(12) United States Patent
Donnelly et al.

(10) Patent No.: US 11,311,610 B2
(45) Date of Patent: Apr. 26, 2022

(54) IMMUNE-MODULATING AGENTS AND USES THEREFOR

(75) Inventors: Sheila Donnelly, Rozelle (AU); Mark William Robinson, Balmain East (AU); John Pius Dalton, Sainte Anne de Bellevue (CA); Joyce To, St. Ives (AU)

(73) Assignee: UNIVERSITY OF TECHNOLOGY SYDNEY, Broadway (AU)

( * ) Notice: Subject to any disclaimer, the term of this patent is extended or adjusted under 35 U.S.C. 154(b) by 820 days.

(21) Appl. No.: 13/882,536

(22) PCT Filed: Nov. 1, 2011

(86) PCT No.: PCT/AU2011/001402
§ 371 (c)(1),
(2), (4) Date: Jul. 15, 2013

(87) PCT Pub. No.: WO2012/058715
PCT Pub. Date: May 10, 2012

(65) Prior Publication Data
US 2013/0287806 A1  Oct. 31, 2013

(30) Foreign Application Priority Data
Nov. 1, 2010 (AU) .............................. 2010904873

(51) Int. Cl.
*A61K 39/00* (2006.01)
*C07K 14/435* (2006.01)
*A61K 45/06* (2006.01)
*A61K 38/00* (2006.01)

(52) U.S. Cl.
CPC .......... *A61K 39/0003* (2013.01); *A61K 45/06* (2013.01); *C07K 14/43559* (2013.01); *A61K 38/00* (2013.01); *Y02A 50/30* (2018.01)

(58) Field of Classification Search
None
See application file for complete search history.

(56) References Cited

FOREIGN PATENT DOCUMENTS

| CN | 1683403 | 10/2005 |
|---|---|---|
| WO | 2005/023979 | 3/2005 |

OTHER PUBLICATIONS

Walsh, K.P., et al. J. Immunol. 2009;183:1577-1586.*
De Olivera et al. Cell Immunol. 1996:170:41-53.*
O'Connell et al., "Unmodified Pancreatic Islet Allograft Rejection Results in the Preferential Expression of Certain T Cell Activation Transcripts," 1993, J. Immunol. 150(3):1093-1104.
O'Doherty et al., "Dendritic cells freshly isolated from human blood express CD4 and mature into typical immunostimulatory dendritic cells after culture in monocyte-conditioned medium," 1993, J Exp Med. 178, 1067-1078.
O'Doherty et al., "Human blood contains two subsets of dendritic cells, one immunologically mature and the other immature," 1994, Immunology 82,487-493.
Oehler et al., "Culture requirements for induction of dendritic cell differentiation in acute myeloid leukemia," 2000, Ann Hematol. 79(7): 355-362.
O'Garra and Arai, "The molecular basis of T helper 1 and T helper 2 cell differentiation," Cell Biology, 2000, 10:542-550.
Pulendran et al., "Flt3-Ligand and Granulocyte Colony-Stimulating Factor Mobilize Distinct Human Dendritic Cell Subsest in Vivo," 2000, J Immunol. 165, 566-572.
Rantapaa-Dahlqvist et al., "Antibodies Against Cyclic Citrullinated Peptide and IgA Rheumatoid Factor Predict the Development of Rheumatoid Arthritis," 2003, Arthritis Rheum. 48:2741.
Ricordi and Strom, "Clinical islet transplantation: advances and immunological challenges," 2004, Nat Rev Immunol. 4:259-268.
Rissoan et al., "Reciprocal Control of T Helper Cell and Dendritic Cell Differentiation," 1999, Science 283, 1183-1186.
Roberge et al., "A strategy for a convergent synthesis of N-linked glycopeptides on a solid support," 1995, Science, 269: 202.
Roberts et al., "Generation of an antibody with enhanced affinity and specificity for its antigen by protein engineering," 1987, Nature 328: 731-734.
Robinson et al., "A family of helminth molecules that modulate innate cell responses via molecular mimicry of host antimicrobial peptides," PLoS Pathog., 2011, 7(5).
Romani et al., "Generation of mature dendritic cells from human blood. An improved method with special regard to clinical applicability," 1996, J Immunol Meth. 196, 137-151.
Schwartz, "Acquisition of immunologic self-tolerance," 1989, Cell 57:1073-1081.
Scofield, "Autoantibodies as predictors of disease," R. H., 2004. Lancet 363, 1544.
Sorg et al., "Phenotypic and functional comparison of monocytes from cord blood and granulocyte colony-stimulating factor—mobilized apheresis products ," 2001, Exp Hematol. 29, 1289-1294.
Strobl et al., "TGF-beta 1 promotes in vitro development of dendritic cells from CD34+ hemopoietic progenitors," 1996, J Immunol. 157, 1499-1507.
Thomas and Lipsky, "Human peripheral blood dendritic cell subsets. Isolation and characterization of precursor and mature antigen-presenting cells," 1994, J Immunol. 153, 4016-4028.
Thomas et al., "Comparative accessory cell function of human peripheral blood dendritic cells and monocytes," 1993, J Immunol. 151(12), 6840-6852.
Thurner et al., "Generation of large Nos. of fully mature and stable dendritic cells from leukapheresis products for clinical application," 1999, J Immunol Methods 223, 1-15.
Truong and Shapiro, "Progress in islet transplantation in patients with type 1 diabetes mellitus," 2006, Treat. Endocrinol. 5:147-158.
Vigna and Naldini, "Lentiviral vectors: excellent tools for experimental gene transfer and promising candidates for gene therapy," 2000, J. Gene Med. 2(5), 308-316.

(Continued)

*Primary Examiner* — G. R. Ewoldt
(74) *Attorney, Agent, or Firm* — K&L Gates LLP; Louis C. Cullman; Michelle Glasky Bergman

(57) ABSTRACT

This invention discloses the use of Heminth Defense Molecules in methods and compositions for modulating immune responses including treating or preventing undesirable or deleterious immune responses.

17 Claims, 15 Drawing Sheets
(7 of 15 Drawing Sheet(s) Filed in Color)
Specification includes a Sequence Listing.

(56) References Cited

OTHER PUBLICATIONS

Vollendweider and Groscurth, "Comparison of four DNA staining fluorescence dyes for measuring cell proliferation of lymphokine-activated killer (LAK) cells," 1992, J Immunol Meth. 149, 133-135.
Vremec and Shortma, "Dendritic cell subtypes in mouse lymphoid organs: cross-correlation of surface markers, changes with incubation, and differences among thymus, spleen, and lymph nodes," 1997, J Immunol. 159, 565-573.
Walther and Stein et al., "Viral vectors for gene transfer: a review of their use in the treatment of human diseases," 2000, Drugs 60(2), 249-271.
Wang et al., "Highly Efficient DNA Delivery Mediated by pH-Sensitive Immunoliposomes," Biochem., 1989 28, 9508-951.
Wang et al., "Combination of adsorption by porous CaCO3 microparticles and encapsulation of polyelectrolyte multilayer films for sustained drug delivery," Int J Pharm., 2006, 308(1-2):160-167.
Weiner, "Oral tolerance: immune mechanisms and the generation of Th3-type TGF-beta-secreting regulatory cells," 2001, Microbes Infect 3:947-954.
Wu and Ataai, "Production of viral vectorsforgene therapy applications," 2000, Curr. Opin. Biotechnol. 11(2), 205-208.
Xu et al., "Distinct roles for B7-1 and B7-2 determinants during priming of effector CD8+ Tc1 and regulatory CD4+ Th2 cells for contact hypersensitivity," 1997, J Immunol 159:4217-4226.
Zhou and Huang et al., "Liposome-Mediated Cytoplasmic Delivery of Proteins: An Effective Means of Accessing the MHC Class I-Restricted Antigen Presentation Pathway," 1994, Immunomethods 4, 229-235.
Zitvogel et al., "Eradication of established murine tumors using a novel cell-free vaccine: dendritic cell derived exosomes," 1998 Nat Med. 4, 594-600.
Cancela et al., Survey of transcripts expressed by the invasive juvenile stage of the liver fluke Fasciola hepatica, BMC Genomics, 2010, 11:227, 14 pages.
Dowling et al., Major Secretory Antigens of the Helminth Fasciola hepatica Activate a Suppressive Dendritic Cell Phenotype That Attenuates Th17 Cells but Fails To Activate Th2 Immune Responses, Infection and Immunity, 2010, 78:793-801.
Lee et al., Purification and Characterization of a 7-KDA Protein From Clonorchis Sinensis Adult Worms, J Parasitology, 2002, 88:499-504.
Miller et al., Immunological Interactions between 2 Common Pathogens, Th1-Inducing Protozoan Toxoplasma gondii and the Th2-Inducing Helminth Fasciola hepatica, PLoS One, 2009, 4(5):e5692, 10 pages.
Rao et al., Cloning and expression of a gene encoding Sm16 an anti-inflammatory protein from Schitosoma mansoni, Mol Biochem Parasitology, 2000, 108:101-108.
Terrazas et al., The Schistosome Oligosaccharide Lacto-N-neotetraose Expands Gr1 Cells That Secrete Anti-inflammatory Cytokines and Inhibit Proliferation of Naive CD4+Cells+: A Potential Mechanism for Immune Polarization in Helminth Infections, J Immunol, 2001, 167:5294-5303.
Valle et al., Stage-specific expression of a Schistosoma mansoni polypeptide similar to the vertebrate regulatory protein stathmin, J Biol Chem, 1999, 274:33869-33874.
Albert et al., "Dendritic cells acquire antigen from apoptotic cells and induce class I-restricted CTLs," Nature, 1998, 392, 86-89.
Albert et al., "Tumor-specific killer cells in paraneoplastic cerebellar degeneration," Nature Med., 1998, 4, 1321-1324.
Altshul et al., "Basic local alignment search tool," J. Mol. Biol, 1990, 215: 403-10.
Arkin and Youvan, "An algorithm for protein engineering: Simulations of recursive ensemble mutagenesis," Proc. Natl. Acad. Sci. USA, 1992, 89: 7811-7815.
Avnir et al., "Enzymes and Other Proteins Entrapped in Sol-Gel Materials," Chem. Mater., 1994, 6, 1605-1614.
Bachmann et al., "Dendritic cells process exogenous viral proteins and virus-like particles for class I presentation to CD8+ cytotoxic T lymphocytes," Eur. J. Immunol., 1996, 26(11), 2595-2600.
Battye and Shortman, "Flow cytometry and cell-separation procedures," Curr. Opin. Immunol, 1991, 3, 238-241.
Benito et al., "Optimizing Saccharide-Directed Molecular Delivery to Biological Receptors: Design, Synthesis, and Biological Evaluation of Glycodendrimer—Cyclodextrin Conjugates," J Am Chem Soc, 2004, 126, 10355-10363.
Berglin et al., "A combination of autoantibodies to cyclic citrullinated peptide (CCP) and HLA-DRB1 locus antigens is strongly associated with future onset of rheumatoid arthritis," 2004, Arthritis Res Ther. 6, R30336.
Bramwell and Perrie, "Particulate Delivery Systems for Vaccines," Crit Rev Ther Drug Carrier Syst, 2005, 22 (2):151-214.
Bramwell and Perrie, "Particulate delivery systems for vaccines: what can we expect," J Pharm Pharmacol., 2006, 58(6):717-728.
Chatenoud et al., "Anti-CD3 antibody induces long-term remission of overt autoimmunity in nonobese diabetic mice," Proc Natl Acad Sci USA, 1994, 91:123-127.
Chatenoud et al., "CD3 Antibody-Induced Dominant Self Tolerance in Overtly Diabetic NOD Mice," J Immunol, 1997, 158:2947-2954.
Chen et al., "Replicative Response, Immunophenotype, and Functional Activity of Monocyte-Derived versus CD34+—Derived Dentdritic Cells Following Exposure to Various Expansion and Maturational Stimuli," Clin Immunol., 2001, 98, 280-292.
Copland et al., "Lipid based particulate formulations for the delivery of antigen," Immunol. Cell Biol., 2005, 83: 95-105.
Corinti et al., "Human Dendritic Cells Very Efficiently Present a Heterologous Antigen Expressed on the Surface of Recombinant Gram-Positive Bacteria to CD4+ T Lymphocytes," J Immunol., 1999, 163(6), 3029-3036.
Cox and Coulter, "Adjuvants—a classification and review of their modes of action," Vaccine, 1997, 15(3), 248-256.
Davis et al., "Assessment of a positive selection technique using an avidin column to isolate human peripheral blood T cell subsets," J Immunol Meth, 1994, 175, 247-257.
Del Hoyo et al., "Characterization of a common precursor population for dendritic cells," Nature, 2002, 415, 1043-1047.
Donnelly et al., "Helminth Cysteine Proteases Inhibit TRIF-dependent Activation of Macrophages via Degradation of TLR3," J. Biol. Chem., 2010, 285, 3383-3392.
Gao et al., "Priming of influenza virus-specific cytotoxic T lymphocytes vivo by short synthetic peptides," 1991, J. Immunol. 147, 3268-3273.
Garderet et al., "In vitro production of dendritic cells from human blood monocytes for therapeutic use," 2001, J Hematother Stem Cell Res. 10, 553-567.
Gillam and Smith, "Site-Specific Mutagenesis Using Synthetic Oligodeoxyribonucleotide Primers: I. Optimum Conditions and Minimum Olgodeoxyribonucleotide Length," Gene, 1979 8: 81-97.
Jain et al., "Nanometer Silica Particles Encapsulating Active Compounds: A Novel Ceramic Drug Carrier," 1998, J. Am. Chem. Soc. 120, 11092-11095.
Jumah et al., "Identification of second harmonic optical effects from vaccine coated gold microparticles," Phys Med. Biol., 2004, 49:3603-3612.
Kawano et al., "CD1d-restricted and TCR-mediated activation of valpha14 NKT cells by glycosylceramides," 1997, Science 278:1626-1629.
Kay et al., "Viral vectors for gene therapy: the art of turning infectious agents into vehicles of therapeutics," 2001, Nat. Med. 7(1), 33-40.
Ke et al., "Gamma delta T lymphocytes regulate the induction and maintenance of oral tolerance," 1997, J Immunol 158:3610-3618.
Kemp et al., "Transplantation of Isolated Pancreatic Islets into the Portal Vein of Diabetic Rats," 1973, Nature 244:447.
Keymeulen et al., "Four-year metabolic outcome of a randomised controlled CD3-antibody trial in recent-onset type 1 diabetic patients depends on their age and baseline residual beta cell mass," 2010, Diabetologia 53:614-623.
Kortesuo et al., "In vitro evaluation of sol-gel processed spray dried silica gel microspheres as carrier in controlled drug delivery," 2000, Int J Pharm.200(2):223-229.

(56) References Cited

OTHER PUBLICATIONS

Kuzu et al., "In vivo priming effect during various stages of ontogeny of an influenza A virus nucleoprotein peptide," 1993, Euro. J. Immunol. 23, 1397-1400.

Lal et al., "Silica Nanobubbles Containing an Organic Dye in a Multilayered Organic/Inorganic Heterostructure with Enhanced Luminescence," 2000, Chem. Mater. 12, 2632-2639.

Lee et al., "Recognition of liposomes by cells: in vitro binding and endocytosis mediated by specific lipid headgroups and surface charge density," 1992, Biochim. Biophys. Acta. 1103, 185-197.

Liu et al., "Role of liposome size and RES blockade in controlling biodistribution and tumor uptake of GM1-containing liposomes," 1992, Biochim. Biophys. Acta. 1104, 95-101.

Loudovaris et al., "Differential effects of autologous serum on CD34(+) or monocyte-derived dendritic cells," 2001, J Hematother Stem Cell Res. 10, 569-578.

Lu et al., "Propagation of Dendritic Cell Progenitors from Normal Mouse Liver Using Granulocyte / Macrophage Colony-stimulating Factor and Their Maturational Development in the Presence of Type-1 Collagen," J Exp Med., 1994, 179, 1823-1834.

Masharani and Becker, "Teplizumab therapy for type 1 diabetes," Expert Opin Biol Ther., 2010, 10:459-465.

Mathiowitz and Langer, "Polyanhydride Microspheres as Drug Carriers I. Hot-Melt Microencapsulation," J. Controlled Release, 1987, 5, 13-22.

Mathiowitz et al., "Polyanydride Microspheres as Drug Carriers. II. Microencapsulation by Solvent Removal, " 1988, J. Appl. Polymer Sci. 35, 755-774.

McIlroy et al., "Investigation of human spleen dendritic cell phenotype and distribution reveals evidence of in vivo activiation in a subset of organ donors," 2001, Blood 97, 3470-3477.

McMenamin et al., "Gamma delta T cells down-regulate primary IgE responses in rats to inhaled soluble protein antigens," 1995, J Immunol 154:4390-4394.

Metcalf and Burgess, "Clonal analysis of progenitor cell commitment to granulocyte or macrophage production," 1982, J Cell Physiol. 111, 275-283.

Moore et al., "Introduction of Soluble Protein into the Class I Pathway of Antigen Processing and Presentation," 1988, Cell 54, 777-785.

Needham and Dewhirst, "The development and testing of a new temperature-sensitive drug delivery system for the treatment of solid tumors," 2001, Advanced Drug Delivery Reviews 53(3): 285-305.

Needleman et al., "A general method applicable to the search for similarities in the amino acid sequence of two proteins," 1970, J. Mol. Biol. 48(3): 443-453.

Nestle et al., "Vaccination of melanoma patients with peptide- or tumorlysate-pulsed dendritic cells," 1998, Nat Med. 4, 328-332.

Nell MJ et al. "Development of novel LL-37 derived antimicrobial peptides with LPS and LTA neutralizing and antimicrobial activities for therapeutic application." Peptides 27:649-660, 2006.

\* cited by examiner

FIGURE 1

Unconserved 0 1 2 3 4 5 6 7 8 9 10 Conserved

```
                      .........10.........20......
C_sinensis_1          YLEKDNLGEK IAEVVKILSE RLTKRIE
O_viverrini_EST       YLEKDGLGEK LADVIKILAE RLTKRME
F_hepatica_Fh6        YLAKDNLGEK ITEVITILLN RLTDRLE
P_westermani_ES       YLEEDGLGDK ISEVIQILLK RLTDRIE
S_japonicum_999       YFKQDDLGEK IAEVLLIFLQ RLNRRLE
S_japonicum_000       YFKQDDLGEK IAEVLLIFLQ RLNRRLE
S_japonicum_998       YFKQDGLGEK LAEVLLILLQ RLNRRLE
S_mansoni_EST         YFREDDLGEK IADVLVVLLK RLNKRLE
S_mansoni_CAZ32       YLEEDNLGEK LAAVVSIYVK RLNKRLD
C_sinensis_2          FFEKDNLGEK IAEVVKILSE PLPKRIE
S_japonicum_EST       YLRKDDLDKK MLEIANILAK RLEKRME
Consistency           9667*5*88* 8779749756 8*56*89
```

FIGURE 2

```
HDM (70mer)        RPSEESREKLRESGRKMVKALRDAVTKAYEKARDRAMAYLAKDNLGEKITEVITILLNRLTDRLEKYAGN  (SEQ ID NO:129)
HDMp1              ---------------------------------KARDRAMAYLAKDNLGEKITEVITILLNRL------  (SEQ ID NO:130)
HDMp2              --------------------------------------NLGEKITEVITILLNRLTDRLEKYAGN      (SEQ ID NO:131)
HDMp3 (34mer)      ----------------------------------AMAYLAKDNLGEKITEVITILLNRLTDRLEKYAG-  (SEQ ID NO:132)
nonHP              ----------------------------------AMAYLAKDNLGEKRTEVQTKRLNRLTDRTEKKAG-  (SEQ ID NO:133)
2Pro               ----------------------------------AMAYLAKDNLGEKPTEVITILLNRPTDRLEKYAG-  (SEQ ID NO:134)
HDMp3_1-13         ----------------------------------AMAYLAKDNLGEK----------------------  (SEQ ID NO:135)
HDMp3_27 (27mer)   -------------------------------------YLAKDNLGEKITEVITILLNRLTDRLE-----  (SEQ ID NO:136)
HDMp3_12-34        -------------------------------------------EKITEVITILLNRLTDRLEKYAG-   (SEQ ID NO:137)
HDMp3_12-32        -------------------------------------------EKITEVITILLNRLTDRLEKY---   (SEQ ID NO:138)
HDMp3_14-34        ---------------------------------------------ITEVITILLNRLTDRLEKYAG-   (SEQ ID NO:139)
HDMp3_14-32        ---------------------------------------------ITEVITILLNRLTDRLEKY---   (SEQ ID NO:140)
Cons_p3            -------------------------IEEYLEKDNLGEKIAEVVKILLERLTRRLEKYVG-           (SEQ ID NO:128)
```

FIGURE 18

```
Unconserved  0 1 2 3 4 5 6 7 8 9 10  Conserved

.........10.........20.
S_japonicum_999     LGEKIAEVLL IFLQRLNRRL E
S_japonicum_000     LGEKIAEVLL IFLQRLNRRL E
S_japonicum_998     LGEKIAEVLL ILLQRLNRRL E
S_mansoni_EST       LGEKIADVLV VLLKRLNKRL E
P_westermani_ES     LGDKISEVIQ ILLKRLTDRL E
F_hepatica_Fh6      LGEKITEVIT ILLNRLTDRL E
Consensus           LGEKIAEVVK ILLERLTRRL E
O_viverrini_EST     LGEKIADVIK ILAERLTKRM E
S_mansoni_CAZ32     LGEKLAAVVS IYVKRLNKRL D
Consistency         **9*887*84 9676**65*8 9
```

FIGURE 19

SEQUENCE LISTING

```
<160> NUMBER OF SEQ ID NOS: 143

<210> SEQ ID NO 1
<211> LENGTH: 81
<212> TYPE: DNA
<213> ORGANISM: Artificial
<220> FEATURE:
<223> OTHER INFORMATION: Nucleotide sequence encoding FhHDM-1 C-terminal
      sequence
<220> FEATURE:
<221> NAME/KEY: CDS
<222> LOCATION: (1)..(81)

<400> SEQUENCE: 1 tac ttg gcg aag gac aat cta gga gaa aag atc act gaa gtg atc acg      48
Tyr Leu Ala Lys Asp Asn Leu Gly Glu Lys Ile Thr Glu Val Ile Thr
1               5                   10                  15 atc tta ctg aat cgg ctc acc gat cgc ttg gag                          81
Ile Leu Leu Asn Arg Leu Thr Asp Arg Leu Glu
            20                  25

<210> SEQ ID NO 2
<211> LENGTH: 27
<212> TYPE: PRT
<213> ORGANISM: Artificial
<220> FEATURE:
<223> OTHER INFORMATION: Synthetic Construct
```

<400> SEQUENCE: 2

Tyr Leu Ala Lys Asp Asn Leu Gly Glu Lys Ile Thr Glu Val Ile Thr
1               5                   10                  15

Ile Leu Leu Asn Arg Leu Thr Asp Arg Leu Glu
            20                  25

<210> SEQ ID NO 3
<211> LENGTH: 81
<212> TYPE: DNA
<213> ORGANISM: Artificial
<220> FEATURE:
<223> OTHER INFORMATION: Nucleotide sequence encoding CsHDM-1 C-terminal
      sequence
<220> FEATURE:
<221> NAME/KEY: CDS
<222> LOCATION: (1)..(81)

<400> SEQUENCE: 3 tat ctt gaa aag gac aac ctg ggc gag aaa ata gct gaa gtc gtg aaa      48
Tyr Leu Glu Lys Asp Asn Leu Gly Glu Lys Ile Ala Glu Val Val Lys
1               5                   10                  15 atc ctg tcc gag cgc ctg acc aaa cgg ata gag                          81
Ile Leu Ser Glu Arg Leu Thr Lys Arg Ile Glu
            20                  25

<210> SEQ ID NO 4
<211> LENGTH: 27
<212> TYPE: PRT
<213> ORGANISM: Artificial
<220> FEATURE:
<223> OTHER INFORMATION: Synthetic Construct

<400> SEQUENCE: 4

Tyr Leu Glu Lys Asp Asn Leu Gly Glu Lys Ile Ala Glu Val Val Lys
1               5                   10                  15

Ile Leu Ser Glu Arg Leu Thr Lys Arg Ile Glu
            20                  25

<210> SEQ ID NO 5
<211> LENGTH: 81
<212> TYPE: DNA
<213> ORGANISM: Artificial
<220> FEATURE:
<223> OTHER INFORMATION: Nucleotide sequence encoding OvHDM-1 C-terminal
      sequence
<220> FEATURE:
<221> NAME/KEY: CDS
<222> LOCATION: (1)..(81)

<400> SEQUENCE: 5 tat ctg gaa aag gac ggt ctc ggc gag aaa tta gct gat gtc att aaa      48
Tyr Leu Glu Lys Asp Gly Leu Gly Glu Lys Leu Ala Asp Val Ile Lys
1               5                   10                  15 atc ctg gcc gag cgc cta acc aaa cgg atg gag                          81
Ile Leu Ala Glu Arg Leu Thr Lys Arg Met Glu
            20                  25

<210> SEQ ID NO 6
<211> LENGTH: 27
<212> TYPE: PRT
<213> ORGANISM: Artificial
<220> FEATURE:
<223> OTHER INFORMATION: Synthetic Construct

<400> SEQUENCE: 6

Tyr Leu Glu Lys Asp Gly Leu Gly Glu Lys Leu Ala Asp Val Ile Lys
1               5                   10                  15

Ile Leu Ala Glu Arg Leu Thr Lys Arg Met Glu
            20                  25

<210> SEQ ID NO 7
<211> LENGTH: 81
<212> TYPE: DNA
<213> ORGANISM: Artificial
<220> FEATURE:
<223> OTHER INFORMATION: Nucleotide sequence encoding PwHDM-1 C-terminal
      sequence
<220> FEATURE:
<221> NAME/KEY: CDS
<222> LOCATION: (1)..(81)

<400> SEQUENCE: 7 tat ttg gag aaa gat gga ctc gga gac aag ata tcg gaa gtg att caa    48
Tyr Leu Glu Lys Asp Gly Leu Gly Asp Lys Ile Ser Glu Val Ile Gln
1               5                   10                  15 atc tta ctg aaa aga cta act gac cga att gag                        81
Ile Leu Leu Lys Arg Leu Thr Asp Arg Ile Glu
            20                  25

<210> SEQ ID NO 8
<211> LENGTH: 27
<212> TYPE: PRT
<213> ORGANISM: Artificial
<220> FEATURE:
<223> OTHER INFORMATION: Synthetic Construct

<400> SEQUENCE: 8

Tyr Leu Glu Lys Asp Gly Leu Gly Asp Lys Ile Ser Glu Val Ile Gln
1               5                   10                  15

Ile Leu Leu Lys Arg Leu Thr Asp Arg Ile Glu
            20                  25

<210> SEQ ID NO 9
<211> LENGTH: 81
<212> TYPE: DNA
<213> ORGANISM: Artificial
<220> FEATURE:
<223> OTHER INFORMATION: Nucleotide sequence encoding SjHDM-1 C-terminal
      sequence
<220> FEATURE:
<221> NAME/KEY: CDS
<222> LOCATION: (1)..(81)

<400> SEQUENCE: 9 tac ttt aaa caa gat gat tta ggc gag aaa ata gca gag gtt cta ctt    48
Tyr Phe Lys Gln Asp Asp Leu Gly Glu Lys Ile Ala Glu Val Leu Leu
1               5                   10                  15 att ttt ctt caa cgt ttg aat aga cgt cta gaa                        81
Ile Phe Leu Gln Arg Leu Asn Arg Arg Leu Glu
            20                  25

<210> SEQ ID NO 10
<211> LENGTH: 27
<212> TYPE: PRT
<213> ORGANISM: Artificial
<220> FEATURE:
<223> OTHER INFORMATION: Synthetic Construct

<400> SEQUENCE: 10

Tyr Phe Lys Gln Asp Asp Leu Gly Glu Lys Ile Ala Glu Val Leu Leu
1               5                   10                  15

```
Ile Phe Leu Gln Arg Leu Asn Arg Arg Leu Glu
            20                  25

<210> SEQ ID NO 11
<211> LENGTH: 81
<212> TYPE: DNA
<213> ORGANISM: Artificial
<220> FEATURE:
<223> OTHER INFORMATION: Nucleotide sequence encoding SjHDM-2 C-terminal
      sequence
<220> FEATURE:
<221> NAME/KEY: CDS
<222> LOCATION: (1)..(81)

<400> SEQUENCE: 11 tac ttt aaa caa gat gat tta gga gag aaa ata gca gag gtt cta ctt       48
Tyr Phe Lys Gln Asp Asp Leu Gly Glu Lys Ile Ala Glu Val Leu Leu
1               5                   10                  15 att ttt ctt caa cgt ttg aat aga cgt cta gaa                          81
Ile Phe Leu Gln Arg Leu Asn Arg Arg Leu Glu
            20                  25

<210> SEQ ID NO 12
<211> LENGTH: 27
<212> TYPE: PRT
<213> ORGANISM: Artificial
<220> FEATURE:
<223> OTHER INFORMATION: Synthetic Construct

<400> SEQUENCE: 12

Tyr Phe Lys Gln Asp Asp Leu Gly Glu Lys Ile Ala Glu Val Leu Leu
1               5                   10                  15

Ile Phe Leu Gln Arg Leu Asn Arg Arg Leu Glu
            20                  25

<210> SEQ ID NO 13
<211> LENGTH: 81
<212> TYPE: DNA
<213> ORGANISM: Artificial
<220> FEATURE:
<223> OTHER INFORMATION: Nucleotide sequence encoding SjHDM-3 C-terminal
      sequence
<220> FEATURE:
<221> NAME/KEY: CDS
<222> LOCATION: (1)..(81)

<400> SEQUENCE: 13 tac ttt aaa caa gat gga tta ggc gag aag tta gca gag gtt cta ctt       48
Tyr Phe Lys Gln Asp Gly Leu Gly Glu Lys Leu Ala Glu Val Leu Leu
1               5                   10                  15 att ctt ctt caa cgt ttg aat aga cgt cta gaa                          81
Ile Leu Leu Gln Arg Leu Asn Arg Arg Leu Glu
            20                  25

<210> SEQ ID NO 14
<211> LENGTH: 27
<212> TYPE: PRT
<213> ORGANISM: Artificial
<220> FEATURE:
<223> OTHER INFORMATION: Synthetic Construct

<400> SEQUENCE: 14

Tyr Phe Lys Gln Asp Gly Leu Gly Glu Lys Leu Ala Glu Val Leu Leu
1               5                   10                  15

Ile Leu Leu Gln Arg Leu Asn Arg Arg Leu Glu
            20                  25
```

-continued

<210> SEQ ID NO 15
<211> LENGTH: 81
<212> TYPE: DNA
<213> ORGANISM: Artificial
<220> FEATURE:
<223> OTHER INFORMATION: Nucleotide sequence encoding SmHDM-1 C-terminal
      sequence
<220> FEATURE:
<221> NAME/KEY: CDS
<222> LOCATION: (1)..(81)

<400> SEQUENCE: 15 tat ttc agg gaa gac gat cta ggt gag aaa ata gca gac gtt tta gtt    48
Tyr Phe Arg Glu Asp Asp Leu Gly Glu Lys Ile Ala Asp Val Leu Val
1               5                   10                  15 gtt tta ctt aaa cgt ttg aat aaa cgc cta gaa                        81
Val Leu Leu Lys Arg Leu Asn Lys Arg Leu Glu
            20                  25

<210> SEQ ID NO 16
<211> LENGTH: 27
<212> TYPE: PRT
<213> ORGANISM: Artificial
<220> FEATURE:
<223> OTHER INFORMATION: Synthetic Construct

<400> SEQUENCE: 16

Tyr Phe Arg Glu Asp Asp Leu Gly Glu Lys Ile Ala Asp Val Leu Val
1               5                   10                  15

Val Leu Leu Lys Arg Leu Asn Lys Arg Leu Glu
            20                  25

<210> SEQ ID NO 17
<211> LENGTH: 81
<212> TYPE: DNA
<213> ORGANISM: Artificial
<220> FEATURE:
<223> OTHER INFORMATION: Nucleotide sequence encoding SmHDM-2 C-terminal
      sequence
<220> FEATURE:
<221> NAME/KEY: CDS
<222> LOCATION: (1)..(81)

<400> SEQUENCE: 17 tat ctt gaa gaa gat aat tta ggt gaa aaa tta gcc gct gtt gta agc    48
Tyr Leu Glu Glu Asp Asn Leu Gly Glu Lys Leu Ala Ala Val Val Ser
1               5                   10                  15 atc tat gtt aag cgt tta aac aag cgt tta gat                        81
Ile Tyr Val Lys Arg Leu Asn Lys Arg Leu Asp
            20                  25

<210> SEQ ID NO 18
<211> LENGTH: 27
<212> TYPE: PRT
<213> ORGANISM: Artificial
<220> FEATURE:
<223> OTHER INFORMATION: Synthetic Construct

<400> SEQUENCE: 18

Tyr Leu Glu Glu Asp Asn Leu Gly Glu Lys Leu Ala Ala Val Val Ser
1               5                   10                  15

Ile Tyr Val Lys Arg Leu Asn Lys Arg Leu Asp
            20                  25

<210> SEQ ID NO 19
<211> LENGTH: 81

```
<212> TYPE: DNA
<213> ORGANISM: Artificial
<220> FEATURE:
<223> OTHER INFORMATION: Nucleotide sequence encoding CsHDM-2 C-terminal
      sequence
<220> FEATURE:
<221> NAME/KEY: CDS
<222> LOCATION: (1)..(81)

<400> SEQUENCE: 19 ttt ttt gaa aag gac aac ctg ggg gag aaa ata gcg gaa gtc gtg aaa      48
Phe Phe Glu Lys Asp Asn Leu Gly Glu Lys Ile Ala Glu Val Val Lys
1               5                   10                  15 atc ctg tcc gag ccc ctg ccc aaa cgg ata gag                           81
Ile Leu Ser Glu Pro Leu Pro Lys Arg Ile Glu
            20                  25

<210> SEQ ID NO 20
<211> LENGTH: 27
<212> TYPE: PRT
<213> ORGANISM: Artificial
<220> FEATURE:
<223> OTHER INFORMATION: Synthetic Construct

<400> SEQUENCE: 20

Phe Phe Glu Lys Asp Asn Leu Gly Glu Lys Ile Ala Glu Val Val Lys
1               5                   10                  15

Ile Leu Ser Glu Pro Leu Pro Lys Arg Ile Glu
            20                  25

<210> SEQ ID NO 21
<211> LENGTH: 81
<212> TYPE: DNA
<213> ORGANISM: Artificial
<220> FEATURE:
<223> OTHER INFORMATION: Nucleotide sequence encoding SjHDM-4 C-terminal
      sequence
<220> FEATURE:
<221> NAME/KEY: CDS
<222> LOCATION: (1)..(81)

<400> SEQUENCE: 21 tac ctc aga aaa gat gat tta gat aag aaa atg ctt gaa atc gcc aat      48
Tyr Leu Arg Lys Asp Asp Leu Asp Lys Lys Met Leu Glu Ile Ala Asn
1               5                   10                  15 att ctt gcc aaa cgt ttg gag aaa cgg atg gag                           81
Ile Leu Ala Lys Arg Leu Glu Lys Arg Met Glu
            20                  25

<210> SEQ ID NO 22
<211> LENGTH: 27
<212> TYPE: PRT
<213> ORGANISM: Artificial
<220> FEATURE:
<223> OTHER INFORMATION: Synthetic Construct

<400> SEQUENCE: 22

Tyr Leu Arg Lys Asp Asp Leu Asp Lys Lys Met Leu Glu Ile Ala Asn
1               5                   10                  15

Ile Leu Ala Lys Arg Leu Glu Lys Arg Met Glu
            20                  25

<210> SEQ ID NO 23
<211> LENGTH: 270
<212> TYPE: DNA
<213> ORGANISM: Fasciola hepatica
<220> FEATURE:
```

<221> NAME/KEY: CDS
<222> LOCATION: (1)..(270)

<400> SEQUENCE: 23

```
atg cgc ttc att gtt ctt ctc tgt ctt gct gag gtc ctt ctt gca gct      48
Met Arg Phe Ile Val Leu Leu Cys Leu Ala Glu Val Leu Leu Ala Ala
1               5                   10                  15 tat gtg gag gct aga cct agc gag gaa agc cgg gaa aaa ttg cgt gaa      96
Tyr Val Glu Ala Arg Pro Ser Glu Glu Ser Arg Glu Lys Leu Arg Glu
            20                  25                  30 agc gga agg aaa atg gtg aaa gcc ctc agg gat gcc gtg acg aag gca     144
Ser Gly Arg Lys Met Val Lys Ala Leu Arg Asp Ala Val Thr Lys Ala
        35                  40                  45 tac gag aag gca cgt gac cga gct atg gct tac ttg gcg aag gac aat     192
Tyr Glu Lys Ala Arg Asp Arg Ala Met Ala Tyr Leu Ala Lys Asp Asn
    50                  55                  60 cta gga gaa aag atc act gaa gtg atc acg atc tta ctg aat cgg ctc     240
Leu Gly Glu Lys Ile Thr Glu Val Ile Thr Ile Leu Leu Asn Arg Leu
65                  70                  75                  80 acc gat cgc ttg gag aaa tac gcg gga aat                             270
Thr Asp Arg Leu Glu Lys Tyr Ala Gly Asn
                85                  90
```

<210> SEQ ID NO 24
<211> LENGTH: 90
<212> TYPE: PRT
<213> ORGANISM: Fasciola hepatica

<400> SEQUENCE: 24

```
Met Arg Phe Ile Val Leu Leu Cys Leu Ala Glu Val Leu Leu Ala Ala
1               5                   10                  15

Tyr Val Glu Ala Arg Pro Ser Glu Glu Ser Arg Glu Lys Leu Arg Glu
            20                  25                  30

Ser Gly Arg Lys Met Val Lys Ala Leu Arg Asp Ala Val Thr Lys Ala
        35                  40                  45

Tyr Glu Lys Ala Arg Asp Arg Ala Met Ala Tyr Leu Ala Lys Asp Asn
    50                  55                  60

Leu Gly Glu Lys Ile Thr Glu Val Ile Thr Ile Leu Leu Asn Arg Leu
65                  70                  75                  80

Thr Asp Arg Leu Glu Lys Tyr Ala Gly Asn
                85                  90
```

<210> SEQ ID NO 25
<211> LENGTH: 270
<212> TYPE: DNA
<213> ORGANISM: Chlonorchis sinensis
<220> FEATURE:
<221> NAME/KEY: CDS
<222> LOCATION: (1)..(270)

<400> SEQUENCE: 25

```
atg cga ctg act gtt ttc atc tgc ttg gtc ttt gtt ctg ttt gtg gcg      48
Met Arg Leu Thr Val Phe Ile Cys Leu Val Phe Val Leu Phe Val Ala
1               5                   10                  15 cac gct gaa gcc cgt ccc agt gag gag acc cgt gcc aaa ctg cga gaa      96
His Ala Glu Ala Arg Pro Ser Glu Glu Thr Arg Ala Lys Leu Arg Glu
            20                  25                  30 tcc ggc cag aaa tta tgg acg gcg gtg gtg gct gct gcg aga aaa tgt     144
Ser Gly Gln Lys Leu Trp Thr Ala Val Val Ala Ala Ala Arg Lys Cys
        35                  40                  45 gcc gaa cgg gtt aga caa cga atc gag gaa tat ctt gaa aag gac aac     192
Ala Glu Arg Val Arg Gln Arg Ile Glu Glu Tyr Leu Glu Lys Asp Asn
```

```
                                              Ala Glu Arg Val Arg Gln Arg Ile Glu Glu Tyr Leu Glu Lys Asp Asn
                                               50                  55                  60 ctg ggc gag aaa ata gct gaa gtc gtg aaa atc ctg tcc gag cgc ctg        240
Leu Gly Glu Lys Ile Ala Glu Val Val Lys Ile Leu Ser Glu Arg Leu
 65                  70                  75                  80 acc aaa cgg ata gag act tac gtt ggg gag                                270
Thr Lys Arg Ile Glu Thr Tyr Val Gly Glu
                 85                  90

<210> SEQ ID NO 26
<211> LENGTH: 90
<212> TYPE: PRT
<213> ORGANISM: Chlonorchis sinensis

<400> SEQUENCE: 26

Met Arg Leu Thr Val Phe Ile Cys Leu Val Phe Val Leu Phe Val Ala
 1               5                  10                  15

His Ala Glu Ala Arg Pro Ser Glu Thr Arg Ala Lys Leu Arg Glu
                20                  25                  30

Ser Gly Gln Lys Leu Trp Thr Ala Val Val Ala Ala Arg Lys Cys
             35                  40                  45

Ala Glu Arg Val Arg Gln Arg Ile Glu Glu Tyr Leu Glu Lys Asp Asn
 50                  55                  60

Leu Gly Glu Lys Ile Ala Glu Val Val Lys Ile Leu Ser Glu Arg Leu
 65                  70                  75                  80

Thr Lys Arg Ile Glu Thr Tyr Val Gly Glu
                 85                  90

<210> SEQ ID NO 27
<211> LENGTH: 270
<212> TYPE: DNA
<213> ORGANISM: Opisthorchis viverrini
<220> FEATURE:
<221> NAME/KEY: CDS
<222> LOCATION: (1)..(270)

<400> SEQUENCE: 27 atg aga ctc act gtt ttc atc tgc ttg gcc ttt gtt ctg ttt gtc gct        48
Met Arg Leu Thr Val Phe Ile Cys Leu Ala Phe Val Leu Phe Val Ala
 1               5                  10                  15 cac gct gaa gcc cgt ccg aat gag gag acc cgt gcc aaa ctg cga gaa        96
His Ala Glu Ala Arg Pro Asn Glu Glu Thr Arg Ala Lys Leu Arg Glu
                20                  25                  30 tcc ggc cag aag cta tgg ggc gca att atg agt gct gcg aaa aaa tgt       144
Ser Gly Gln Lys Leu Trp Gly Ala Ile Met Ser Ala Ala Lys Lys Cys
             35                  40                  45 gca gat cgg gtc aaa caa cga atc gaa gaa tat ctg gaa aag gac ggt       192
Ala Asp Arg Val Lys Gln Arg Ile Glu Glu Tyr Leu Glu Lys Asp Gly
 50                  55                  60 ctc ggc gag aaa tta gct gat gtc att aaa atc ctg gcc gag cgc cta       240
Leu Gly Glu Lys Leu Ala Asp Val Ile Lys Ile Leu Ala Glu Arg Leu
 65                  70                  75                  80 acc aaa cgg atg gag acc tat gtc aag gag                                270
Thr Lys Arg Met Glu Thr Tyr Val Lys Glu
                 85                  90

<210> SEQ ID NO 28
<211> LENGTH: 90
<212> TYPE: PRT
<213> ORGANISM: Opisthorchis viverrini

<400> SEQUENCE: 28
```

```
Met Arg Leu Thr Val Phe Ile Cys Leu Ala Phe Val Leu Phe Val Ala
1               5                   10                  15

His Ala Glu Ala Arg Pro Asn Glu Glu Thr Arg Ala Lys Leu Arg Glu
                20                  25                  30

Ser Gly Gln Lys Leu Trp Gly Ala Ile Met Ser Ala Ala Lys Lys Cys
            35                  40                  45

Ala Asp Arg Val Lys Gln Arg Ile Glu Glu Tyr Leu Glu Lys Asp Gly
        50                  55                  60

Leu Gly Glu Lys Leu Ala Asp Val Ile Lys Ile Leu Ala Glu Arg Leu
65                  70                  75                  80

Thr Lys Arg Met Glu Thr Tyr Val Lys Glu
                85                  90

<210> SEQ ID NO 29
<211> LENGTH: 264
<212> TYPE: DNA
<213> ORGANISM: Paragonimus westermani
<220> FEATURE:
<221> NAME/KEY: CDS
<222> LOCATION: (1)..(264)

<400> SEQUENCE: 29 gag ggg ctg ctg gtg ttt ctc tgc ttg gtt att gct ttg ttc att gtc      48
Glu Gly Leu Leu Val Phe Leu Cys Leu Val Ile Ala Leu Phe Ile Val
1               5                   10                  15 tac gcc gag gct cgt ccg gat tcg caa gaa cag ctg cgt gaa act gga      96
Tyr Ala Glu Ala Arg Pro Asp Ser Gln Glu Gln Leu Arg Glu Thr Gly
                20                  25                  30 aaa aac ctg tat gaa gcg att cga aaa gcc gtc atg aaa att gct caa     144
Lys Asn Leu Tyr Glu Ala Ile Arg Lys Ala Val Met Lys Ile Ala Gln
            35                  40                  45 aaa tgc aaa gca aag att gat gcc tat ttg gag aaa gat gga ctc gga     192
Lys Cys Lys Ala Lys Ile Asp Ala Tyr Leu Glu Lys Asp Gly Leu Gly
        50                  55                  60 gac aag ata tcg gaa gtg att caa atc tta ctg aaa aga cta act gac     240
Asp Lys Ile Ser Glu Val Ile Gln Ile Leu Leu Lys Arg Leu Thr Asp
65                  70                  75                  80 cga att gag aaa tat gtt gag aac                                     264
Arg Ile Glu Lys Tyr Val Glu Asn
                85

<210> SEQ ID NO 30
<211> LENGTH: 88
<212> TYPE: PRT
<213> ORGANISM: Paragonimus westermani

<400> SEQUENCE: 30

Glu Gly Leu Leu Val Phe Leu Cys Leu Val Ile Ala Leu Phe Ile Val
1               5                   10                  15

Tyr Ala Glu Ala Arg Pro Asp Ser Gln Glu Gln Leu Arg Glu Thr Gly
                20                  25                  30

Lys Asn Leu Tyr Glu Ala Ile Arg Lys Ala Val Met Lys Ile Ala Gln
            35                  40                  45

Lys Cys Lys Ala Lys Ile Asp Ala Tyr Leu Glu Lys Asp Gly Leu Gly
        50                  55                  60

Asp Lys Ile Ser Glu Val Ile Gln Ile Leu Leu Lys Arg Leu Thr Asp
65                  70                  75                  80

Arg Ile Glu Lys Tyr Val Glu Asn
                85
```

<210> SEQ ID NO 31
<211> LENGTH: 273
<212> TYPE: DNA
<213> ORGANISM: Schistosoma japonicum
<220> FEATURE:
<221> NAME/KEY: CDS
<222> LOCATION: (1)..(273)

<400> SEQUENCE: 31

```
atg aaa ttc att gta gct atc agt tta tta gtt ctt atg aca tta atc      48
Met Lys Phe Ile Val Ala Ile Ser Leu Leu Val Leu Met Thr Leu Ile
1               5                  10                  15 tat aca gaa gca agt cct gaa aat ttg cga ttt caa ttg caa aaa acc      96
Tyr Thr Glu Ala Ser Pro Glu Asn Leu Arg Phe Gln Leu Gln Lys Thr
                20                  25                  30 tta atg gat acc ggc gaa aaa ttt aaa act tta tct cta aga cta ttg     144
Leu Met Asp Thr Gly Glu Lys Phe Lys Thr Leu Ser Leu Arg Leu Leu
            35                  40                  45 aca aga tgt cga aat cgt gta aga gaa tac ttt aaa caa gat gat tta     192
Thr Arg Cys Arg Asn Arg Val Arg Glu Tyr Phe Lys Gln Asp Asp Leu
        50                  55                  60 ggc gag aaa ata gca gag gtt cta ctt att ttt ctt caa cgt ttg aat     240
Gly Glu Lys Ile Ala Glu Val Leu Leu Ile Phe Leu Gln Arg Leu Asn
65                  70                  75                  80 aga cgt cta gaa aaa tat tta tca aga cct gaa                         273
Arg Arg Leu Glu Lys Tyr Leu Ser Arg Pro Glu
                85                  90
```

<210> SEQ ID NO 32
<211> LENGTH: 91
<212> TYPE: PRT
<213> ORGANISM: Schistosoma japonicum

<400> SEQUENCE: 32

```
Met Lys Phe Ile Val Ala Ile Ser Leu Leu Val Leu Met Thr Leu Ile
1               5                  10                  15

Tyr Thr Glu Ala Ser Pro Glu Asn Leu Arg Phe Gln Leu Gln Lys Thr
                20                  25                  30

Leu Met Asp Thr Gly Glu Lys Phe Lys Thr Leu Ser Leu Arg Leu Leu
            35                  40                  45

Thr Arg Cys Arg Asn Arg Val Arg Glu Tyr Phe Lys Gln Asp Asp Leu
        50                  55                  60

Gly Glu Lys Ile Ala Glu Val Leu Leu Ile Phe Leu Gln Arg Leu Asn
65                  70                  75                  80

Arg Arg Leu Glu Lys Tyr Leu Ser Arg Pro Glu
                85                  90
```

<210> SEQ ID NO 33
<211> LENGTH: 273
<212> TYPE: DNA
<213> ORGANISM: Schistosoma japonicum
<220> FEATURE:
<221> NAME/KEY: CDS
<222> LOCATION: (1)..(273)

<400> SEQUENCE: 33

```
atg aaa ttc att gta gct atc agt tta tta gtt ctt atg aca tta atc      48
Met Lys Phe Ile Val Ala Ile Ser Leu Leu Val Leu Met Thr Leu Ile
1               5                  10                  15 tat aca gaa gca agt cct gaa aat ttg cga ttt caa ttg caa aaa acc      96
Tyr Thr Glu Ala Ser Pro Glu Asn Leu Arg Phe Gln Leu Gln Lys Thr
                20                  25                  30
```

```
                    20                  25                  30 tta atg gat acc ggc gaa aaa ttt aaa act tta tct cta aga cta ttg      144
Leu Met Asp Thr Gly Glu Lys Phe Lys Thr Leu Ser Leu Arg Leu Leu
            35                  40                  45 aca aga tgt cga aat cgt gta aga gaa tac ttt aaa caa gat gat tta      192
Thr Arg Cys Arg Asn Arg Val Arg Glu Tyr Phe Lys Gln Asp Asp Leu
 50                  55                  60 gga gag aaa ata gca gag gtt cta ctt att ttt ctt caa cgt ttg aat      240
Gly Glu Lys Ile Ala Glu Val Leu Leu Ile Phe Leu Gln Arg Leu Asn
 65                  70                  75                  80 aga cgt cta gaa aaa tat tta tta aga cct gaa                          273
Arg Arg Leu Glu Lys Tyr Leu Leu Arg Pro Glu
                 85                  90

<210> SEQ ID NO 34
<211> LENGTH: 91
<212> TYPE: PRT
<213> ORGANISM: Schistosoma japonicum

<400> SEQUENCE: 34

Met Lys Phe Ile Val Ala Ile Ser Leu Leu Val Leu Met Thr Leu Ile
1               5                   10                  15

Tyr Thr Glu Ala Ser Pro Glu Asn Leu Arg Phe Gln Leu Gln Lys Thr
            20                  25                  30

Leu Met Asp Thr Gly Glu Lys Phe Lys Thr Leu Ser Leu Arg Leu Leu
        35                  40                  45

Thr Arg Cys Arg Asn Arg Val Arg Glu Tyr Phe Lys Gln Asp Asp Leu
    50                  55                  60

Gly Glu Lys Ile Ala Glu Val Leu Leu Ile Phe Leu Gln Arg Leu Asn
65                  70                  75                  80

Arg Arg Leu Glu Lys Tyr Leu Leu Arg Pro Glu
                85                  90

<210> SEQ ID NO 35
<211> LENGTH: 273
<212> TYPE: DNA
<213> ORGANISM: Schistosoma japonicum
<220> FEATURE:
<221> NAME/KEY: CDS
<222> LOCATION: (1)..(273)

<400> SEQUENCE: 35 atg aaa atc att gta gct atc agt tta tta gtt ctt atg aca tta atc      48
Met Lys Ile Ile Val Ala Ile Ser Leu Leu Val Leu Met Thr Leu Ile
1               5                   10                  15 tat aca gaa gca agt cct gaa aat tca cga ctt cta tta caa aaa gct     96
Tyr Thr Glu Ala Ser Pro Glu Asn Ser Arg Leu Leu Leu Gln Lys Ala
            20                  25                  30 tta atg gat acc ggc gaa aaa ttt aaa act tta tct cta aga cta ttg     144
Leu Met Asp Thr Gly Glu Lys Phe Lys Thr Leu Ser Leu Arg Leu Leu
        35                  40                  45 gca aga tgt cga gat cgt gta aga gaa tac ttt aaa caa gat gga tta    192
Ala Arg Cys Arg Asp Arg Val Arg Glu Tyr Phe Lys Gln Asp Gly Leu
    50                  55                  60 ggc gag aag tta gca gag gtt cta ctt att ctt ctt caa cgt ttg aat    240
Gly Glu Lys Leu Ala Glu Val Leu Leu Ile Leu Leu Gln Arg Leu Asn
65                  70                  75                  80 aga cgt cta gaa aaa tat tta cca aga tct gaa                         273
Arg Arg Leu Glu Lys Tyr Leu Pro Arg Ser Glu
                85                  90
```

<210> SEQ ID NO 36
<211> LENGTH: 91
<212> TYPE: PRT
<213> ORGANISM: Schistosoma japonicum

<400> SEQUENCE: 36

Met Lys Ile Ile Val Ala Ile Ser Leu Leu Val Leu Met Thr Leu Ile
1               5                   10                  15

Tyr Thr Glu Ala Ser Pro Glu Asn Ser Arg Leu Leu Leu Gln Lys Ala
            20                  25                  30

Leu Met Asp Thr Gly Glu Lys Phe Lys Thr Leu Ser Leu Arg Leu Leu
        35                  40                  45

Ala Arg Cys Arg Asp Arg Val Arg Glu Tyr Phe Lys Gln Asp Gly Leu
    50                  55                  60

Gly Glu Lys Leu Ala Glu Val Leu Leu Ile Leu Leu Gln Arg Leu Asn
65                  70                  75                  80

Arg Arg Leu Glu Lys Tyr Leu Pro Arg Ser Glu
                85                  90

<210> SEQ ID NO 37
<211> LENGTH: 258
<212> TYPE: DNA
<213> ORGANISM: Schistosoma mansoni
<220> FEATURE:
<221> NAME/KEY: CDS
<222> LOCATION: (1)..(258)

<400> SEQUENCE: 37 tca tta gtc ctt gta aca tta gtt tgt gtt gaa gca aca cct gaa gtt       48
Ser Leu Val Leu Val Thr Leu Val Cys Val Glu Ala Thr Pro Glu Val
1               5                   10                  15 ggt gat gaa atg cta ctg aaa aga atg gta cta gat act gct gat aaa       96
Gly Asp Glu Met Leu Leu Lys Arg Met Val Leu Asp Thr Ala Asp Lys
            20                  25                  30 ctc aaa atg tta act tta aaa cac ata gcc gca tgt cgt aat aaa gtg      144
Leu Lys Met Leu Thr Leu Lys His Ile Ala Ala Cys Arg Asn Lys Val
        35                  40                  45 caa act tat ttc agg gaa gac gat cta ggt gag aaa ata gca gac gtt      192
Gln Thr Tyr Phe Arg Glu Asp Asp Leu Gly Glu Lys Ile Ala Asp Val
    50                  55                  60 tta gtt gtt tta ctt aaa cgt ttg aat aaa cgc cta gaa aat tgt tta      240
Leu Val Val Leu Leu Lys Arg Leu Asn Lys Arg Leu Glu Asn Cys Leu
65                  70                  75                  80 aaa tca tct aat tta gaa                                              258
Lys Ser Ser Asn Leu Glu
                85

<210> SEQ ID NO 38
<211> LENGTH: 86
<212> TYPE: PRT
<213> ORGANISM: Schistosoma mansoni

<400> SEQUENCE: 38

Ser Leu Val Leu Val Thr Leu Val Cys Val Glu Ala Thr Pro Glu Val
1               5                   10                  15

Gly Asp Glu Met Leu Leu Lys Arg Met Val Leu Asp Thr Ala Asp Lys
            20                  25                  30

Leu Lys Met Leu Thr Leu Lys His Ile Ala Ala Cys Arg Asn Lys Val
        35                  40                  45

Gln Thr Tyr Phe Arg Glu Asp Asp Leu Gly Glu Lys Ile Ala Asp Val

```
                  50                   55                  60
Leu Val Leu Leu Lys Arg Leu Asn Lys Arg Leu Glu Asn Cys Leu
 65                  70                  75                  80

Lys Ser Ser Asn Leu Glu
                85

<210> SEQ ID NO 39
<211> LENGTH: 291
<212> TYPE: DNA
<213> ORGANISM: Schistosoma mansoni
<220> FEATURE:
<221> NAME/KEY: CDS
<222> LOCATION: (1)..(291)

<400> SEQUENCE: 39 cac att tca ata atg aaa ctc atc tta ata ttt gca cta att att tcg    48
His Ile Ser Ile Met Lys Leu Ile Leu Ile Phe Ala Leu Ile Ile Ser
  1               5                  10                  15 ttg ctg tta aat gta act gct gaa tcc caa gct agt caa aag gaa cta    96
Leu Leu Leu Asn Val Thr Ala Glu Ser Gln Ala Ser Gln Lys Glu Leu
                 20                  25                  30 ttt act gaa agt gtg aag tta tgg aag tca atc aca gaa ctt tgg aag   144
Phe Thr Glu Ser Val Lys Leu Trp Lys Ser Ile Thr Glu Leu Trp Lys
             35                  40                  45 aga ttt gaa cat aac tgt cga gtt aaa att cga aaa tat ctt gaa gaa   192
Arg Phe Glu His Asn Cys Arg Val Lys Ile Arg Lys Tyr Leu Glu Glu
         50                  55                  60 gat aat tta ggt gaa aaa tta gcc gct gtt gta agc atc tat gtt aag   240
Asp Asn Leu Gly Glu Lys Leu Ala Ala Val Val Ser Ile Tyr Val Lys
 65                  70                  75                  80 cgt tta aac aag cgt tta gat atg cgt tta tca gaa gac aga gca gaa   288
Arg Leu Asn Lys Arg Leu Asp Met Arg Leu Ser Glu Asp Arg Ala Glu
                 85                  90                  95 taa                                                               291

<210> SEQ ID NO 40
<211> LENGTH: 96
<212> TYPE: PRT
<213> ORGANISM: Schistosoma mansoni

<400> SEQUENCE: 40

His Ile Ser Ile Met Lys Leu Ile Leu Ile Phe Ala Leu Ile Ile Ser
  1               5                  10                  15

Leu Leu Leu Asn Val Thr Ala Glu Ser Gln Ala Ser Gln Lys Glu Leu
                 20                  25                  30

Phe Thr Glu Ser Val Lys Leu Trp Lys Ser Ile Thr Glu Leu Trp Lys
             35                  40                  45

Arg Phe Glu His Asn Cys Arg Val Lys Ile Arg Lys Tyr Leu Glu Glu
         50                  55                  60

Asp Asn Leu Gly Glu Lys Leu Ala Ala Val Val Ser Ile Tyr Val Lys
 65                  70                  75                  80

Arg Leu Asn Lys Arg Leu Asp Met Arg Leu Ser Glu Asp Arg Ala Glu
                 85                  90                  95

<210> SEQ ID NO 41
<211> LENGTH: 270
<212> TYPE: DNA
<213> ORGANISM: Chlonorchis sinensis
<220> FEATURE:
<221> NAME/KEY: CDS
<222> LOCATION: (1)..(270)
```

<400> SEQUENCE: 41

| | |
|---|---|
| atg gga cgg act gtt ttc ttt tgc ttg gtt ttt gtt ctg ttt ggg gcc<br>Met Gly Arg Thr Val Phe Phe Cys Leu Val Phe Val Leu Phe Gly Ala<br>1               5                   10                  15 | 48 |
| cac gct gaa gcc cgt ccc agt gag gag acc cgt gcc aaa ctg ggg gaa<br>His Ala Glu Ala Arg Pro Ser Glu Glu Thr Arg Ala Lys Leu Gly Glu<br>            20                  25                  30 | 96 |
| tcc ggc cag aaa tta tgg acg gcg gtg ggg gct gtt ggg aga aaa tgt<br>Ser Gly Gln Lys Leu Trp Thr Ala Val Gly Ala Val Gly Arg Lys Cys<br>        35                  40                  45 | 144 |
| gcc gaa cgg gtt aga caa gga atc gag gaa ttt ttt gaa aag gac aac<br>Ala Glu Arg Val Arg Gln Gly Ile Glu Glu Phe Phe Glu Lys Asp Asn<br>    50                  55                  60 | 192 |
| ctg ggg gag aaa ata gcg gaa gtc gtg aaa atc ctg tcc gag ccc ctg<br>Leu Gly Glu Lys Ile Ala Glu Val Val Lys Ile Leu Ser Glu Pro Leu<br>65                  70                  75                  80 | 240 |
| ccc aaa cgg ata gag act tac gtt ggg gag<br>Pro Lys Arg Ile Glu Thr Tyr Val Gly Glu<br>                85                  90 | 270 |

<210> SEQ ID NO 42
<211> LENGTH: 90
<212> TYPE: PRT
<213> ORGANISM: Chlonorchis sinensis

<400> SEQUENCE: 42

Met Gly Arg Thr Val Phe Phe Cys Leu Val Phe Val Leu Phe Gly Ala
1               5                   10                  15

His Ala Glu Ala Arg Pro Ser Glu Glu Thr Arg Ala Lys Leu Gly Glu
            20                  25                  30

Ser Gly Gln Lys Leu Trp Thr Ala Val Gly Ala Val Gly Arg Lys Cys
        35                  40                  45

Ala Glu Arg Val Arg Gln Gly Ile Glu Glu Phe Phe Glu Lys Asp Asn
    50                  55                  60

Leu Gly Glu Lys Ile Ala Glu Val Val Lys Ile Leu Ser Glu Pro Leu
65                  70                  75                  80

Pro Lys Arg Ile Glu Thr Tyr Val Gly Glu
                85                  90

<210> SEQ ID NO 43
<211> LENGTH: 378
<212> TYPE: DNA
<213> ORGANISM: Schistosoma japonicum
<220> FEATURE:
<221> NAME/KEY: CDS
<222> LOCATION: (1)..(378)

<400> SEQUENCE: 43

| | |
|---|---|
| atg aaa gtg ata ata tta ctt tgc atg gtt tat act gca ttg acc tat<br>Met Lys Val Ile Ile Leu Leu Cys Met Val Tyr Thr Ala Leu Thr Tyr<br>1               5                   10                  15 | 48 |
| gca aca tta ata agt aaa gtt gat gat acc aac aaa aag aac gat gat<br>Ala Thr Leu Ile Ser Lys Val Asp Asp Thr Asn Lys Lys Asn Asp Asp<br>            20                  25                  30 | 96 |
| gca gcc gaa gta aag aaa gag gat aag gac gag aat gag gaa ggg gaa<br>Ala Ala Glu Val Lys Lys Glu Asp Lys Asp Glu Asn Glu Glu Gly Glu<br>        35                  40                  45 | 144 |
| aca gat gaa gat gaa ggc gag tca aaa cgt gga atg aaa gca ata tac<br>Thr Asp Glu Asp Glu Gly Glu Ser Lys Arg Gly Met Lys Ala Ile Tyr<br>    50                  55                  60 | 192 |

```
aaa gtt cta aag aaa tcc tat aag act gga cgt aaa aaa ata tgc aaa      240
Lys Val Leu Lys Lys Ser Tyr Lys Thr Gly Arg Lys Lys Ile Cys Lys
 65              70                  75                  80 acg ttt gat aaa tac ctc aga aaa gat gat tta gat aag aaa atg ctt      288
Thr Phe Asp Lys Tyr Leu Arg Lys Asp Asp Leu Asp Lys Lys Met Leu
                 85                  90                  95 gaa atc gcc aat att ctt gcc aaa cgt ttg gag aaa cgg atg gag tat      336
Glu Ile Ala Asn Ile Leu Ala Lys Arg Leu Glu Lys Arg Met Glu Tyr
                100                 105                 110 cta tca cag tcg ttg gct gat atg tta aca tat gaa aca tct              378
Leu Ser Gln Ser Leu Ala Asp Met Leu Thr Tyr Glu Thr Ser
                115                 120                 125
```

<210> SEQ ID NO 44
<211> LENGTH: 126
<212> TYPE: PRT
<213> ORGANISM: Schistosoma japonicum

<400> SEQUENCE: 44

```
Met Lys Val Ile Ile Leu Leu Cys Met Val Tyr Thr Ala Leu Thr Tyr
 1               5                  10                  15

Ala Thr Leu Ile Ser Lys Val Asp Asp Thr Asn Lys Lys Asn Asp Asp
                20                  25                  30

Ala Ala Glu Val Lys Lys Glu Asp Lys Asp Glu Asn Glu Glu Gly Glu
            35                  40                  45

Thr Asp Glu Asp Glu Gly Glu Ser Lys Arg Gly Met Lys Ala Ile Tyr
        50                  55                  60

Lys Val Leu Lys Lys Ser Tyr Lys Thr Gly Arg Lys Lys Ile Cys Lys
 65              70                  75                  80

Thr Phe Asp Lys Tyr Leu Arg Lys Asp Asp Leu Asp Lys Lys Met Leu
                 85                  90                  95

Glu Ile Ala Asn Ile Leu Ala Lys Arg Leu Glu Lys Arg Met Glu Tyr
                100                 105                 110

Leu Ser Gln Ser Leu Ala Asp Met Leu Thr Tyr Glu Thr Ser
                115                 120                 125
```

<210> SEQ ID NO 45
<211> LENGTH: 21
<212> TYPE: PRT
<213> ORGANISM: Artificial
<220> FEATURE:
<223> OTHER INFORMATION: Partial amino acid sequence of prior art
      peptide disclosed in McGonigle et al., (1995, Parasitology 111 (Pt
      2):209-215)

<400> SEQUENCE: 45

```
Ser Glu Glu Ser Arg Glu Lys Leu Arg Glu Ser Gly Gly Lys Met Val
 1               5                  10                  15

Lys Ala Leu Arg Asp
                20
```

<210> SEQ ID NO 46
<211> LENGTH: 34
<212> TYPE: PRT
<213> ORGANISM: Artificial
<220> FEATURE:
<223> OTHER INFORMATION: FhHDM-1 peptide 3, comprising the complete
      amphipathic helix contained in FhHDM-1

<400> SEQUENCE: 46

```
Ala Met Ala Tyr Leu Ala Lys Asp Asn Leu Gly Glu Lys Ile Thr Glu
```

```
                1               5                   10                  15
Val Ile Thr Ile Leu Leu Asn Arg Leu Thr Asp Arg Leu Glu Lys Tyr
                20                  25                  30
Ala Gly

<210> SEQ ID NO 47
<211> LENGTH: 30
<212> TYPE: PRT
<213> ORGANISM: Artificial
<220> FEATURE:
<223> OTHER INFORMATION: FhHDM-1 peptide 1 comprising a truncated
      amphipathic helix contained in FhHDM-1

<400> SEQUENCE: 47

Lys Ala Arg Asp Arg Ala Met Ala Tyr Leu Ala Lys Asp Asn Leu Gly
1               5                   10                  15

Glu Lys Ile Thr Glu Val Ile Thr Ile Leu Leu Asn Arg Leu
                20                  25                  30

<210> SEQ ID NO 48
<211> LENGTH: 585
<212> TYPE: DNA
<213> ORGANISM: Fasciola hepatica
<220> FEATURE:
<221> NAME/KEY: CDS
<222> LOCATION: (1)..(585)

<400> SEQUENCE: 48 atg ttg cag cct aat atg ccc gcc ccg aat ttt tct gga cag gcg gta        48
Met Leu Gln Pro Asn Met Pro Ala Pro Asn Phe Ser Gly Gln Ala Val
1               5                   10                  15 gtg ggc aag gag ttc gaa acc atc agt tta tca gac tac aag ggc aaa        96
Val Gly Lys Glu Phe Glu Thr Ile Ser Leu Ser Asp Tyr Lys Gly Lys
                20                  25                  30 tgg gtg att ctc gcc ttc tat cca ctt gat ttc acg ttc gtg tgt cca       144
Trp Val Ile Leu Ala Phe Tyr Pro Leu Asp Phe Thr Phe Val Cys Pro
            35                  40                  45 acg gaa ata atc gcg atc agt gat cag atg gag cag ttc gca caa cgt       192
Thr Glu Ile Ile Ala Ile Ser Asp Gln Met Glu Gln Phe Ala Gln Arg
        50                  55                  60 aac tgc gcc gtc atc ttc tgc tct act gac tcg gtt tat tcg cat ctg       240
Asn Cys Ala Val Ile Phe Cys Ser Thr Asp Ser Val Tyr Ser His Leu
65                  70                  75                  80 caa tgg acc aaa atg gat cgt aag gtt ggc ggt ata ggc cag ctg aac       288
Gln Trp Thr Lys Met Asp Arg Lys Val Gly Gly Ile Gly Gln Leu Asn
                85                  90                  95 ttc ccg ctg ctg gca gac aag aat atg tct gtc tct cgc gcc ttt ggt       336
Phe Pro Leu Leu Ala Asp Lys Asn Met Ser Val Ser Arg Ala Phe Gly
            100                 105                 110 gtt ctg gat gag gaa cag ggt aat acc tac cgt ggc aat ttc ctc atc       384
Val Leu Asp Glu Glu Gln Gly Asn Thr Tyr Arg Gly Asn Phe Leu Ile
        115                 120                 125 gat ccc aag ggg gtc ctg cgc cag atc acg gtg aat gac gac ccg gtg       432
Asp Pro Lys Gly Val Leu Arg Gln Ile Thr Val Asn Asp Asp Pro Val
    130                 135                 140 ggc cgt tcc gtt gaa gaa gcc ttg cgt ctg ctc gat gca ttc ata ttc       480
Gly Arg Ser Val Glu Glu Ala Leu Arg Leu Leu Asp Ala Phe Ile Phe
145                 150                 155                 160 cac gag gag cat gga gag gtc tgc ccg gcg aac tgg aag cct aaa agc       528
His Glu Glu His Gly Glu Val Cys Pro Ala Asn Trp Lys Pro Lys Ser
                165                 170                 175
```

```
aag acc atc gtg cct act ccg gat gga tcc aaa gca tat ttc tcc tca    576
Lys Thr Ile Val Pro Thr Pro Asp Gly Ser Lys Ala Tyr Phe Ser Ser
            180                 185                 190 gcc aac tag                                                        585
Ala Asn

<210> SEQ ID NO 49
<211> LENGTH: 194
<212> TYPE: PRT
<213> ORGANISM: Fasciola hepatica

<400> SEQUENCE: 49

Met Leu Gln Pro Asn Met Pro Ala Pro Asn Phe Ser Gly Gln Ala Val
1               5                   10                  15

Val Gly Lys Glu Phe Glu Thr Ile Ser Leu Ser Asp Tyr Lys Gly Lys
            20                  25                  30

Trp Val Ile Leu Ala Phe Tyr Pro Leu Asp Phe Thr Phe Val Cys Pro
        35                  40                  45

Thr Glu Ile Ile Ala Ile Ser Asp Gln Met Glu Gln Phe Ala Gln Arg
    50                  55                  60

Asn Cys Ala Val Ile Phe Cys Ser Thr Asp Ser Val Tyr Ser His Leu
65                  70                  75                  80

Gln Trp Thr Lys Met Asp Arg Lys Val Gly Ile Gly Gln Leu Asn
                85                  90                  95

Phe Pro Leu Leu Ala Asp Lys Asn Met Ser Val Ser Arg Ala Phe Gly
            100                 105                 110

Val Leu Asp Glu Glu Gln Gly Asn Thr Tyr Arg Gly Asn Phe Leu Ile
        115                 120                 125

Asp Pro Lys Gly Val Leu Arg Gln Ile Thr Val Asn Asp Asp Pro Val
    130                 135                 140

Gly Arg Ser Val Glu Glu Ala Leu Arg Leu Leu Asp Ala Phe Ile Phe
145                 150                 155                 160

His Glu Glu His Gly Glu Val Cys Pro Ala Asn Trp Lys Pro Lys Ser
                165                 170                 175

Lys Thr Ile Val Pro Thr Pro Asp Gly Ser Lys Ala Tyr Phe Ser Ser
            180                 185                 190

Ala Asn

<210> SEQ ID NO 50
<211> LENGTH: 657
<212> TYPE: DNA
<213> ORGANISM: Fasciola gigantica
<220> FEATURE:
<221> NAME/KEY: CDS
<222> LOCATION: (1)..(657)

<400> SEQUENCE: 50 atg tgt gat cgc gat cag tgc tct ccg ggg cgc cat cca ctt ccc cac    48
Met Cys Asp Arg Asp Gln Cys Ser Pro Gly Arg His Pro Leu Pro His
1               5                   10                  15 tct cat ccg cat ttg caa aga ccg atg ttg cag cct aac atg ccc gcc    96
Ser His Pro His Leu Gln Arg Pro Met Leu Gln Pro Asn Met Pro Ala
            20                  25                  30 ccg aat ttt tct gga cag gcg gta gtg ggc aag gag ttc aaa acc atc    144
Pro Asn Phe Ser Gly Gln Ala Val Val Gly Lys Glu Phe Lys Thr Ile
        35                  40                  45 agt tta tca gac tac aag ggc aaa tgg gtg att ctc gcc ttc tat cca    192
Ser Leu Ser Asp Tyr Lys Gly Lys Trp Val Ile Leu Ala Phe Tyr Pro
    50                  55                  60
```

```
ctt gat ttc acg ttc gtg tgt cca acg gaa ata atc gcg ttc agt gat    240
Leu Asp Phe Thr Phe Val Cys Pro Thr Glu Ile Ile Ala Phe Ser Asp
 65                  70                  75                  80 cag atg gag cag ttc gca cga cgt aac tgt gcc gtc atc ttt tgc tct    288
Gln Met Glu Gln Phe Ala Arg Arg Asn Cys Ala Val Ile Phe Cys Ser
                 85                  90                  95 act gac tcg gtt tat tcg cat ctg caa tgg acc aaa atg gat cgt aag    336
Thr Asp Ser Val Tyr Ser His Leu Gln Trp Thr Lys Met Asp Arg Lys
            100                 105                 110 gtt ggc ggt ata ggc cag ctg aac ttc ccg ctg ctg gca gac aag aat    384
Val Gly Gly Ile Gly Gln Leu Asn Phe Pro Leu Leu Ala Asp Lys Asn
        115                 120                 125 atg tct atc tct cgc gcc tat ggt gtt ctg gat gag gag cag ggt aat    432
Met Ser Ile Ser Arg Ala Tyr Gly Val Leu Asp Glu Glu Gln Gly Asn
    130                 135                 140 acc tac cgt ggc aat ttc ctc atc gat ccc aag ggg gtc ctg cgc cag    480
Thr Tyr Arg Gly Asn Phe Leu Ile Asp Pro Lys Gly Val Leu Arg Gln
145                 150                 155                 160 atc acg gtg aat gac cga ccg gtg ggc cgt tcc gtt gaa gaa gcc ttg    528
Ile Thr Val Asn Asp Arg Pro Val Gly Arg Ser Val Glu Glu Ala Leu
                165                 170                 175 cgt ctg ctc gat gca ttc ata ttc cac gag gag cat gga gag gtc tgc    576
Arg Leu Leu Asp Ala Phe Ile Phe His Glu Glu His Gly Glu Val Cys
            180                 185                 190 ccg gcg aac tgg aag cct aaa agc aag acc atc gtg cct act ccg gat    624
Pro Ala Asn Trp Lys Pro Lys Ser Lys Thr Ile Val Pro Thr Pro Asp
        195                 200                 205 gga tcc aaa gca tat ttc tcc tca gcc aac tag                        657
Gly Ser Lys Ala Tyr Phe Ser Ser Ala Asn
    210                 215
```

<210> SEQ ID NO 51
<211> LENGTH: 218
<212> TYPE: PRT
<213> ORGANISM: Fasciola gigantica

<400> SEQUENCE: 51

```
Met Cys Asp Arg Asp Gln Cys Ser Pro Gly Arg His Pro Leu Pro His
  1               5                  10                  15

Ser His Pro His Leu Gln Arg Pro Met Leu Gln Pro Asn Met Pro Ala
             20                  25                  30

Pro Asn Phe Ser Gly Gln Ala Val Val Gly Lys Glu Phe Lys Thr Ile
         35                  40                  45

Ser Leu Ser Asp Tyr Lys Gly Lys Trp Val Ile Leu Ala Phe Tyr Pro
 50                  55                  60

Leu Asp Phe Thr Phe Val Cys Pro Thr Glu Ile Ile Ala Phe Ser Asp
 65                  70                  75                  80

Gln Met Glu Gln Phe Ala Arg Arg Asn Cys Ala Val Ile Phe Cys Ser
                 85                  90                  95

Thr Asp Ser Val Tyr Ser His Leu Gln Trp Thr Lys Met Asp Arg Lys
            100                 105                 110

Val Gly Gly Ile Gly Gln Leu Asn Phe Pro Leu Leu Ala Asp Lys Asn
        115                 120                 125

Met Ser Ile Ser Arg Ala Tyr Gly Val Leu Asp Glu Glu Gln Gly Asn
    130                 135                 140

Thr Tyr Arg Gly Asn Phe Leu Ile Asp Pro Lys Gly Val Leu Arg Gln
145                 150                 155                 160
```

```
Ile Thr Val Asn Asp Arg Pro Val Gly Arg Ser Val Glu Glu Ala Leu
            165                 170                 175

Arg Leu Leu Asp Ala Phe Ile Phe His Glu Glu His Gly Glu Val Cys
        180                 185                 190

Pro Ala Asn Trp Lys Pro Lys Ser Lys Thr Ile Val Pro Thr Pro Asp
    195                 200                 205

Gly Ser Lys Ala Tyr Phe Ser Ser Ala Asn
210                 215

<210> SEQ ID NO 52
<211> LENGTH: 585
<212> TYPE: DNA
<213> ORGANISM: Fasciola gigantica
<220> FEATURE:
<221> NAME/KEY: CDS
<222> LOCATION: (1)..(585)

<400> SEQUENCE: 52 atg ttg cag cct aat atg ccc gcc ccg aat ttt tct ggg cag gcg gta      48
Met Leu Gln Pro Asn Met Pro Ala Pro Asn Phe Ser Gly Gln Ala Val
1               5                   10                  15 gtg ggc aag gag ttc aaa acc atc agt ttg tca gac tac aaa ggc aaa      96
Val Gly Lys Glu Phe Lys Thr Ile Ser Leu Ser Asp Tyr Lys Gly Lys
            20                  25                  30 tgg gtg att ctc gcc ttc tat cca ctt gat ttc acg ttc gtg tgt cca     144
Trp Val Ile Leu Ala Phe Tyr Pro Leu Asp Phe Thr Phe Val Cys Pro
        35                  40                  45 acg gaa ata atc gcg ttc agt gat cag atg gag cag ttc gcg cga cgt     192
Thr Glu Ile Ile Ala Phe Ser Asp Gln Met Glu Gln Phe Ala Arg Arg
    50                  55                  60 aac tgt gcc gta atc ttc tgc tct act gat tcg gtt tat tcg cat ctg     240
Asn Cys Ala Val Ile Phe Cys Ser Thr Asp Ser Val Tyr Ser His Leu
65                  70                  75                  80 caa tgg acc aaa atg gat cgt aaa gtt ggc ggt ata ggt cag ctg aac     288
Gln Trp Thr Lys Met Asp Arg Lys Val Gly Gly Ile Gly Gln Leu Asn
                85                  90                  95 ttc ccg ctg ctg gca gac aag aat atg tct atc tct cgc gcc tat ggt     336
Phe Pro Leu Leu Ala Asp Lys Asn Met Ser Ile Ser Arg Ala Tyr Gly
            100                 105                 110 gtt ctg gat gag gaa cag ggt aat acc tac cgt ggc aat ttc ctc atc     384
Val Leu Asp Glu Glu Gln Gly Asn Thr Tyr Arg Gly Asn Phe Leu Ile
        115                 120                 125 gat ccc aag ggg gtc ttg cgc cag atc acg gtg aat gac cgg ccg gtg     432
Asp Pro Lys Gly Val Leu Arg Gln Ile Thr Val Asn Asp Arg Pro Val
    130                 135                 140 ggc cgt tct gtt gaa gaa gcc ttg cgt ctg ctc gac gca ttc ata ttc     480
Gly Arg Ser Val Glu Glu Ala Leu Arg Leu Leu Asp Ala Phe Ile Phe
145                 150                 155                 160 cac gag gag cat gga gag gtc tgc ccg gct aac tgg aag cct aaa agc     528
His Glu Glu His Gly Glu Val Cys Pro Ala Asn Trp Lys Pro Lys Ser
                165                 170                 175 aag acc atc gtg cct gat ccg gat gga tcc aaa gca tat ttc tcc tca     576
Lys Thr Ile Val Pro Asp Pro Asp Gly Ser Lys Ala Tyr Phe Ser Ser
            180                 185                 190 gcc aac tag                                                         585
Ala Asn

<210> SEQ ID NO 53
<211> LENGTH: 194
<212> TYPE: PRT
<213> ORGANISM: Fasciola gigantica
```

<400> SEQUENCE: 53

```
Met Leu Gln Pro Asn Met Pro Ala Pro Asn Phe Ser Gly Gln Ala Val
1               5                   10                  15

Val Gly Lys Glu Phe Lys Thr Ile Ser Leu Ser Asp Tyr Lys Gly Lys
            20                  25                  30

Trp Val Ile Leu Ala Phe Tyr Pro Leu Asp Phe Thr Phe Val Cys Pro
        35                  40                  45

Thr Glu Ile Ile Ala Phe Ser Asp Gln Met Glu Gln Phe Ala Arg Arg
    50                  55                  60

Asn Cys Ala Val Ile Phe Cys Ser Thr Asp Ser Val Tyr Ser His Leu
65                  70                  75                  80

Gln Trp Thr Lys Met Asp Arg Lys Val Gly Gly Ile Gly Gln Leu Asn
                85                  90                  95

Phe Pro Leu Leu Ala Asp Lys Asn Met Ser Ile Ser Arg Ala Tyr Gly
            100                 105                 110

Val Leu Asp Glu Glu Gln Gly Asn Thr Tyr Arg Gly Asn Phe Leu Ile
        115                 120                 125

Asp Pro Lys Gly Val Leu Arg Gln Ile Thr Val Asn Asp Arg Pro Val
    130                 135                 140

Gly Arg Ser Val Glu Glu Ala Leu Arg Leu Leu Asp Ala Phe Ile Phe
145                 150                 155                 160

His Glu Glu His Gly Glu Val Cys Pro Ala Asn Trp Lys Pro Lys Ser
                165                 170                 175

Lys Thr Ile Val Pro Asp Pro Asp Gly Ser Lys Ala Tyr Phe Ser Ser
            180                 185                 190

Ala Asn
```

<210> SEQ ID NO 54
<211> LENGTH: 585
<212> TYPE: DNA
<213> ORGANISM: Fasciola hepatica
<220> FEATURE:
<221> NAME/KEY: CDS
<222> LOCATION: (1)..(585)

<400> SEQUENCE: 54

```
atg ttg cag cct aat atg ccc gcc ccg aat ttt tct gga cag gcg gta    48
Met Leu Gln Pro Asn Met Pro Ala Pro Asn Phe Ser Gly Gln Ala Val
1               5                   10                  15 gtg ggc aag gag ttc aaa acc atc agt tta tca gac tac aag ggc aaa    96
Val Gly Lys Glu Phe Lys Thr Ile Ser Leu Ser Asp Tyr Lys Gly Lys
            20                  25                  30 tgg gtg att ctc gcc ttc tat cca ctt gat ttc acg ttc gtg tgt cca   144
Trp Val Ile Leu Ala Phe Tyr Pro Leu Asp Phe Thr Phe Val Cys Pro
        35                  40                  45 acg gaa ata atc gcg ttc agt gat cag atg gag cag ttc gca cga cgt   192
Thr Glu Ile Ile Ala Phe Ser Asp Gln Met Glu Gln Phe Ala Arg Arg
    50                  55                  60 aac tgt gcc gtc atc ttc tgc tct act gac tcg gtt tat tcg cat ctg   240
Asn Cys Ala Val Ile Phe Cys Ser Thr Asp Ser Val Tyr Ser His Leu
65                  70                  75                  80 caa tgg acc aaa atg gat cgt aag gtt ggc ggt ata ggc cag ctg aac   288
Gln Trp Thr Lys Met Asp Arg Lys Val Gly Gly Ile Gly Gln Leu Asn
                85                  90                  95 ttc ccg ctg ctg gca gag aag aat atg tct atc tct cgc gcc tat ggt   336
Phe Pro Leu Leu Ala Glu Lys Asn Met Ser Ile Ser Arg Ala Tyr Gly
            100                 105                 110
```

```
gtt ctg gat gag gaa cag ggt aat acc tac cgt ggc aat ttc ctc atc      384
Val Leu Asp Glu Glu Gln Gly Asn Thr Tyr Arg Gly Asn Phe Leu Ile
        115                 120                 125 gat ccc aag ggg gtc ctg ccc cag atc acg gtg aat gac cga ccg gtg      432
Asp Pro Lys Gly Val Leu Pro Gln Ile Thr Val Asn Asp Arg Pro Val
    130                 135                 140 ggc cgt tcc gtt gaa gaa gcc ttg cgt ctg ctc gat gca ttc ata ttc      480
Gly Arg Ser Val Glu Glu Ala Leu Arg Leu Leu Asp Ala Phe Ile Phe
145                 150                 155                 160 cac gag gag cat gga gag gtc tgc ccg gcg aac tgg aag cct aaa agc      528
His Glu Glu His Gly Glu Val Cys Pro Ala Asn Trp Lys Pro Lys Ser
                165                 170                 175 aag acc atc gtg cct act ccg gat gga tcc aaa gca tat ttc tcc tca      576
Lys Thr Ile Val Pro Thr Pro Asp Gly Ser Lys Ala Tyr Phe Ser Ser
            180                 185                 190 gcc aac tag                                                          585
Ala Asn
```

<210> SEQ ID NO 55
<211> LENGTH: 194
<212> TYPE: PRT
<213> ORGANISM: Fasciola hepatica

<400> SEQUENCE: 55

Met Leu Gln Pro Asn Met Pro Ala Pro Asn Phe Ser Gly Gln Ala Val
1               5                   10                  15

Val Gly Lys Glu Phe Lys Thr Ile Ser Leu Ser Asp Tyr Lys Gly Lys
            20                  25                  30

Trp Val Ile Leu Ala Phe Tyr Pro Leu Asp Phe Thr Phe Val Cys Pro
        35                  40                  45

Thr Glu Ile Ile Ala Phe Ser Asp Gln Met Glu Gln Phe Ala Arg Arg
    50                  55                  60

Asn Cys Ala Val Ile Phe Cys Ser Thr Asp Ser Val Tyr Ser His Leu
65                  70                  75                  80

Gln Trp Thr Lys Met Asp Arg Lys Val Gly Ile Gly Gln Leu Asn
                85                  90                  95

Phe Pro Leu Leu Ala Glu Lys Asn Met Ser Ile Ser Arg Ala Tyr Gly
            100                 105                 110

Val Leu Asp Glu Glu Gln Gly Asn Thr Tyr Arg Gly Asn Phe Leu Ile
        115                 120                 125

Asp Pro Lys Gly Val Leu Pro Gln Ile Thr Val Asn Asp Arg Pro Val
    130                 135                 140

Gly Arg Ser Val Glu Glu Ala Leu Arg Leu Leu Asp Ala Phe Ile Phe
145                 150                 155                 160

His Glu Glu His Gly Glu Val Cys Pro Ala Asn Trp Lys Pro Lys Ser
                165                 170                 175

Lys Thr Ile Val Pro Thr Pro Asp Gly Ser Lys Ala Tyr Phe Ser Ser
            180                 185                 190

Ala Asn

<210> SEQ ID NO 56
<211> LENGTH: 588
<212> TYPE: DNA
<213> ORGANISM: Clonorchis sinensis
<220> FEATURE:
<221> NAME/KEY: CDS
<222> LOCATION: (1)..(588)

<400> SEQUENCE: 56

```
atg gct ctc ctg ccg aac caa ccc gca ccg gag ttc tca gga atg gca      48
Met Ala Leu Leu Pro Asn Gln Pro Ala Pro Glu Phe Ser Gly Met Ala
1               5                   10                  15 gtt gtt aat ggc gag ttc aag aat atc agc cta aag gat tac cgt gga      96
Val Val Asn Gly Glu Phe Lys Asn Ile Ser Leu Lys Asp Tyr Arg Gly
            20                  25                  30 aaa tac gtc att ttg ctg ttc tac cca ctg gac ttc acg ttc gtc tgt     144
Lys Tyr Val Ile Leu Leu Phe Tyr Pro Leu Asp Phe Thr Phe Val Cys
        35                  40                  45 cca aca gag ttg att gct ttc agc gat gct gct gaa gag ttc aag tcc     192
Pro Thr Glu Leu Ile Ala Phe Ser Asp Ala Ala Glu Glu Phe Lys Ser
    50                  55                  60 aaa aac tgc gtg att ata ggt tgc tcc acg gac tct gtc tat gca cat     240
Lys Asn Cys Val Ile Ile Gly Cys Ser Thr Asp Ser Val Tyr Ala His
65                  70                  75                  80 ctg caa tgg acc aaa atg gat aga aag gtt ggt ggc ctg gga aag atg     288
Leu Gln Trp Thr Lys Met Asp Arg Lys Val Gly Gly Leu Gly Lys Met
                85                  90                  95 aac atc ccg ctt ttg tcg gat aag aac atg aag atc tct cgc gca tac     336
Asn Ile Pro Leu Leu Ser Asp Lys Asn Met Lys Ile Ser Arg Ala Tyr
            100                 105                 110 cat gtg ctg gac gag gaa gag gga cac gca ttt cga ggg caa ttt ttg     384
His Val Leu Asp Glu Glu Glu Gly His Ala Phe Arg Gly Gln Phe Leu
        115                 120                 125 att gac ccg aag ggt gtt ttg cgt cag ata act gtc aat gat cgt cca     432
Ile Asp Pro Lys Gly Val Leu Arg Gln Ile Thr Val Asn Asp Arg Pro
    130                 135                 140 gtt ggt cgt tct gtt gaa gaa gcg atc cgc ttg ttg gaa gcc ttt cat     480
Val Gly Arg Ser Val Glu Glu Ala Ile Arg Leu Leu Glu Ala Phe His
145                 150                 155                 160 ttc cat gag caa cat ggc gat gtg tgt cca gcg aat tgg aag ccg aaa     528
Phe His Glu Gln His Gly Asp Val Cys Pro Ala Asn Trp Lys Pro Lys
                165                 170                 175 ggc aag act atg aag gca gac ccg gtt gcc gcc cag gag tat ttc tcg     576
Gly Lys Thr Met Lys Ala Asp Pro Val Ala Ala Gln Glu Tyr Phe Ser
            180                 185                 190 tcc gtt aac tag                                                     588
Ser Val Asn
        195
```

<210> SEQ ID NO 57
<211> LENGTH: 195
<212> TYPE: PRT
<213> ORGANISM: Clonorchis sinensis

<400> SEQUENCE: 57

```
Met Ala Leu Leu Pro Asn Gln Pro Ala Pro Glu Phe Ser Gly Met Ala
1               5                   10                  15

Val Val Asn Gly Glu Phe Lys Asn Ile Ser Leu Lys Asp Tyr Arg Gly
            20                  25                  30

Lys Tyr Val Ile Leu Leu Phe Tyr Pro Leu Asp Phe Thr Phe Val Cys
        35                  40                  45

Pro Thr Glu Leu Ile Ala Phe Ser Asp Ala Ala Glu Glu Phe Lys Ser
    50                  55                  60

Lys Asn Cys Val Ile Ile Gly Cys Ser Thr Asp Ser Val Tyr Ala His
65                  70                  75                  80

Leu Gln Trp Thr Lys Met Asp Arg Lys Val Gly Gly Leu Gly Lys Met
                85                  90                  95
```

```
Asn Ile Pro Leu Leu Ser Asp Lys Asn Met Lys Ile Ser Arg Ala Tyr
            100                 105                 110

His Val Leu Asp Glu Glu Gly His Ala Phe Arg Gly Gln Phe Leu
        115                 120                 125

Ile Asp Pro Lys Gly Val Leu Arg Gln Ile Thr Val Asn Asp Arg Pro
        130                 135                 140

Val Gly Arg Ser Val Glu Glu Ala Ile Arg Leu Leu Glu Ala Phe His
145                 150                 155                 160

Phe His Glu Gln His Gly Asp Val Cys Pro Ala Asn Trp Lys Pro Lys
                165                 170                 175

Gly Lys Thr Met Lys Ala Asp Pro Val Ala Ala Gln Glu Tyr Phe Ser
            180                 185                 190

Ser Val Asn
        195

<210> SEQ ID NO 58
<211> LENGTH: 639
<212> TYPE: DNA
<213> ORGANISM: Opisthorchis viverrini
<220> FEATURE:
<221> NAME/KEY: CDS
<222> LOCATION: (1)..(639)

<400> SEQUENCE: 58 atg ggt tgc gca ctc ttg atc gtc ctg tgc acg gtc ggt cta gtc aac      48
Met Gly Cys Ala Leu Leu Ile Val Leu Cys Thr Val Gly Leu Val Asn
1               5                   10                  15 gcg atg gct ctc ctg ccg aac caa ccc gca ccg gag ttt tca gga atg      96
Ala Met Ala Leu Leu Pro Asn Gln Pro Ala Pro Glu Phe Ser Gly Met
            20                  25                  30 gca gta gtt aat ggc gaa ttc aag aat atc agc cta aag gat tac cgt     144
Ala Val Val Asn Gly Glu Phe Lys Asn Ile Ser Leu Lys Asp Tyr Arg
        35                  40                  45 gga aaa tac gtc att ttg ctg ttc tac cca ctg gat ttc acg ttc gtc     192
Gly Lys Tyr Val Ile Leu Leu Phe Tyr Pro Leu Asp Phe Thr Phe Val
    50                  55                  60 tgc cca aca gag ttg att gct ttc agc gat gct gct gaa gag ttc aag     240
Cys Pro Thr Glu Leu Ile Ala Phe Ser Asp Ala Ala Glu Glu Phe Lys
65                  70                  75                  80 tcc aaa aac tgc gtg att ata ggt tgt tcc acg gac tct gtc tat gca     288
Ser Lys Asn Cys Val Ile Ile Gly Cys Ser Thr Asp Ser Val Tyr Ala
                85                  90                  95 cac ctg caa tgg acc aag atg gat agg aaa gct ggt ggc ctg gga aag     336
His Leu Gln Trp Thr Lys Met Asp Arg Lys Ala Gly Gly Leu Gly Lys
            100                 105                 110 atg aac att ccc ctt ttg tcg gat aag aac atg aag att tct cgc gca     384
Met Asn Ile Pro Leu Leu Ser Asp Lys Asn Met Lys Ile Ser Arg Ala
        115                 120                 125 tac cat gtg ctg gac gag gaa gag gga cac gca ttt cga ggg caa ttc     432
Tyr His Val Leu Asp Glu Glu Glu Gly His Ala Phe Arg Gly Gln Phe
    130                 135                 140 tta att gac ccg aag ggc att ttg cgt cag ata act gtc aat gat cgt     480
Leu Ile Asp Pro Lys Gly Ile Leu Arg Gln Ile Thr Val Asn Asp Arg
145                 150                 155                 160 cca gtt ggt cgt tct gtt gaa gaa gca atc cgc ttg ttg gaa gcc ttt     528
Pro Val Gly Arg Ser Val Glu Glu Ala Ile Arg Leu Leu Glu Ala Phe
                165                 170                 175 cat ttc cac gat caa cat ggc gat gtg tgt cca gcg aat tgg aag ccg     576
His Phe His Asp Gln His Gly Asp Val Cys Pro Ala Asn Trp Lys Pro
```

```
aag ggc aag act atg aag gca gac ccg gtc ggc gcc cag gag tat ttc    624
Lys Gly Lys Thr Met Lys Ala Asp Pro Val Gly Ala Gln Glu Tyr Phe
        195                 200                 205 tcg tcc gtt aac tag                                                639
Ser Ser Val Asn
    210
```

<210> SEQ ID NO 59
<211> LENGTH: 212
<212> TYPE: PRT
<213> ORGANISM: Opisthorchis viverrini

<400> SEQUENCE: 59

```
Met Gly Cys Ala Leu Leu Ile Val Leu Cys Thr Val Gly Leu Val Asn
1               5                   10                  15

Ala Met Ala Leu Leu Pro Asn Gln Pro Ala Pro Glu Phe Ser Gly Met
            20                  25                  30

Ala Val Val Asn Gly Glu Phe Lys Asn Ile Ser Leu Lys Asp Tyr Arg
        35                  40                  45

Gly Lys Tyr Val Ile Leu Leu Phe Tyr Pro Leu Asp Phe Thr Phe Val
    50                  55                  60

Cys Pro Thr Glu Leu Ile Ala Phe Ser Asp Ala Ala Glu Glu Phe Lys
65                  70                  75                  80

Ser Lys Asn Cys Val Ile Ile Gly Cys Ser Thr Asp Ser Val Tyr Ala
                85                  90                  95

His Leu Gln Trp Thr Lys Met Asp Arg Lys Ala Gly Gly Leu Gly Lys
            100                 105                 110

Met Asn Ile Pro Leu Leu Ser Asp Lys Asn Met Lys Ile Ser Arg Ala
        115                 120                 125

Tyr His Val Leu Asp Glu Glu Glu Gly His Ala Phe Arg Gly Gln Phe
    130                 135                 140

Leu Ile Asp Pro Lys Gly Ile Leu Arg Gln Ile Thr Val Asn Asp Arg
145                 150                 155                 160

Pro Val Gly Arg Ser Val Glu Glu Ala Ile Arg Leu Leu Glu Ala Phe
                165                 170                 175

His Phe His Asp Gln His Gly Asp Val Cys Pro Ala Asn Trp Lys Pro
            180                 185                 190

Lys Gly Lys Thr Met Lys Ala Asp Pro Val Gly Ala Gln Glu Tyr Phe
        195                 200                 205

Ser Ser Val Asn
    210
```

<210> SEQ ID NO 60
<211> LENGTH: 585
<212> TYPE: DNA
<213> ORGANISM: Schistosoma japonicum
<220> FEATURE:
<221> NAME/KEY: CDS
<222> LOCATION: (1)..(585)

<400> SEQUENCE: 60

```
atg ttg ttg cca aat caa cct gct ccc gat ttt gaa ggt aca gct gtt    48
Met Leu Leu Pro Asn Gln Pro Ala Pro Asp Phe Glu Gly Thr Ala Val
1               5                   10                  15 att gga aca gaa ttc cat cca att acc ttg cgt cag ttt cgc ggg agt    96
Ile Gly Thr Glu Phe His Pro Ile Thr Leu Arg Gln Phe Arg Gly Ser
            20                  25                  30
```

```
tat gtg tta ttg gta ttt tat cca ctt gac ttc acg ttt gtt tgc cca    144
Tyr Val Leu Leu Val Phe Tyr Pro Leu Asp Phe Thr Phe Val Cys Pro
         35                  40                  45 act gag ctg att gcg ttt agt gaa aga gct gcg gaa ttc aag tcc aga    192
Thr Glu Leu Ile Ala Phe Ser Glu Arg Ala Ala Glu Phe Lys Ser Arg
 50                  55                  60 ggt tgt caa gtg att gca tgc tca act gat tcg att tat tca cat ctg    240
Gly Cys Gln Val Ile Ala Cys Ser Thr Asp Ser Ile Tyr Ser His Leu
 65                  70                  75                  80 gca tgg aca aaa tta gat cga aaa gct ggt gga tta gga caa atg aat    288
Ala Trp Thr Lys Leu Asp Arg Lys Ala Gly Gly Leu Gly Gln Met Asn
                 85                  90                  95 ata cct ctg ctt tca gac aaa aat ttg aaa ata tca cga gct tac gga    336
Ile Pro Leu Leu Ser Asp Lys Asn Leu Lys Ile Ser Arg Ala Tyr Gly
                100                 105                 110 gtt ctt gat gaa gaa gag ggt cat gca ttc aga ggg atg ttc ctc att    384
Val Leu Asp Glu Glu Glu Gly His Ala Phe Arg Gly Met Phe Leu Ile
            115                 120                 125 gat cct aat ggt gtt tta cgt cag att acc gtt aac gat cgc ccc gta    432
Asp Pro Asn Gly Val Leu Arg Gln Ile Thr Val Asn Asp Arg Pro Val
130                 135                 140 ggg aga tca gtt gat gag gcg att cgt ctt ctg gat gct ttc att ttc    480
Gly Arg Ser Val Asp Glu Ala Ile Arg Leu Leu Asp Ala Phe Ile Phe
145                 150                 155                 160 ttc gag aaa aac ggt gaa gtt tgt cca gca aat tgg aaa cca aag tcg    528
Phe Glu Lys Asn Gly Glu Val Cys Pro Ala Asn Trp Lys Pro Lys Ser
                165                 170                 175 gca aca ata aaa cct gat cct aca gct gct ctc tcg tac ttt tcc tct    576
Ala Thr Ile Lys Pro Asp Pro Thr Ala Ala Leu Ser Tyr Phe Ser Ser
                180                 185                 190 gta aac tga                                                         585
Val Asn

<210> SEQ ID NO 61
<211> LENGTH: 194
<212> TYPE: PRT
<213> ORGANISM: Schistosoma japonicum

<400> SEQUENCE: 61

Met Leu Leu Pro Asn Gln Pro Ala Pro Asp Phe Glu Gly Thr Ala Val
1               5                   10                  15

Ile Gly Thr Glu Phe His Pro Ile Thr Leu Arg Gln Phe Arg Gly Ser
            20                  25                  30

Tyr Val Leu Leu Val Phe Tyr Pro Leu Asp Phe Thr Phe Val Cys Pro
         35                  40                  45

Thr Glu Leu Ile Ala Phe Ser Glu Arg Ala Ala Glu Phe Lys Ser Arg
 50                  55                  60

Gly Cys Gln Val Ile Ala Cys Ser Thr Asp Ser Ile Tyr Ser His Leu
 65                  70                  75                  80

Ala Trp Thr Lys Leu Asp Arg Lys Ala Gly Gly Leu Gly Gln Met Asn
                 85                  90                  95

Ile Pro Leu Leu Ser Asp Lys Asn Leu Lys Ile Ser Arg Ala Tyr Gly
                100                 105                 110

Val Leu Asp Glu Glu Glu Gly His Ala Phe Arg Gly Met Phe Leu Ile
            115                 120                 125

Asp Pro Asn Gly Val Leu Arg Gln Ile Thr Val Asn Asp Arg Pro Val
130                 135                 140

Gly Arg Ser Val Asp Glu Ala Ile Arg Leu Leu Asp Ala Phe Ile Phe
```

```
                145                 150                 155                 160
Phe Glu Lys Asn Gly Glu Val Cys Pro Ala Asn Trp Lys Pro Lys Ser
                165                 170                 175
Ala Thr Ile Lys Pro Asp Pro Thr Ala Ala Leu Ser Tyr Phe Ser Ser
            180                 185                 190
Val Asn

<210> SEQ ID NO 62
<211> LENGTH: 585
<212> TYPE: DNA
<213> ORGANISM: Schistosoma mansoni
<220> FEATURE:
<221> NAME/KEY: CDS
<222> LOCATION: (1)..(585)

<400> SEQUENCE: 62 atg ttg tta cca aat caa cct gct cct gat ttt gaa ggt act gct gtt      48
Met Leu Leu Pro Asn Gln Pro Ala Pro Asp Phe Glu Gly Thr Ala Val
1               5                   10                  15 att ggc acg gaa tta cgt cca att agt ttg agt caa ttt caa gga aaa      96
Ile Gly Thr Glu Leu Arg Pro Ile Ser Leu Ser Gln Phe Gln Gly Lys
            20                  25                  30 tat gtg tta ctg gta ttt tat cca ctt gac ttc act ttt gtt tgt ccc     144
Tyr Val Leu Leu Val Phe Tyr Pro Leu Asp Phe Thr Phe Val Cys Pro
        35                  40                  45 acg gaa cta att gca ttc agt gaa aga gct gct gag ttt caa tct aga     192
Thr Glu Leu Ile Ala Phe Ser Glu Arg Ala Ala Glu Phe Gln Ser Arg
    50                  55                  60 gga tgt caa gta atc gca tgc tca act gat tca gtt tat gct cat ttg     240
Gly Cys Gln Val Ile Ala Cys Ser Thr Asp Ser Val Tyr Ala His Leu
65                  70                  75                  80 gca tgg aca aaa ttg gat cgc aaa gct ggt ggt ttg ggg caa atg aat     288
Ala Trp Thr Lys Leu Asp Arg Lys Ala Gly Gly Leu Gly Gln Met Asn
                85                  90                  95 ata cct ttg ctg tcc gat aaa aac cta agg ata tca cga gcg tac gag     336
Ile Pro Leu Leu Ser Asp Lys Asn Leu Arg Ile Ser Arg Ala Tyr Glu
            100                 105                 110 gtt ctt gac gaa cag gaa ggt cat gca ttc aga ggt atg ttc ctc att     384
Val Leu Asp Glu Gln Glu Gly His Ala Phe Arg Gly Met Phe Leu Ile
        115                 120                 125 gat cgc aaa ggg att tta cgt caa att acc gtt aac gat cgc cct gta     432
Asp Arg Lys Gly Ile Leu Arg Gln Ile Thr Val Asn Asp Arg Pro Val
    130                 135                 140 ggt aga tca gtt gat gag gcg att cgt ctc ttg gat gct ttt att ttc     480
Gly Arg Ser Val Asp Glu Ala Ile Arg Leu Leu Asp Ala Phe Ile Phe
145                 150                 155                 160 ttt gag aaa cat ggc gaa gtt tgt cca gcg aac tgg aaa cca aat tca     528
Phe Glu Lys His Gly Glu Val Cys Pro Ala Asn Trp Lys Pro Asn Ser
                165                 170                 175 gca aca ata aaa cct gat cct gtt gct tct ctc tcc tac ttc tcc tct     576
Ala Thr Ile Lys Pro Asp Pro Val Ala Ser Leu Ser Tyr Phe Ser Ser
            180                 185                 190 gtg cac tga                                                         585
Val His

<210> SEQ ID NO 63
<211> LENGTH: 194
<212> TYPE: PRT
<213> ORGANISM: Schistosoma mansoni

<400> SEQUENCE: 63
```

```
Met Leu Leu Pro Asn Gln Pro Ala Pro Asp Phe Glu Gly Thr Ala Val
1               5                   10                  15

Ile Gly Thr Glu Leu Arg Pro Ile Ser Leu Ser Gln Phe Gln Gly Lys
                20                  25                  30

Tyr Val Leu Leu Val Phe Tyr Pro Leu Asp Phe Thr Phe Val Cys Pro
            35                  40                  45

Thr Glu Leu Ile Ala Phe Ser Glu Arg Ala Ala Glu Phe Gln Ser Arg
        50                  55                  60

Gly Cys Gln Val Ile Ala Cys Ser Thr Asp Ser Val Tyr Ala His Leu
65                  70                  75                  80

Ala Trp Thr Lys Leu Asp Arg Lys Ala Gly Gly Leu Gly Gln Met Asn
                85                  90                  95

Ile Pro Leu Leu Ser Asp Lys Asn Leu Arg Ile Ser Arg Ala Tyr Glu
                100                 105                 110

Val Leu Asp Glu Gln Glu Gly His Ala Phe Arg Gly Met Phe Leu Ile
            115                 120                 125

Asp Arg Lys Gly Ile Leu Arg Gln Ile Thr Val Asn Asp Arg Pro Val
        130                 135                 140

Gly Arg Ser Val Asp Glu Ala Ile Arg Leu Leu Asp Ala Phe Ile Phe
145                 150                 155                 160

Phe Glu Lys His Gly Glu Val Cys Pro Ala Asn Trp Lys Pro Asn Ser
                165                 170                 175

Ala Thr Ile Lys Pro Asp Pro Val Ala Ser Leu Ser Tyr Phe Ser Ser
                180                 185                 190

Val His

<210> SEQ ID NO 64
<211> LENGTH: 585
<212> TYPE: DNA
<213> ORGANISM: Schistosoma mansoni
<220> FEATURE:
<221> NAME/KEY: CDS
<222> LOCATION: (1)..(585)

<400> SEQUENCE: 64
```

| | |
|---|---|
| atg ctt att cca aca aaa cct gca cct aat ttc aaa gga aaa gct gta<br>Met Leu Ile Pro Thr Lys Pro Ala Pro Asn Phe Lys Gly Lys Ala Val<br>1                   5                     10               15 | 48 |
| att aat ggt gca ttt aaa caa atc aat tta cat gat tat ttg ggc aaa<br>Ile Asn Gly Ala Phe Lys Gln Ile Asn Leu His Asp Tyr Leu Gly Lys<br>                20                   25               30 | 96 |
| tat gtg gta cta ttc ttt tat cct gca gat ttt acg ttt gtc tgt cca<br>Tyr Val Val Leu Phe Phe Tyr Pro Ala Asp Phe Thr Phe Val Cys Pro<br>             35                   40              45 | 144 |
| act gaa att ata gca tat agt gaa cgc gtt gaa gag ttt gaa aaa aga<br>Thr Glu Ile Ile Ala Tyr Ser Glu Arg Val Glu Glu Phe Glu Lys Arg<br>     50                 55                  60 | 192 |
| aat tgt caa gtt att gcc tgt tca aca gat tct gaa tat tgt cat tta<br>Asn Cys Gln Val Ile Ala Cys Ser Thr Asp Ser Glu Tyr Cys His Leu<br>65                    70                   75              80 | 240 |
| gca tgg aca aat atg gat cgt aaa gca ggt gga tta ggt cca atg aaa<br>Ala Trp Thr Asn Met Asp Arg Lys Ala Gly Gly Leu Gly Pro Met Lys<br>                85                   90               95 | 288 |
| ata cca ctt tta gct gat aca aca aaa tgt att tca cga tca tat ggt<br>Ile Pro Leu Leu Ala Asp Thr Thr Lys Cys Ile Ser Arg Ser Tyr Gly<br>                100             105            110 | 336 |
| gta ctt gat gaa gaa gag ggt aat gca ttc aga gga tta ttt ata att | 384 |

```
Val Leu Asp Glu Glu Gly Asn Ala Phe Arg Gly Leu Phe Ile Ile
            115                 120                 125 gat ggt aaa gga ata ctc cgt cag ata acg gta aat gat cgt cca gtt        432
Asp Gly Lys Gly Ile Leu Arg Gln Ile Thr Val Asn Asp Arg Pro Val
            130                 135                 140 ggt cgg tct gtc gat gaa act ata cga ttg ttg gat gca ttt cag ttc        480
Gly Arg Ser Val Asp Glu Thr Ile Arg Leu Leu Asp Ala Phe Gln Phe
145                 150                 155                 160 gta gaa aaa cac ggt gaa gta tgt cca gct aac tgg aaa gct ggt aag        528
Val Glu Lys His Gly Glu Val Cys Pro Ala Asn Trp Lys Ala Gly Lys
            165                 170                 175 aaa aca att aaa cca gat cca aat gct agt aaa gag ttt ttt gct tcg        576
Lys Thr Ile Lys Pro Asp Pro Asn Ala Ser Lys Glu Phe Phe Ala Ser
            180                 185                 190 cct aca taa                                                            585
Pro Thr <210> SEQ ID NO 65
<211> LENGTH: 194
<212> TYPE: PRT
<213> ORGANISM: Schistosoma mansoni

<400> SEQUENCE: 65

Met Leu Ile Pro Thr Lys Pro Ala Pro Asn Phe Lys Gly Lys Ala Val
1               5                   10                  15

Ile Asn Gly Ala Phe Lys Gln Ile Asn Leu His Asp Tyr Leu Gly Lys
            20                  25                  30

Tyr Val Val Leu Phe Phe Tyr Pro Ala Asp Phe Thr Phe Val Cys Pro
        35                  40                  45

Thr Glu Ile Ile Ala Tyr Ser Glu Arg Val Glu Glu Phe Glu Lys Arg
    50                  55                  60

Asn Cys Gln Val Ile Ala Cys Ser Thr Asp Ser Glu Tyr Cys His Leu
65                  70                  75                  80

Ala Trp Thr Asn Met Asp Arg Lys Ala Gly Gly Leu Gly Pro Met Lys
                85                  90                  95

Ile Pro Leu Leu Ala Asp Thr Thr Lys Cys Ile Ser Arg Ser Tyr Gly
            100                 105                 110

Val Leu Asp Glu Glu Glu Gly Asn Ala Phe Arg Gly Leu Phe Ile Ile
        115                 120                 125

Asp Gly Lys Gly Ile Leu Arg Gln Ile Thr Val Asn Asp Arg Pro Val
    130                 135                 140

Gly Arg Ser Val Asp Glu Thr Ile Arg Leu Leu Asp Ala Phe Gln Phe
145                 150                 155                 160

Val Glu Lys His Gly Glu Val Cys Pro Ala Asn Trp Lys Ala Gly Lys
                165                 170                 175

Lys Thr Ile Lys Pro Asp Pro Asn Ala Ser Lys Glu Phe Phe Ala Ser
            180                 185                 190

Pro Thr

<210> SEQ ID NO 66
<211> LENGTH: 600
<212> TYPE: DNA
<213> ORGANISM: Loa loa
<220> FEATURE:
<221> NAME/KEY: CDS
<222> LOCATION: (1)..(600)

<400> SEQUENCE: 66
```

| | |
|---|---|
| atg aca ctt gcc gga agt aaa gca ttt att ggt cag cca gct cct acc<br>Met Thr Leu Ala Gly Ser Lys Ala Phe Ile Gly Gln Pro Ala Pro Thr<br>1                    5                    10                 15 | 48 |
| ttc aaa aca aca gcg gtt ctg aat ggt gat ttc aag gag att tca ctt<br>Phe Lys Thr Thr Ala Val Leu Asn Gly Asp Phe Lys Glu Ile Ser Leu<br>                   20                   25                   30 | 96 |
| agt cag tat aag ggg aaa tat gtg gtg ctc ttc ttt tat cca ctt gat<br>Ser Gln Tyr Lys Gly Lys Tyr Val Val Leu Phe Phe Tyr Pro Leu Asp<br>               35                   40                   45 | 144 |
| ttc aca ttc gtt tgc cca acg gag ata att gct ttt tct gat cgt att<br>Phe Thr Phe Val Cys Pro Thr Glu Ile Ile Ala Phe Ser Asp Arg Ile<br>     50                   55                   60 | 192 |
| gcg gag ttc aaa caa ttg gat gtc gct gtt atg gca tgc tca aca gac<br>Ala Glu Phe Lys Gln Leu Asp Val Ala Val Met Ala Cys Ser Thr Asp<br>65                    70                   75                   80 | 240 |
| tcg cac ttc tcg cac ctt gct tgg gta aat act gat cga aaa atg ggt<br>Ser His Phe Ser His Leu Ala Trp Val Asn Thr Asp Arg Lys Met Gly<br>                   85                   90                   95 | 288 |
| gga ctt ggt cag atg aat ata cct att ctt tcc gat acg aat cat gca<br>Gly Leu Gly Gln Met Asn Ile Pro Ile Leu Ser Asp Thr Asn His Ala<br>             100                  105                 110 | 336 |
| atc agc cga gca tat ggt gtg ctc aag gaa gat gat ggg att gcc tat<br>Ile Ser Arg Ala Tyr Gly Val Leu Lys Glu Asp Asp Gly Ile Ala Tyr<br>         115                  120                  125 | 384 |
| cgt gga tta ttc atc att gat cca aat ggg att ttg cgg cag atc act<br>Arg Gly Leu Phe Ile Ile Asp Pro Asn Gly Ile Leu Arg Gln Ile Thr<br>130                   135                  140 | 432 |
| gtt aat gat ctt cca gtg ggt cgt tct gta gac gaa act tta cgt ctg<br>Val Asn Asp Leu Pro Val Gly Arg Ser Val Asp Glu Thr Leu Arg Leu<br>145                   150                   155                 160 | 480 |
| att caa gct ttc cag ttt gtt gat aag cat ggt gaa gtg tgt cca gct<br>Ile Gln Ala Phe Gln Phe Val Asp Lys His Gly Glu Val Cys Pro Ala<br>             165                  170                  175 | 528 |
| aac tgg cat ccg gga tct gaa acg att aag cca gga gtg aaa gaa agc<br>Asn Trp His Pro Gly Ser Glu Thr Ile Lys Pro Gly Val Lys Glu Ser<br>             180                  185                 190 | 576 |
| aag gcg tat ttt gaa aag cac tga<br>Lys Ala Tyr Phe Glu Lys His<br>         195 | 600 |

<210> SEQ ID NO 67
<211> LENGTH: 199
<212> TYPE: PRT
<213> ORGANISM: Loa loa

<400> SEQUENCE: 67

Met Thr Leu Ala Gly Ser Lys Ala Phe Ile Gly Gln Pro Ala Pro Thr
1               5                   10                  15

Phe Lys Thr Thr Ala Val Leu Asn Gly Asp Phe Lys Glu Ile Ser Leu
            20                  25                  30

Ser Gln Tyr Lys Gly Lys Tyr Val Val Leu Phe Phe Tyr Pro Leu Asp
        35                  40                  45

Phe Thr Phe Val Cys Pro Thr Glu Ile Ile Ala Phe Ser Asp Arg Ile
    50                  55                  60

Ala Glu Phe Lys Gln Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Gln Met Asn Ile Pro Ile Leu Ser Asp Thr Asn His Ala

```
            100                 105                 110
Ile Ser Arg Ala Tyr Gly Val Leu Lys Glu Asp Asp Gly Ile Ala Tyr
        115                 120                 125

Arg Gly Leu Phe Ile Ile Asp Pro Asn Gly Ile Leu Arg Gln Ile Thr
    130                 135                 140

Val Asn Asp Leu Pro Val Gly Arg Ser Val Asp Glu Thr Leu Arg Leu
145                 150                 155                 160

Ile Gln Ala Phe Gln Phe Val Asp Lys His Gly Glu Val Cys Pro Ala
                165                 170                 175

Asn Trp His Pro Gly Ser Glu Thr Ile Lys Pro Gly Val Lys Glu Ser
            180                 185                 190

Lys Ala Tyr Phe Glu Lys His
        195

<210> SEQ ID NO 68
<211> LENGTH: 600
<212> TYPE: DNA
<213> ORGANISM: Dirofilaria immitis
<220> FEATURE:
<221> NAME/KEY: CDS
<222> LOCATION: (1)..(600)

<400> SEQUENCE: 68 atg act ctt gct gga agc aaa gca ttc att ggt caa ccg gcc cct aat      48
Met Thr Leu Ala Gly Ser Lys Ala Phe Ile Gly Gln Pro Ala Pro Asn
1               5                  10                  15 ttc aaa aca aca gcg gtt gtg aat ggc gat ttc aag gaa att tca ctt      96
Phe Lys Thr Thr Ala Val Val Asn Gly Asp Phe Lys Glu Ile Ser Leu
            20                  25                  30 tgt cag ttc aaa gga aaa tat gtg gtc ctc ttc ttt tat cct ctc gat     144
Cys Gln Phe Lys Gly Lys Tyr Val Val Leu Phe Phe Tyr Pro Leu Asp
        35                  40                  45 ttc act ttc gtt tgc cca aca gag ata att gct ttt tct gat cgt att     192
Phe Thr Phe Val Cys Pro Thr Glu Ile Ile Ala Phe Ser Asp Arg Ile
    50                  55                  60 gcg gag ttc aaa aaa tta gat gta gct gtt atg gca tgc tca act gat     240
Ala Glu Phe Lys Lys Leu Asp Val Ala Val Met Ala Cys Ser Thr Asp
65                  70                  75                  80 tca cat ttt tca cac ctt gca tgg gta aat acc gac cga aaa atg ggt     288
Ser His Phe Ser His Leu Ala Trp Val Asn Thr Asp Arg Lys Met Gly
                85                  90                  95 gga ctc ggt cag atg aat ata cca att ctt gct gat acc aat cat aca     336
Gly Leu Gly Gln Met Asn Ile Pro Ile Leu Ala Asp Thr Asn His Thr
            100                 105                 110 att agt agg gca tat ggc gtg ctc aag gaa gat gat ggc att gct tac     384
Ile Ser Arg Ala Tyr Gly Val Leu Lys Glu Asp Asp Gly Ile Ala Tyr
        115                 120                 125 cgt gga tta ttc atc att gat cca aaa ggg att ttg cga caa atc aca     432
Arg Gly Leu Phe Ile Ile Asp Pro Lys Gly Ile Leu Arg Gln Ile Thr
    130                 135                 140 atc aat gat ctt cca gtt ggt cgt tct gta gat gaa act tta cgt ctg     480
Ile Asn Asp Leu Pro Val Gly Arg Ser Val Asp Glu Thr Leu Arg Leu
145                 150                 155                 160 att caa gct ttt caa ttt gtc gac aat cac ggt gaa gta tgt ccg gcc     528
Ile Gln Ala Phe Gln Phe Val Asp Asn His Gly Glu Val Cys Pro Ala
                165                 170                 175 aat tgg cag cca gga tct gaa gca atc aaa cct gga gtg aaa gaa agc     576
Asn Trp Gln Pro Gly Ser Glu Ala Ile Lys Pro Gly Val Lys Glu Ser
            180                 185                 190
```

```
aaa gcg tac ttc gaa aag cac tga                                          600
Lys Ala Tyr Phe Glu Lys His
        195
```

<210> SEQ ID NO 69
<211> LENGTH: 199
<212> TYPE: PRT
<213> ORGANISM: Dirofilaria immitis

<400> SEQUENCE: 69

```
Met Thr Leu Ala Gly Ser Lys Ala Phe Ile Gly Gln Pro Ala Pro Asn
1               5                   10                  15

Phe Lys Thr Thr Ala Val Val Asn Gly Asp Phe Lys Glu Ile Ser Leu
            20                  25                  30

Cys Gln Phe Lys Gly Lys Tyr Val Val Leu Phe Phe Tyr Pro Leu Asp
        35                  40                  45

Phe Thr Phe Val Cys Pro Thr Glu Ile Ile Ala Phe Ser Asp Arg Ile
    50                  55                  60

Ala Glu Phe Lys Lys Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Gln Met Asn Ile Pro Ile Leu Ala Asp Thr Asn His Thr
            100                 105                 110

Ile Ser Arg Ala Tyr Gly Val Leu Lys Glu Asp Asp Gly Ile Ala Tyr
        115                 120                 125

Arg Gly Leu Phe Ile Ile Asp Pro Lys Gly Ile Leu Arg Gln Ile Thr
    130                 135                 140

Ile Asn Asp Leu Pro Val Gly Arg Ser Val Asp Glu Thr Leu Arg Leu
145                 150                 155                 160

Ile Gln Ala Phe Gln Phe Val Asp Asn His Gly Glu Val Cys Pro Ala
                165                 170                 175

Asn Trp Gln Pro Gly Ser Glu Ala Ile Lys Pro Gly Val Lys Glu Ser
            180                 185                 190

Lys Ala Tyr Phe Glu Lys His
        195
```

<210> SEQ ID NO 70
<211> LENGTH: 666
<212> TYPE: DNA
<213> ORGANISM: Ixodes scapularis
<220> FEATURE:
<221> NAME/KEY: CDS
<222> LOCATION: (1)..(666)

<400> SEQUENCE: 70

```
atg ggt gct cgg caa gtt gtg ttg cag tgt gcc ggt cgt caa ttt gga         48
Met Gly Ala Arg Gln Val Val Leu Gln Cys Ala Gly Arg Gln Phe Gly
1               5                   10                  15 ttt ttg tcc ttc ctg cgc aaa gta cga gag atg gca ctt ccc aag ctg         96
Phe Leu Ser Phe Leu Arg Lys Val Arg Glu Met Ala Leu Pro Lys Leu
            20                  25                  30 acc cac ccc gct ccg gac ttc agc ggt acc gca gtc gtc ggc gga caa        144
Thr His Pro Ala Pro Asp Phe Ser Gly Thr Ala Val Val Gly Gly Gln
        35                  40                  45 ttc aag gac atc aag ctc tcg gac tac aag gga aaa tac ctg gtt ctc        192
Phe Lys Asp Ile Lys Leu Ser Asp Tyr Lys Gly Lys Tyr Leu Val Leu
    50                  55                  60 ttc ttc tat ccc ctt gac ttc acc ttt gtg tgt ccc acg gag atc att        240
Phe Phe Tyr Pro Leu Asp Phe Thr Phe Val Cys Pro Thr Glu Ile Ile
```

```
Phe Phe Tyr Pro Leu Asp Phe Thr Phe Val Cys Pro Thr Glu Ile Ile
 65                  70                  75                  80 gcc ttc agc gac cat gtg gag gag ttt agg aag atc aac tgc gaa gtg     288
Ala Phe Ser Asp His Val Glu Glu Phe Arg Lys Ile Asn Cys Glu Val
                     85                  90                  95 gtg gcg tgc tcg acg gac agt cac ttc tgc cat ctc gcc tgg atc aac     336
Val Ala Cys Ser Thr Asp Ser His Phe Cys His Leu Ala Trp Ile Asn
                100                 105                 110 aca tcc agg aaa gag ggc ggt ctg ggc aac atg aac atc cct ctc ctt     384
Thr Ser Arg Lys Glu Gly Gly Leu Gly Asn Met Asn Ile Pro Leu Leu
            115                 120                 125 gct gac aag acc tgc aag att tcc cgg gac tat ggt gtc ctc aag gaa     432
Ala Asp Lys Thr Cys Lys Ile Ser Arg Asp Tyr Gly Val Leu Lys Glu
        130                 135                 140 gac gag ggc atc ccc ttc cgg ggc ctg ttc atc atc gat gac aag ggc     480
Asp Glu Gly Ile Pro Phe Arg Gly Leu Phe Ile Ile Asp Asp Lys Gly
145                 150                 155                 160 agg ctg cgc cag atg acc atc aat gat ctg ccc gtc gga cgt tcg gtt     528
Arg Leu Arg Gln Met Thr Ile Asn Asp Leu Pro Val Gly Arg Ser Val
                165                 170                 175 gac gag act ctg cgg ctc gtc cag gct ttc cag tac acg gac aag cac     576
Asp Glu Thr Leu Arg Leu Val Gln Ala Phe Gln Tyr Thr Asp Lys His
            180                 185                 190 ggt gaa gtg tgc cct gcc aac tgg aag cct ggg ggt gac acc atg aag     624
Gly Glu Val Cys Pro Ala Asn Trp Lys Pro Gly Gly Asp Thr Met Lys
        195                 200                 205 ccc gac ccc aag gga agc aag gac tac ttc tcc aag cac tag             666
Pro Asp Pro Lys Gly Ser Lys Asp Tyr Phe Ser Lys His
210                 215                 220

<210> SEQ ID NO 71
<211> LENGTH: 221
<212> TYPE: PRT
<213> ORGANISM: Ixodes scapularis

<400> SEQUENCE: 71

Met Gly Ala Arg Gln Val Val Leu Gln Cys Ala Gly Arg Gln Phe Gly
1                   5                   10                  15

Phe Leu Ser Phe Leu Arg Lys Val Arg Glu Met Ala Leu Pro Lys Leu
                20                  25                  30

Thr His Pro Ala Pro Asp Phe Ser Gly Thr Ala Val Val Gly Gly Gln
            35                  40                  45

Phe Lys Asp Ile Lys Leu Ser Asp Tyr Lys Gly Lys Tyr Leu Val Leu
        50                  55                  60

Phe Phe Tyr Pro Leu Asp Phe Thr Phe Val Cys Pro Thr Glu Ile Ile
 65                  70                  75                  80

Ala Phe Ser Asp His Val Glu Glu Phe Arg Lys Ile Asn Cys Glu Val
                 85                  90                  95

Val Ala Cys Ser Thr Asp Ser His Phe Cys His Leu Ala Trp Ile Asn
                100                 105                 110

Thr Ser Arg Lys Glu Gly Gly Leu Gly Asn Met Asn Ile Pro Leu Leu
            115                 120                 125

Ala Asp Lys Thr Cys Lys Ile Ser Arg Asp Tyr Gly Val Leu Lys Glu
        130                 135                 140

Asp Glu Gly Ile Pro Phe Arg Gly Leu Phe Ile Ile Asp Asp Lys Gly
145                 150                 155                 160

Arg Leu Arg Gln Met Thr Ile Asn Asp Leu Pro Val Gly Arg Ser Val
                165                 170                 175
```

Asp Glu Thr Leu Arg Leu Val Gln Ala Phe Gln Tyr Thr Asp Lys His
                180                 185                 190

Gly Glu Val Cys Pro Ala Asn Trp Lys Pro Gly Gly Asp Thr Met Lys
            195                 200                 205

Pro Asp Pro Lys Gly Ser Lys Asp Tyr Phe Ser Lys His
    210                 215                 220

<210> SEQ ID NO 72
<211> LENGTH: 591
<212> TYPE: DNA
<213> ORGANISM: Cristaria plicata
<220> FEATURE:
<221> NAME/KEY: CDS
<222> LOCATION: (1)..(591)

<400> SEQUENCE: 72

| | |
|---|---|
| atg tct cag ctg aaa ctg acc aaa cca gcc cca gag tgg agt gga act<br>Met Ser Gln Leu Lys Leu Thr Lys Pro Ala Pro Glu Trp Ser Gly Thr<br>1               5                   10                  15 | 48 |
| gcc gtt gtc aat gga gaa ttt aaa gat att tca ttg gca gat tat agg<br>Ala Val Val Asn Gly Glu Phe Lys Asp Ile Ser Leu Ala Asp Tyr Arg<br>            20                  25                  30 | 96 |
| ggc aaa tac ctc gtc ctg ttt ttc tat cca ttg gat ttc act ttt gtt<br>Gly Lys Tyr Leu Val Leu Phe Phe Tyr Pro Leu Asp Phe Thr Phe Val<br>        35                  40                  45 | 144 |
| tgc cca aca gag atc ata gcc ttc agt gac agg gtg gaa gaa ttc cga<br>Cys Pro Thr Glu Ile Ile Ala Phe Ser Asp Arg Val Glu Glu Phe Arg<br>    50                  55                  60 | 192 |
| gcc atc aac tgt gaa gtt gta gcc tgc tcc aca gat agc cat ttc tct<br>Ala Ile Asn Cys Glu Val Val Ala Cys Ser Thr Asp Ser His Phe Ser<br>65                  70                  75                  80 | 240 |
| cac ttg gca tgg atc aat acg ccg aga aag cag ggt ggc ttg ggc agc<br>His Leu Ala Trp Ile Asn Thr Pro Arg Lys Gln Gly Gly Leu Gly Ser<br>                85                  90                  95 | 288 |
| atg aat ata cct ctt ctg gcc gac aaa acc tgt gag atc tcc agc gct<br>Met Asn Ile Pro Leu Leu Ala Asp Lys Thr Cys Glu Ile Ser Ser Ala<br>            100                 105                 110 | 336 |
| tat gga gtt ctt aag gaa gat gag gga gtg gca ttc aga gga ctg ttt<br>Tyr Gly Val Leu Lys Glu Asp Glu Gly Val Ala Phe Arg Gly Leu Phe<br>        115                 120                 125 | 384 |
| ata att gat gga aag gga aac ctg cga cag atc aca gtg aat gat atg<br>Ile Ile Asp Gly Lys Gly Asn Leu Arg Gln Ile Thr Val Asn Asp Met<br>    130                 135                 140 | 432 |
| ccc gtg ggt cga tca gtt gac gaa acc ttg aga cta gtt cag gct ttc<br>Pro Val Gly Arg Ser Val Asp Glu Thr Leu Arg Leu Val Gln Ala Phe<br>145                 150                 155                 160 | 480 |
| cag ttc aca gat aag cat gga gaa gtc tgt cca gct aat tgg aag cct<br>Gln Phe Thr Asp Lys His Gly Glu Val Cys Pro Ala Asn Trp Lys Pro<br>                165                 170                 175 | 528 |
| ggt tcc gac acg atg aag ccc agc cct aaa gaa agc cag agc tat ttc<br>Gly Ser Asp Thr Met Lys Pro Ser Pro Lys Glu Ser Gln Ser Tyr Phe<br>            180                 185                 190 | 576 |
| aag gcc cat cac taa<br>Lys Ala His His<br>        195 | 591 |

<210> SEQ ID NO 73
<211> LENGTH: 196
<212> TYPE: PRT
<213> ORGANISM: Cristaria plicata

<400> SEQUENCE: 73

```
Met Ser Gln Leu Lys Leu Thr Lys Pro Ala Pro Glu Trp Ser Gly Thr
1               5                   10                  15

Ala Val Val Asn Gly Glu Phe Lys Asp Ile Ser Leu Ala Asp Tyr Arg
            20                  25                  30

Gly Lys Tyr Leu Val Leu Phe Phe Tyr Pro Leu Asp Phe Thr Phe Val
        35                  40                  45

Cys Pro Thr Glu Ile Ile Ala Phe Ser Asp Arg Val Glu Glu Phe Arg
50                  55                  60

Ala Ile Asn Cys Glu Val Val Ala Cys Ser Thr Asp Ser His Phe Ser
65                  70                  75                  80

His Leu Ala Trp Ile Asn Thr Pro Arg Lys Gln Gly Gly Leu Gly Ser
                85                  90                  95

Met Asn Ile Pro Leu Leu Ala Asp Lys Thr Cys Glu Ile Ser Ser Ala
            100                 105                 110

Tyr Gly Val Leu Lys Glu Asp Glu Gly Val Ala Phe Arg Gly Leu Phe
        115                 120                 125

Ile Ile Asp Gly Lys Gly Asn Leu Arg Gln Ile Thr Val Asn Asp Met
130                 135                 140

Pro Val Gly Arg Ser Val Asp Glu Thr Leu Arg Leu Val Gln Ala Phe
145                 150                 155                 160

Gln Phe Thr Asp Lys His Gly Glu Val Cys Pro Ala Asn Trp Lys Pro
                165                 170                 175

Gly Ser Asp Thr Met Lys Pro Ser Pro Lys Glu Ser Gln Ser Tyr Phe
            180                 185                 190

Lys Ala His His
        195
```

<210> SEQ ID NO 74
<211> LENGTH: 744
<212> TYPE: DNA
<213> ORGANISM: Acanthocheilonema viteae
<220> FEATURE:
<221> NAME/KEY: CDS
<222> LOCATION: (1)..(744)

<400> SEQUENCE: 74

```
atg aca ctt gct gga agc aaa gcg ttt att ggt caa cca gct ccc aac      48
Met Thr Leu Ala Gly Ser Lys Ala Phe Ile Gly Gln Pro Ala Pro Asn
1               5                   10                  15 ttt aaa aca aca gcg gtt atg aat ggc gat ttc aag gag att tca ctt      96
Phe Lys Thr Thr Ala Val Met Asn Gly Asp Phe Lys Glu Ile Ser Leu
            20                  25                  30 tgt cag ttt aaa ggg aaa tat gtg gtc ctc ttc ttt tat cca ctc gat     144
Cys Gln Phe Lys Gly Lys Tyr Val Val Leu Phe Phe Tyr Pro Leu Asp
        35                  40                  45 ttc act ttt gtt tgt cca aca gag ata atc gca ttt tcc gat cgt att     192
Phe Thr Phe Val Cys Pro Thr Glu Ile Ile Ala Phe Ser Asp Arg Ile
50                  55                  60 gcg gaa ttc aag cag tta gat gtg gct gtt atg gcg tgt tca act gac     240
Ala Glu Phe Lys Gln Leu Asp Val Ala Val Met Ala Cys Ser Thr Asp
65                  70                  75                  80 tcg cat ttc tcg cat ctt gca tgg gta aat acc gat cga aaa atg ggt     288
Ser His Phe Ser His Leu Ala Trp Val Asn Thr Asp Arg Lys Met Gly
                85                  90                  95 gga ctt gga ccg atg aat ata cca att ctt gct gat acg aat cat gaa     336
Gly Leu Gly Pro Met Asn Ile Pro Ile Leu Ala Asp Thr Asn His Glu
            100                 105                 110
```

| | | | | | | | | | | | | | | | | |
|---|---|---|---|---|---|---|---|---|---|---|---|---|---|---|---|---|
| atc | agc | agg | gcc | tat | ggt | gtg | ctc | aaa | gaa | gac | gat | gga | att | gct | tat | 384 |
| Ile | Ser | Arg | Ala | Tyr | Gly | Val | Leu | Lys | Glu | Asp | Asp | Gly | Ile | Ala | Tyr | |
| | | 115 | | | | 120 | | | | | 125 | | | | | |
| cgg | gga | tta | ttc | atc | att | gat | cca | aaa | ggg | att | tta | cgg | cag | atc | aca | 432 |
| Arg | Gly | Leu | Phe | Ile | Ile | Asp | Pro | Lys | Gly | Ile | Leu | Arg | Gln | Ile | Thr | |
| | 130 | | | | | 135 | | | | | 140 | | | | | |
| atc | aat | gat | ctc | cca | gtg | ggt | cgt | tct | gta | gat | gag | act | tta | cgt | ctc | 480 |
| Ile | Asn | Asp | Leu | Pro | Val | Gly | Arg | Ser | Val | Asp | Glu | Thr | Leu | Arg | Leu | |
| 145 | | | | | 150 | | | | | 155 | | | | | 160 | |
| att | cag | gct | ttt | caa | ttt | gtc | gat | aag | cac | ggt | gaa | gta | tgt | ccg | gcc | 528 |
| Ile | Gln | Ala | Phe | Gln | Phe | Val | Asp | Lys | His | Gly | Glu | Val | Cys | Pro | Ala | |
| | | | | 165 | | | | | 170 | | | | | 175 | | |
| aat | tgg | cat | ccg | gga | tct | gag | acg | att | aaa | cct | ggg | gtg | aaa | gaa | agc | 576 |
| Asn | Trp | His | Pro | Gly | Ser | Glu | Thr | Ile | Lys | Pro | Gly | Val | Lys | Glu | Ser | |
| | | | 180 | | | | | 185 | | | | | 190 | | | |
| aaa | gcg | tat | ttc | caa | aac | att | gaa | aat | gaa | ccg | ttg | tat | aat | gtc | gat | 624 |
| Lys | Ala | Tyr | Phe | Gln | Asn | Ile | Glu | Asn | Glu | Pro | Leu | Tyr | Asn | Val | Asp | |
| | | 195 | | | | | 200 | | | | | 205 | | | | |
| caa | ctc | agt | aat | ttt | ttc | aat | ata | tgc | gtg | tta | aat | acc | ttt | gat | gaa | 672 |
| Gln | Leu | Ser | Asn | Phe | Phe | Asn | Ile | Cys | Val | Leu | Asn | Thr | Phe | Asp | Glu | |
| | 210 | | | | | 215 | | | | | 220 | | | | | |
| tat | ggc | att | tct | gct | tta | ctg | tac | tcc | gta | ata | tta | att | gtc | ctt | gat | 720 |
| Tyr | Gly | Ile | Ser | Ala | Leu | Leu | Tyr | Ser | Val | Ile | Leu | Ile | Val | Leu | Asp | |
| 225 | | | | | 230 | | | | | 235 | | | | | 240 | |
| gat | att | ata | tgc | cga | ttt | tta | tag | | | | | | | | | 744 |
| Asp | Ile | Ile | Cys | Arg | Phe | Leu | | | | | | | | | | |
| | | | | 245 | | | | | | | | | | | | |

<210> SEQ ID NO 75
<211> LENGTH: 247
<212> TYPE: PRT
<213> ORGANISM: Acanthocheilonema viteae

<400> SEQUENCE: 75

Met Thr Leu Ala Gly Ser Lys Ala Phe Ile Gly Gln Pro Ala Pro Asn
1               5                   10                  15

Phe Lys Thr Thr Ala Val Met Asn Gly Asp Phe Lys Glu Ile Ser Leu
            20                  25                  30

Cys Gln Phe Lys Gly Lys Tyr Val Val Leu Phe Phe Tyr Pro Leu Asp
        35                  40                  45

Phe Thr Phe Val Cys Pro Thr Glu Ile Ile Ala Phe Ser Asp Arg Ile
    50                  55                  60

Ala Glu Phe Lys Gln Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Pro Met Asn Ile Pro Ile Leu Ala Asp Thr Asn His Glu
            100                 105                 110

Ile Ser Arg Ala Tyr Gly Val Leu Lys Glu Asp Asp Gly Ile Ala Tyr
        115                 120                 125

Arg Gly Leu Phe Ile Ile Asp Pro Lys Gly Ile Leu Arg Gln Ile Thr
    130                 135                 140

Ile Asn Asp Leu Pro Val Gly Arg Ser Val Asp Glu Thr Leu Arg Leu
145                 150                 155                 160

Ile Gln Ala Phe Gln Phe Val Asp Lys His Gly Glu Val Cys Pro Ala
                165                 170                 175

Asn Trp His Pro Gly Ser Glu Thr Ile Lys Pro Gly Val Lys Glu Ser

```
              180                 185                 190
Lys Ala Tyr Phe Gln Asn Ile Glu Asn Glu Pro Leu Tyr Asn Val Asp
        195                 200                 205

Gln Leu Ser Asn Phe Phe Asn Ile Cys Val Leu Asn Thr Phe Asp Glu
    210                 215                 220

Tyr Gly Ile Ser Ala Leu Leu Tyr Ser Val Ile Leu Ile Val Leu Asp
225                 230                 235                 240

Asp Ile Ile Cys Arg Phe Leu
                245

<210> SEQ ID NO 76
<211> LENGTH: 600
<212> TYPE: DNA
<213> ORGANISM: Onchocerca ochengi
<220> FEATURE:
<221> NAME/KEY: CDS
<222> LOCATION: (1)..(600)

<400> SEQUENCE: 76
```

| | | | | | | | | | | | | | | | | |
|---|---|---|---|---|---|---|---|---|---|---|---|---|---|---|---|---|
| atg | aca | ctt | gct | gga | agc | aaa | gca | ttc | att | gga | caa | cca | gct | cct | aac | 48 |
| Met | Thr | Leu | Ala | Gly | Ser | Lys | Ala | Phe | Ile | Gly | Gln | Pro | Ala | Pro | Asn | |
| 1 | | | | 5 | | | | | 10 | | | | | 15 | | |
| ttc | aag | aca | aca | gcg | gtt | gtg | aat | ggc | gat | ttc | aag | gaa | att | tca | ctt | 96 |
| Phe | Lys | Thr | Thr | Ala | Val | Val | Asn | Gly | Asp | Phe | Lys | Glu | Ile | Ser | Leu | |
| | | | 20 | | | | | 25 | | | | | 30 | | | |
| aat | cag | ttt | aaa | ggg | aaa | tat | gtg | gtc | ctc | ttc | ttc | tat | cca | ctc | gac | 144 |
| Asn | Gln | Phe | Lys | Gly | Lys | Tyr | Val | Val | Leu | Phe | Phe | Tyr | Pro | Leu | Asp | |
| | | 35 | | | | | 40 | | | | | 45 | | | | |
| ttc | act | ttc | gtt | tgc | cca | acg | gag | ata | att | gcg | ttt | tct | gat | cgt | att | 192 |
| Phe | Thr | Phe | Val | Cys | Pro | Thr | Glu | Ile | Ile | Ala | Phe | Ser | Asp | Arg | Ile | |
| | 50 | | | | | 55 | | | | | 60 | | | | | |
| tcg | gaa | ttc | aaa | aaa | tta | gat | gta | gct | gtt | atg | gcg | tgt | tca | act | gac | 240 |
| Ser | Glu | Phe | Lys | Lys | Leu | Asp | Val | Ala | Val | Met | Ala | Cys | Ser | Thr | Asp | |
| 65 | | | | | 70 | | | | | 75 | | | | | 80 | |
| tcg | cat | ttc | tcg | cat | ctt | gca | tgg | gta | aat | acc | gac | cga | aaa | atg | ggt | 288 |
| Ser | His | Phe | Ser | His | Leu | Ala | Trp | Val | Asn | Thr | Asp | Arg | Lys | Met | Gly | |
| | | | | 85 | | | | | 90 | | | | | 95 | | |
| gga | ctt | ggt | cag | atg | aat | ata | cca | att | ctt | gct | gat | acc | aat | cat | gca | 336 |
| Gly | Leu | Gly | Gln | Met | Asn | Ile | Pro | Ile | Leu | Ala | Asp | Thr | Asn | His | Ala | |
| | | | 100 | | | | | 105 | | | | | 110 | | | |
| atc | agc | aag | gca | tat | ggt | gtg | ctc | aag | gaa | gat | gaa | gga | att | gct | tat | 384 |
| Ile | Ser | Lys | Ala | Tyr | Gly | Val | Leu | Lys | Glu | Asp | Glu | Gly | Ile | Ala | Tyr | |
| | | 115 | | | | | 120 | | | | | 125 | | | | |
| cgt | gga | cta | ttc | atc | att | gat | tca | aaa | ggg | att | ttg | cgg | cag | atc | aca | 432 |
| Arg | Gly | Leu | Phe | Ile | Ile | Asp | Ser | Lys | Gly | Ile | Leu | Arg | Gln | Ile | Thr | |
| | 130 | | | | | 135 | | | | | 140 | | | | | |
| gtc | aat | gat | ctt | cca | gtt | ggt | cgt | tcc | gta | gac | gaa | act | tta | cgt | ctg | 480 |
| Val | Asn | Asp | Leu | Pro | Val | Gly | Arg | Ser | Val | Asp | Glu | Thr | Leu | Arg | Leu | |
| 145 | | | | | 150 | | | | | 155 | | | | | 160 | |
| att | caa | gct | ttt | cag | ttt | gtc | gat | aat | cat | ggt | gaa | gta | tgt | ccg | gcc | 528 |
| Ile | Gln | Ala | Phe | Gln | Phe | Val | Asp | Asn | His | Gly | Glu | Val | Cys | Pro | Ala | |
| | | | | 165 | | | | | 170 | | | | | 175 | | |
| aac | tgg | caa | cca | gga | tct | gaa | acg | att | aag | cct | gaa | gtg | aaa | gaa | agc | 576 |
| Asn | Trp | Gln | Pro | Gly | Ser | Glu | Thr | Ile | Lys | Pro | Glu | Val | Lys | Glu | Ser | |
| | | | 180 | | | | | 185 | | | | | 190 | | | |
| aag | gaa | tat | ttt | gga | aag | cat | tga | | | | | | | | | 600 |
| Lys | Glu | Tyr | Phe | Gly | Lys | His | | | | | | | | | | |
| | | 195 | | | | | | | | | | | | | | |

```
<210> SEQ ID NO 77
```

```
<211> LENGTH: 199
<212> TYPE: PRT
<213> ORGANISM: Onchocerca ochengi

<400> SEQUENCE: 77

Met Thr Leu Ala Gly Ser Lys Ala Phe Ile Gly Gln Pro Ala Pro Asn
1               5                   10                  15

Phe Lys Thr Thr Ala Val Val Asn Gly Asp Phe Lys Glu Ile Ser Leu
            20                  25                  30

Asn Gln Phe Lys Gly Lys Tyr Val Val Leu Phe Phe Tyr Pro Leu Asp
        35                  40                  45

Phe Thr Phe Val Cys Pro Thr Glu Ile Ile Ala Phe Ser Asp Arg Ile
    50                  55                  60

Ser Glu Phe Lys Lys Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Gln Met Asn Ile Pro Ile Leu Ala Asp Thr Asn His Ala
            100                 105                 110

Ile Ser Lys Ala Tyr Gly Val Leu Lys Glu Asp Glu Gly Ile Ala Tyr
        115                 120                 125

Arg Gly Leu Phe Ile Ile Asp Ser Lys Gly Ile Leu Arg Gln Ile Thr
    130                 135                 140

Val Asn Asp Leu Pro Val Gly Arg Ser Val Asp Glu Thr Leu Arg Leu
145                 150                 155                 160

Ile Gln Ala Phe Gln Phe Val Asp Asn His Gly Glu Val Cys Pro Ala
                165                 170                 175

Asn Trp Gln Pro Gly Ser Glu Thr Ile Lys Pro Glu Val Lys Glu Ser
            180                 185                 190

Lys Glu Tyr Phe Gly Lys His
        195

<210> SEQ ID NO 78
<211> LENGTH: 600
<212> TYPE: DNA
<213> ORGANISM: Dirofilaria immitis
<220> FEATURE:
<221> NAME/KEY: CDS
<222> LOCATION: (1)..(600)

<400> SEQUENCE: 78 atg act ctt gct gga agc aaa gca ttc att ggt caa ccg gcc cct aat     48
Met Thr Leu Ala Gly Ser Lys Ala Phe Ile Gly Gln Pro Ala Pro Asn
1               5                   10                  15 ttc aaa aca aca gcg gtt gtg aat ggc gat ttc aag gaa att tca ctt     96
Phe Lys Thr Thr Ala Val Val Asn Gly Asp Phe Lys Glu Ile Ser Leu
            20                  25                  30 tgt cag ttc aaa gga aaa tat gtg gtc ctc ttc ttt tat cct ctc gat    144
Cys Gln Phe Lys Gly Lys Tyr Val Val Leu Phe Phe Tyr Pro Leu Asp
        35                  40                  45 ttc act ttc gtt tgc cca aca gag ata att gct ttt tct gat cgt att    192
Phe Thr Phe Val Cys Pro Thr Glu Ile Ile Ala Phe Ser Asp Arg Ile
    50                  55                  60 gcg gag ttc aaa caa ttg gat gta gtt gtt atg gca tgc tca act gat    240
Ala Glu Phe Lys Gln Leu Asp Val Val Val Met Ala Cys Ser Thr Asp
65                  70                  75                  80 tca cat ttt tca cac ctt gca tgg ata aat act gac cga aaa atg ggt    288
Ser His Phe Ser His Leu Ala Trp Ile Asn Thr Asp Arg Lys Met Gly
                85                  90                  95
```

```
ggc ctc ggt cag atg aat ata cca att ctt gct gat acc aat cat aca    336
Gly Leu Gly Gln Met Asn Ile Pro Ile Leu Ala Asp Thr Asn His Thr
            100                 105                 110 att agt agg gca tat ggc gtg ctc aag gaa gat gat ggc att gct tac    384
Ile Ser Arg Ala Tyr Gly Val Leu Lys Glu Asp Asp Gly Ile Ala Tyr
            115                 120                 125 cgt gga tta ttc atc att gat cca gaa gga att ttg cgg cag att acg    432
Arg Gly Leu Phe Ile Ile Asp Pro Glu Gly Ile Leu Arg Gln Ile Thr
    130                 135                 140 gtc aat gat ctc cca gtt ggt cgc tct gtg gac gaa act tta cgt ctg    480
Val Asn Asp Leu Pro Val Gly Arg Ser Val Asp Glu Thr Leu Arg Leu
145                 150                 155                 160 atc caa gct ttt caa ttt gtc gac aat cat ggt gaa gta tgt ccg gcc    528
Ile Gln Ala Phe Gln Phe Val Asp Asn His Gly Glu Val Cys Pro Ala
                165                 170                 175 aat tgg cat cca gga tct gaa gca atc aaa cct gga gtg aaa gaa agc    576
Asn Trp His Pro Gly Ser Glu Ala Ile Lys Pro Gly Val Lys Glu Ser
            180                 185                 190 aaa gcg tac ttc gaa aag cac tga                                    600
Lys Ala Tyr Phe Glu Lys His
        195
```

<210> SEQ ID NO 79
<211> LENGTH: 199
<212> TYPE: PRT
<213> ORGANISM: Dirofilaria immitis

<400> SEQUENCE: 79

Met Thr Leu Ala Gly Ser Lys Ala Phe Ile Gly Gln Pro Ala Pro Asn
1               5                   10                  15

Phe Lys Thr Thr Ala Val Val Asn Gly Asp Phe Lys Glu Ile Ser Leu
            20                  25                  30

Cys Gln Phe Lys Gly Lys Tyr Val Val Leu Phe Phe Tyr Pro Leu Asp
        35                  40                  45

Phe Thr Phe Val Cys Pro Thr Glu Ile Ile Ala Phe Ser Asp Arg Ile
    50                  55                  60

Ala Glu Phe Lys Gln Leu Asp Val Val Met Ala Cys Ser Thr Asp
65                  70                  75                  80

Ser His Phe Ser His Leu Ala Trp Ile Asn Thr Asp Arg Lys Met Gly
                85                  90                  95

Gly Leu Gly Gln Met Asn Ile Pro Ile Leu Ala Asp Thr Asn His Thr
            100                 105                 110

Ile Ser Arg Ala Tyr Gly Val Leu Lys Glu Asp Asp Gly Ile Ala Tyr
            115                 120                 125

Arg Gly Leu Phe Ile Ile Asp Pro Glu Gly Ile Leu Arg Gln Ile Thr
    130                 135                 140

Val Asn Asp Leu Pro Val Gly Arg Ser Val Asp Glu Thr Leu Arg Leu
145                 150                 155                 160

Ile Gln Ala Phe Gln Phe Val Asp Asn His Gly Glu Val Cys Pro Ala
                165                 170                 175

Asn Trp His Pro Gly Ser Glu Ala Ile Lys Pro Gly Val Lys Glu Ser
            180                 185                 190

Lys Ala Tyr Phe Glu Lys His
        195

<210> SEQ ID NO 80
<211> LENGTH: 588

<212> TYPE: DNA
<213> ORGANISM: Ornithodoros parkeri
<220> FEATURE:
<221> NAME/KEY: CDS
<222> LOCATION: (1)..(588)

<400> SEQUENCE: 80

```
atg tct ctc cca aag ctg acc gag ccc gcc ccg tac ttt gcg ggt act        48
Met Ser Leu Pro Lys Leu Thr Glu Pro Ala Pro Tyr Phe Ala Gly Thr
1               5                   10                  15 gct gtc gtc gac ggt gaa ttc aag gaa atc aag ctc acg gac tac aaa        96
Ala Val Val Asp Gly Glu Phe Lys Glu Ile Lys Leu Thr Asp Tyr Lys
                20                  25                  30 ggg aaa tac ctg gtt ttg ttc ttc tac ccc ctg gat ttc aca ttc gtc       144
Gly Lys Tyr Leu Val Leu Phe Phe Tyr Pro Leu Asp Phe Thr Phe Val
            35                  40                  45 tgc ccc acg gaa atc att gcc ttc agc gac agt gcc gaa gag ttc aga       192
Cys Pro Thr Glu Ile Ile Ala Phe Ser Asp Ser Ala Glu Glu Phe Arg
50                  55                  60 aaa atc aac tgt gaa atc gtc gcc tgc tct gct gac agt cac ttc tgc       240
Lys Ile Asn Cys Glu Ile Val Ala Cys Ser Ala Asp Ser His Phe Cys
65                  70                  75                  80 cat ctg gca tgg att aat aca cct cgc aag gag ggt ggt ctt ggc agc       288
His Leu Ala Trp Ile Asn Thr Pro Arg Lys Glu Gly Gly Leu Gly Ser
                85                  90                  95 atg aac att cct ctc ctg gct gac aaa tcc tgt gca gtg tca cga gcg       336
Met Asn Ile Pro Leu Leu Ala Asp Lys Ser Cys Ala Val Ser Arg Ala
            100                 105                 110 tat ggt gtg ctg aag gag gac gaa gga atc cca ttc agg ggc ctg ttt       384
Tyr Gly Val Leu Lys Glu Asp Glu Gly Ile Pro Phe Arg Gly Leu Phe
        115                 120                 125 atc att gac gac aag caa cgt ctg cga cag ata acc gtt aac gac ctg       432
Ile Ile Asp Asp Lys Gln Arg Leu Arg Gln Ile Thr Val Asn Asp Leu
    130                 135                 140 cct gtc ggc cgt tct gtc gaa gaa aca ctt cgc ctc gtc cag gca ttc       480
Pro Val Gly Arg Ser Val Glu Glu Thr Leu Arg Leu Val Gln Ala Phe
145                 150                 155                 160 caa ttc acg gac aag aat gga gaa gtg tgc cca gcc aac tgg aag cct       528
Gln Phe Thr Asp Lys Asn Gly Glu Val Cys Pro Ala Asn Trp Lys Pro
                165                 170                 175 gga gga gac acc atg agg cca gat ccc aag ggt agc aag gct tac ttc       576
Gly Gly Asp Thr Met Arg Pro Asp Pro Lys Gly Ser Lys Ala Tyr Phe
            180                 185                 190 tca aag cag tag                                                        588
Ser Lys Gln
        195
```

<210> SEQ ID NO 81
<211> LENGTH: 195
<212> TYPE: PRT
<213> ORGANISM: Ornithodoros parkeri

<400> SEQUENCE: 81

```
Met Ser Leu Pro Lys Leu Thr Glu Pro Ala Pro Tyr Phe Ala Gly Thr
1               5                   10                  15

Ala Val Val Asp Gly Glu Phe Lys Glu Ile Lys Leu Thr Asp Tyr Lys
                20                  25                  30

Gly Lys Tyr Leu Val Leu Phe Phe Tyr Pro Leu Asp Phe Thr Phe Val
            35                  40                  45

Cys Pro Thr Glu Ile Ile Ala Phe Ser Asp Ser Ala Glu Glu Phe Arg
        50                  55                  60
```

```
Lys Ile Asn Cys Glu Ile Val Ala Cys Ser Ala Asp Ser His Phe Cys
 65                  70                  75                  80

His Leu Ala Trp Ile Asn Thr Pro Arg Lys Glu Gly Gly Leu Gly Ser
                 85                  90                  95

Met Asn Ile Pro Leu Leu Ala Asp Lys Ser Cys Ala Val Ser Arg Ala
            100                 105                 110

Tyr Gly Val Leu Lys Glu Asp Glu Gly Ile Pro Phe Arg Gly Leu Phe
        115                 120                 125

Ile Ile Asp Asp Lys Gln Arg Leu Arg Gln Ile Thr Val Asn Asp Leu
    130                 135                 140

Pro Val Gly Arg Ser Val Glu Glu Thr Leu Arg Leu Val Gln Ala Phe
145                 150                 155                 160

Gln Phe Thr Asp Lys Asn Gly Glu Val Cys Pro Ala Asn Trp Lys Pro
                165                 170                 175

Gly Gly Asp Thr Met Arg Pro Asp Pro Lys Gly Ser Lys Ala Tyr Phe
            180                 185                 190

Ser Lys Gln
        195

<210> SEQ ID NO 82
<211> LENGTH: 600
<212> TYPE: DNA
<213> ORGANISM: Leishmania major
<220> FEATURE:
<221> NAME/KEY: CDS
<222> LOCATION: (1)..(600)

<400> SEQUENCE: 82 atg tcc tgc ggt aac gcc aag atc aac tct ccc gcg ccg tcc ttc gag     48
Met Ser Cys Gly Asn Ala Lys Ile Asn Ser Pro Ala Pro Ser Phe Glu
  1               5                  10                  15 gag gtg gcg ctc atg ccc aac ggc agc ttc aag aag atc agc ctc tcc     96
Glu Val Ala Leu Met Pro Asn Gly Ser Phe Lys Lys Ile Ser Leu Ser
             20                  25                  30 tcc tac aag ggc aag tgg gtc gtg ctc ttc ttc tac ccg ctc gac ttc    144
Ser Tyr Lys Gly Lys Trp Val Val Leu Phe Phe Tyr Pro Leu Asp Phe
         35                  40                  45 acc ttc gtg tgc ccg aca gag gtc atc gcg ttc tcc gac agc gtg agt    192
Thr Phe Val Cys Pro Thr Glu Val Ile Ala Phe Ser Asp Ser Val Ser
     50                  55                  60 cgc ttc aac gag ctc aac tgc gag gtc ctc gcg tgc tcg ata gac agc    240
Arg Phe Asn Glu Leu Asn Cys Glu Val Leu Ala Cys Ser Ile Asp Ser
 65                  70                  75                  80 gag tac gcg cac ctg cag tgg acg ctg cag gac cgc aag aag ggc ggc    288
Glu Tyr Ala His Leu Gln Trp Thr Leu Gln Asp Arg Lys Lys Gly Gly
                 85                  90                  95 ctc ggg acc atg gcg atc cca atg cta gcc gac aag acc aag agc atc    336
Leu Gly Thr Met Ala Ile Pro Met Leu Ala Asp Lys Thr Lys Ser Ile
            100                 105                 110 gct cgt tcc tac ggc gtg ctg gag gag agc cgg ggc gtg gcc tac cgc    384
Ala Arg Ser Tyr Gly Val Leu Glu Glu Ser Arg Gly Val Ala Tyr Arg
        115                 120                 125 ggt ctc ttc atc atc gac ccc cat ggc atg ctg cgt cag atc acc gtc    432
Gly Leu Phe Ile Ile Asp Pro His Gly Met Leu Arg Gln Ile Thr Val
    130                 135                 140 aat gac atg ccg gtg ggc cgc agc gtg gag gag gtt cta cgc ctg ctg    480
Asn Asp Met Pro Val Gly Arg Ser Val Glu Glu Val Leu Arg Leu Leu
145                 150                 155                 160
```

|  |  |
|---|---|
| gag gct ttt cag ttc gtg gag aag cac ggc gag gtg tgc ccc gcg aac<br>Glu Ala Phe Gln Phe Val Glu Lys His Gly Glu Val Cys Pro Ala Asn<br>              165                    170                  175 | 528 |
| tgg aag aag ggc gcc ccc acg atg aag ccg gaa ccg aag gcg tct gtc<br>Trp Lys Lys Gly Ala Pro Thr Met Lys Pro Glu Pro Lys Ala Ser Val<br>              180                    185                  190 | 576 |
| gag gga tac ttc agc aag cag taa<br>Glu Gly Tyr Phe Ser Lys Gln<br>           195 | 600 |

<210> SEQ ID NO 83
<211> LENGTH: 199
<212> TYPE: PRT
<213> ORGANISM: Leishmania major

<400> SEQUENCE: 83

Met Ser Cys Gly Asn Ala Lys Ile Asn Ser Pro Ala Pro Ser Phe Glu
1               5                   10                  15

Glu Val Ala Leu Met Pro Asn Gly Ser Phe Lys Lys Ile Ser Leu Ser
            20                  25                  30

Ser Tyr Lys Gly Lys Trp Val Leu Phe Phe Tyr Pro Leu Asp Phe
        35                  40                  45

Thr Phe Val Cys Pro Thr Glu Val Ile Ala Phe Ser Asp Ser Val Ser
    50                  55                  60

Arg Phe Asn Glu Leu Asn Cys Glu Val Leu Ala Cys Ser Ile Asp Ser
65                  70                  75                  80

Glu Tyr Ala His Leu Gln Trp Thr Leu Gln Asp Arg Lys Lys Gly Gly
                85                  90                  95

Leu Gly Thr Met Ala Ile Pro Met Leu Ala Asp Lys Thr Lys Ser Ile
            100                 105                 110

Ala Arg Ser Tyr Gly Val Leu Glu Ser Arg Gly Val Ala Tyr Arg
        115                 120                 125

Gly Leu Phe Ile Ile Asp Pro His Gly Met Leu Arg Gln Ile Thr Val
    130                 135                 140

Asn Asp Met Pro Val Gly Arg Ser Val Glu Glu Val Leu Arg Leu Leu
145                 150                 155                 160

Glu Ala Phe Gln Phe Val Glu Lys His Gly Glu Val Cys Pro Ala Asn
                165                 170                 175

Trp Lys Lys Gly Ala Pro Thr Met Lys Pro Glu Pro Lys Ala Ser Val
            180                 185                 190

Glu Gly Tyr Phe Ser Lys Gln
        195

<210> SEQ ID NO 84
<211> LENGTH: 600
<212> TYPE: DNA
<213> ORGANISM: Onchocerca volvulus
<220> FEATURE:
<221> NAME/KEY: CDS
<222> LO

```
                Asn Gln Phe Lys Gly Lys Tyr Val Leu Phe Phe Tyr Pro Leu Asp
                             35                  40                  45 ttc act ttt gtt tgc ccc acg gag ata att gcg ttt tct gat cgt att        192
Phe Thr Phe Val Cys Pro Thr Glu Ile Ile Ala Phe Ser Asp Arg Ile
 50                  55                  60 tcg gaa ttc aaa aaa tta gat gtt gct gtt atg gcg tgt tca act gac        240
Ser Glu Phe Lys Lys Leu Asp Val Ala Val Met Ala Cys Ser Thr Asp
 65                  70                  75                  80 tcg cat ttc tcg cat ctt gca tgg gta aat acc gac cga aaa atg ggt        288
Ser His Phe Ser His Leu Ala Trp Val Asn Thr Asp Arg Lys Met Gly
                 85                  90                  95 gga ctt ggt caa atg aat ata cca att ctt gct gat acc aat cat gca        336
Gly Leu Gly Gln Met Asn Ile Pro Ile Leu Ala Asp Thr Asn His Ala
            100                 105                 110 atc agc aag gca tat ggt gtg ctc aag gaa gat gaa gga att gct tat        384
Ile Ser Lys Ala Tyr Gly Val Leu Lys Glu Asp Glu Gly Ile Ala Tyr
        115                 120                 125 cgt gga tta tca atc att gat tca aaa ggg att ttg cgg cag atc aca        432
Arg Gly Leu Ser Ile Ile Asp Ser Lys Gly Ile Leu Arg Gln Ile Thr
130                 135                 140 gtc aat gat ctt cca gtt ggt cgt tcc gta gac gaa act tta cgt ctg        480
Val Asn Asp Leu Pro Val Gly Arg Ser Val Asp Glu Thr Leu Arg Leu
145                 150                 155                 160 gtt caa gct ttt cag ttt gtc gat aat cat ggt gaa gta tgt ccg gcc        528
Val Gln Ala Phe Gln Phe Val Asp Asn His Gly Glu Val Cys Pro Ala
                165                 170                 175 aac tgg caa cca gga tct gaa acg att aag ccc gaa gtg aaa gaa agc        576
Asn Trp Gln Pro Gly Ser Glu Thr Ile Lys Pro Glu Val Lys Glu Ser
            180                 185                 190 aag gaa tat ttt gga aag cat tga                                        600
Lys Glu Tyr Phe Gly Lys His
        195

<210> SEQ ID NO 85
<211> LENGTH: 199
<212> TYPE: PRT
<213> ORGANISM: Onchocerca volvulus

<400> SEQUENCE: 85

Met Thr Leu Ala Gly Ser Lys Ala Phe Ile Gly Gln Pro Ala Pro Asn
1               5                   10                  15

Phe Lys Thr Thr Ala Val Val Asn Gly Asp Phe Lys Glu Ile Ser Leu
                20                  25                  30

Asn Gln Phe Lys Gly Lys Tyr Val Val Leu Phe Phe Tyr Pro Leu Asp
            35                  40                  45

Phe Thr Phe Val Cys Pro Thr Glu Ile Ile Ala Phe Ser Asp Arg Ile
    50                  55                  60

Ser Glu Phe Lys Lys Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Gln Met Asn Ile Pro Ile Leu Ala Asp Thr Asn His Ala
            100                 105                 110

Ile Ser Lys Ala Tyr Gly Val Leu Lys Glu Asp Glu Gly Ile Ala Tyr
        115                 120                 125

Arg Gly Leu Ser Ile Ile Asp Ser Lys Gly Ile Leu Arg Gln Ile Thr
    130                 135                 140

Val Asn Asp Leu Pro Val Gly Arg Ser Val Asp Glu Thr Leu Arg Leu
```

```
                145                 150                 155                 160
Val Gln Ala Phe Gln Phe Val Asp Asn His Gly Glu Val Cys Pro Ala
                165                 170                 175

Asn Trp Gln Pro Gly Ser Glu Thr Ile Lys Pro Glu Val Lys Glu Ser
                180                 185                 190

Lys Glu Tyr Phe Gly Lys His
            195

<210> SEQ ID NO 86
<211> LENGTH: 582
<212> TYPE: DNA
<213> ORGANISM: Litomosoides sigmodontis
<220> FEATURE:
<221> NAME/KEY: CDS
<222> LOCATION: (1)..(582)

<400> SEQUENCE: 86 atg aca ctt gct gga agc aaa gct ttc att ggt cag cca gcc cct aac      48
Met Thr Leu Ala Gly Ser Lys Ala Phe Ile Gly Gln Pro Ala Pro Asn
1               5                   10                  15 ttc aag aca acc gcg gtt gtg aat ggc gat ttc aag gag att tca ctg      96
Phe Lys Thr Thr Ala Val Val Asn Gly Asp Phe Lys Glu Ile Ser Leu
                20                  25                  30 tgc caa ttc aag ggg aaa tat gtg gtc ctt ttc ttc tac ccg ctt gat     144
Cys Gln Phe Lys Gly Lys Tyr Val Val Leu Phe Phe Tyr Pro Leu Asp
            35                  40                  45 ttc act ttt gtt tgt ccg acg gag ata atc gcg ttt tct gac cgc att     192
Phe Thr Phe Val Cys Pro Thr Glu Ile Ile Ala Phe Ser Asp Arg Ile
        50                  55                  60 gcg gaa ttc aag cag ttg gat gta gcc gtt atg gcg tgc tca act gac     240
Ala Glu Phe Lys Gln Leu Asp Val Ala Val Met Ala Cys Ser Thr Asp
65                  70                  75                  80 tct cac ttc tcg cac ctt gcg tgg gta aat acg gac cgg aag atg ggt     288
Ser His Phe Ser His Leu Ala Trp Val Asn Thr Asp Arg Lys Met Gly
                85                  90                  95 ggc ctc ggt gcg atg aat ata cct ata ctt gct gat acg aat cac acg     336
Gly Leu Gly Ala Met Asn Ile Pro Ile Leu Ala Asp Thr Asn His Thr
                100                 105                 110 atc agc agg gcc tat ggt gtg ctt aag gaa gac gat gga att gct tat     384
Ile Ser Arg Ala Tyr Gly Val Leu Lys Glu Asp Asp Gly Ile Ala Tyr
            115                 120                 125 cgt gga tta ttc atc att gat cca aaa ggc att tta cgg caa atc acg     432
Arg Gly Leu Phe Ile Ile Asp Pro Lys Gly Ile Leu Arg Gln Ile Thr
        130                 135                 140 gtc aat gac ctg cca gtg ggt cgt tct gtc gat gag acg ttg cgt ctg     480
Val Asn Asp Leu Pro Val Gly Arg Ser Val Asp Glu Thr Leu Arg Leu
145                 150                 155                 160 att caa gct ttt cag ttt gtt gat aaa cat ggt gaa tta tgt ccg gcg     528
Ile Gln Ala Phe Gln Phe Val Asp Lys His Gly Glu Leu Cys Pro Ala
                165                 170                 175 aat tgg caa cca ggt tct gaa acg att aag ccc gga gtg aaa gaa agc     576
Asn Trp Gln Pro Gly Ser Glu Thr Ile Lys Pro Gly Val Lys Glu Ser
                180                 185                 190 aaa taa                                                             582
Lys

<210> SEQ ID NO 87
<211> LENGTH: 193
<212> TYPE: PRT
<213> ORGANISM: Litomosoides sigmodontis
```

<400> SEQUENCE: 87

```
Met Thr Leu Ala Gly Ser Lys Ala Phe Ile Gly Gln Pro Ala Pro Asn
1               5                   10                  15

Phe Lys Thr Thr Ala Val Val Asn Gly Asp Phe Lys Glu Ile Ser Leu
            20                  25                  30

Cys Gln Phe Lys Gly Lys Tyr Val Leu Phe Phe Tyr Pro Leu Asp
        35                  40                  45

Phe Thr Phe Val Cys Pro Thr Glu Ile Ile Ala Phe Ser Asp Arg Ile
    50                  55                  60

Ala Glu Phe Lys Gln Leu Asp Val Ala Val Met Ala Cys Ser Thr Asp
65                  70                  75                  80

Ser His Phe Ser His Leu Ala Trp Val Asn Thr Asp Arg Lys Met Gly
                85                  90                  95

Gly Leu Gly Ala Met Asn Ile Pro Ile Leu Ala Asp Thr Asn His Thr
            100                 105                 110

Ile Ser Arg Ala Tyr Gly Val Leu Lys Glu Asp Asp Gly Ile Ala Tyr
        115                 120                 125

Arg Gly Leu Phe Ile Ile Asp Pro Lys Gly Ile Leu Arg Gln Ile Thr
    130                 135                 140

Val Asn Asp Leu Pro Val Gly Arg Ser Val Asp Glu Thr Leu Arg Leu
145                 150                 155                 160

Ile Gln Ala Phe Gln Phe Val Asp Lys His Gly Glu Leu Cys Pro Ala
                165                 170                 175

Asn Trp Gln Pro Gly Ser Glu Thr Ile Lys Pro Gly Val Lys Glu Ser
            180                 185                 190

Lys
```

<210> SEQ ID NO 88
<211> LENGTH: 597
<212> TYPE: DNA
<213> ORGANISM: Branchiostoma belcheri tsingtaunese
<220> FEATURE:
<221> NAME/KEY: CDS
<222> LOCATION: (1)..(597)

<400> SEQUENCE: 88

```
atg tct gct gga aat gcc aag ctc caa cac ccc gct cca aac ttc gag    48
Met Ser Ala Gly Asn Ala Lys Leu Gln His Pro Ala Pro Asn Phe Glu
1               5                   10                  15 agc acg gct gta cta ccc tct ggg gag ttc aag acc ata aaa ctc tcg    96
Ser Thr Ala Val Leu Pro Ser Gly Glu Phe Lys Thr Ile Lys Leu Ser
            20                  25                  30 gac tat aaa gga aag tac ttg gtc atc ttc ttc tac cct ctg gat ttc    144
Asp Tyr Lys Gly Lys Tyr Leu Val Ile Phe Phe Tyr Pro Leu Asp Phe
        35                  40                  45 aca ttt gtg tgc ccg aca gaa atc atc gcc ttc agc gat cgc gtg gag    192
Thr Phe Val Cys Pro Thr Glu Ile Ile Ala Phe Ser Asp Arg Val Glu
    50                  55                  60 gag ttt cgt aag atc aac tgc gag gtg gtg gcg tgt tca aca gac tcc    240
Glu Phe Arg Lys Ile Asn Cys Glu Val Val Ala Cys Ser Thr Asp Ser
65                  70                  75                  80 caa ttc tcc cac ttg gcc tgg acg aac acc ccc aga aag cag ggt gga    288
Gln Phe Ser His Leu Ala Trp Thr Asn Thr Pro Arg Lys Gln Gly Gly
                85                  90                  95 ctg ggc cag atg aag atc cca atc ctg gcc gac aaa gcg atg acc ata    336
Leu Gly Gln Met Lys Ile Pro Ile Leu Ala Asp Lys Ala Met Thr Ile
            100                 105                 110
```

```
tcc cgg gac tac ggc gtg ttg atg gag cct gag ggc atc gcg ttc cgt    384
Ser Arg Asp Tyr Gly Val Leu Met Glu Pro Glu Gly Ile Ala Phe Arg
        115                 120                 125 ggt ttg ttc atc att gac gac aag ggt acc ctg cgc caa atc acg atc    432
Gly Leu Phe Ile Ile Asp Asp Lys Gly Thr Leu Arg Gln Ile Thr Ile
130                 135                 140 aac gac ctg cct gtc ggg cgt tcg gtc gac gag acg ctg cgt ctg gtt    480
Asn Asp Leu Pro Val Gly Arg Ser Val Asp Glu Thr Leu Arg Leu Val
145                 150                 155                 160 cag gcc ttc cag ttc aca gac aaa cac ggg gaa gtg tgt cct gct ggc    528
Gln Ala Phe Gln Phe Thr Asp Lys His Gly Glu Val Cys Pro Ala Gly
                165                 170                 175 tgg aag ccc ggt gca gac acc atc aaa ccc gac gtt aag aac agc aaa    576
Trp Lys Pro Gly Ala Asp Thr Ile Lys Pro Asp Val Lys Asn Ser Lys
            180                 185                 190 gaa tat ttc tcc aag cag taa                                        597
Glu Tyr Phe Ser Lys Gln
        195
```

<210> SEQ ID NO 89
<211> LENGTH: 198
<212> TYPE: PRT
<213> ORGANISM: Branchiostoma belcheri tsingtaunese

<400> SEQUENCE: 89

```
Met Ser Ala Gly Asn Ala Lys Leu Gln His Pro Ala Pro Asn Phe Glu
1               5                   10                  15

Ser Thr Ala Val Leu Pro Ser Gly Glu Phe Lys Thr Ile Lys Leu Ser
            20                  25                  30

Asp Tyr Lys Gly Lys Tyr Leu Val Ile Phe Phe Tyr Pro Leu Asp Phe
        35                  40                  45

Thr Phe Val Cys Pro Thr Glu Ile Ile Ala Phe Ser Asp Arg Val Glu
    50                  55                  60

Glu Phe Arg Lys Ile Asn Cys Glu Val Val Ala Cys Ser Thr Asp Ser
65                  70                  75                  80

Gln Phe Ser His Leu Ala Trp Thr Asn Thr Pro Arg Lys Gln Gly Gly
                85                  90                  95

Leu Gly Gln Met Lys Ile Pro Ile Leu Ala Asp Lys Ala Met Thr Ile
            100                 105                 110

Ser Arg Asp Tyr Gly Val Leu Met Glu Pro Glu Gly Ile Ala Phe Arg
        115                 120                 125

Gly Leu Phe Ile Ile Asp Asp Lys Gly Thr Leu Arg Gln Ile Thr Ile
    130                 135                 140

Asn Asp Leu Pro Val Gly Arg Ser Val Asp Glu Thr Leu Arg Leu Val
145                 150                 155                 160

Gln Ala Phe Gln Phe Thr Asp Lys His Gly Glu Val Cys Pro Ala Gly
                165                 170                 175

Trp Lys Pro Gly Ala Asp Thr Ile Lys Pro Asp Val Lys Asn Ser Lys
            180                 185                 190

Glu Tyr Phe Ser Lys Gln
        195
```

<210> SEQ ID NO 90
<211> LENGTH: 597
<212> TYPE: DNA
<213> ORGANISM: Rhipicephalus sanguineus
<220> FEATURE:
<221> NAME/KEY: CDS
<222> LOCATION: (1)..(597)

```
<400> SEQUENCE: 90 gac atg aca ctt cct cag ttg acc aag ccc gcc cca gac ttc tgc ggt    48
Asp Met Thr Leu Pro Gln Leu Thr Lys Pro Ala Pro Asp Phe Cys Gly
1               5                   10                  15 acc gcc gta gtc gat ggc caa ttc aag gaa atc aag ctg tcg gac tac    96
Thr Ala Val Val Asp Gly Gln Phe Lys Glu Ile Lys Leu Ser Asp Tyr
            20                  25                  30 aag gac aag tac ctg gtc ctc ttc ttc tac ccg ctt gac ttc acc ttt    144
Lys Asp Lys Tyr Leu Val Leu Phe Phe Tyr Pro Leu Asp Phe Thr Phe
        35                  40                  45 gtc tgc ccc acg gag atc atc gca ttc agc gac cgt gct gaa gag ttc    192
Val Cys Pro Thr Glu Ile Ile Ala Phe Ser Asp Arg Ala Glu Glu Phe
    50                  55                  60 cgc aag atc aac tgc gag gtg gtt gcc tgc tcc acc gac agc cac ttc    240
Arg Lys Ile Asn Cys Glu Val Val Ala Cys Ser Thr Asp Ser His Phe
65                  70                  75                  80 tgc cat ctt gca tgg ata aac aca ccc cgc aag gaa ggt ggc ctt ggc    288
Cys His Leu Ala Trp Ile Asn Thr Pro Arg Lys Glu Gly Gly Leu Gly
                85                  90                  95 gag atg aag atc cca ctt ctg gcc gac aag acc agc aag atc gcg aga    336
Glu Met Lys Ile Pro Leu Leu Ala Asp Lys Thr Ser Lys Ile Ala Arg
            100                 105                 110 gcc tac ggg gtc ctg aag gag gac gac ggt gtt cct ttc cgt ggc ctc    384
Ala Tyr Gly Val Leu Lys Glu Asp Asp Gly Val Pro Phe Arg Gly Leu
        115                 120                 125 ttc atc atc gat gac aag ggc ctt ctg cgc cag atc acc atg aac gac    432
Phe Ile Ile Asp Asp Lys Gly Leu Leu Arg Gln Ile Thr Met Asn Asp
    130                 135                 140 ctc ccc gtc ggc cgc tct gtc gat gag acc ctc aga ctt gtc cag gcc    480
Leu Pro Val Gly Arg Ser Val Asp Glu Thr Leu Arg Leu Val Gln Ala
145                 150                 155                 160 ttc cag tac aca gac aag tac gga gaa gtc tgc cca gcc aac tgg aag    528
Phe Gln Tyr Thr Asp Lys Tyr Gly Glu Val Cys Pro Ala Asn Trp Lys
                165                 170                 175 cct ggc gga gac acc atg aag cca gac ccc aag ggt agc aag gcc tac    576
Pro Gly Gly Asp Thr Met Lys Pro Asp Pro Lys Gly Ser Lys Ala Tyr
            180                 185                 190 ttt gca aag agt gat cac tga                                        597
Phe Ala Lys Ser Asp His
        195

<210> SEQ ID NO 91
<211> LENGTH: 198
<212> TYPE: PRT
<213> ORGANISM: Rhipicephalus sanguineus

<400> SEQUENCE: 91

Asp Met Thr Leu Pro Gln Leu Thr Lys Pro Ala Pro Asp Phe Cys Gly
1               5                   10                  15

Thr Ala Val Val Asp Gly Gln Phe Lys Glu Ile Lys Leu Ser Asp Tyr
            20                  25                  30

Lys Asp Lys Tyr Leu Val Leu Phe Phe Tyr Pro Leu Asp Phe Thr Phe
        35                  40                  45

Val Cys Pro Thr Glu Ile Ile Ala Phe Ser Asp Arg Ala Glu Glu Phe
    50                  55                  60

Arg Lys Ile Asn Cys Glu Val Val Ala Cys Ser Thr Asp Ser His Phe
65                  70                  75                  80

Cys His Leu Ala Trp Ile Asn Thr Pro Arg Lys Glu Gly Gly Leu Gly
```

|  |  |  |  |  |  |  |  |  |  |  |  |  |
|---|---|---|---|---|---|---|---|---|---|---|---|---|
|  |  |  | 85 |  |  |  | 90 |  |  |  | 95 |  |

Glu Met Lys Ile Pro Leu Leu Ala Asp Lys Thr Ser Lys Ile Ala Arg
         100               105              110

Ala Tyr Gly Val Leu Lys Glu Asp Gly Val Pro Phe Arg Gly Leu
        115               120              125

Phe Ile Ile Asp Asp Lys Gly Leu Leu Arg Gln Ile Thr Met Asn Asp
         130               135              140

Leu Pro Val Gly Arg Ser Val Asp Glu Thr Leu Arg Leu Val Gln Ala
145              150              155              160

Phe Gln Tyr Thr Asp Lys Tyr Gly Glu Val Cys Pro Ala Asn Trp Lys
         165               170              175

Pro Gly Gly Asp Thr Met Lys Pro Asp Pro Lys Gly Ser Lys Ala Tyr
        180               185              190

Phe Ala Lys Ser Asp His
        195

<210> SEQ ID NO 92
<211> LENGTH: 600
<212> TYPE: DNA
<213> ORGANISM: Leishmania tropica
<220> FEATURE:
<221> NAME/KEY: CDS
<222> LOCATION: (1)..(600)

<400> SEQUENCE: 92

```
atg tcc tgc ggt gaa acc aag atc aac tct ccc gcg ccg ccc ttc gag      48
Met Ser Cys Gly Glu Thr Lys Ile Asn Ser Pro Ala Pro Pro Phe Glu
1               5                   10                  15 gag atg gcg ctc atg ccc aac ggc agc ttc aag aag atc agc ctc tcc      96
Glu Met Ala Leu Met Pro Asn Gly Ser Phe Lys Lys Ile Ser Leu Ser
            20                  25                  30 gcc tac aag ggc aag tgg gtc gtg ctc ttc ttc tac ccg ctc gac ttc     144
Ala Tyr Lys Gly Lys Trp Val Val Leu Phe Phe Tyr Pro Leu Asp Phe
        35                  40                  45 acc ttc gtg tgc ccg aca gag atc atc gcg ttc tcc gac aac gtg agt     192
Thr Phe Val Cys Pro Thr Glu Ile Ile Ala Phe Ser Asp Asn Val Ser
    50                  55                  60 cgc ttc aac gag ctc aac tgc gag gtc ctc gcg tgc tcg atg gac agc     240
Arg Phe Asn Glu Leu Asn Cys Glu Val Leu Ala Cys Ser Met Asp Ser
65                  70                  75                  80 gag tac gcg cac ctg cag tgg acg ctg cag gac cgc aag aag ggc ggc     288
Glu Tyr Ala His Leu Gln Trp Thr Leu Gln Asp Arg Lys Lys Gly Gly
                85                  90                  95 ctc ggg gcc atg gcg atc cca atg ctg gcc gac aag acc aag agc atc     336
Leu Gly Ala Met Ala Ile Pro Met Leu Ala Asp Lys Thr Lys Ser Ile
            100                 105                 110 gct cgt tcc tac ggc gtg ctg gag gag agc cag ggc gtg gcc tac cgc     384
Ala Arg Ser Tyr Gly Val Leu Glu Glu Ser Gln Gly Val Ala Tyr Arg
        115                 120                 125 ggt ctc ttc atc atc gac ccc cat ggc atg gtg cgt cag atc acc gtc     432
Gly Leu Phe Ile Ile Asp Pro His Gly Met Val Arg Gln Ile Thr Val
    130                 135                 140 aac gac atg ccg gtg ggc cgc aac gtg gag gag gtt ctg cgc ctg ctg     480
Asn Asp Met Pro Val Gly Arg Asn Val Glu Glu Val Leu Arg Leu Leu
145                 150                 155                 160 gag gct ttg cag ttc gtg gag aag cac ggc gag gtg tgc ccc gcg aac     528
Glu Ala Leu Gln Phe Val Glu Lys His Gly Glu Val Cys Pro Ala Asn
                165                 170                 175 tgg aag aag ggc gcc ccc acg atg aag ccg gaa ccg aag gcg tct gtc     576
Trp Lys Lys Gly Ala Pro Thr Met Lys Pro Glu Pro Lys Ala Ser Val
```

```
Trp Lys Lys Gly Ala Pro Thr Met Lys Pro Glu Pro Lys Ala Ser Val
            180                 185                 190 gag ggg tac ttc agc aaa cag taa                                    600
Glu Gly Tyr Phe Ser Lys Gln
        195
```

<210> SEQ ID NO 93
<211> LENGTH: 199
<212> TYPE: PRT
<213> ORGANISM: Leishmania tropica

<400> SEQUENCE: 93

```
Met Ser Cys Gly Glu Thr Lys Ile Asn Ser Pro Ala Pro Pro Phe Glu
1               5                   10                  15

Glu Met Ala Leu Met Pro Asn Gly Ser Phe Lys Lys Ile Ser Leu Ser
            20                  25                  30

Ala Tyr Lys Gly Lys Trp Val Val Leu Phe Phe Tyr Pro Leu Asp Phe
        35                  40                  45

Thr Phe Val Cys Pro Thr Glu Ile Ile Ala Phe Ser Asp Asn Val Ser
    50                  55                  60

Arg Phe Asn Glu Leu Asn Cys Glu Val Leu Ala Cys Ser Met Asp Ser
65                  70                  75                  80

Glu Tyr Ala His Leu Gln Trp Thr Leu Gln Asp Arg Lys Lys Gly Gly
                85                  90                  95

Leu Gly Ala Met Ala Ile Pro Met Leu Ala Asp Lys Thr Lys Ser Ile
            100                 105                 110

Ala Arg Ser Tyr Gly Val Leu Glu Glu Ser Gln Gly Val Ala Tyr Arg
        115                 120                 125

Gly Leu Phe Ile Ile Asp Pro His Gly Met Val Arg Gln Ile Thr Val
    130                 135                 140

Asn Asp Met Pro Val Gly Arg Asn Val Glu Glu Val Leu Arg Leu Leu
145                 150                 155                 160

Glu Ala Leu Gln Phe Val Glu Lys His Gly Glu Val Cys Pro Ala Asn
                165                 170                 175

Trp Lys Lys Gly Ala Pro Thr Met Lys Pro Glu Pro Lys Ala Ser Val
            180                 185                 190

Glu Gly Tyr Phe Ser Lys Gln
        195
```

<210> SEQ ID NO 94
<211> LENGTH: 594
<212> TYPE: DNA
<213> ORGANISM: Meloidogyne incognita
<220> FEATURE:
<221> NAME/KEY: CDS
<222> LOCATION: (1)..(594)

<400> SEQUENCE: 94

```
atg atg tct gga caa gca aaa att gga aaa ctt gct cct gaa ttc aca    48
Met Met Ser Gly Gln Ala Lys Ile Gly Lys Leu Ala Pro Glu Phe Thr
1               5                   10                  15 act gat gct gtt gtt gat tct gac ttt aag gct gtt tct ttg tct gac    96
Thr Asp Ala Val Val Asp Ser Asp Phe Lys Ala Val Ser Leu Ser Asp
            20                  25                  30 tac aag ggc aaa tat gtt gtg ctc ttc ttt tat ccg ctt gac ttt act   144
Tyr Lys Gly Lys Tyr Val Val Leu Phe Phe Tyr Pro Leu Asp Phe Thr
        35                  40                  45 ttt gtt tgt ccg act gaa ata att gca ttt tct gag aga aac ggt gac   192
Phe Val Cys Pro Thr Glu Ile Ile Ala Phe Ser Glu Arg Asn Gly Asp
    50                  55                  60
```

```
                    50                  55                  60
ttt acc aaa att aac gtt caa tta ttg gct tgt tct act gac tct aaa       240
Phe Thr Lys Ile Asn Val Gln Leu Leu Ala Cys Ser Thr Asp Ser Lys
 65                  70                  75                  80 ttt agc cat ttt gaa tgg atc aat aag cca cgt aag gag gga gga ctt       288
Phe Ser His Phe Glu Trp Ile Asn Lys Pro Arg Lys Glu Gly Gly Leu
                     85                  90                  95 gga gaa atg aaa att cct gtt ctt tct gat cga aat atg aaa att gct       336
Gly Glu Met Lys Ile Pro Val Leu Ser Asp Arg Asn Met Lys Ile Ala
                100                 105                 110 cgt gat tat gga gtt ctt aaa gag gat gag gga att gcc tat cgt gga       384
Arg Asp Tyr Gly Val Leu Lys Glu Asp Glu Gly Ile Ala Tyr Arg Gly
            115                 120                 125 ttg ttt atc att gat cct aaa gga att ctt cgt caa att act att aat       432
Leu Phe Ile Ile Asp Pro Lys Gly Ile Leu Arg Gln Ile Thr Ile Asn
        130                 135                 140 gac ctt cct gtt gga cgc tct gtt gat gag act ctt cgt ctc gtt caa       480
Asp Leu Pro Val Gly Arg Ser Val Asp Glu Thr Leu Arg Leu Val Gln
145                 150                 155                 160 gct ttt caa tat acg gac aag cat gga gaa gtt tgt cca gct aat tgg       528
Ala Phe Gln Tyr Thr Asp Lys His Gly Glu Val Cys Pro Ala Asn Trp
                165                 170                 175 aag cca gga agt gat act att aaa cca gat cct aac aaa agt aaa gaa       576
Lys Pro Gly Ser Asp Thr Ile Lys Pro Asp Pro Asn Lys Ser Lys Glu
            180                 185                 190 tat ttt ggt aaa caa taa                                               594
Tyr Phe Gly Lys Gln
        195

<210> SEQ ID NO 95
<211> LENGTH: 197
<212> TYPE: PRT
<213> ORGANISM: Meloidogyne incognita

<400> SEQUENCE: 95

Met Met Ser Gly Gln Ala Lys Ile Gly Lys Leu Ala Pro Glu Phe Thr
 1               5                   10                  15

Thr Asp Ala Val Val Asp Ser Asp Phe Lys Ala Val Ser Leu Ser Asp
                20                  25                  30

Tyr Lys Gly Lys Tyr Val Val Leu Phe Phe Tyr Pro Leu Asp Phe Thr
            35                  40                  45

Phe Val Cys Pro Thr Glu Ile Ile Ala Phe Ser Glu Arg Asn Gly Asp
        50                  55                  60

Phe Thr Lys Ile Asn Val Gln Leu Leu Ala Cys Ser Thr Asp Ser Lys
65                  70                  75                  80

Phe Ser His Phe Glu Trp Ile Asn Lys Pro Arg Lys Glu Gly Gly Leu
                85                  90                  95

Gly Glu Met Lys Ile Pro Val Leu Ser Asp Arg Asn Met Lys Ile Ala
            100                 105                 110

Arg Asp Tyr Gly Val Leu Lys Glu Asp Glu Gly Ile Ala Tyr Arg Gly
        115                 120                 125

Leu Phe Ile Ile Asp Pro Lys Gly Ile Leu Arg Gln Ile Thr Ile Asn
    130                 135                 140

Asp Leu Pro Val Gly Arg Ser Val Asp Glu Thr Leu Arg Leu Val Gln
145                 150                 155                 160

Ala Phe Gln Tyr Thr Asp Lys His Gly Glu Val Cys Pro Ala Asn Trp
                165                 170                 175
```

```
Lys Pro Gly Ser Asp Thr Ile Lys Pro Asp Pro Asn Lys Ser Lys Glu
            180                 185                 190

Tyr Phe Gly Lys Gln
        195
```

<210> SEQ ID NO 96
<211> LENGTH: 600
<212> TYPE: DNA
<213> ORGANISM: Globodera rostochiensis
<220> FEATURE:
<221> NAME/KEY: CDS
<222> LOCATION: (1)..(600)

<400> SEQUENCE: 96

```
atg tct tcc aac tca aag gca ttc atc ggt aag cca gca ccc aag ttc        48
Met Ser Ser Asn Ser Lys Ala Phe Ile Gly Lys Pro Ala Pro Lys Phe
1               5                   10                  15 agt gct gat gcg gtg gta aac ggc gac ttc aag aca att tcc ttg gac        96
Ser Ala Asp Ala Val Val Asn Gly Asp Phe Lys Thr Ile Ser Leu Asp
                20                  25                  30 gac tac aag ggg aaa tat gtg gtg cta ttc ttc tac ccg ctc gat ttc       144
Asp Tyr Lys Gly Lys Tyr Val Val Leu Phe Phe Tyr Pro Leu Asp Phe
            35                  40                  45 act ttc gtt tgc cca acc gaa ata att gct ttc tct gac cgt gct gac       192
Thr Phe Val Cys Pro Thr Glu Ile Ile Ala Phe Ser Asp Arg Ala Asp
        50                  55                  60 gaa ttc aag aag atc gac act cag ctt att gcg tgt tca acc gat tcc       240
Glu Phe Lys Lys Ile Asp Thr Gln Leu Ile Ala Cys Ser Thr Asp Ser
65                  70                  75                  80 aaa ttt agt cac ctt gaa tgg atc aac aaa ccg cga aag cat ggc gga       288
Lys Phe Ser His Leu Glu Trp Ile Asn Lys Pro Arg Lys His Gly Gly
                85                  90                  95 ctg ggc gag atg aaa att ccg gta ttg gca gac acc aac cac aaa atc       336
Leu Gly Glu Met Lys Ile Pro Val Leu Ala Asp Thr Asn His Lys Ile
            100                 105                 110 agc cgc gac tac gga gtg ttg atg gaa gaa gct ggc att gct ttt cgt       384
Ser Arg Asp Tyr Gly Val Leu Met Glu Glu Ala Gly Ile Ala Phe Arg
        115                 120                 125 ggg ttg ttc atc att gac gac aaa ggc att ctt cgt cag atc acc atc       432
Gly Leu Phe Ile Ile Asp Asp Lys Gly Ile Leu Arg Gln Ile Thr Ile
    130                 135                 140 aac gat ttg cct gtt ggt cgc tcg gtt gac gag acg ctt cgt ttg gtg       480
Asn Asp Leu Pro Val Gly Arg Ser Val Asp Glu Thr Leu Arg Leu Val
145                 150                 155                 160 caa gcc ttc aag tac act gat aca cat ggc gag gtt tgt ccg gcc aac       528
Gln Ala Phe Lys Tyr Thr Asp Thr His Gly Glu Val Cys Pro Ala Asn
                165                 170                 175 tgg cag cct gga gag gac act atc aag cca gac ccg gag gga agt cag       576
Trp Gln Pro Gly Glu Asp Thr Ile Lys Pro Asp Pro Glu Gly Ser Gln
            180                 185                 190 aca ttt ttc ggc aag aag cgc tga                                       600
Thr Phe Phe Gly Lys Lys Arg
        195
```

<210> SEQ ID NO 97
<211> LENGTH: 199
<212> TYPE: PRT
<213> ORGANISM: Globodera rostochiensis

<400> SEQUENCE: 97

```
Met Ser Ser Asn Ser Lys Ala Phe Ile Gly Lys Pro Ala Pro Lys Phe
1               5                   10                  15
```

```
Ser Ala Asp Ala Val Val Asn Gly Asp Phe Lys Thr Ile Ser Leu Asp
            20                  25                  30

Asp Tyr Lys Gly Lys Tyr Val Leu Phe Phe Tyr Pro Leu Asp Phe
        35                  40                  45

Thr Phe Val Cys Pro Thr Glu Ile Ile Ala Phe Ser Asp Arg Ala Asp
    50                  55                  60

Glu Phe Lys Lys Ile Asp Thr Gln Leu Ile Ala Cys Ser Thr Asp Ser
65                  70                  75                  80

Lys Phe Ser His Leu Glu Trp Ile Asn Lys Pro Arg Lys His Gly Gly
                85                  90                  95

Leu Gly Glu Met Lys Ile Pro Val Leu Ala Asp Thr Asn His Lys Ile
            100                 105                 110

Ser Arg Asp Tyr Gly Val Leu Met Glu Glu Ala Gly Ile Ala Phe Arg
        115                 120                 125

Gly Leu Phe Ile Ile Asp Asp Lys Gly Ile Leu Arg Gln Ile Thr Ile
    130                 135                 140

Asn Asp Leu Pro Val Gly Arg Ser Val Asp Glu Thr Leu Arg Leu Val
145                 150                 155                 160

Gln Ala Phe Lys Tyr Thr Asp Thr His Gly Glu Val Cys Pro Ala Asn
                165                 170                 175

Trp Gln Pro Gly Glu Asp Thr Ile Lys Pro Asp Pro Glu Gly Ser Gln
            180                 185                 190

Thr Phe Phe Gly Lys Lys Arg
            195

<210> SEQ ID NO 98
<211> LENGTH: 600
<212> TYPE: DNA
<213> ORGANISM: Leishmania aethiopica
<220> FEATURE:
<221> NAME/KEY: CDS
<222> LOCATION: (1)..(600)

<400> SEQUENCE: 98 atg tcc tgc ggt gac gcc aag atc aac tct ccc gcg ccg ccc ttc gag      48
Met Ser Cys Gly Asp Ala Lys Ile Asn Ser Pro Ala Pro Pro Phe Glu
1               5                   10                  15 gag gtg gcg ctc atg ccc aac ggc agc ttc aag aag atc agc ctc tcc      96
Glu Val Ala Leu Met Pro Asn Gly Ser Phe Lys Lys Ile Ser Leu Ser
            20                  25                  30 gcc tac aag ggc aag tgg gtc gtg ctc ttc ttc tac ccg ctc gac ttc     144
Ala Tyr Lys Gly Lys Trp Val Val Leu Phe Phe Tyr Pro Leu Asp Phe
        35                  40                  45 acc ttc gtg tgc ccg aca gag atc atc gcg ttc tcc gac agc gtg agt     192
Thr Phe Val Cys Pro Thr Glu Ile Ile Ala Phe Ser Asp Ser Val Ser
    50                  55                  60 cgc ttc aac gag ctc aac tgc gag gtc ctc gcg tgc tcg atg gac agc     240
Arg Phe Asn Glu Leu Asn Cys Glu Val Leu Ala Cys Ser Met Asp Ser
65                  70                  75                  80 gag tac gcg cac ctg cag tgg acg ctg cag gac cgc cag aag ggc ggc     288
Glu Tyr Ala His Leu Gln Trp Thr Leu Gln Asp Arg Gln Lys Gly Gly
                85                  90                  95 ctc ggg gcc atg gcg atc cca atg ctg gcc gac aag acc aag tgc atc     336
Leu Gly Ala Met Ala Ile Pro Met Leu Ala Asp Lys Thr Lys Cys Ile
            100                 105                 110 gct cgt tcc tac ggc gtg ctg gag gag agc cag ggc gtg gcc tac cgc     384
Ala Arg Ser Tyr Gly Val Leu Glu Glu Ser Gln Gly Val Ala Tyr Arg
        115                 120                 125
```

```
ggt ctc ttc atc atc gac ccc cat ggc atg gtg cgt cag atc acc gtc      432
Gly Leu Phe Ile Ile Asp Pro His Gly Met Val Arg Gln Ile Thr Val
    130                 135                 140 aac gac atg ccg gtg ggc cgc agc gtg gag gag gtt ctg cgc ctg ctg      480
Asn Asp Met Pro Val Gly Arg Ser Val Glu Glu Val Leu Arg Leu Leu
145                 150                 155                 160 gag gct ttt cag ttc gtg gag aag cac ggc gag gtg tgc ccc gcg aac      528
Glu Ala Phe Gln Phe Val Glu Lys His Gly Glu Val Cys Pro Ala Asn
                165                 170                 175 tgg aag aag ggc gcc ccc acg atg aag ccg gaa ccg aag gcg tct gtc      576
Trp Lys Lys Gly Ala Pro Thr Met Lys Pro Glu Pro Lys Ala Ser Val
            180                 185                 190 gag ggg tac ttc agc aaa cag taa                                      600
Glu Gly Tyr Phe Ser Lys Gln
            195
```

<210> SEQ ID NO 99
<211> LENGTH: 199
<212> TYPE: PRT
<213> ORGANISM: Leishmania aethiopica

<400> SEQUENCE: 99

```
Met Ser Cys Gly Asp Ala Lys Ile Asn Ser Pro Ala Pro Pro Phe Glu
1               5                   10                  15

Glu Val Ala Leu Met Pro Asn Gly Ser Phe Lys Lys Ile Ser Leu Ser
            20                  25                  30

Ala Tyr Lys Gly Lys Trp Val Val Leu Phe Phe Tyr Pro Leu Asp Phe
        35                  40                  45

Thr Phe Val Cys Pro Thr Glu Ile Ile Ala Phe Ser Asp Ser Val Ser
    50                  55                  60

Arg Phe Asn Glu Leu Asn Cys Glu Val Leu Ala Cys Ser Met Asp Ser
65                  70                  75                  80

Glu Tyr Ala His Leu Gln Trp Thr Leu Gln Asp Arg Gln Lys Gly Gly
                85                  90                  95

Leu Gly Ala Met Ala Ile Pro Met Leu Ala Asp Lys Thr Lys Cys Ile
            100                 105                 110

Ala Arg Ser Tyr Gly Val Leu Glu Glu Ser Gln Gly Val Ala Tyr Arg
        115                 120                 125

Gly Leu Phe Ile Ile Asp Pro His Gly Met Val Arg Gln Ile Thr Val
    130                 135                 140

Asn Asp Met Pro Val Gly Arg Ser Val Glu Glu Val Leu Arg Leu Leu
145                 150                 155                 160

Glu Ala Phe Gln Phe Val Glu Lys His Gly Glu Val Cys Pro Ala Asn
                165                 170                 175

Trp Lys Lys Gly Ala Pro Thr Met Lys Pro Glu Pro Lys Ala Ser Val
            180                 185                 190

Glu Gly Tyr Phe Ser Lys Gln
            195
```

<210> SEQ ID NO 100
<211> LENGTH: 583
<212> TYPE: DNA
<213> ORGANISM: Ostertagia ostertagi
<220> FEATURE:
<221> NAME/KEY: CDS
<222> LOCATION: (2)..(583)

<400> SEQUENCE: 100

```
g gct ttt atc gga aaa ccc gca ccc gac ttc gcc aca aag gcc gtc tat      49
  Ala Phe Ile Gly Lys Pro Ala Pro Asp Phe Ala Thr Lys Ala Val Tyr
  1               5                   10                  15 aat ggc gac ttc atc gac gtg aaa ctg tct gac tac aag ggc aag tac        97
Asn Gly Asp Phe Ile Asp Val Lys Leu Ser Asp Tyr Lys Gly Lys Tyr
                20                  25                  30 acc gtc ctc ttc ttc tat cca ctg gat ttc acg ttt gtc tgt cct acg       145
Thr Val Leu Phe Phe Tyr Pro Leu Asp Phe Thr Phe Val Cys Pro Thr
                35                  40                  45 gaa atc atc gcc ttt tcc gac cgt gtc gaa gaa ttc aaa aaa atc gat       193
Glu Ile Ile Ala Phe Ser Asp Arg Val Glu Glu Phe Lys Lys Ile Asp
        50                  55                  60 gct gcg gtc ctc gct tgt tca amt gat tcc gtt ttc tct cat ctg gcg       241
Ala Ala Val Leu Ala Cys Ser Xaa Asp Ser Val Phe Ser His Leu Ala
65                  70                  75                  80 tgg atc aat act cct cgc aag atg ggc ggc ctt ggt gac atg aac att       289
Trp Ile Asn Thr Pro Arg Lys Met Gly Gly Leu Gly Asp Met Asn Ile
                85                  90                  95 ccc gtt ctt gct gac acc aac cac caa att gca aag gac tat ggt gta       337
Pro Val Leu Ala Asp Thr Asn His Gln Ile Ala Lys Asp Tyr Gly Val
                100                 105                 110 ctg aaa gaa gac gaa gga atc gct tac aga ggt ctt ttc att att gac       385
Leu Lys Glu Asp Glu Gly Ile Ala Tyr Arg Gly Leu Phe Ile Ile Asp
            115                 120                 125 cct aag gga att ctg cga cag atc act gtc aat gac ctt cct gtc ggt       433
Pro Lys Gly Ile Leu Arg Gln Ile Thr Val Asn Asp Leu Pro Val Gly
        130                 135                 140 cgc tct gtg gat gag act ctc cgt ctg gtg cag gcc ttc caa tac gtt       481
Arg Ser Val Asp Glu Thr Leu Arg Leu Val Gln Ala Phe Gln Tyr Val
145                 150                 155                 160 gac aag cat ggt gag gtg tgc cca gct ggt tgg act cct gga aaa gct       529
Asp Lys His Gly Glu Val Cys Pro Ala Gly Trp Thr Pro Gly Lys Ala
                165                 170                 175 acc atc aag cca ggt gtc aag gac agc aag gag tac ttc agc aaa gca       577
Thr Ile Lys Pro Gly Val Lys Asp Ser Lys Glu Tyr Phe Ser Lys Ala
                180                 185                 190 aac taa                                                                583
Asn

<210> SEQ ID NO 101
<211> LENGTH: 193
<212> TYPE: PRT
<213> ORGANISM: Ostertagia ostertagi
<220> FEATURE:
<221> NAME/KEY: misc_feature
<222> LOCATION: (72)..(72)
<223> OTHER INFORMATION: The 'Xaa' at location 72 stands for Asn, or
      Thr.

<400> SEQUENCE: 101

Ala Phe Ile Gly Lys Pro Ala Pro Asp Phe Ala Thr Lys Ala Val Tyr
1               5                   10                  15

Asn Gly Asp Phe Ile Asp Val Lys Leu Ser Asp Tyr Lys Gly Lys Tyr
                20                  25                  30

Thr Val Leu Phe Phe Tyr Pro Leu Asp Phe Thr Phe Val Cys Pro Thr
                35                  40                  45

Glu Ile Ile Ala Phe Ser Asp Arg Val Glu Glu Phe Lys Lys Ile Asp
        50                  55                  60

Ala Ala Val Leu Ala Cys Ser Xaa Asp Ser Val Phe Ser His Leu Ala
65                  70                  75                  80
```

```
Trp Ile Asn Thr Pro Arg Lys Met Gly Gly Leu Gly Asp Met Asn Ile
                 85                  90                  95

Pro Val Leu Ala Asp Thr Asn His Gln Ile Ala Lys Tyr Gly Val
            100                 105                 110

Leu Lys Glu Asp Glu Gly Ile Ala Tyr Arg Gly Leu Phe Ile Ile Asp
        115                 120                 125

Pro Lys Gly Ile Leu Arg Gln Ile Thr Val Asn Asp Leu Pro Val Gly
    130                 135                 140

Arg Ser Val Asp Glu Thr Leu Arg Leu Val Gln Ala Phe Gln Tyr Val
145                 150                 155                 160

Asp Lys His Gly Glu Val Cys Pro Ala Gly Trp Thr Pro Gly Lys Ala
                165                 170                 175

Thr Ile Lys Pro Gly Val Lys Asp Ser Lys Glu Tyr Phe Ser Lys Ala
            180                 185                 190

Asn

<210> SEQ ID NO 102
<211> LENGTH: 702
<212> TYPE: DNA
<213> ORGANISM: Ixodes scapularis
<220> FEATURE:
<221> NAME/KEY: CDS
<222> LOCATION: (1)..(702)

<400> SEQUENCE: 102 atg gct cgt ctc ctc gca tcg gcg ttc cga ttg gga gtt tca cgt gct      48
Met Ala Arg Leu Leu Ala Ser Ala Phe Arg Leu Gly Val Ser Arg Ala
1               5                   10                  15 tgc gtg caa ctt ccg agc gac gcc ggc att tcc tcc aag cgc ctg ttc      96
Cys Val Gln Leu Pro Ser Asp Ala Gly Ile Ser Ser Lys Arg Leu Phe
            20                  25                  30 cac gtc gct ccg agg ctc ctg ggt ccc gaa gtt ctt aag cct gcg ccg     144
His Val Ala Pro Arg Leu Leu Gly Pro Glu Val Leu Lys Pro Ala Pro
        35                  40                  45 gcg ttc aaa ggt aaa gcc gtc gta gac ggt cag ttc aag gac ata tct     192
Ala Phe Lys Gly Lys Ala Val Val Asp Gly Gln Phe Lys Asp Ile Ser
    50                  55                  60 ctg gcc gat tac aaa ggc aaa tac ctc gtg ctc ttc ttc tac ccg ctt     240
Leu Ala Asp Tyr Lys Gly Lys Tyr Leu Val Leu Phe Phe Tyr Pro Leu
65                  70                  75                  80 gac ttc acc ttc gtg tgc ccg acg gag atc atc gcg ttc agc gat cgc     288
Asp Phe Thr Phe Val Cys Pro Thr Glu Ile Ile Ala Phe Ser Asp Arg
                85                  90                  95 gcc gac gag ttc cgc aag atc aac acc gag ctg gtc gcc gtc tcc gtc     336
Ala Asp Glu Phe Arg Lys Ile Asn Thr Glu Leu Val Ala Val Ser Val
            100                 105                 110 gac tcg cac ttc tcc cac ctc gcc tgg acc aac acc ccc cgc aag caa     384
Asp Ser His Phe Ser His Leu Ala Trp Thr Asn Thr Pro Arg Lys Gln
        115                 120                 125 ggc ggg ctg ggc aag atg aac att ccg ctc ctc tcg gac ttc aac aag     432
Gly Gly Leu Gly Lys Met Asn Ile Pro Leu Leu Ser Asp Phe Asn Lys
    130                 135                 140 cag att gcc cgg gac tac ggt gtg ctg ttg gaa gac gcc ggc ctg gcg     480
Gln Ile Ala Arg Asp Tyr Gly Val Leu Leu Glu Asp Ala Gly Leu Ala
145                 150                 155                 160 ctc cgc ggg ctg ttt atc atc gac ccc aag gga gtc gtc cga caa atc     528
Leu Arg Gly Leu Phe Ile Ile Asp Pro Lys Gly Val Val Arg Gln Ile
                165                 170                 175 acc gtc aac gac ttg ccc gtc gga aga tcg gtg gac gaa acg ctg agg     576
Thr Val Asn Asp Leu Pro Val Gly Arg Ser Val Asp Glu Thr Leu Arg
```

```
Thr Val Asn Asp Leu Pro Val Gly Arg Ser Val Asp Glu Thr Leu Arg
            180                 185                 190 ctt gtc aag gcg ttt cag ttt gtg gag aag cac ggc gaa gtg tgc ccg       624
Leu Val Lys Ala Phe Gln Phe Val Glu Lys His Gly Glu Val Cys Pro
        195                 200                 205 gcc ggc tgg cag ccg gac tcc ccc acg atc aag ccg gac ccg aag aac       672
Ala Gly Trp Gln Pro Asp Ser Pro Thr Ile Lys Pro Asp Pro Lys Asn
210                 215                 220 tcg cag gag tac ttc agc aaa gtc aac tga                               702
Ser Gln Glu Tyr Phe Ser Lys Val Asn
225                 230
```

<210> SEQ ID NO 103
<211> LENGTH: 233
<212> TYPE: PRT
<213> ORGANISM: Ixodes scapularis

<400> SEQUENCE: 103

```
Met Ala Arg Leu Leu Ala Ser Ala Phe Arg Leu Gly Val Ser Arg Ala
1               5                   10                  15

Cys Val Gln Leu Pro Ser Asp Ala Gly Ile Ser Ser Lys Arg Leu Phe
            20                  25                  30

His Val Ala Pro Arg Leu Leu Gly Pro Glu Val Leu Lys Pro Ala Pro
        35                  40                  45

Ala Phe Lys Gly Lys Ala Val Val Asp Gly Gln Phe Lys Asp Ile Ser
    50                  55                  60

Leu Ala Asp Tyr Lys Gly Lys Tyr Leu Val Leu Phe Phe Tyr Pro Leu
65                  70                  75                  80

Asp Phe Thr Phe Val Cys Pro Thr Glu Ile Ile Ala Phe Ser Asp Arg
                85                  90                  95

Ala Asp Glu Phe Arg Lys Ile Asn Thr Glu Leu Val Ala Val Ser Val
            100                 105                 110

Asp Ser His Phe Ser His Leu Ala Trp Thr Asn Thr Pro Arg Lys Gln
        115                 120                 125

Gly Gly Leu Gly Lys Met Asn Ile Pro Leu Leu Ser Asp Phe Asn Lys
    130                 135                 140

Gln Ile Ala Arg Asp Tyr Gly Val Leu Leu Glu Asp Ala Gly Leu Ala
145                 150                 155                 160

Leu Arg Gly Leu Phe Ile Ile Asp Pro Lys Gly Val Val Arg Gln Ile
                165                 170                 175

Thr Val Asn Asp Leu Pro Val Gly Arg Ser Val Asp Glu Thr Leu Arg
            180                 185                 190

Leu Val Lys Ala Phe Gln Phe Val Glu Lys His Gly Glu Val Cys Pro
        195                 200                 205

Ala Gly Trp Gln Pro Asp Ser Pro Thr Ile Lys Pro Asp Pro Lys Asn
    210                 215                 220

Ser Gln Glu Tyr Phe Ser Lys Val Asn
225                 230
```

<210> SEQ ID NO 104
<211> LENGTH: 63
<212> TYPE: DNA
<213> ORGANISM: Artificial
<220> FEATURE:
<223> OTHER INFORMATION: FhHDM-1 C-terminal sequence 2
<220> FEATURE:
<221> NAME/KEY: CDS
<222> LOCATION: (1)..(63)

-continued

```
<400> SEQUENCE: 104 cta gga gaa aag atc act gaa gtg atc acg atc tta ctg aat cgg ctc      48
Leu Gly Glu Lys Ile Thr Glu Val Ile Thr Ile Leu Leu Asn Arg Leu
1               5                   10                  15 acc gat cgc ttg gag                                                  63
Thr Asp Arg Leu Glu
            20

<210> SEQ ID NO 105
<211> LENGTH: 21
<212> TYPE: PRT
<213> ORGANISM: Artificial
<220> FEATURE:
<223> OTHER INFORMATION: Synthetic Construct

<400> SEQUENCE: 105

Leu Gly Glu Lys Ile Thr Glu Val Ile Thr Ile Leu Leu Asn Arg Leu
1               5                   10                  15

Thr Asp Arg Leu Glu
            20

<210> SEQ ID NO 106
<211> LENGTH: 63
<212> TYPE: DNA
<213> ORGANISM: Artificial
<220> FEATURE:
<223> OTHER INFORMATION: OvHDM-1 C-terminal sequence 2
<220> FEATURE:
<221> NAME/KEY: CDS
<222> LOCATION: (1)..(63)

<400> SEQUENCE: 106 ctc ggc gag aaa tta gct gat gtc att aaa atc ctg gcc gag cgc cta      48
Leu Gly Glu Lys Leu Ala Asp Val Ile Lys Ile Leu Ala Glu Arg Leu
1               5                   10                  15 acc aaa cgg atg gag                                                  63
Thr Lys Arg Met Glu
            20

<210> SEQ ID NO 107
<211> LENGTH: 21
<212> TYPE: PRT
<213> ORGANISM: Artificial
<220> FEATURE:
<223> OTHER INFORMATION: Synthetic Construct

<400> SEQUENCE: 107

Leu Gly Glu Lys Leu Ala Asp Val Ile Lys Ile Leu Ala Glu Arg Leu
1               5                   10                  15

Thr Lys Arg Met Glu
            20

<210> SEQ ID NO 108
<211> LENGTH: 63
<212> TYPE: DNA
<213> ORGANISM: Artificial
<220> FEATURE:
<223> OTHER INFORMATION: PwHDM-1 C-terminal sequence 2
<220> FEATURE:
<221> NAME/KEY: CDS
<222> LOCATION: (1)..(63)

<400> SEQUENCE: 108 ctc gga gac aag ata tcg gaa gtg att caa atc tta ctg aaa aga cta      48
Leu Gly Asp Lys Ile Ser Glu Val Ile Gln Ile Leu Leu Lys Arg Leu
1               5                   10                  15
```

```
act gac cga att gag                                              63
Thr Asp Arg Ile Glu
         20

<210> SEQ ID NO 109
<211> LENGTH: 21
<212> TYPE: PRT
<213> ORGANISM: Artificial
<220> FEATURE:
<223> OTHER INFORMATION: Synthetic Construct

<400> SEQUENCE: 109

Leu Gly Asp Lys Ile Ser Glu Val Ile Gln Ile Leu Leu Lys Arg Leu
1               5                  10                  15

Thr Asp Arg Ile Glu
         20

<210> SEQ ID NO 110
<211> LENGTH: 63
<212> TYPE: DNA
<213> ORGANISM: Artificial
<220> FEATURE:
<223> OTHER INFORMATION: SjHDM-1 C-terminal sequence 2
<220> FEATURE:
<221> NAME/KEY: CDS
<222> LOCATION: (1)..(63)

<400> SEQUENCE: 110 tta ggc gag aaa ata gca gag gtt cta ctt att ttt ctt caa cgt ttg    48
Leu Gly Glu Lys Ile Ala Glu Val Leu Leu Ile Phe Leu Gln Arg Leu
1               5                  10                  15 aat aga cgt cta gaa                                              63
Asn Arg Arg Leu Glu
         20

<210> SEQ ID NO 111
<211> LENGTH: 21
<212> TYPE: PRT
<213> ORGANISM: Artificial
<220> FEATURE:
<223> OTHER INFORMATION: Synthetic Construct

<400> SEQUENCE: 111

Leu Gly Glu Lys Ile Ala Glu Val Leu Leu Ile Phe Leu Gln Arg Leu
1               5                  10                  15

Asn Arg Arg Leu Glu
         20

<210> SEQ ID NO 112
<211> LENGTH: 63
<212> TYPE: DNA
<213> ORGANISM: Artificial
<220> FEATURE:
<223> OTHER INFORMATION: SjHDM-2 C-terminal sequence 2
<220> FEATURE:
<221> NAME/KEY: CDS
<222> LOCATION: (1)..(63)

<400> SEQUENCE: 112 tta gga gag aaa ata gca gag gtt cta ctt att ttt ctt caa cgt ttg    48
Leu Gly Glu Lys Ile Ala Glu Val Leu Leu Ile Phe Leu Gln Arg Leu
1               5                  10                  15 aat aga cgt cta gaa                                              63
Asn Arg Arg Leu Glu
         20
```

<210> SEQ ID NO 113
<211> LENGTH: 21
<212> TYPE: PRT
<213> ORGANISM: Artificial
<220> FEATURE:
<223> OTHER INFORMATION: Synthetic Construct

<400> SEQUENCE: 113

Leu Gly Glu Lys Ile Ala Glu Val Leu Leu Ile Phe Leu Gln Arg Leu
1               5                   10                  15

Asn Arg Arg Leu Glu
            20

<210> SEQ ID NO 114
<211> LENGTH: 63
<212> TYPE: DNA
<213> ORGANISM: Artificial
<220> FEATURE:
<223> OTHER INFORMATION: SjHDM-3 C-terminal sequence 2
<220> FEATURE:
<221> NAME/KEY: CDS
<222> LOCATION: (1)..(63)

<400> SEQUENCE: 114 tta ggc gag aag tta gca gag gtt cta ctt att ctt ctt caa cgt ttg      48
Leu Gly Glu Lys Leu Ala Glu Val Leu Leu Ile Leu Leu Gln Arg Leu
1               5                   10                  15 aat aga cgt cta gaa                                                  63
Asn Arg Arg Leu Glu
            20

<210> SEQ ID NO 115
<211> LENGTH: 21
<212> TYPE: PRT
<213> ORGANISM: Artificial
<220> FEATURE:
<223> OTHER INFORMATION: Synthetic Construct

<400> SEQUENCE: 115

Leu Gly Glu Lys Leu Ala Glu Val Leu Leu Ile Leu Leu Gln Arg Leu
1               5                   10                  15

Asn Arg Arg Leu Glu
            20

<210> SEQ ID NO 116
<211> LENGTH: 63
<212> TYPE: DNA
<213> ORGANISM: Artificial
<220> FEATURE:
<223> OTHER INFORMATION: SmHDM-1 C-terminal sequence 2
<220> FEATURE:
<221> NAME/KEY: CDS
<222> LOCATION: (1)..(63)

<400> SEQUENCE: 116 cta ggt gag aaa ata gca gac gtt tta gtt gtt tta ctt aaa cgt ttg      48
Leu Gly Glu Lys Ile Ala Asp Val Leu Val Val Leu Leu Lys Arg Leu
1               5                   10                  15 aat aaa cgc cta gaa                                                  63
Asn Lys Arg Leu Glu
            20

<210> SEQ ID NO 117
<211> LENGTH: 21
<212> TYPE: PRT
<213> ORGANISM: Artificial

```
<220> FEATURE:
<223> OTHER INFORMATION: Synthetic Construct

<400> SEQUENCE: 117

Leu Gly Glu Lys Ile Ala Asp Val Leu Val Val Leu Leu Lys Arg Leu
1               5                   10                  15

Asn Lys Arg Leu Glu
            20

<210> SEQ ID NO 118
<211> LENGTH: 63
<212> TYPE: DNA
<213> ORGANISM: Artificial
<220> FEATURE:
<223> OTHER INFORMATION: SmHDM-2 C-terminal sequence 2
<220> FEATURE:
<221> NAME/KEY: CDS
<222> LOCATION: (1)..(63)

<400> SEQUENCE: 118 tta ggt gaa aaa tta gcc gct gtt gta agc atc tat gtt aag cgt tta      48
Leu Gly Glu Lys Leu Ala Ala Val Val Ser Ile Tyr Val Lys Arg Leu
1               5                   10                  15 aac aag cgt tta gat                                                  63
Asn Lys Arg Leu Asp
            20

<210> SEQ ID NO 119
<211> LENGTH: 21
<212> TYPE: PRT
<213> ORGANISM: Artificial
<220> FEATURE:
<223> OTHER INFORMATION: Synthetic Construct

<400> SEQUENCE: 119

Leu Gly Glu Lys Leu Ala Ala Val Val Ser Ile Tyr Val Lys Arg Leu
1               5                   10                  15

Asn Lys Arg Leu Asp
            20

<210> SEQ ID NO 120
<211> LENGTH: 63
<212> TYPE: DNA
<213> ORGANISM: Artificial
<220> FEATURE:
<223> OTHER INFORMATION: Consensus   C-terminal sequence 2
<220> FEATURE:
<221> NAME/KEY: CDS
<222> LOCATION: (1)..(63)

<400> SEQUENCE: 120 ctg ggc gag aag atc gcc gag gtg gtg aag atc ctg ctg gag aga ctg      48
Leu Gly Glu Lys Ile Ala Glu Val Val Lys Ile Leu Leu Glu Arg Leu
1               5                   10                  15 acc aga aga ctg gag                                                  63
Thr Arg Arg Leu Glu
            20

<210> SEQ ID NO 121
<211> LENGTH: 21
<212> TYPE: PRT
<213> ORGANISM: Artificial
<220> FEATURE:
<223> OTHER INFORMATION: Synthetic Construct

<400> SEQUENCE: 121
```

Leu Gly Glu Lys Ile Ala Glu Val Val Lys Ile Leu Leu Glu Arg Leu
1               5                   10                  15

Thr Arg Arg Leu Glu
            20

<210> SEQ ID NO 122
<211> LENGTH: 27
<212> TYPE: PRT
<213> ORGANISM: Artificial
<220> FEATURE:
<223> OTHER INFORMATION: FhHDM-1 peptide 2

<400> SEQUENCE: 122

Asn Leu Gly Glu Lys Ile Thr Glu Val Ile Thr Ile Leu Leu Asn Arg
1               5                   10                  15

Leu Thr Asp Arg Leu Glu Lys Tyr Ala Gly Asn
            20                  25

<210> SEQ ID NO 123
<211> LENGTH: 27
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Y or F
<220> FEATURE:
<221> NAME/KEY: MISC_FEATURE
<222> LOCATION: (2)..(2)
<223> OTHER INFORMATION: Xaa = L or F
<220> FEATURE:
<221> NAME/KEY: MISC_FEATURE
<222> LOCATION: (3)..(3)
<223> OTHER INFORMATION: Xaa = A, E, K or R
<220> FEATURE:
<221> NAME/KEY: MISC_FEATURE
<222> LOCATION: (4)..(4)
<223> OTHER INFORMATION: Xaa = Q, K or E
<220> FEATURE:
<221> NAME/KEY: MISC_FEATURE
<222> LOCATION: (6)..(6)
<223> OTHER INFORMATION: Xaa = G, N or D
<220> FEATURE:
<221> NAME/KEY: MISC_FEATURE
<222> LOCATION: (8)..(8)
<223> OTHER INFORMATION: Xaa = G or D
<220> FEATURE:
<221> NAME/KEY: MISC_FEATURE
<222> LOCATION: (9)..(9)
<223> OTHER INFORMATION: Xaa = E, D or K
<220> FEATURE:
<221> NAME/KEY: MISC_FEATURE
<222> LOCATION: (11)..(11)
<223> OTHER INFORMATION: Xaa = L, I or M
<220> FEATURE:
<221> NAME/KEY: MISC_FEATURE
<222> LOCATION: (12)..(12)
<223> OTHER INFORMATION: Xaa = A, S, T or L
<220> FEATURE:
<221> NAME/KEY: MISC_FEATURE
<222> LOCATION: (13)..(13)
<223> OTHER INFORMATION: Xaa = E, D or A
<220> FEATURE:
<221> NAME/KEY: MISC_FEATURE
<222> LOCATION: (14)..(14)
<223> OTHER INFORMATION: Xaa = V or I
<220> FEATURE:
<221> NAME/KEY: MISC_FEATURE
<222> LOCATION: (15)..(15)
<223> OTHER INFORMATION: Xaa = I, L, V or A
<220> FEATURE:
<221> NAME/KEY: MISC_FEATURE -continued

```
<222> LOCATION: (16)..(16)
<223> OTHER INFORMATION: Xaa = K, Q, N, S, T, L or V
<220> FEATURE:
<221> NAME/KEY: MISC_FEATURE
<222> LOCATION: (17)..(17)
<223> OTHER INFORMATION: Xaa = I or V
<220> FEATURE:
<221> NAME/KEY: MISC_FEATURE
<222> LOCATION: (18)..(18)
<223> OTHER INFORMATION: Xaa = Y, F or L
<220> FEATURE:
<221> NAME/KEY: MISC_FEATURE
<222> LOCATION: (19)..(19)
<223> OTHER INFORMATION: Xaa = A, S, L or V
<220> FEATURE:
<221> NAME/KEY: MISC_FEATURE
<222> LOCATION: (20)..(20)
<223> OTHER INFORMATION: Xaa = E, K, Q or N
<220> FEATURE:
<221> NAME/KEY: MISC_FEATURE
<222> LOCATION: (21)..(21)
<223> OTHER INFORMATION: Xaa = R or P
<220> FEATURE:
<221> NAME/KEY: MISC_FEATURE
<222> LOCATION: (23)..(23)
<223> OTHER INFORMATION: Xaa = T, P, N or E
<220> FEATURE:
<221> NAME/KEY: MISC_FEATURE
<222> LOCATION: (24)..(24)
<223> OTHER INFORMATION: Xaa = K, R or D
<220> FEATURE:
<221> NAME/KEY: MISC_FEATURE
<222> LOCATION: (26)..(26)
<223> OTHER INFORMATION: Xaa = M, I or L
<220> FEATURE:
<221> NAME/KEY: MISC_FEATURE
<222> LOCATION: (27)..(27)
<223> OTHER INFORMATION: Xaa = E or D

<400> SEQUENCE: 123

Xaa Xaa Xaa Xaa Asp Xaa Leu Xaa Xaa Lys Xaa Xaa Xaa Xaa Xaa Xaa
1               5                   10                  15

Xaa Xaa Xaa Xaa Xaa Leu Xaa Xaa Arg Xaa Xaa
            20                  25

<210> SEQ ID NO 124
<211> LENGTH: 4
<212> TYPE: PRT
<213> ORGANISM: Artificial
<220> FEATURE:
<223> OTHER INFORMATION: proteinaceous moiety
<220> FEATURE:
<221> NAME/KEY: MISC_FEATURE
<222> LOCATION: (1)..(1)
<223> OTHER INFORMATION: Xaa = T, A, K, N or M
<220> FEATURE:
<221> NAME/KEY: MISC_FEATURE
<222> LOCATION: (2)..(2)
<223> OTHER INFORMATION: Xaa = Y, C or R
<220> FEATURE:
<221> NAME/KEY: MISC_FEATURE
<222> LOCATION: (3)..(3)
<223> OTHER INFORMATION: Xaa = V, L or A
<220> FEATURE:
<221> NAME/KEY: MISC_FEATURE
<222> LOCATION: (4)..(4)
<223> OTHER INFORMATION: Xaa = G, S, P, E, K or L

<400> SEQUENCE: 124

Xaa Xaa Xaa Xaa
1

<210> SEQ ID NO 125
<211> LENGTH: 68
```

```
<212> TYPE: PRT
<213> ORGANISM: Fasciola hepatica

<400> SEQUENCE: 125

Ser Glu Glu Ser Arg Glu Lys Leu Arg Glu Ser Gly Arg Lys Met Val
1               5                   10                  15

Lys Ala Leu Arg Asp Ala Val Thr Lys Ala Tyr Glu Lys Ala Arg Asp
            20                  25                  30

Arg Ala Met Ala Tyr Leu Ala Lys Asp Asn Leu Gly Glu Lys Ile Thr
        35                  40                  45

Glu Val Ile Thr Ile Leu Leu Asn Arg Leu Thr Asp Arg Leu Glu Lys
    50                  55                  60

Tyr Ala Gly Asn
65

<210> SEQ ID NO 126
<211> LENGTH: 204
<212> TYPE: DNA
<213> ORGANISM: Fasciola hepatica
<220> FEATURE:
<221> NAME/KEY: CDS
<222> LOCATION: (1)..(204)

<400> SEQUENCE: 126 agc gag gaa agc cgg gaa aaa ttg cgt gaa agc gga agg aaa atg gtg      48
Ser Glu Glu Ser Arg Glu Lys Leu Arg Glu Ser Gly Arg Lys Met Val
1               5                   10                  15 aaa gcc ctc agg gat gcc gtg acg aag gca tac gag aag gca cgt gac      96
Lys Ala Leu Arg Asp Ala Val Thr Lys Ala Tyr Glu Lys Ala Arg Asp
            20                  25                  30 cga gct atg gct tac ttg gcg aag gac aat cta gga gaa aag atc act     144
Arg Ala Met Ala Tyr Leu Ala Lys Asp Asn Leu Gly Glu Lys Ile Thr
        35                  40                  45 gaa gtg atc acg atc tta ctg aat cgg ctc acc gat cgc ttg gag aaa     192
Glu Val Ile Thr Ile Leu Leu Asn Arg Leu Thr Asp Arg Leu Glu Lys
    50                  55                  60 tac gcg gga aat                                                     204
Tyr Ala Gly Asn
65

<210> SEQ ID NO 127
<211> LENGTH: 68
<212> TYPE: PRT
<213> ORGANISM: Fasciola hepatica

<400> SEQUENCE: 127

Ser Glu Glu Ser Arg Glu Lys Leu Arg Glu Ser Gly Arg Lys Met Val
1               5                   10                  15

Lys Ala Leu Arg Asp Ala Val Thr Lys Ala Tyr Glu Lys Ala Arg Asp
            20                  25                  30

Arg Ala Met Ala Tyr Leu Ala Lys Asp Asn Leu Gly Glu Lys Ile Thr
        35                  40                  45

Glu Val Ile Thr Ile Leu Leu Asn Arg Leu Thr Asp Arg Leu Glu Lys
    50                  55                  60

Tyr Ala Gly Asn
65

<210> SEQ ID NO 128
<211> LENGTH: 34
<212> TYPE: PRT
<213> ORGANISM: Artificial sequence
```

<220> FEATURE:
<223> OTHER INFORMATION: Synthetic peptide

<400> SEQUENCE: 128

Ile Glu Glu Tyr Leu Glu Lys Asp Asn Leu Gly Lys Ile Ala Glu
1               5                   10                  15

Val Val Lys Ile Leu Leu Glu Arg Leu Thr Arg Arg Leu Glu Lys Tyr
            20                  25                  30

Val Gly

<210> SEQ ID NO 129
<211> LENGTH: 70
<212> TYPE: PRT
<213> ORGANISM: Artificial sequence
<220> FEATURE:
<223> OTHER INFORMATION: Synthetic peptide

<400> SEQUENCE: 129

Arg Pro Ser Glu Glu Ser Arg Glu Lys Leu Arg Glu Ser Gly Arg Lys
1               5                   10                  15

Met Val Lys Ala Leu Arg Asp Ala Val Thr Lys Ala Tyr Glu Lys Ala
            20                  25                  30

Arg Asp Arg Ala Met Ala Tyr Leu Ala Lys Asp Asn Leu Gly Glu Lys
        35                  40                  45

Ile Thr Glu Val Ile Thr Ile Leu Leu Asn Arg Leu Thr Asp Arg Leu
    50                  55                  60

Glu Lys Tyr Ala Gly Asn
65                  70

<210> SEQ ID NO 130
<211> LENGTH: 30
<212> TYPE: PRT
<213> ORGANISM: Artificial sequence
<220> FEATURE:
<223> OTHER INFORMATION: Synthetic peptide

<400> SEQUENCE: 130

Lys Ala Arg Asp Arg Ala Met Ala Tyr Leu Ala Lys Asp Asn Leu Gly
1               5                   10                  15

Glu Lys Ile Thr Glu Val Ile Thr Ile Leu Leu Asn Arg Leu
            20                  25                  30

<210> SEQ ID NO 131
<211> LENGTH: 27
<212> TYPE: PRT
<213> ORGANISM: Artificial sequence
<220> FEATURE:
<223> OTHER INFORMATION: Synthetic peptide

<400> SEQUENCE: 131

Asn Leu Gly Glu Lys Ile Thr Glu Val Ile Thr Ile Leu Leu Asn Arg
1               5                   10                  15

Leu Thr Asp Arg Leu Glu Lys Tyr Ala Gly Asn
            20                  25

<210> SEQ ID NO 132
<211> LENGTH: 34
<212> TYPE: PRT
<213> ORGANISM: Artificial sequence
<220> FEATURE:
<223> OTHER INFORMATION: Synthetic peptide

<400> SEQUENCE: 132

```
Ala Met Ala Tyr Leu Ala Lys Asp Asn Leu Gly Glu Lys Ile Thr Glu
1               5                   10                  15

Val Ile Thr Ile Leu Leu Asn Arg Leu Thr Asp Arg Leu Glu Lys Tyr
            20                  25                  30

Ala Gly

<210> SEQ ID NO 133
<211> LENGTH: 34
<212> TYPE: PRT
<213> ORGANISM: Artificial sequence
<220> FEATURE:
<223> OTHER INFORMATION: Synthetic peptide

<400> SEQUENCE: 133

Ala Met Ala Tyr Leu Ala Lys Asp Asn Leu Gly Glu Lys Arg Thr Glu
1               5                   10                  15

Val Gln Thr Lys Arg Leu Asn Arg Leu Thr Asp Arg Thr Glu Lys Lys
            20                  25                  30

Ala Gly

<210> SEQ ID NO 134
<211> LENGTH: 34
<212> TYPE: PRT
<213> ORGANISM: Artificial sequence
<220> FEATURE:
<223> OTHER INFORMATION: Synthetic peptide

<400> SEQUENCE: 134

Ala Met Ala Tyr Leu Ala Lys Asp Asn Leu Gly Glu Lys Pro Thr Glu
1               5                   10                  15

Val Ile Thr Ile Leu Leu Asn Arg Pro Thr Asp Arg Leu Glu Lys Tyr
            20                  25                  30

Ala Gly

<210> SEQ ID NO 135
<211> LENGTH: 13
<212> TYPE: PRT
<213> ORGANISM: Artificial sequence
<220> FEATURE:
<223> OTHER INFORMATION: Synthetic peptide

<400> SEQUENCE: 135

Ala Met Ala Tyr Leu Ala Lys Asp Asn Leu Gly Glu Lys
1               5                   10

<210> SEQ ID NO 136
<211> LENGTH: 27
<212> TYPE: PRT
<213> ORGANISM: Artificial sequence
<220> FEATURE:
<223> OTHER INFORMATION: Synthetic peptide

<400> SEQUENCE: 136

Tyr Leu Ala Lys Asp Asn Leu Gly Glu Lys Ile Thr Glu Val Ile Thr
1               5                   10                  15

Ile Leu Leu Asn Arg Leu Thr Asp Arg Leu Glu
            20                  25

<210> SEQ ID NO 137
<211> LENGTH: 23
<212> TYPE: PRT
<213> ORGANISM: Artificial sequence
```

```
<220> FEATURE:
<223> OTHER INFORMATION: Synthetic peptide

<400> SEQUENCE: 137

Glu Lys Ile Thr Glu Val Ile Thr Ile Leu Leu Asn Arg Leu Thr Asp
1               5                   10                  15

Arg Leu Glu Lys Tyr Ala Gly
            20

<210> SEQ ID NO 138
<211> LENGTH: 21
<212> TYPE: PRT
<213> ORGANISM: Artificial sequence
<220> FEATURE:
<223> OTHER INFORMATION: Synthetic peptide

<400> SEQUENCE: 138

Glu Lys Ile Thr Glu Val Ile Thr Ile Leu Leu Asn Arg Leu Thr Asp
1               5                   10                  15

Arg Leu Glu Lys Tyr
            20

<210> SEQ ID NO 139
<211> LENGTH: 21
<212> TYPE: PRT
<213> ORGANISM: Artificial sequence
<220> FEATURE:
<223> OTHER INFORMATION: Synthetic peptide

<400> SEQUENCE: 139

Ile Thr Glu Val Ile Thr Ile Leu Leu Asn Arg Leu Thr Asp Arg Leu
1               5                   10                  15

Glu Lys Tyr Ala Gly
            20

<210> SEQ ID NO 140
<211> LENGTH: 19
<212> TYPE: PRT
<213> ORGANISM: Artificial sequence
<220> FEATURE:
<223> OTHER INFORMATION: Synthetic peptide

<400> SEQUENCE: 140

Ile Thr Glu Val Ile Thr Ile Leu Leu Asn Arg Leu Thr Asp Arg Leu
1               5                   10                  15

Glu Lys Tyr

<210> SEQ ID NO 141
<211> LENGTH: 11
<212> TYPE: PRT
<213> ORGANISM: Artificial Sequence
<220> FEATURE:
<223> OTHER INFORMATION: FhHDM-1 LC-MS/MS peptide

<400> SEQUENCE: 141

Ile Thr Glu Val Ile Thr Ile Leu Leu Asn Arg
1               5                   10

<210> SEQ ID NO 142
<211> LENGTH: 10
<212> TYPE: PRT
<213> ORGANISM: Artificial Sequence
<220> FEATURE:
<223> OTHER INFORMATION: FhHDM-1 LC-MS/MS N-terminal peptide
```

-continued

<400> SEQUENCE: 142

Ser Glu Glu Ser Arg Glu Lys Leu Arg Glu
1               5                   10

<210> SEQ ID NO 143
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = I, V, F or A
<220> FEATURE:
<221> NAME/KEY: MISC_FEATURE
<222> LOCATION: (2)..(2)
<223> OTHER INFORMATION: Xaa = E, D, M, Q or R
<220> FEATURE:
<221> NAME/KEY: MISC_FEATURE
<222> LOCATION: (3)..(3)
<223> OTHER INFORMATION: Xaa = E, A, T or K
<220> FEATURE:
<221> NAME/KEY: MISC_FEATURE
<222> LOCATION: (4)..(4)
<223> OTHER INFORMATION: Xaa = Y or F
<220> FEATURE:
<221> NAME/KEY: MISC_FEATURE
<222> LOCATION: (5)..(5)
<223> OTHER INFORMATION: Xaa = L or F
<220> FEATURE:
<221> NAME/KEY: MISC_FEATURE
<222> LOCATION: (6)..(6)
<223> OTHER INFORMATION: Xaa = A, E, K or R
<220> FEATURE:
<221> NAME/KEY: MISC_FEATURE
<222> LOCATION: (7)..(7)
<223> OTHER INFORMATION: Xaa = Q, K or E
<220> FEATURE:
<221> NAME/KEY: MISC_FEATURE
<222> LOCATION: (9)..(9)
<223> OTHER INFORMATION: Xaa = G, N or D
<220> FEATURE:
<221> NAME/KEY: MISC_FEATURE
<222> LOCATION: (11)..(11)
<223> OTHER INFORMATION: Xaa = G or D
<220> FEATURE:
<221> NAME/KEY: MISC_FEATURE
<222> LOCATION: (12)..(12)
<223> OTHER INFORMATION: Xaa = E, D or K
<220> FEATURE:
<221> NAME/KEY: MISC_FEATURE
<222> LOCATION: (14)..(14)
<223> OTHER INFORMATION: Xaa = L, I or M
<220> FEATURE:
<221> NAME/KEY: MISC_FEATURE
<222> LOCATION: (15)..(15)
<223> OTHER INFORMATION: Xaa = A, S, T or L
<220> FEATURE:
<221> NAME/KEY: MISC_FEATURE
<222> LOCATION: (16)..(16)
<223> OTHER INFORMATION: Xaa = E, D or A
<220> FEATURE:
<221> NAME/KEY: MISC_FEATURE
<222> LOCATION: (17)..(17)
<223> OTHER INFORMATION: Xaa = V or I
<220> FEATURE:
<221> NAME/KEY: MISC_FEATURE
<222> LOCATION: (18)..(18)
<223> OTHER INFORMATION: Xaa = I, L, V or A
<220> FEATURE:
<221> NAME/KEY: MISC_FEATURE
<222> LOCATION: (19)..(19)
<223> OTHER INFORMATION: Xaa = K, Q, N, S, T, L or V
<220> FEATURE:
<221> NAME/KEY: MISC_FEATURE
<222> LOCATION: (20)..(20)

```
<223> OTHER INFORMATION: Xaa = I or V
<220> FEATURE:
<221> NAME/KEY: MISC_FEATURE
<222> LOCATION: (21)..(21)
<223> OTHER INFORMATION: Xaa = Y, F or L
<220> FEATURE:
<221> NAME/KEY: MISC_FEATURE
<222> LOCATION: (22)..(22)
<223> OTHER INFORMATION: Xaa = A, S, L or V
<220> FEATURE:
<221> NAME/KEY: MISC_FEATURE
<222> LOCATION: (23)..(23)
<223> OTHER INFORMATION: Xaa = E, K, Q or N
<220> FEATURE:
<221> NAME/KEY: MISC_FEATURE
<222> LOCATION: (24)..(24)
<223> OTHER INFORMATION: Xaa = R or P
<220> FEATURE:
<221> NAME/KEY: MISC_FEATURE
<222> LOCATION: (26)..(26)
<223> OTHER INFORMATION: Xaa = T, P, N or E
<220> FEATURE:
<221> NAME/KEY: MISC_FEATURE
<222> LOCATION: (27)..(27)
<223> OTHER INFORMATION: Xaa = K, R or D
<220> FEATURE:
<221> NAME/KEY: MISC_FEATURE
<222> LOCATION: (29)..(29)
<223> OTHER INFORMATION: Xaa = M, I or L
<220> FEATURE:
<221> NAME/KEY: MISC_FEATURE
<222> LOCATION: (30)..(30)
<223> OTHER INFORMATION: Xaa = E or D
<220> FEATURE:
<221> NAME/KEY: MISC_FEATURE
<222> LOCATION: (31)..(31)
<223> OTHER INFORMATION: Xaa = M, N, K, A, T or Y
<220> FEATURE:
<221> NAME/KEY: MISC_FEATURE
<222> LOCATION: (32)..(32)
<223> OTHER INFORMATION: Xaa = R, C, Y or L
<220> FEATURE:
<221> NAME/KEY: MISC_FEATURE
<222> LOCATION: (33)..(33)
<223> OTHER INFORMATION: Xaa = A, L, V or S
<220> FEATURE:
<221> NAME/KEY: MISC_FEATURE
<222> LOCATION: (34)..(34)
<223> OTHER INFORMATION: Xaa = L, K, E, P, S, Q or G

<400> SEQUENCE: 143

Xaa Xaa Xaa Xaa Xaa Xaa Xaa Asp Xaa Leu Xaa Xaa Lys Xaa Xaa Xaa
1               5                   10                  15

Xaa Xaa Xaa Xaa Xaa Xaa Xaa Xaa Leu Xaa Xaa Arg Xaa Xaa Xaa Xaa
            20                  25                  30

Xaa Xaa
```

IMMUNE-MODULATING AGENTS AND USES THEREFOR

This application is a 371 National Entry of International Patent Application PCT/AU2011/001402, filed Nov. 1, 2011, which is incorporated by reference, and which claims priority to Australian Patent Application 2010904873, filed Nov. 1, 2010.

FIELD OF THE INVENTION

This invention relates generally to methods and compositions for modulating immune responses. More particularly, the present invention relates to proteinaceous agents having one or more activities selected from stimulating or inducing an antigen-specific Th2 response, suppressing the development of an antigen-specific Th1 response, stimulating the development in antigen-presenting cells of an alternatively activated phenotype, preventing or inhibiting the activation of antigen-presenting cells by an inflammatory stimulus, binding to lipopolysaccharide, preventing or inhibiting binding of lipopolysaccharide to lipopolysaccharide-binding protein, preventing or inhibiting binding of toll-like receptor (TLR) ligands (e.g., lipopolysaccharide) to antigen-presenting cells (e.g., macrophages), interacting with the plasma membrane of antigen-presenting cells, and down-regulating or impairing lysosome function in antigen-presenting cells, as well as nucleic acid molecules encoding the proteinaceous agents. The present invention further relates to the use of these agents and molecules for treating or preventing undesirable or deleterious immune responses in a range of conditions including transplant rejection, graft versus host disease, allergies, parasitic diseases, inflammatory diseases and autoimmune diseases.

BACKGROUND OF THE INVENTION

Autoimmune diseases are caused by T and B lymphocytes that attack self-molecules ("autoantigens") causing damage to the body's cells and/or tissues. These immune cells are normally inactive but become activated through a break in immune tolerance, which is a process by which the immune system does not attack an antigen.

Immune tolerance can be divided into 'self tolerance,' where the body does not mount an immune response to its autoantigens, and 'induced tolerance,' where the immune system is manipulated to tolerate external antigens ("alloantigens"). Self tolerance is mediated by central and peripheral mechanisms. In central tolerance, immature lymphocytes that recognize self antigens in generative lymphoid organs (the bone marrow for B cells and the thymus for T cells) die by apoptosis. However, in peripheral tolerance, mature self-reactive lymphocytes encounter self antigens in peripheral tissues and are killed or become inactivated. The principal mechanisms of peripheral tolerance are anergy (functional unresponsiveness), deletion (apoptotic cell death), and suppression by regulatory T cells.

Although the mechanisms by which immune tolerance is broken are not entirely known, autoimmunity is thought to result from a combination of genetic variants, acquired environmental triggers such as infections, and stochastic events.

Type I diabetes mellitus is an autoimmune-mediated disease resulting in the specific destruction of the insulin producing pancreatic β cells. Nonobese diabetic (NOD) mice are the most widely used model for studying the disease mechanisms of T1D because they exhibit many characteristics of the human disease. Disease onset is preceded by an extensive period of asymptomatic pre-diabetes, ending at approximately 4 weeks of age, when immune cells reactive against beta cell autoantigens begin to infiltrate the islets (insulitis) and destroy β cells (Giarratana et al., 2007, *Methods Mol Biol* 380:285-311). Autoimmune destruction of β-cells in the NOD mouse model can be divided into 3 distinct phases (You et al., 2008, *Ann NY Acad Sci* 1150: 300-310). In phase 1, antigen presenting cells (APCs; classically activated macrophages and dendritic cells (DCs)) accumulate within the islets, prior to observable inflammation. In phase 2, autoreactive T cells are activated and expanded, initially in the draining pancreatic lymph nodes (PLN), and subsequently in the pancreas itself. At this time, lymphocytic infiltrates, containing T and B cells as well as macrophages, DCs and NK cells, are evident. Finally, in phase 3, $CD8^+$ (cytotoxic) T cells and inflammatory scavenger macrophages invade the islets and, by immune-mediated effector mechanisms, cause the final wave of β-cell destruction that precipitates clinical disease.

Since the 1980s, strategies to induce immune cell tolerance to β-cell antigens have been the primary therapeutic goal in the prevention and treatment of T1D. Immune tolerance is a state of immune system unresponsiveness to an antigen, and is maintained by a number of mechanisms including deletion, inactivation, and regulation (Schwartz, 1989, *Cell* 57:1073-1081). Results of early randomized trials showed that suppression of T cell activation by cyclosporine (Stiller et al., 1984, *Science* 223:1362-1367) and azathioprine (Silverstein et al., 1988, *N Engl J Med.* 319:599-604.) were effective at reversing established T1D with approximately 50% of treated patients becoming independent of insulin therapy (Feutren et al., 1986, *Lancet* 2:119-124). Despite this significant success, relapse of T1D occurred upon withdrawal of treatment, which implied that indefinite administration would be necessary. Additionally, these therapies induced global immunosuppression per se, and, given the associated side effects, would be undesirable treatment regimes for children. In other studies, depletion of B lymphocytes, by administration of Rituximab to patients with newly diagnosed T1D, initially reduced insulin requirements in these patients. However, due to the global depletion of B lymphocytes, ancillary antibody responses were severely compromised (Pescovitz et al., 2009, *N Engl J Med.* 361:2143-2152). While the risk-to-benefit ratio in these cases was not in favour of developing the therapies as applicable treatments for T1D, the results provided proof-of-principle for the intervention of developing inflammatory immune responses as an effective treatment of T1D.

With this in mind, the potential of anti-CD3 monoclonal antibodies (mAbs) as a treatment for T1D was investigated. Anti-CD3 mAbs are potent immunosuppressive agents that act by antigenic modulation of the CD3/T-cell receptor complex and result in the transient depletion of T-cells. Since 1985, anti-CD3 mAb had been licensed for use in transplantation as it successfully induced alloantigen tolerance and thus prevented graft rejection (Strohl, W. Therapeutic Monoclonal Antibodies: Past, Present, and Future. In: Zhiqiang, A. N. *Therapeutic Monoclonal Antibodies: From Bench to Clinic*. New Jersey: John Wiley and Sons, Inc. 28-29). The first demonstration that anti-CD3 antibody could also affect the development of T1D was reported in the mid-1990s. A 5-day anti-CD3 antibody treatment in NOD mice with new onset diabetes restored normoglycemia permanently in 72% of treated mice (Chatenoud et al., 1994, *Proc Natl Acad Sci USA* 91:123-127; Chatenoud et al., 1997, *J Immunol* 158:2947-2954). On the basis of these results, therapeutic trials were launched using humanized anti-CD3 mAbs (Herold et al., 2002, *N Engl J Med.* 346:1692-1698; Herold et al., 2005, *Diabetes.* 54:1763-1769; Bolt et al., 1993, *Eur J Immunol.* 23:403-411). In Phase I/II randomized control trials, patients with new onset T1D showed a reduced rate of loss of 0-cell function following treatment combined with better glycemic control and lower insulin requirements (Herold et al., 2009, *Clin Immunol.* 132:166-173; Keymeulen et al., 2010, *Diabetologia* 53:614-623). Phase III clinical trials are underway to confirm these results and to optimize the treatment regime for greater efficacy in arresting loss of 0-cell function (Masharani et al., 2010, *Expert Opin Biol Ther.* 10:459-465).

A major obstacle to the clinical applicability of these therapies is the requirement for heavy immune-suppression to preserve 0 cell mass remaining at diagnosis (approximately 10%). To overcome this, the development of strategies to achieve immune-modulation, through the regulation of specific immunological signals (such as innate cell modulation or regulatory T cell activation) is required.

A successful outcome (i.e., reversion to normoglycemia) of any immune therapy protocol for T1D is dependent on the presence and/or maintenance of a sufficient functional mass of β-cells at the initiation of treatment. This could be achieved at the point of auto-antibody conversion, indicative of the beta cell destruction process occurring; at diagnosis, when 10% of functional beta cell mass remains; or after islet transplantation. Due to the extensive, yet silent, preclinical period and the absence of a definitive marker of disease progression, the vast majority of immune-modulatory treatments for T1D have been targeted at preserving beta cell mass after pancreas or islet transplantation.

Since the studies of Ballinger et al. and Lacy et al. (Ballinger, 1976, *Annals of the Royal Colleges of Surgeons of England* 58: 327; Ballinger et al., 1973, *Br. J Surg.* 60: 313; Kemp et al., 1973, *Nature* 244:447) during the 1970s, which showed that islet transplantation could cure diabetes in rodents, islet transplantation for humans has been regarded as a potential cure for T1D. The first series of successful transplants in Edmonton, Canada (Shapiro et al., 2000, *N. Engl. J Med.* 343: 230-238; Truong et al., 2006, *Treat. Endocrinol.* 5:147-158), has established transplantation of islets as a viable therapeutic option for the cure of T1D. This successful treatment, however, comes at the cost of using intense immunosuppression (Shapiro et al., 2000, supra; Ricordi et al., 2004, *Nat Rev Immunol.* 4:259-268), which carries adverse side-effects and exerts cytotoxic effects on transplanted beta cells such that the recipient generally requires multiple transplants to remain insulin-free. These drawbacks preclude the widespread application of islet transplantation for children; the main group for which such a treatment would be most beneficial as disease onset typically occurs in childhood and a cure shortly after diagnosis would prevent the chronic complications of T1D, which greatly increase mortality and morbidity.

As in the development of T1D, islet graft rejection is characterized by a robust pro-inflammatory T helper (Th)1-driven inflammatory response directed at donor alloantigens (O'Connell et al., 1993, *J. Immunol.* 150(3):1093-1104). Manipulations that modulate or control T cell activation, and thus alter the phenotype of immune response (pro-inflammatory Th1 versus anti-inflammatory Th2/regulatory T cell), alter disease outcome in rodent T1D models and improve islet graft survival (Makhlouf et al., 2004, *Transplantation* 77(7):990-997; Nanji et al., 2006, *Diabetes* 55(1):27-33; Pop et al., 2007, *Diabetes* 56(5):1395-1402; Rapoport et al., 1993, *J Exp. Med.* 178(1):87-99). These studies support the idea that modulation of lymphocyte activation, such as by way of immune-deviation, can lead to the development of therapies that allow successful islet engraftment in the absence of systemic immunosuppression. Such an outcome constitutes a viable transplant-based alternative to daily administration of insulin, and prevents the deleterious chronic effects of hyperglycemia. However, to date there has been little progress towards the development of prophylactic and therapeutic strategies to divert Th1 responses towards Th2/Treg responses required for preservation of beta cell mass.

SUMMARY OF THE INVENTION

The present invention arises from the unexpected discovery of an immunomodulatory peptide from *Fasciola hepatica*, referred to herein as *F. hepatica* Helminth Defense Molecule-1 (FhHDM-1) and fragments thereof that have at least one activity selected from: stimulating or inducing an antigen-specific Th2 response, suppressing the development of an antigen-specific Th1 response, stimulating the development in antigen-presenting cells of an alternatively activated phenotype, preventing or inhibiting the activation of antigen-presenting cells by an inflammatory stimulus, binding to lipopolysaccharide, preventing or inhibiting binding of lipopolysaccharide to lipopolysaccharide-binding protein, preventing or inhibiting binding of toll-like receptor (TLR) ligands (e.g., lipopolysaccharide) to antigen-presenting cells, interacting with the plasma membrane of antigen-presenting cells, and down-regulating or impairing lysosome function in antigen-presenting cells. When administered to diabetic animals, these molecules are surprisingly effective in reducing immune cell invasion of pancreatic islets and are considered, therefore, to be useful as a preventative treatment for T1D and in permitting the acceptance of islet grafts in the context of established disease. The present inventors have also identified various structurally related homologs of FhHDM-1, which are considered to have similar activity. These discoveries have been reduced to practice in novel compositions and methods for treating or preventing undesirable immune responses including autoimmune diseases, allergies and transplantation associated diseases.

Accordingly, in one aspect, the present invention provides isolated or purified proteinaceous molecules for modulating an undesirable or deleterious immune response. These molecules generally comprise, consists or consist essentially of an amino acid sequence represented by formula I (SEQ ID NO:123):

$$X_1X_2X_3X_4DX_5LX_6X_7KX_8X_9X_{10}X_{11}X_{12}X_{13}X_{14}X_{15}X_{16}X_{17}X_{18}LX_{19}X_{20}RX_{21}X_{22} \qquad (I)$$

wherein:

$X_1$ is selected from aromatic amino acid residues (e.g., Y or F, or modified forms thereof);

$X_2$ is selected from hydrophobic amino acid residues (e.g., aliphatic amino acid residues such as L or modified forms thereof, or aromatic amino acid residues such as F, or modified forms thereof);

$X_3$ is selected from any amino acid residue (e.g., acidic amino acid residues such as E, or modified forms thereof, or small amino acid residues such as A, or modified forms thereof, or basic amino acid residues such as K or R, or modified forms thereof);

$X_4$ is selected from neutral/polar amino acid residues (e.g., Q or modified forms thereof), or charged amino acid residues (e.g., basic amino acid residues such as K, or modified forms thereof, or acidic amino acid residues such as E, or modified forms thereof);

X$_5$ is selected from any amino acid residue (e.g., small amino acid residues such as G, or modified forms thereof, or neutral/polar amino acid residues such as N, or modified forms thereof, or acidic amino acid residues such as D, or modified forms thereof);

X$_6$ is selected from any amino acid residue (e.g., small amino acid residues such as G, or modified forms thereof, or acidic amino acid residues such as D, or modified forms thereof);

X$_7$ is selected from charged amino acid residues (e.g., acidic amino acid residues such as E or D, or modified forms thereof, or basic amino acid residues such as K, or modified forms thereof);

X$_8$ is selected from hydrophobic amino acid residues (e.g., aliphatic amino acid residues such as L, I or M, or modified forms thereof);

X$_9$ is selected from any amino acid residue (e.g., small amino acid residues such as A, S or T, or modified forms thereof, or hydrophobic amino acid residues including aliphatic amino acid residues such as L, or modified forms thereof);

X$_{10}$ is selected from any amino acid residue (e.g., acidic amino acid residues such as E or D, or modified forms thereof, or small amino acid residues such as A, or modified forms thereof);

X$_{11}$ is selected from hydrophobic amino acid residues (e.g., aliphatic amino acid residues such as V or I, or modified forms thereof);

X$_{12}$ is selected from any amino acid residue (e.g., hydrophobic amino acid residues including aliphatic amino acid residues such as I, L or V, or modified forms thereof, or small amino acid residues such as A, or modified forms thereof);

X$_{13}$ is selected from any amino acid residue (e.g., basic amino acid residues such as K, or modified forms thereof, or neutral/polar amino acid residues such as Q or N, or modified forms thereof, or small amino acid residues such as S or T, or modified forms thereof, or hydrophobic amino acid residues including aliphatic amino acid residues such as L or V, or modified forms thereof);

X$_{14}$ is selected from hydrophobic amino acid residues (e.g., aliphatic amino acid residues such as I or V, or modified forms thereof);

X$_{15}$ is selected from hydrophobic amino acid residues (e.g., aromatic amino acid residues such as Y or F, or modified forms thereof, or aliphatic amino acid residues such as L or modified forms thereof);

X$_{16}$ is selected from any amino acid residue (e.g., small amino acid residues such as A or S, or modified forms thereof, or hydrophobic amino acid residues including aliphatic amino acid residues such as L or V, or modified forms thereof);

X$_{17}$ is selected from any amino acid residue (e.g., acid amino acid residues such as E, or modified forms thereof, or basic amino acid residues such as K, or modified forms thereof, or neutral/polar amino acid residues such as Q or N, or modified forms thereof);

X$_{18}$ is selected from any amino acid residue (e.g., basic amino acid residues such as R, or modified forms thereof, or small acid residues such as P, or modified forms thereof);

X$_{19}$ is selected from any amino acid residue (e.g., small amino acid residues such as T or P, or modified forms thereof, or neutral/polar amino acid residues such as N, or modified forms thereof, or acidic amino acid residues such as E, or modified forms thereof);

X$_{20}$ is selected from charged amino acid residues (e.g., basic amino acid residues such as K or R, or modified forms thereof, or acidic amino acid residues such as D, or modified forms thereof);

X$_{21}$ is selected from hydrophobic amino acid residues (e.g., aliphatic amino acid residues such as M, I or L, or modified forms thereof); and X$_{22}$ is selected from acidic amino acid residues (e.g., E or D, or modified forms thereof).

In some embodiments, the proteinaceous molecules are represented by formula II (SEQ ID NO:123):

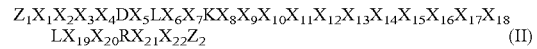

$$Z_1X_1X_2X_3X_4DX_5LX_6X_7KX_8X_9X_{10}X_{11}X_{12}X_{13}X_{14}X_{15}X_{16}X_{17}X_{18}LX_{19}X_{20}RX_{21}X_{22}Z_2 \quad (II)$$

wherein:

X$_1$-X$_{22}$ are as broadly defined above;

Z$_1$ is absent or is selected from at least one of a proteinaceous moiety comprising from about 1 to about 50 amino acid residues (and all integers therebetween), and a protecting moiety (e.g., an N-terminal blocking residue such as pyroglutamate); and Z$_2$ is absent or is a proteinaceous moiety comprising from about 1 to about 50 amino acid residues (and all integers therebetween).

In some embodiments, Z$_1$ comprises, consists or consists essentially of an amino acid sequence represented by formula III:

$$B_1X_{23}X_{24}X_{25} \quad (III)$$

wherein:

B$_1$ is absent or is an N-terminal blocking residue;

X$_{23}$ is absent or is selected from any amino acid residue (e.g., hydrophobic amino acid residues including aliphatic amino acid residues such as I or V, or modified forms thereof, or aromatic amino acid residues such as F, or modified forms thereof, or small amino acid residues such as A, or modified forms thereof), wherein X$_{23}$ is present in some embodiments with the proviso that X$_{24}$ is also present;

X$_{24}$ is absent or is selected from any amino acid residue (e.g., acidic amino acid residues such as E or D, or modified forms thereof, or hydrophobic amino acid residues including aliphatic amino acid residues such as M, or modified forms thereof, or modified forms thereof, or basic residues such as R, or modified forms thereof), wherein X$_{24}$ is present in some embodiments with the proviso that X$_{25}$ is also present; and X$_{25}$ is selected from any amino acid residue (e.g., acidic amino acid residues such as E, or modified forms thereof, or small amino acid residues such as A or T, or modified forms thereof, or basic amino acid residues such as K, or modified forms thereof).

In some embodiments, Z$_2$ comprises, consists or consists essentially of an amino acid sequence represented by formula IV (SEQ ID NO:124):

$$X_{26}X_{27}X_{28}X_{29} \quad (IV)$$

wherein:

X$_{26}$ is absent or is selected from any amino acid residue (e.g., small amino acid residues such as T or A, or modified forms thereof, or basic amino acid residues such as K, or modified forms thereof, or neutral/polar amino acid residues such as N, or modified forms thereof, or hydrophobic amino acid residues including aliphatic amino acid residues such as M, or modified forms thereof);

X$_{27}$ is absent or is selected from any amino acid residue (e.g., hydrophobic amino acid residues including aromatic amino acid residues such as Y or modified forms thereof, or aliphatic amino acid residues such as C, or modified forms thereof, or basic amino acid residues such as R, or modified forms thereof), wherein $X_{27}$ is present in some embodiments with the proviso that $X_{26}$ is also present;

$X_{28}$ is absent or is selected from any amino acid residue (e.g., hydrophobic amino acid residues including aliphatic amino acid residues such as V or L, or modified forms thereof, or small amino acid residues such as A, or modified forms thereof), wherein $X_{28}$ is present in some embodiments with the proviso that $X_{27}$ is also present; and $X_{29}$ is absent or is selected from any amino acid residue (e.g., small amino acid residues such as G, S or P, or modified forms thereof, or acidic amino acid residues such as E, or modified forms thereof, or basic acid residues such as K, or modified forms thereof, hydrophobic amino acid residues including aliphatic amino acid residues such as L, or modified forms thereof), wherein $X_{29}$ is present in some embodiments with the proviso that $X_{28}$ is also present.

In illustrative examples, the proteinaceous molecules comprise, consist or consist essentially of an amino acid sequence selected from the group consisting of:

(a) an amino acid sequence selected from: YLAKDNLGEKITEVITILLNRLTDRLE [SEQ ID NO:2, C terminal sequence of FhHDM-1 from *F. hepatica*]; YLEKDNLGEKIAEV VKILSERLTKRIE [SEQ ID NO:4, C-terminal sequence of FhHDM-1 homolog CsHDM-1 from *Clonorchis sinensis* under GenBank Accession AAM55183.1]; YLEKDGLGEKLADVI KILAERLTKRME [SEQ ID NO:6, C-terminal sequence of FhHDM-1 homolog OvHDM-1 from *Opisthorchis viverrini*]; YLEEDGLGDKISEVIQILLKRLTDRIE [SEQ ID NO:8, C-terminal sequence of FhHDM-1 homolog PwHDM-1 from *Paragonimus westermani*]; YFKQDDLGEKIAEVLLIFLQRLNRRLE [SEQ ID NO:10, C-terminal sequence of FhHDM-1 homolog SjHDM-1 from *Schistosoma japonicum* under GenBank Accession CAX69999.1]; YFKQDDLGEKIAEVLLIFLQRLNRRLE [SEQ ID NO:12, C-terminal sequence of FhHDM-1 homolog SjHDM-2 from *S. japonicum* under GenBank Accession CAX70000.1]; YFKQDGLGEKLAEVLLILLQRLNRRLE [SEQ ID NO:14, C-terminal sequence of FhHDM-1 homolog SjHDM-3 from *S. japonicum* under GenBank Accession CAX69998.1]; YFREDDLGEKIADVLVVLLKRLNKRLE [SEQ ID NO:16, C-terminal sequence of FhHDM-1 homolog SmHDM-1 from *Schistosoma mansoni*]; YLEEDN LGEKLAAVVSIYVKRLNKRLD [SEQ ID NO:18, C-terminal sequence of FhHDM-1 homolog SmHDM-2 from *S. mansoni* under GenBank Accession CAZ32864.1]; FFEKDNLG EKIAEVVKILSEPLPKRIE [SEQ ID NO:20, C-terminal sequence of FhHDM-1 homolog CsHDM-2 from *C. sinensis*] or YLRKDDLDKKMLEIANILAKRLEKRME [SEQ ID NO:22, C-terminal sequence of FhHDM-1 homolog SjHDM-4 from *S. japonicum*];

(b) an amino acid sequence that shares at least 50% (and at least 51% to at least 99% and all integer percentages in between) sequence similarity or sequence identity with the sequence set forth in any one of SEQ ID NO: 2, 4, 6, 8, 10, 12, 14, 16, 18, 20 or 22; or (c) an amino acid sequence which is encoded by the nucleotide sequence set forth in any one of SEQ ID NO:1 (nucleotide sequence encoding C-terminal sequence of FhHDM-1 from *F. hepatica*), SEQ ID NO:3 (nucleotide sequence encoding C-terminal sequence of FhHDM-1 homolog from *C. sinensis* AAM55183.1), SEQ ID NO:5 (nucleotide sequence encoding C-terminal sequence of FhHDM-1 homolog from *O. viverrini*), SEQ ID NO:7 (nucleotide sequence encoding C-terminal sequence of FhHDM-1 homolog from *P. westermani*), SEQ ID NO:9 (nucleotide sequence encoding C-terminal sequence of FhHDM-1 homolog from *S. japonicum* CAX69999.1), SEQ ID NO:11 (nucleotide sequence encoding C-terminal sequence of FhHDM-1 homolog from *S. japonicum* CAX70000.1), SEQ ID NO:13 (nucleotide sequence encoding C-terminal sequence of FhHDM-1 homolog from *S. japonicum* CAX69998.1), SEQ ID NO:15 (nucleotide sequence encoding C-terminal sequence of FhHDM-1 homolog from *S. mansoni*), SEQ ID NO:17 (nucleotide sequence encoding C-terminal sequence of FhHDM-1 homolog from *S. mansoni* CAZ32864.1), SEQ ID NO:19 (nucleotide sequence encoding C-terminal sequence of FhHDM-1 homolog from *C. sinensis*) or SEQ ID NO:21 (nucleotide sequence encoding C-terminal sequence of FhHDM-1 homolog from *S. japonicum*);

(d) an amino acid sequence which is encoded by a nucleotide sequence that shares at least 50% (and at least 51% to at least 99% and all integer percentages in between) sequence identity with the sequence set forth in any one of SEQ ID NO: 1, 3, 5, 7, 9, 11, 13, 15, 17, 19 or 21, or a complement thereof; or (e) an amino acid sequence which is encoded by a nucleotide sequence that hybridizes under at least low, medium or high stringency conditions to the sequence set forth in any one of SEQ ID NO: 1, 3, 5, 7, 9, 11, 13, 15, 17, 19 or 21, or a complement thereof, wherein the amino acid sequence of (a), (b), (c), (d) or (e) has any one or more activities selected from the group consisting of: stimulating or inducing an antigen specific Th2 response, suppressing the development of a Th1 response to an antigen (e.g., parasite antigens or bystander Th1 inducing antigens), stimulating the development in antigen-presenting cells (e.g., macrophages, dendritic cells, Langerhans cells etc) of an alternatively activated phenotype (e.g., increased expression of any one or more of Arg1, Fizz, Ym1, IL-10, TGF-β, CD206 and CD163), preventing or inhibiting the activation of antigen-presenting cells (e.g., macrophages, dendritic cells Langerhans cells etc) by an inflammatory stimulus (e.g., exposure to a TLR ligand such as lipopolysaccharide), binding to lipopolysaccharide, preventing binding of lipopolysaccharide to lipopolysaccharide-binding protein, preventing or inhibiting binding of a TLR ligand (e.g., lipopolysaccharide) to antigen-presenting cells (e.g., macrophages, dendritic cells, Langerhans cells etc), interacting with the plasma membrane of antigen-presenting cells (e.g., macrophages, dendritic cells, Langerhans cells etc) and down-regulating or impairing lysosome function in antigen-presenting cells (e.g., macrophages, dendritic cells, Langerhans cells etc).

In some embodiments, the proteinaceous molecules comprise, consist or consist essentially of an amino acid sequence selected from the group consisting of:

(A) an amino acid sequence selected from any one of SEQ ID NO:24 (a putatively full-length HDM from *F. hepatica* designated FhHDM-1), SEQ ID NO:26 (a putatively full-length HDM from *C. sinensis* designated CsHDM-1), SEQ ID NO:28 (a putatively full-length HDM from *O. viverrini* designated OvHDM-1), SEQ ID NO:30 (a putatively full-length HDM from *P. westermani* designated PwHDM-1), SEQ ID NO:32 (a putatively full-length HDM from *S. japonicum* designated SjHDM-1), SEQ ID NO:34 (a putatively full-length HDM from *S. japonicum* designated SjHDM-2), SEQ ID NO:36 (a putatively full-length HDM from *S. japonicum* designated SjHDM-4), SEQ ID NO:38 (a putatively full-length HDM from *S. mansoni* designated SmHDM-1), SEQ ID NO:40 (a putatively full-length HDM from *S. mansoni* designated SmHDM-2), SEQ ID NO:42 (a putatively full-length HDM from *C. sinensis* designated CsHDM-2) or SEQ ID NO:44 (a putatively full-length HDM from *S. japonicum* designated SjHDM-4);

(B) an amino acid sequence that shares at least 50% (and at least 51% to at least 99% and all integer percentages in between) sequence similarity or sequence identity with the sequence set forth in any one of SEQ ID NO: 24, 26, 28, 30, 32, 34, 36, 38, 40, 42 or 44; or (C) an amino acid sequence which is encoded by the nucleotide sequence set forth in any one of SEQ ID NO:23 (nucleotide sequence encoding FhHDM-1 from *F. hepatica*), SEQ ID NO:25 (nucleotide sequence encoding CsHDM-1 from *C. sinensis* AAM55183.1), SEQ ID NO:27 (nucleotide sequence encoding OvHDM-1 from *O. viverrini*), SEQ ID NO:29 (nucleotide sequence encoding PwHDM-1 from *P. westermani*), SEQ ID NO:31 (nucleotide sequence encoding SjHDM-1 from *S. japonicum* CAX69999.1), SEQ ID NO:33 (nucleotide sequence encoding SjHDM-2 from *S. japonicum* CAX70000.1), SEQ ID NO:35 (nucleotide sequence encoding SjHDM-3 from *S. japonicum* CAX69998.1), SEQ ID NO:37 (nucleotide sequence encoding SmHDM-1 from *S. mansoni*), SEQ ID NO:39 (nucleotide sequence encoding SmHDM-1 from *S. mansoni* CAZ32864.1), SEQ ID NO:41 (nucleotide sequence encoding CsHDM-2 from *C. sinensis*) or SEQ ID NO:43 (nucleotide sequence encoding SjHDM-4 homolog from *S. japonicum*);

(D) an amino acid sequence which is encoded by a nucleotide sequence that shares at least 50% (and at least 510% to at least 99% and all integer percentages in between) sequence identity with the sequence set forth in any one of SEQ ID NO: 23, 25, 27, 29, 31, 33, 35, 37, 39, 41 or 43, or a complement thereof; or (E) an amino acid sequence which is encoded by a nucleotide sequence that hybridizes under at least low, medium or high stringency conditions to the sequence set forth in any one of SEQ ID NO: 23, 25, 27, 29, 31, 33, 35, 37, 39, 41 or 43, or a complement thereof, wherein the amino acid sequence of (A), (B), (C), (D) or (E) has any one or more activities selected from the group consisting of: stimulating or inducing an antigen specific Th2 response, suppressing the development of a Th1 response to an antigen (e.g., parasite antigens or bystander Th1 inducing antigens), stimulating the development in antigen-presenting cells (e.g., macrophages, dendritic cells, Langerhans cells etc) of an alternatively activated phenotype (e.g., increased expression of any one or more of Arg1, Fizz, Ym1, IL-10, TGF-β, CD206 and CD163), preventing or inhibiting the activation of antigen-presenting cells (e.g., macrophages, dendritic cells Langerhans cells etc) by an inflammatory stimulus (e.g., exposure to a TLR ligand such as lipopolysaccharide), binding to lipopolysaccharide, preventing binding of lipopolysaccharide to lipopolysaccharide-binding protein, preventing or inhibiting binding of a TLR ligand (e.g., lipopolysaccharide) to antigen-presenting cells (e.g., macrophages, dendritic cells, Langerhans cells etc), interacting with the plasma membrane of antigen-presenting cells (e.g., macrophages, dendritic cells, Langerhans cells etc) and down-regulating or impairing lysosome function in antigen-presenting cells (e.g., macrophages, dendritic cells, Langerhans cells etc).

In some embodiments, the proteinaceous molecule is other than one consisting of an amino acid sequence selected from:

[SEQ ID NO: 26]
MRLTVFICLVFVLFVAHAEARPSEETRAKLRESGQKLWTAVVAAARKCA

ERVRQRIEEYLEKDNLGEKIAEVVKILSERLTKRIETYVGE;

[SEQ ID NO: 32]
MKFIVAISLLVLMTLIYTEASPENLRFQLQKTLMDTGEKFKTLSLRLLT

RCRNRVREYFKQDDLGEKIAEVLLIFLQRLNRRLEKYLSRPE;

[SEQ ID NO: 34]
MKFIVAISLLVLMTLIYTEASPENLRFQLQKTLMDTGEKFKTLSLRLLT

RCRNRVREYFKQDDLGEKIAEVLLIFLQRLNRRLEKYLLRPE;

[SEQ ID NO: 36]
MKIIVAISLLVLMTLIYTEASPENSRLLLQKALMDTGEKFKTLSLRLLA

RCRDRVREYFKQDGLGEKLAEVLLILLQRLNRRLEKYLPRSE;
and/or

[SEQ ID NO: 40]
HISIMKLILIFALIISLLLNVTAESQASQKELFTESVKLWKSITELWKR

FEHNCRVKIRKYLEEDNLGEKLAAVVSIYVKRLNKRLDMRLSEDRAE.

In some embodiments, the proteinaceous molecule is other than one consisting of the amino acid sequence SEES-REKLRESGGKMVKALRD [SEQ ID NO:45].

In a related aspect, the present invention provides proteinaceous molecules comprising, consisting or consisting essentially of an amino acid sequence selected from the group consisting of (a) to (e) or (A) to (E), as broadly defined above.

Another aspect of the present invention provides isolated nucleic acid molecules that comprise, consist or consist essentially of a nucleotide sequence encoding the amino acid sequence of a proteinaceous molecule as broadly defined above. In some embodiments, the nucleic acid molecules comprise, consist or consist essentially of a nucleotide sequence selected from:

(a) a nucleotide sequence selected from: TACTTGGCGAAGGACAATCTAGGAGAA AAGAT-CACTGAAGTGATCACGATCTTACTGAATCGGCTCA-CCGATCGCTTGGAG [SEQ ID NO:1; nucleotide sequence encoding C-terminal sequence of FhHDM-1 from *F. hepatica*]; TATCTTGAAAAGGACAACCT- GGGCGA-GAAAATAGCTGAAGTCG TGAAAATCCTGTCCG-AGCGCCTGACCAAACGGATAGAG [SEQ ID NO:3; nucleotide sequence encoding C-terminal sequence of FhHDM-1 homolog from *C. sinensis* AAM55183.1]; TATCTGGAAAAGGACGGTCTCGGCGAGAAATTAG-CTGATGTCATTAAAATCCTGGCCGAGCGCCTAAC-CAAACGGATGGAG [SEQ ID NO:5; nucleotide sequence encoding C-terminal sequence of FhHDM-1 homolog from *O. viverrini*]; TATTTGGAGAAAGATGGACTCGGA-GACAAGATATCGGAAGTGATTCAAATCTTACTGAA-AAGACTAACTGAC- CGAATTGAG [SEQ ID NO:7; nucleotide sequence encoding C-terminal sequence of FhHDM-1 homolog from *P. westermani*]; TACTT-TAAACAAGATGATTTAGGCGAGAAAATAGCAGAG-GTTCTACTTATTTTTCTTCAAC-GTTTGAATAGACG-TCTAGAA [SEQ ID NO:9; nucleotide sequence encoding C-terminal sequence of FhHDM-1 homolog from *S. japonicum* CAX69999.1]; TACTTTAAACAAGATGATTTAG-GAGAGAAAATAGCAGAGGTTCTA CTTATTTTTCTT- CAACGTTTGAATAGACGTCTAGAA [SEQ ID NO:11; nucleotide sequence encoding C-terminal sequence of FhHDM-1 homolog from *S. japonicum* CAX70000.1]; TACTTTAAACAAGATGGATTAGGCGAGAAGTTAG-CAGAGGTTCTAC TTATTCTTCTTCAACGTTTGAATA-GACGTCTAGAA [SEQ ID NO:13; nucleotide sequence encoding C-terminal sequence of FhHDM-1 homolog from *S. japonicum* CAX69998.1]; TATTTCAGGGAAGAC-GATCTAGGTGAGAAAATAGCAGACGTTTTA GTTGT-TTTACTTAAACGTTTGAATAAACGCCTAGAA [SEQ ID NO:15; nucleotide sequence encoding C-terminal sequence of FhHDM-1 homolog from *S. mansoni*]; TATCTTG AAGAAGATAATTTAGGTGAAAAATTAG-CCGCTGTTGTAAGCATCTATGTTAAGCG TTTAAA-CAAGCGTTTAGAT [SEQ ID NO:17; nucleotide sequence encoding C-terminal sequence of FhHDM-1 homolog from *S. mansoni* CAZ32864.1]; TTTTTTGAAAAGGACAA CCTGGGGGAGAAAATAGCGGAAGTCGTGAAAAT-CCTGTCCGAGCCCCTGCCCAA ACGGATAGAG [SEQ ID NO: 19; nucleotide sequence encoding C-terminal sequence of FhHDM-1 homolog from *C. sinensis*]; or TACCTCAGAAAAGATGATTTAGATAAGAAA ATGCT-TGAAATCGCCAATATTCTTGCCAAACGTTTGGAGA-AACGGATGGAG [SEQ ID NO:21; nucleotide sequence encoding C-terminal sequence of FhHDM-1 homolog from *S. japonicum*];

(b) a nucleotide sequence that shares at least 50% (and at least 510% to at least 99% and all integer percentages in between) sequence identity with the sequence set forth in any one of SEQ ID NO: 1, 3, 5, 7, 9, 11, 13, 15, 17, 19 or 21, or a complement thereof;

(c) a nucleotide sequence that hybridizes under at least low, medium or high stringency conditions to the sequence set forth in any one of SEQ ID NO: 1, 3, 5, 7, 9, 11, 13, 15, 17, 19 or 21, or a complement thereof, wherein the amino acid sequence encoded by the nucleotide sequence of (a), (b) or (c) has any one or more activities selected from the group consisting of: stimulating or inducing an antigen specific Th2 response, suppressing the development of a Th1 response to an antigen (e.g., parasite antigens or bystander Th1 inducing antigens), stimulating the development in antigen-presenting cells (e.g., macrophages, dendritic cells, Langerhans cells etc) of an alternatively activated phenotype (e.g., increased expression of any one or more of Arg1, Fizz, Ym1, IL-10, TGF-β, CD206 and CD163), preventing or inhibiting the activation of antigen-presenting cells (e.g., macrophages, dendritic cells, Langerhans cells etc) by an inflammatory stimulus (e.g., exposure to a TLR ligand such as lipopolysaccharide), binding to lipopolysaccharide, preventing binding of lipopolysaccharide to lipopolysaccharide-binding protein, and preventing or inhibiting binding of a TLR ligand (e.g., lipopolysaccharide) to antigen-presenting cells (e.g., macrophages, dendritic cells, Langerhans cells etc), interacting with the plasma membrane of antigen-presenting cells (e.g., macrophages, dendritic cells, Langerhans cells etc) and down-regulating or impairing lysosome function in antigen-presenting cells (e.g., macrophages, dendritic cells, Langerhans cells etc).

In some embodiments, the nucleic acid molecules comprise, consist or consist essentially of a nucleotide sequence selected from:

(a) a nucleotide sequence selected from any one of SEQ ID NO: 23, 25, 27, 29, 31, 33, 35, 37, 39, 41 or 43, or a complement thereof;

(b) a nucleotide sequence that shares at least 50% (and at least 51% to at least 99% and all integer percentages in between) sequence identity with the sequence set forth in any one of SEQ ID NO: 23, 25, 27, 29, 31, 33, 35, 37, 39, 41 or 43, or a complement thereof;

(c) a nucleotide sequence that hybridizes under at least low, medium or high stringency conditions to the sequence set forth in any one of SEQ ID NO: 23, 25, 27, 29, 31, 33, 35, 37, 39, 41 or 43, or a complement thereof, wherein the amino acid sequence encoded by the nucleotide sequence of (a), (b) or (c) has any one or more activities selected from the group consisting of: stimulating or inducing an antigen specific Th2 response, suppressing the development of a Th1 response to an antigen (e.g., parasite antigens or bystander Th1 inducing antigens), stimulating the development in antigen-presenting cells (e.g., macrophages, dendritic cells, Langerhans cells etc) of an alternatively activated phenotype (e.g., increased expression of any one or more of Arg1, Fizz, Ym1, IL-10, TGF-β, CD206 and CD163), preventing or inhibiting the activation of antigen-presenting cells (e.g., macrophages, dendritic cells, Langerhans cells etc) by an inflammatory stimulus (e.g., exposure to a TLR ligand such as lipopolysaccharide), binding to lipopolysaccharide, preventing binding of lipopolysaccharide to lipopolysaccharide-binding protein, and preventing or inhibiting binding of a TLR ligand (e.g., lipopolysaccharide) to antigen-presenting cells (e.g., macrophages, dendritic cells, Langerhans cells etc), interacting with the plasma membrane of antigen-presenting cells (e.g., macrophages, dendritic cells, Langerhans cells etc) and down-regulating or impairing lysosome function in antigen-presenting cells (e.g., macrophages, dendritic cells, Langerhans cells etc).

The present inventors have also determined that certain fragments of FhHDM-1 and its homologues are capable of down-regulating or impairing lysosome function in antigen-presenting cells. Accordingly, in yet another aspect of the present invention, isolated or purified proteinaceous molecules are provided for down-regulating or impairing lysosome function in antigen-presenting cells or for modulating an undesirable or deleterious immune response. These molecules generally comprise, consists or consist essentially of an amino acid sequence represented by formula V:

$$LGJ_1KJ_2J_3J_4VJ_5J_6J_7J_8J_9J_{10}RLJ_{11}J_{12}RJ_{13}J_{14} \qquad (V)$$

wherein:

$J_1$ is selected from acidic amino acid residues such as E or D, or modified forms thereof;

$J_2$ is selected from hydrophobic amino acid residues (e.g., aliphatic amino acid residues such as L or I, or modified forms thereof);

$J_3$ is selected from small amino acid residues such as A, S or T, or modified forms thereof, $J_4$ is selected from any amino acid residue (e.g., acidic amino acid residues such as E or D, or modified forms thereof, or small amino acid residues such as A, or modified forms thereof);

$J_5$ is selected from hydrophobic amino acid residues including aliphatic amino acid residues such as I, L or V, or modified forms thereof;

$J_6$ is selected from any amino acid residue (e.g., basic amino acid residues such as K, or modified forms thereof, or neutral/polar amino acid residues such as Q, or modified forms thereof, or small amino acid residues such as S or T, or modified forms thereof, or hydrophobic amino acid residues including aliphatic amino acid residues such as L or V, or modified forms thereof);

$J_7$ is selected from hydrophobic amino acid residues (e.g., aliphatic amino acid residues such as I or V, or modified forms thereof);

$J_8$ is selected from hydrophobic amino acid residues (e.g., aromatic amino acid residues such as Y or F, or modified forms thereof, or aliphatic amino acid residues such as L or modified forms thereof);

$J_9$ is selected from any amino acid residue (e.g., small amino acid residues such as A or S, or modified forms thereof, or hydrophobic amino acid residues including aliphatic amino acid residues such as L or V, or modified forms thereof);

$J_{10}$ is selected from any amino acid residue (e.g., acidic amino acid residues such as E, or modified forms thereof, or basic amino acid residues such as K, or modified forms thereof, or neutral/polar amino acid residues such as Q or N, or modified forms thereof);

$J_{11}$ is selected from any amino acid residue (e.g., small amino acid residues such as T or P, or modified forms thereof, or neutral/polar amino acid residues such as N, or modified forms thereof);

$J_{12}$ is selected from charged amino acid residues (e.g., basic amino acid residues such as K or R, or modified forms thereof, or acidic amino acid residues such as D, or modified forms thereof);

$J_{13}$ is selected from hydrophobic amino acid residues (e.g., aliphatic amino acid residues such as M or L, or modified forms thereof); and $J_{14}$ is selected from acidic amino acid residues (e.g., E or D, or modified forms thereof).

In some embodiments, the proteinaceous molecules are represented by formula VI:

$$Z_1 LGJ_1 KJ_2 J_3 J_4 VJ_5 J_6 J_7 J_8 J_9 J_{10} RLJ_{11} J_{12} RJ_{13} J_{14} Z_2 \quad\quad (VI)$$

wherein:

$J_1$-$J_{14}$ are as broadly defined above;

$Z_1$ is absent or is selected from at least one of a proteinaceous moiety comprising from about 1 to about 50 amino acid residues (and all integers therebetween), and a protecting moiety (e.g., an N-terminal blocking residue such as pyroglutamate); and $Z_2$ is absent or is a proteinaceous moiety comprising from about 1 to about 50 amino acid residues (and all integers therebetween).

In some embodiments, $Z_1$ comprises, consists, or consists essentially of an amino acid sequence represented by formula VII:

$$B_1 J_{15} \quad\quad (VII)$$

wherein:

$B_1$ is absent or is an N-terminal blocking residue; and $J_{15}$ is selected from any amino acid residue (e.g., neutral/polar amino acid residues such as N, or modified forms thereof, or small amino acid residues such as G, or modified forms thereof, or acid amino acid residues such as D, or modified forms thereof).

In some embodiments, $Z_2$ comprises, consists or consists essentially of an amino acid sequence represented by formula VIII:

$$J_{16} J_{17} J_{18} J_{19} \quad\quad (VIII)$$

wherein:

$J_{16}$ is selected from any amino acid residue (e.g., small amino acid residues such as T or A, or modified forms thereof, or basic amino acid residues such as K, or modified forms thereof, or neutral/polar amino acid residues such as N, or modified forms thereof, or hydrophobic amino acid residues including aliphatic amino acid residues such as M, or modified forms thereof);

$J_{17}$ is absent or is selected from any amino acid residue (e.g., hydrophobic amino acid residues including aromatic amino acid residues such as Y or modified forms thereof, or aliphatic amino acid residues such as C, or modified forms thereof, or basic amino acid residues such as R, or modified forms thereof), wherein $J_{17}$ is present in some embodiments with the proviso that $J_{16}$ is also present;

$J_{18}$ is absent or is selected from any amino acid residue (e.g., hydrophobic amino acid residues including aliphatic amino acid residues such as V or L, or modified forms thereof, or small amino acid residues such as A, or modified forms thereof), wherein $J_{18}$ is present in some embodiments with the proviso that $J_{17}$ is also present; and $J_{19}$ is absent or is selected from any amino acid residue (e.g., small amino acid residues such as G, S or P, or modified forms thereof, or acidic amino acid residues such as E, or modified forms thereof, or basic acid residues such as K, or modified forms thereof, hydrophobic amino acid residues including aliphatic amino acid residues such as L, or modified forms thereof), wherein $J_{19}$ is present in some embodiments with the proviso that $J_{18}$ is also present.

In illustrative examples, the proteinaceous molecules comprise, consist or consist essentially of an amino acid sequence selected from the group consisting of:

(1) an amino acid sequence selected from: LGEKITEVITILLNRLTDRLE [SEQ ID NO:105, another embodiment of a C terminal sequence of FhHDM-1 from *F. hepatica*]; LGEKLADVIKILAERLTKRME [SEQ ID NO:107, another embodiment of a C-terminal sequence of FhHDM-1 homolog OvHDM-1 from *Opisthorchis viverrini*]; LGDKISE VIQILLKRLTDRIE [SEQ ID NO:109, another embodiment of a C-terminal sequence of FhHDM-1 homolog PwHDM-1 from *Paragonimus westermani*]; LGEKIAEVLLIFLQRLNR RLE [SEQ ID NO:111, another embodiment of a C-terminal sequence of FhHDM-1 homolog SjHDM-1 from *Schistosoma japonicum* under GenBank Accession CAX69999.1]; LGEKIAE VLLIFLQRLNRRLE [SEQ ID NO:113, another embodiment of a C-terminal sequence of FhHDM-1 homolog SjHDM-2 from *S japonicum* under GenBank Accession CAX70000.1]; LGEKLAEVLLILLQRLNRRLE [SEQ ID NO:115, another embodiment of a C-terminal sequence of FhHDM-1 homolog SjHDM-3 from *S. japonicum* under GenBank Accession CAX69998.1]; LGEKIADVLVVLLKRLNKRLE [SEQ ID NO:117, another embodiment of a C-terminal sequence of FhHDM-1 homolog SmHDM-1 from *Schistosoma mansoni*]; LGEK LAAVVSIYVKRLNKRLD [SEQ ID NO:119, another embodiment of a C-terminal sequence of FhHDM-1 homolog SmHDM-2 from *S. mansoni* under GenBank Accession CAZ32864.1] or LGEKIAEVVKILLERLTRRLE [SEQ ID NO:121, an embodiment of a FhHDM-1 homolog consensus C-terminal sequence];

(2) an amino acid sequence that shares at least 50% (and at least 51% to at least 99% and all integer percentages in between) sequence similarity or sequence identity with the sequence set forth in any one of SEQ ID NO: 105, 107, 109, 111, 113, 115, 117, 119 or 121; or (3) an amino acid sequence which is encoded by the nucleotide sequence set forth in any one of SEQ ID NO:104 (nucleotide sequence encoding another embodiment of a C-terminal sequence of a FhHDM-1 from *F. hepatica*), SEQ ID NO:106 (nucleotide sequence encoding another embodiment of a C-terminal sequence of FhHDM-1 homolog OvHDM-1 from *O. viverrini*), SEQ ID NO:108 (nucleotide sequence encoding another embodiment of a C-terminal sequence of FhHDM-1 homolog PwHDM-1 from *P. westermani*), SEQ ID NO:110 (nucleotide sequence encoding another embodiment of a C-terminal sequence of FhHDM-1 homolog SjHDM-1 from *S. japonicum* CAX69999.1), SEQ ID NO:112 (nucleotide sequence encoding another embodiment of a C-terminal sequence of FhHDM-1 homolog SjHDM-2 from *S. japonicum* CAX70000.1), SEQ ID NO:114 (nucleotide sequence encoding another embodiment of a C-terminal sequence of FhHDM-1 homolog SjHDM-3 from *S. japonicum* CAX69998.1), SEQ ID NO:116 (nucleotide sequence encoding another embodiment of a C-terminal sequence of FhHDM-1 homolog SmHDM-1 from *S. mansoni*), SEQ ID NO:118 (nucleotide sequence encoding another embodiment of a C-terminal sequence of FhHDM-1 homolog SmHDM-2 from *S. mansoni* CAZ32864.1) or SEQ ID NO:120 (nucleotide sequence encoding an embodiment of a consensus FhHDM-1 homolog C-terminal sequence);

(4) an amino acid sequence which is encoded by a nucleotide sequence that shares at least 50% (and at least 51% to at least 99% and all integer percentages in between) sequence identity with the sequence set forth in any one of SEQ ID NO: 104, 106, 108, 110, 112, 114, 116, 118 or 120, or a complement thereof; or (5) an amino acid sequence which is encoded by a nucleotide sequence that hybridizes under at least low, medium or high stringency conditions to the sequence set forth in any one of SEQ ID NO: 104, 106, 108, 110, 112, 114, 116, 118 or 120, or a complement thereof, wherein the amino acid sequence of (1), (2), (3), (4) or (5) has any one or more activities selected from the group consisting of: stimulating or inducing an antigen specific Th2 response, suppressing the development of a Th1 response to an antigen (e.g., parasite antigens or bystander Th1 inducing antigens), stimulating the development in antigen-presenting cells (e.g., macrophages, dendritic cells, Langerhans cells etc) of an alternatively activated phenotype (e.g., increased expression of any one or more of Arg1, Fizz, Ym1, IL-10, TGF-β, CD206 and CD163), preventing or inhibiting the activation of antigen-presenting cells (e.g., macrophages, dendritic cells Langerhans cells etc) by an inflammatory stimulus (e.g., exposure to a TLR ligand such as lipopolysaccharide), binding to lipopolysaccharide, preventing binding of lipopolysaccharide to lipopolysaccharide-binding protein, preventing or inhibiting binding of a TLR ligand (e.g., lipopolysaccharide) to antigen-presenting cells (e.g., macrophages, dendritic cells, Langerhans cells etc), interacting with the plasma membrane of antigen-presenting cells (e.g., macrophages, dendritic cells, Langerhans cells etc), and down-regulating or impairing lysosome function in antigen-presenting cells (e.g., macrophages, dendritic cells, Langerhans cells etc).

In some embodiments, the proteinaceous molecule comprising, consisting or consisting essentially of an amino acid sequence represented by Formula V or Formula VI is other than one consisting of an amino acid sequence selected from:

[SEQ ID NO: 26]
MRLTVFICLVFVLFVAHAEARPSEETRAKLRESGQKLWTAVVAAARKCA

ERVRQRIEEYLEKDNLGEKIAEVVKILSERLTKRIETYVGE;

[SEQ ID NO: 32]
MKFIVAISLLVLMTLIYTEASPENLRFQLQKTLMDTGEKFKTLSLRLLT

RCRNRVREYFKQDDLGEKIAEVLLIFLQRLNRRLEKYLSRPE;

[SEQ ID NO: 34]
MKFIVAISLLVLMTLIYTEASPENLRFQLQKTLMDTGEKFKTLSLRLLT

RCRNRVREYFKQDDLGEKIAEVLLIFLQRLNRRLEKYLLRPE;

[SEQ ID NO: 36]
MKIIVAISLLVLMTLIYTEASPENSRLLLQKALMDTGEKFKTLSLRLLA

RCRDRVREYFKQDGLGEKLAEVLLILLQRLNRRLEKYLPRSE;
and/or

[SEQ ID NO: 40]
HISIMKLILIFALIISLLLNVTAESQASQKELFTESVKLWKSITELWKR

FEHNCRVKIRKYLEEDNLGEKLAAVVSIYVKRLNKRLDMRLSEDRAE.

In some embodiments, the proteinaceous molecule is other than one consisting of the amino acid sequence SEESREKLRESGGKMVKALRD [SEQ ID NO:45].

In a related aspect, the present invention provides proteinaceous molecules comprising, consisting or consisting essentially of an amino acid sequence selected from the group consisting of (1) to (5), as broadly defined above.

In a related aspect, the present invention provides isolated nucleic acid molecules that comprise, consist or consist essentially of a nucleotide sequence encoding the amino acid sequence of a proteinaceous molecule comprising, consisting or consisting essentially of an amino acid sequence represented by Formula V or Formula VI. In some embodiments, the nucleic acid molecules comprise, consist or consist essentially of a nucleotide sequence selected from:

(a) a nucleotide sequence selected from: CTAGGAGAAAAGATCACTGAAGTGATC ACGATCTTACTGAATCGGCTCACCGATCGCTTGGAG [SEQ ID NO:104; nucleotide sequence encoding another embodiment of a C-terminal sequence of FhHDM-1 from *F. hepatica*]; CTCGGCGAGAAATTAGCTGATGTCATTAAAATCCTGGCCGAGCG CCTAACCAAACGGATGGAG [SEQ ID NO:106; nucleotide sequence encoding another embodiment of a C-terminal sequence of FhHDM-1 homolog OvHDM-1 from *O. viverrini*]; CTCGGAGACAAGATATCGGAAGTGATTCAAATCTTACTGAAAAGACTAACTGACC GAATTGAG [SEQ ID NO:108; nucleotide sequence encoding another embodiment of a C-terminal sequence of FhHDM-1 homolog PwHDM-1 from *P. westermani*]; TTAGGCGAGA AAATAGCAGAGGTTCTACTTATTTTTCTTCAACGTTTGAATAGACGTCTAGAA [SEQ ID NO:110; nucleotide sequence encoding another embodiment of a C-terminal sequence of FhHDM-1 homolog SjHDM-1 from *S. japonicum* CAX69999.1]; TTAGGAGAG AAAATAGCAGAGGTTCTACTTATTTTTCTTCAACGTTTGAATAGACGTCTAGAA [SEQ ID NO:112; nucleotide sequence encoding another embodiment of a C-terminal sequence of FhHDM-1 homolog SjHDM-2 from *S. japonicum* CAX70000.1]; TTAGGCGAG AAGTAGCAGAGGTTCTACTTATTCTTCTTCAACGTTTGAATAGACGTCTAGAA [SEQ ID NO:114; nucleotide sequence encoding another embodiment of a C-terminal sequence of FhHDM-1 homolog SjHDM-3 from *S. japonicum* CAX69998.1]; CTAGGTGAG AAAATAGCAGACGTTTTAGTTGTTTTACTTAAACGTTTGAATAAACGCCTAGAA [SEQ ID NO:116; nucleotide sequence encoding another embodiment of a C-terminal sequence of FhHDM-1 homolog SmHDM-1 from *S. mansoni*]; TTAGGTGAAAAATTAGC CGCTGTTGTAAGCATCTATGTTAAGCGTTTAAACAAGCGTTTAGAT [SEQ ID NO:118; nucleotide sequence encoding another embodiment of a C-terminal sequence of FhHDM-1 homolog SmHDM-2 from *S. mansoni* CAZ32864.1] or CTGGGCGAGAAGATCGCCGAG GTGGTGAAGATCCTGCTGGAGAGACTGACCAGAAGACTGGAG [SEQ ID NO:120; nucleotide sequence encoding a consensus FhHDM-1 homolog C-terminal sequence];

(b) a nucleotide sequence that shares at least 50% (and at least 51% to at least 99% and all integer percentages in between) sequence identity with the sequence set forth in any one of SEQ ID NO: 104, 106, 108, 110, 112, 114, 116, 118 or 120, or a complement thereof;

(c) a nucleotide sequence that hybridizes under at least low, medium or high stringency conditions to the sequence set forth in any one of SEQ ID NO: 104, 106, 108, 110, 112, 114, 116, 118 or 120, or a complement thereof, wherein the amino acid sequence encoded by the nucleotide sequence of (a), (b) or (c) has any one or more activities selected from the group consisting of: stimulating or inducing an antigen specific Th2 response, suppressing the development of a Th1 response to an antigen (e.g., parasite antigens or bystander Th1 inducing antigens), stimulating the development in antigen-presenting cells (e.g., macrophages, dendritic cells, Langerhans cells etc) of an alternatively activated phenotype (e.g., increased expression of any one or more of Arg1, Fizz, Ym1, IL-10, TGF-β, CD206 and CD163), preventing or inhibiting the activation of antigen-presenting cells (e.g., macrophages, dendritic cells, Langerhans cells etc) by an inflammatory stimulus (e.g., exposure to a TLR ligand such as lipopolysaccharide), binding to lipopolysaccharide, preventing binding of lipopolysaccharide to lipopolysaccharide-binding protein, and preventing or inhibiting binding of a TLR ligand (e.g., lipopolysaccharide) to antigen-presenting cells (e.g., macrophages, dendritic cells, Langerhans cells etc), interacting with the plasma membrane of antigen-presenting cells (e.g., macrophages, dendritic cells, Langerhans cells etc) and down-regulating or impairing lysosome function in antigen-presenting cells (e.g., macrophages, dendritic cells, Langerhans cells etc).

Still another aspect of the present invention provides constructs for expressing the nucleic acid molecules broadly described above. These constructs generally comprise a nucleic acid molecule as broadly described above operably connected to a regulatory sequence.

In yet another aspect, the present invention provides compositions for modulating an undesirable or deleterious immune response. These compositions generally comprise a Helminth Defense Molecule (HDM) agent selected from a proteinaceous molecule as broadly described above or a nucleic acid molecule as broadly described above or a construct as broadly described above and a pharmaceutically acceptable carrier or diluent. The compositions may be administered by injection, by topical or mucosal application, by inhalation or via the oral route including modified-release modes of administration, over a period of time and in amounts which are effective to modulate the immune response to the target antigen. In specific embodiments, the composition is administered systemically.

The compositions of the present invention are especially useful for stimulating or inducing a tolerogenic response including the suppression of a future or existing immune response, to a specified antigen or group of antigens. For example, the immune response includes, but is not limited to, a response mediated by immunoglobulin molecules (e.g., IgE) and/or T lymphocytes (e.g., cytotoxic T lymphocytes (CTLs) and T helper lymphocytes). The immune response is typically but not exclusively directed to an antigen selected from a protein antigen, a particulate antigen, an alloantigen, an autoantigen, an allergen, a bacterial antigen, a viral antigen, a parasitic antigen or an immune complex. In illustrative examples of this type, the compositions further include an antigen that corresponds to at least a portion of a target antigen associated with the undesirable or deleterious immune response. Suitably, the antigen that corresponds to at least a portion of the target antigen is selected from allergens, autoantigens and alloantigens. The antigen may be selected from proteinaceous antigens, lipid antigens, glycolipid antigens and carbohydrate antigens. In some embodiments, the antigen is in nucleic acid form (e.g., from which the antigen is expressible).

The present inventors have also found that the activity of the proteinaceous molecules of the invention may be enhanced by polypeptides with peroxiredoxin activity. Accordingly, in some embodiments, the compositions further comprise a polypeptide having peroxiredoxin activity or a nucleic acid molecule from which that polypeptide is expressible. In illustrative examples of this type, the polypeptide comprises an amino acid sequence selected from:

```
                                    [SEQ ID NO: 49]
(1) MLQPNMPAPNFSGQAVVGKEFETISLSDYKGKWVILAFYPLDFTF

VCPTEIIAISDQMEQFAQRNCAVIFCSTDSVYSHLQWTKMDRKVGGIGQ

LNFPLLADKNMSVSRAFGVLDEEQGNTYRGNFLIDPKGVLRQITVNDDP

VGRSVEEALRLLDAFIFHEEHGEVCPANWKPKSKTIVPTPDGSKAYFSS

AN;
```

(2) an amino acid sequence that shares at least 50% (and at least 51% to at least 99% and all integer percentages in between) sequence similarity or sequence identity with the sequence set forth in SEQ ID NO:49;

(3) an amino acid sequence which is encoded by a nucleotide sequence that shares at least 50% (and at least 51% to at least 99% and all integer percentages in between) sequence identity with the sequence set forth in SEQ ID NO:48, or a complement thereof, or (4) an amino acid sequence which is encoded by a nucleotide sequence that hybridizes under at least low, medium or high stringency conditions to the sequence set forth in SEQ ID NO:48, or a complement thereof, wherein the amino acid sequence of (1), (2), (3), (4) or (5) has peroxiredoxin activity (e.g., reduces hydrogen peroxide, peroxynitrite, and organic hydroperoxides).

Non-limiting examples of polypeptides comprising amino acid sequences according to (2), (3), (4) and (5) are set forth in SEQ ID NO: 51, 53, 55, 57, 59, 61, 63, 65, 67, 69, 71, 73, 75, 77, 79, 81, 83, 85, 87, 89, 91, 93, 95, 97, 99, 101 and 103. Representative nucleotide sequences as defined in (3) and (4) are set out in SEQ ID NO: 50, 52, 54, 56, 58, 60, 62, 64, 66, 68, 70, 72, 74, 76, 78, 80, 82, 84, 86, 88, 90, 92, 94, 96, 98, 100 and 102. Suitably, these polypeptides and nucleotide sequences are obtained from parasites including protozoa (e.g., helminths).

In some embodiments, the HDM agent and optionally at least one ancillary agent selected from an antigen that corresponds to a target antigen, a nucleic acid molecule from which an antigen that corresponds to the target antigen is expressible, a polypeptide having peroxiredoxin activity or a nucleic acid molecule from which a polypeptide having peroxiredoxin activity is expressible, are in particulate form. In illustrative examples of this type, the HDM agent is contained in or otherwise associated with a particle (e.g., nanoparticles, microparticles etc). In some embodiments in which the compositions comprise an HDM agent as broadly described above and one or more ancillary agents selected from an antigen that corresponds to a target antigen, a nucleic acid molecule from which an antigen that corresponds to a target antigen is expressible, a polypeptide having peroxiredoxin activity or a nucleic acid molecule from which a polypeptide having peroxiredoxin activity is expressible, the HDM agent and the ancillary agent(s) are contained in the same particle or in different particles. Desirably, the or each particle is capable of being taken up (e.g., endocytosis or phagocytosis) by an immune cell such as, but not limited to, an antigen presenting cell (e.g., a dendritic cell, macrophage or Langerhans cell).

A further aspect of the present invention provides methods for modulating the activity of an antigen-presenting cell (e.g., macrophages, dendritic cells etc). These methods generally comprise contacting the antigen-presenting cell with an HDM agent as broadly described above or with a composition as broadly described above for a time and under conditions sufficient to stimulate the development in the antigen-presenting cell of an alternatively activated phenotype (e.g., increased expression of any one or more of Arg1, Fizz, Ym1, IL-10, TGF-β, CD206 and CD163) or to prevent or inhibit the activation of the antigen-presenting cell by an inflammatory stimulus (e.g., exposure to a TLR ligand such as lipopolysaccharide).

In some embodiments, the methods further comprise contacting the antigen-presenting cell with an antigen of interest or a nucleic acid construct from which the antigen is expressible for a time and under conditions sufficient for the antigen-presenting cell to present the antigen or processed form thereof ("antigen-specific antigen-presenting cell") and to stimulate the development of a Th2 response to the antigen and/or to suppress the development of a Th1 response to the antigen.

Antigen-specific antigen-presenting cells as broadly described above are also useful for producing antigen-specific regulatory lymphocytes" (e.g., Treg cells) for suppression of an immune response to that antigen. Accordingly, in a related aspect, the invention provides methods for producing antigen-specific regulatory lymphocytes that suppress an immune response to a target antigen ("antigen-specific regulatory lymphocytes"), wherein the methods generally comprise contacting a population of regulatory lymphocytes, or their precursors, with an antigen-specific antigen-presenting cell as broadly described above for a time and under conditions sufficient for the antigen-presenting cells to stimulate the development of antigen-specific regulatory lymphocytes.

Another aspect of the present invention provides cellular compositions for modulating an undesirable or deleterious immune response to a target antigen. These compositions generally comprise an antigen-presenting cell (e.g., macrophages, dendritic cells etc) and an HDM agent as broadly described above. In some embodiments, the cellular compositions further comprise at least one ancillary agent as broadly described above. Suitably, the cellular compositions are formulated for systemic administration (e.g., intravenous administration).

In yet another aspect, the present invention provides methods for treating or preventing an undesirable or deleterious immune response in a subject. These methods generally comprise administering to the subject an effective amount of an HDM agent as broadly described above or a composition as broadly described above. In some embodiments, when an HDM agent as broadly described above and one or more ancillary agents as broadly described above, are co-administered, they are concurrently administered to the subject. Typically, the immune response is associated with a condition selected from transplant rejection, graft versus host disease, allergies, parasitic diseases, inflammatory diseases and autoimmune diseases.

Thus, in a related aspect, the present invention provides methods for treating or preventing a condition whose symptoms or etiology are associated with the presence or risk of development of an undesirable or deleterious immune response in a subject. These methods generally comprise administering to the subject an effective amount of an HDM agent as broadly described above, or a composition as broadly described above, or an antigen-presenting cell as broadly described above, or a regulatory lymphocyte as broadly described above. In some embodiments, the subject has a condition as broadly described above whilst in others the subject is at risk of developing such a condition.

In a related aspect, the invention extends to the use of an HDM agent as broadly described above or a composition as broadly described above or an antigen-presenting cell as broadly described above, or a regulatory lymphocyte as broadly described above, for modulating (e.g., suppressing) an immune response, or for treating or preventing an undesirable or deleterious immune response.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a diagrammatic representation showing the results of a PRALINE sequence alignment of the following putatively full-length HDM amino acid sequences: CsHDM-1 from *C. sinensis* under GenBank Accession AAM55183.1 [SEQ ID NO:26]; OvHDM-1 from *O. viverrini* [SEQ ID NO:28]; CsHDM-2 from *C. sinensis* [SEQ ID NO:42]; FhHDM-1 from *F. hepatica* [SEQ ID NO:24]; PwHDM-1 from *P. westermani* [SEQ ID NO:30]; SmHDM-2 from *S. mansoni* under GenBank Accession CAZ32864.1 [SEQ ID NO:40]; SjHDM-1 from *S. japonicum* under GenBank Accession CAX69999.1 [SEQ ID NO: 32]; SjHDM-2 from *S. japonicum* under GenBank Accession CAX70000.1 [SEQ ID NO: 34]; SjHDM-3 from *S. japonicum* under GenBank Accession CAX69998.1 [SEQ ID NO:36]; SjHDM-4 from *S. japonicum* [SEQ ID NO:44]; and SmHDM-1 from *S. mansoni* [SEQ ID NO:38].

FIG. 2 is a diagrammatic representation showing the results of a PRALINE sequence alignment of the following HDM amino acid sequences: C-terminal amino acid sequence of CsHDM-1 from *C. sinensis* under GenBank Accession AAM55183.1 [SEQ ID NO:4]; C-terminal amino acid sequence of OvHDM-1 from *O. viverrini* [SEQ ID NO:6]; C-terminal amino acid sequence of FhHDM-1 from *F. hepatica* [SEQ ID NO:2]; C-terminal amino acid sequence of PwHDM-1 from *P. westermani* [SEQ ID NO: 8]; C-terminal amino acid sequence of SjHDM-1 from *S. japonicum* under GenBank Accession CAX69999.1 [SEQ ID NO: 10]; C-terminal amino acid sequence of SjHDM-2 from *S. japonicum* under GenBank Accession CAX70000.1 [SEQ ID NO:12]; C-terminal amino acid sequence of SjHDM-3 from *S. japonicum* under GenBank Accession CAX69998.1 [SEQ ID NO:14]; C-terminal amino acid sequence of SmHDM-1 from *S. mansoni* [SEQ ID NO:16]; C-terminal amino acid sequence of SmHDM-2 from *S. mansoni* under GenBank Accession CAZ32864.1 [SEQ ID NO:18]; C-terminal amino acid sequence of CsHDM-2 from C. sinensis [SEQ ID NO:20]; and C-terminal amino acid sequence of SjHDM-4 from S. japonicum [SEQ ID NO:22].

FIG. 18 is a diagrammatic representation showing a sequence alignment of various synthetic HDM peptides. The amphipathic helix is shaded in grey as are the mutated residues in peptides nonHP and 2Pro. NonHP is a variant of FhHDM-1 P3 in which the hydrophobic face of the FhHDM-1 amphipathic helix was removed. 2Pro is a variant of FhHDM-1 P3 in which two prolines substitutions were incorporated to disrupt the alpha-helix. Cons_p3 is a consensus peptide corresponding to various FhHDM-1 homologs. All peptides in the alignment were tested for their ability to inhibit the ATPase activity associated with enriched lysosomal membranes (prepared from RAW macrophages). Those with inhibitory activity are shown in bold text.

FIG. 19 is a diagrammatic representation showing the results of a PRALINE sequence alignment of the following HDM amino acid sequences predicted to inhibit the ATPase activity associated with enriched lysosomal membranes: a 21-aa C-terminal sequence of SjHDM-1 from S. japonicum under GenBank Accession CAX69999.1 [SEQ ID NO:111]; a 21-aa C-terminal sequence of SjHDM-2 from S. japonicum under GenBank Accession CAX70000.1 [SEQ ID NO:113]; a 21-aa C-terminal sequence of SjHDM-3 from S. japonicum under GenBank Accession CAX69998.1 [SEQ ID NO:115]; a 21-aa C-terminal sequence SmHDM-1 from S. mansoni [SEQ ID NO:117]; a 21-aa C-terminal sequence of PwHDM-1 from P. westermani [SEQ ID NO:109]; a 21-aa C-terminal sequence of FhHDM-1 from F. hepatica [SEQ ID NO:105]; a 21-aa consensus C-terminal sequence of various FhHDM-1 homologs [SEQ ID NO:121]; a 21-aa C-terminal sequence of OvHDM-1 from O. viverrini [SEQ ID NO:107]; and a 21-aa C-terminal sequence of SmHDM-2 from S. mansoni under GenBank Accession CAZ32864.1 [SEQ ID NO:119].

TABLE 1

Figure 3:
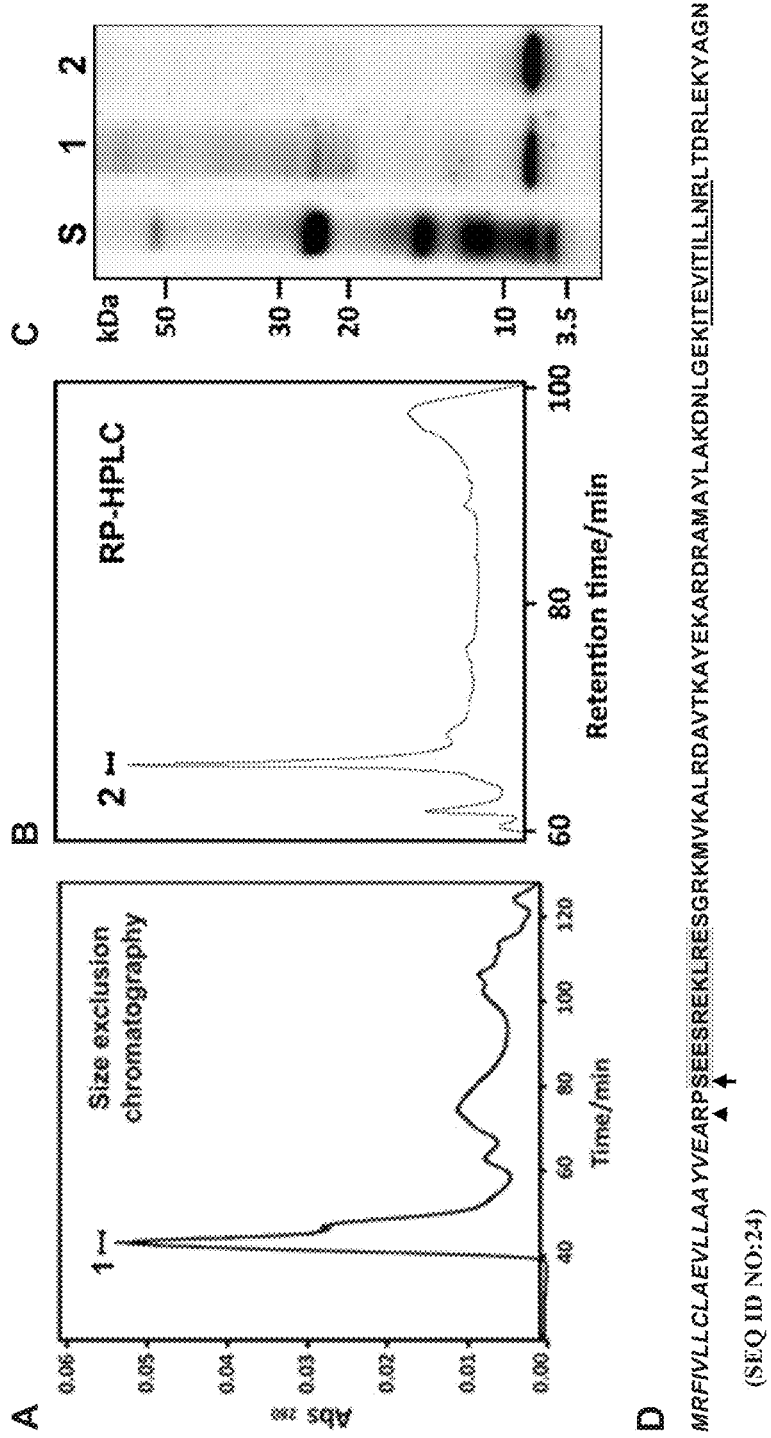
FIG. 3 is a graphical and photographic representation characterizing various physical features of FhHDM-1. Chromatographic traces are shown in panels (A) and (B) depicting the separation of total adult F. hepatica secretory proteins (ES) by size exclusion chromatography (A) and purification of FhHDM-1 to homogeneity using RP-HPLC (B). Panel C shows total ES proteins (S), peak 1 (1) and HPLC-pure native FhHDM-1 (2). Panel D shows the primary sequence of FhHDM-1 (SEQ ID NO:24). The predicted signal peptide for classical secretion is shown in italics and the experimentally determined N-terminal sequence is highlighted. LC-MS/MS analysis of purified FhHDM-1 identified peptide ITEVITILLNR (SEQ ID NO:141), which is underlined.

| BRIEF DESCRIPTION OF THE SEQUENCES | | |
|---|---|---|
| SEQUENCE ID NUMBER | SEQUENCE | LENGTH |
| SEQ ID NO: 1 | Nucleotide sequence from F. hepatica, which encodes a C-terminal sequence of FhHDM-1 | 81 nts |
| SEQ ID NO: 2 | Peptide encoded by SEQ ID NO: 1 | 27 aa |
| SEQ ID NO: 3 | Nucleotide sequence from C. sinensis under GenBank Accession AF281362.1, which encodes a C-terminal sequence of a FhHDM-1 homolog (CsHDM-1) | 81 nts |
| SEQ ID NO: 4 | Peptide encoded by SEQ ID NO: 3 | 27 aa |
| SEQ ID NO: 5 | Nucleotide sequence from O. viverrini, which encodes a C-terminal sequence of a FhHDM-1 homolog (OvHDM-1) | 81 nts |
| SEQ ID NO: 6 | Peptide encoded by SEQ ID NO: 5 | 27 aa |
| SEQ ID NO: 7 | Nucleotide sequence from P. westermani, which encodes a C-terminal sequence of a FhHDM-1 homolog (PwHDM-1) | 81 nts |
| SEQ ID NO: 8 | Peptide encoded by SEQ ID NO: 7 | 27 aa |
| SEQ ID NO: 9 | Nucleotide sequence from S. japonicum under GenBank Accession FN314266.1, which encodes a C-terminal sequence of a FhHDM-1 homolog (SjHDM-1) | 81 nts |
| SEQ ID NO: 10 | Peptide encoded by SEQ ID NO: 9 | 27 aa |
| SEQ ID NO: 11 | Nucleotide sequence from S. japonicum under GenBank Accession FN314267.1, which encodes a C-terminal sequence of a FhHDM-1 homolog (SjHDM-2) | 81 nts |
| SEQ ID NO: 12 | Peptide encoded by SEQ ID NO: 11 | 27 aa |
| SEQ ID NO: 13 | Nucleotide sequence from S. japonicum under GenBank Accession FN314265.1, which encodes a C-terminal sequence of a FhHDM-1 homolog (SjHDM-3) | 81 nts |
| SEQ ID NO: 14 | Peptide encoded by SEQ ID NO: 13 | 27 aa |
| SEQ ID NO: 15 | Nucleotide sequence from S. mansoni, which encodes a C-terminal sequence of a FhHDM-1 homolog (SmHDM-1) | 81 nts |
| SEQ ID NO: 16 | Peptide encoded by SEQ ID NO: 15 | 27 aa |
| SEQ ID NO: 17 | Nucleotide sequence from S. mansoni under GenBank Accession FN357430.1, which encodes a C-terminal sequence of a FhHDM-1 homolog (SmHDM-2) | 81 nts |
| SEQ ID NO: 18 | Peptide encoded by SEQ ID NO: 17 | 27 aa |
| SEQ ID NO: 19 | Nucleotide sequence from C. sinensis, which encodes a C-terminal sequence of a FhHDM-1 homolog (CsHDM-2) | 81 nts |
| SEQ ID NO: 20 | Peptide encoded by SEQ ID NO: 19 | 27 aa |
| SEQ ID NO: 21 | Nucleotide sequence from S. japonicum, which encodes a C-terminal sequence of a FhHDM-1 homolog (SjHDM-4) | 81 nts |

TABLE 1-continued

BRIEF DESCRIPTION OF THE SEQUENCES

| SEQUENCE ID NUMBER | SEQUENCE | LENGTH |
|---|---|---|
| SEQ ID NO: 22 | Peptide encoded by SEQ ID NO: 21 | 27 aa |
| SEQ ID NO: 23 | Nucleotide sequence from *F. hepatica* encoding putatively full-length FhHDM-1 | 270 nts |
| SEQ ID NO: 24 | Polypeptide encoded by SEQ ID NO: 23 | 90 aa |
| SEQ ID NO: 25 | Nucleotide sequence from *C. sinensis* under GenBank Accession AF281362.1, which encodes putatively full-length CsHDM-1 | 270 nts |
| SEQ ID NO: 26 | Polypeptide encoded by SEQ ID NO: 25, whose amino acid sequence is set out under GenBank Accession AAM55183.1 | 90 aa |
| SEQ ID NO: 27 | Nucleotide sequence from *O. viverrini*, which putatively encodes full-length OvHDM-1 | 270 nts |
| SEQ ID NO: 28 | Polypeptide encoded by SEQ ID NO: 27 | 90 aa |
| SEQ ID NO: 29 | Nucleotide sequence from *P. westermani*, which encodes putatively full-length PwHDM-1 | 264 nts |
| SEQ ID NO: 30 | Polypeptide encoded by SEQ ID NO: 29 | 88 aa |
| SEQ ID NO: 31 | Nucleotide sequence from *S. japonicum* under GenBank Accession FN314266.1, which encodes putatively full-length SjHDM-1 | 273 nts |
| SEQ ID NO: 32 | Polypeptide encoded by SEQ ID NO: 31, whose amino acid sequence is set out under GenBank Accession CAX69999.1 | 91 aa |
| SEQ ID NO: 33 | Nucleotide sequence from *S. japonicum* under GenBank Accession FN314267.1, which encodes putatively full-length SjHDM-2 | 273 nts |
| SEQ ID NO: 34 | Polypeptide encoded by SEQ ID NO: 33, whose amino acid sequence is set out under GenBank Accession CAX70000.1 | 91 aa |
| SEQ ID NO: 35 | Nucleotide sequence from *S. japonicum* under GenBank Accession FN314265.1, which encodes putatively full-length SjHDM-3 | 273 nts |
| SEQ ID NO: 36 | Polypeptide encoded by SEQ ID NO: 35, whose amino acid sequence is set out under GenBank Accession CAX69998.1 | 91 aa |
| SEQ ID NO: 37 | Nucleotide sequence from *S. mansoni*, which encodes putatively full-length SmHDM-1 | 258 nts |
| SEQ ID NO: 38 | Polypeptide encoded by SEQ ID NO: 37 | 86 aa |
| SEQ ID NO: 39 | Nucleotide sequence from *S. mansoni* under GenBank Accession FN357430.1, which encodes putatively full-length SmHDM-2 | 291 nts |
| SEQ ID NO: 40 | Polypeptide encoded by SEQ ID NO: 39, whose amino acid sequence is set out under GenBank Accession CAZ32864.1 | 96 aa |
| SEQ ID NO: 41 | Nucleotide sequence from *C. sinensis*, which encodes putatively CsHDM-2 | 270 nts |
| SEQ ID NO: 42 | Polypeptide encoded by SEQ ID NO: 41 | 90 aa |
| SEQ ID NO: 43 | Nucleotide sequence from *S. japonicum*, which encodes putatively full-length SjHDM-4 | 378 nts |
| SEQ ID NO: 44 | Polypeptide encoded by SEQ ID NO: 43 | 126 aa |
| SEQ ID NO: 45 | Partial amino acid sequence disclosed in McGonigle et al. (1995, *Parasitology* 111 (Pt 2): 209-215) | 21 aa |
| SEQ ID NO: 46 | FhHDM-1 peptide 3, comprising the complete amphipathic helix contained in FhHDM-1 | 34 aa |
| SEQ ID NO: 47 | FhHDM-1 peptide 1 comprising a truncated amphipathic helix contained in FhHDM-1 | 30 aa |
| SEQ ID NO: 48 | Nucleotide sequence from *F. hepatica* under GenBank Accession U88577, which encodes a polypeptide with peroxiredoxin activity | 585 nts |
| SEQ ID NO: 49 | Polypeptide encoded by SEQ ID NO: 48, whose amino acid sequence is set out under GenBank Accession AAB71727.1 | 194 aa |
| SEQ ID NO: 50 | Nucleotide sequence from *F. gigantica* under GenBank Accession EU372005, which encodes a polypeptide with peroxiredoxin activity | 657 nts |
| SEQ ID NO: 51 | Polypeptide encoded by SEQ ID NO: 50, whose amino acid sequence is set out under GenBank Accession ABY85785.1 | 218 aa |
| SEQ ID NO: 52 | Nucleotide sequence from *F. gigantica* under GenBank Accession GQ845012, which encodes a polypeptide with peroxiredoxin activity | 585 nts |
| SEQ ID NO: 53 | Polypeptide encoded by SEQ ID NO: 52, whose amino acid sequence is set out under GenBank Accession ACV91889.1 | 194 aa |

TABLE 1-continued

BRIEF DESCRIPTION OF THE SEQUENCES

| SEQUENCE ID NUMBER | SEQUENCE | LENGTH |
|---|---|---|
| SEQ ID NO: 54 | Nucleotide sequence from *F. hepatica* under GenBank Accession AJ004822, which encodes a polypeptide with peroxiredoxin activity | 585 nts |
| SEQ ID NO: 55 | Polypeptide encoded by SEQ ID NO: 54, whose amino acid sequence is set out under GenBank Accession CAA06158.1 | 194 aa |
| SEQ ID NO: 56 | Nucleotide sequence from *C. sinensis* under GenBank Accession HQ216221, which encodes a polypeptide with peroxiredoxin activity | 588 nts |
| SEQ ID NO: 57 | Polypeptide encoded by SEQ ID NO: 56, whose amino acid sequence is set out under GenBank Accession ADN65138.1 | 195 aa |
| SEQ ID NO: 58 | Nucleotide sequence from *O. viverrini* under GenBank Accession EU376958, which encodes a polypeptide with peroxiredoxin activity | 639 nts |
| SEQ ID NO: 59 | Polypeptide encoded by SEQ ID NO: 58, whose amino acid sequence is set out under GenBank Accession ACB13822.1 | 212 aa |
| SEQ ID NO: 60 | Nucleotide sequence from *S. japonicum* under GenBank Accession FN315053, which encodes a polypeptide with peroxiredoxin activity | 585 nts |
| SEQ ID NO: 61 | Polypeptide encoded by SEQ ID NO: 60, whose amino acid sequence is set out under GenBank Accession CAX70785.1 | 194 aa |
| SEQ ID NO: 62 | Nucleotide sequence from *S. mansoni* under GenBank Accession XM_002577840, which encodes a polypeptide with peroxiredoxin activity | 585 nts |
| SEQ ID NO: 63 | Polypeptide encoded by SEQ ID NO: 62, whose amino acid sequence is set out under GenBank Accession XP_002577886.1 | 194 aa |
| SEQ ID NO: 64 | Nucleotide sequence from *S. mansoni* under GenBank Accession XM_002577526, which encodes a polypeptide with peroxiredoxin activity | 585 nts |
| SEQ ID NO: 65 | Polypeptide encoded by SEQ ID NO: 64, whose amino acid sequence is set out under GenBank Accession XP_002577572.1 | 194 aa |
| SEQ ID NO: 66 | Nucleotide sequence from *Loa loa* under GenBank Accession ADBU01000127, which encodes a polypeptide with peroxiredoxin activity | 600 nts |
| SEQ ID NO: 67 | Polypeptide encoded by SEQ ID NO: 66, whose amino acid sequence is set out under GenBank Accession EFO27148.1 | 199 aa |
| SEQ ID NO: 68 | Nucleotide sequence from *Dirofilaria immitis* under GenBank Accession AF004167, which encodes a polypeptide with peroxiredoxin activity | 600 nts |
| SEQ ID NO: 69 | Polypeptide encoded by SEQ ID NO: 68, whose amino acid sequence is set out under GenBank Accession AAC38831.1.1 | 199 aa |
| SEQ ID NO: 70 | Nucleotide sequence from *Ixodes scapularis* under GenBank Accession DS886467, which encodes a polypeptide with peroxiredoxin activity | 666 nts |
| SEQ ID NO: 71 | Polypeptide encoded by SEQ ID NO: 70, whose amino acid sequence is set out under GenBank Accession EEC15288.1 | 221 aa |
| SEQ ID NO: 72 | Nucleotide sequence from *Cristaria plicata* under GenBank Accession HQ166838, which encodes a polypeptide with peroxiredoxin activity | 591 nts |
| SEQ ID NO: 73 | Polypeptide encoded by SEQ ID NO: 72, whose amino acid sequence is set out under GenBank Accession ADM88874.1 | 196 aa |
| SEQ ID NO: 74 | Nucleotide sequence from *Acanthocheilonema viteae* under GenBank Accession AY080902, which encodes a polypeptide with peroxiredoxin activity | 744 nts |
| SEQ ID NO: 75 | Polypeptide encoded by SEQ ID NO: 74, whose amino acid sequence is set out under GenBank Accession AAL91102.1 | 247 aa |
| SEQ ID NO: 76 | Nucleotide sequence from *Onchocerca ochengi* under GenBank Accession AF068946, which encodes a polypeptide with peroxiredoxin activity | 600 nts |
| SEQ ID NO: 77 | Polypeptide encoded by SEQ ID NO: 76, whose amino acid sequence is set out under GenBank Accession AAC77922.1 | 199 aa |
| SEQ ID NO: 78 | Nucleotide sequence from *Dirofilaria immitis* under GenBank Accession AF001007, which encodes a polypeptide with peroxiredoxin activity | 600 nts |

TABLE 1-continued

BRIEF DESCRIPTION OF THE SEQUENCES

| SEQUENCE ID NUMBER | SEQUENCE | LENGTH |
|---|---|---|
| SEQ ID NO: 79 | Polypeptide encoded by SEQ ID NO: 78, whose amino acid sequence is set out under GenBank Accession AAB68798.1 | 199 aa |
| SEQ ID NO: 80 | Nucleotide sequence from *Ornithodoros parkeri* under GenBank Accession EF633887, which encodes a polypeptide with peroxiredoxin activity | 588 nts |
| SEQ ID NO: 81 | Polypeptide encoded by SEQ ID NO: 80, whose amino acid sequence is set out under GenBank Accession ABR23404.1 | 195 aa |
| SEQ ID NO: 82 | Nucleotide sequence from *Leishmania major* under GenBank Accession AF069386, which encodes a polypeptide with peroxiredoxin activity | 600 nts |
| SEQ ID NO: 83 | Polypeptide encoded by SEQ ID NO: 82, whose amino acid sequence is set out under GenBank Accession AAC79432.1 | 199 aa |
| SEQ ID NO: 84 | Nucleotide sequence from *Onchocerca volvulus* under GenBank Accession AF043415, which encodes a polypeptide with peroxiredoxin activity | 600 nts |
| SEQ ID NO: 85 | Polypeptide encoded by SEQ ID NO: 84, whose amino acid sequence is set out under GenBank Accession AAC32810.1 | 199 aa |
| SEQ ID NO: 86 | Nucleotide sequence from *Litomosoides sigmodontis* under GenBank Accession AF105258, which encodes a polypeptide with peroxiredoxin activity | 582 nts |
| SEQ ID NO: 87 | Polypeptide encoded by SEQ ID NO: 86, whose amino acid sequence is set out under GenBank Accession AAG10102.1 | 193 aa |
| SEQ ID NO: 88 | Nucleotide sequence from *Branchiostoma belcheri tsingtaunese* under GenBank Accession AY737279, which encodes a polypeptide with peroxiredoxin activity | 597 nts |
| SEQ ID NO: 89 | Polypeptide encoded by SEQ ID NO: 88, whose amino acid sequence is set out under GenBank Accession AAU84951.1 | 198 aa |
| SEQ ID NO: 90 | Nucleotide sequence from *Rhipicephalus sanguineus* under GenBank Accession EZ406230, which encodes a polypeptide with peroxiredoxin activity | 597 nts |
| SEQ ID NO: 91 | Polypeptide encoded by SEQ ID NO: 90, whose amino acid sequence is set out under GenBank Accession ACX54025.1 | 198 aa |
| SEQ ID NO: 92 | Nucleotide sequence from *Leishmania tropica* under GenBank Accession DQ071683, which encodes a polypeptide with peroxiredoxin activity | 600 nts |
| SEQ ID NO: 93 | Polypeptide encoded by SEQ ID NO: 92, whose amino acid sequence is set out under GenBank Accession AAZ23601.1 | 199 aa |
| SEQ ID NO: 94 | Nucleotide sequence from *Meloidogyne incognita* under GenBank Accession GU144285, which encodes a polypeptide with peroxiredoxin activity | 594 nts |
| SEQ ID NO: 95 | Polypeptide encoded by SEQ ID NO: 94, whose amino acid sequence is set out under GenBank Accession ACZ67203.1 | 197 aa |
| SEQ ID NO: 96 | Nucleotide sequence from *Globodera rostochiensis* under GenBank Accession AJ243736, which encodes a polypeptide with peroxiredoxin activity | 600 nts |
| SEQ ID NO: 97 | Polypeptide encoded by SEQ ID NO: 96, whose amino acid sequence is set out under GenBank Accession CAB48391.1 | 199 aa |
| SEQ ID NO: 98 | Nucleotide sequence from *Leishmania aethiopica* under GenBank Accession DQ071684, which encodes a polypeptide with peroxiredoxin activity | 600 nts |
| SEQ ID NO: 99 | Polypeptide encoded by SEQ ID NO: 98, whose amino acid sequence is set out under GenBank Accession AAZ23602.1 | 199 aa |
| SEQ ID NO: 100 | Nucleotide sequence from *Ostertagia ostertagi* under GenBank Accession AJ427630, which encodes a polypeptide with peroxiredoxin activity | 583 nts |
| SEQ ID NO: 101 | Polypeptide encoded by SEQ ID NO: 100, whose amino acid sequence is set out under GenBank Accession CAD20737.1 | 193 aa |
| SEQ ID NO: 102 | Nucleotide sequence from *Ixodes scapularis* under GenBank Accession XM_002400474, which encodes a polypeptide with peroxiredoxin activity | 702 nts |
| SEQ ID NO: 103 | Polypeptide encoded by SEQ ID NO: 102, whose amino acid sequence is set out under GenBank Accession XP_002400518.1 | 233 aa |

TABLE 1-continued

BRIEF DESCRIPTION OF THE SEQUENCES

| SEQUENCE ID NUMBER | SEQUENCE | LENGTH |
|---|---|---|
| SEQ ID NO: 104 | Nucleotide sequence encoding another embodiment of a C terminal sequence of FhHDM-1 from *F. hepatica* | 63 nts |
| SEQ ID NO: 105 | Peptide encoded by SEQ ID NO: 104 | 21 aa |
| SEQ ID NO: 106 | Nucleotide sequence encoding another embodiment of a C terminal sequence of an FhHDM-1 homolog OvHDM-1 from *O. viverrini* | 63 nts |
| SEQ ID NO: 107 | Peptide encoded by SEQ ID NO: 106 | 21 aa |
| SEQ ID NO: 108 | Nucleotide sequence encoding another embodiment of a C terminal sequence of FhHDM-1 homolog PwHDM-1 from *P. westermani* | 63 nts |
| SEQ ID NO: 109 | Peptide encoded by SEQ ID NO: 108 | 21 aa |
| SEQ ID NO: 110 | Nucleotide sequence encoding another embodiment of a C terminal sequence of FhHDM-1 homolog SjHDM-1 from *S. japonicum* CAX69999.1 | 63 nts |
| SEQ ID NO: 111 | Peptide encoded by SEQ ID NO: 110 | 21 aa |
| SEQ ID NO: 112 | Nucleotide sequence encoding another embodiment of a C terminal sequence of FhHDM-1 homolog SjHDM-2 from *S. japonicum* CAX70000.1 | 63 nts |
| SEQ ID NO: 113 | Peptide encoded by SEQ ID NO: 112 | 21 aa |
| SEQ ID NO: 114 | Nucleotide sequence encoding another embodiment of a C terminal sequence of FhHDM-1 homolog SjHDM-3 from *S. japonicum* CAX69998.1 | 63 nts |
| SEQ ID NO: 115 | Peptide encoded by SEQ ID NO: 114 | 21 aa |
| SEQ ID NO: 116 | Nucleotide sequence encoding another embodiment of a C terminal sequence of FhHDM-1 homolog SmHDM-1 from *S. mansoni* | 63 nts |
| SEQ ID NO: 117 | Peptide encoded by SEQ ID NO: 116 | 21 aa |
| SEQ ID NO: 118 | Nucleotide sequence encoding another embodiment of a C terminal sequence of FhHDM-1 homolog SmHDM-2 from *S. mansoni* CAZ32864.1 | 63 nts |
| SEQ ID NO: 119 | Peptide encoded by SEQ ID NO: 118 | 21 aa |
| SEQ ID NO: 120 | Nucleotide sequence encoding a consensus FhHDM-1 homolog C terminal sequence | 63 nts |
| SEQ ID NO: 121 | Peptide encoded by SEQ ID NO: 120 | 21 aa |
| SEQ ID NO: 122 | FhHDM-1 peptide 2, comprising a shorter amphipathic helix than the amphipathic helix contained in FhHDM-1 peptide 3 | 27 aa |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much 15, 14, 13, 12, 11, 10, 9, 8, 7, 6, 5, 4, 3, 2 or 1% to a reference quantity, level, value, number, frequency, percentage, dimension, size, amount, weight or length.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and preferably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

By "antigen" is meant all, or part of, a molecule (e.g., a protein, peptide, or other molecule or macromolecule) capable of being bound by an antibody or a T cell receptor (TCR) if presented by MHC molecules An antigen may be additionally capable of being recognized by the immune system and/or being capable of stimulating or inducing a humoral immune response and/or cellular immune response leading to the activation of B- and/or T-lymphocytes. An antigen may have one or more epitopes (B- and T-epitopes). Antigens as used herein may also be mixtures of several individual antigens.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

The term "autoantigen" refers to a constituent of self that binds an autoantibody or that induces a cellular response.

By "autologous" is meant something (e.g., cells, tissues etc) derived from the same organism.

The term "allogeneic" as used herein refers to cells, tissues, organisms etc that are of different genetic constitution.

By "alloantigen" is meant an antigen found only in some members of a species, such as blood group antigens. By contrast a "xenoantigen" refers to an antigen that is present in members of one species but not members of another. Correspondingly, an "allograft" is a graft between members of the same species and a "xenograft" is a graft between members of a different species.

The term "biologically active fragment," as applied to fragments of a reference or full-length polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99% of the activity of a reference sequence. Suitably, the biologically-active fragment has no less than about 1%, 10%, 25% 50% of an activity of the full-length polypeptide from which it is derived. Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 250, 300, 400, 500, 600, 700, 800, 900, 1000, 1500, 2000 nucleotides or residues in length, which comprise or encode an activity of a reference polynucleotide or polypeptide. Representative biologically active fragments generally participate in an interaction, e.g., an intramolecular or an inter-molecular interaction. An inter-molecular interaction can be a specific binding interaction or an enzymatic interaction (e.g., the interaction can be transient and a covalent bond is formed or broken). Biologically active fragments of a full-length HDM polypeptide include peptides comprising amino acid sequences sufficiently similar to or derived from the amino acid sequences of a (putative) full-length HDM polypeptide. For example, biologically active portions of a HDM proteinaceous molecule (e.g., peptide or polypeptide) include peptides or polypeptides comprising amino acid sequences with sufficient similarity or identity to or derived from the amino acid sequence of the HDM proteinaceous molecules of the present invention, as for example set forth in SEQ ID NO: 2, 4, 6, 8, 10, 12, 14, 16, 18, 20, 22, 24, 26, 28, 30, 32, 34, 36, 38, 40, 42, 44, 105, 107, 109, 111, 113, 115, 117, 119, 121 or 122 and comprise at least one domain or motif with at least one activity selected from stimulating or inducing an antigen-specific Th2 response, suppressing the development of an antigen-specific Th1 response, stimulating the development in antigen-presenting cells of an alternatively activated phenotype, preventing or inhibiting the activation of antigen-presenting cells by an inflammatory stimulus, binding to lipopolysaccharide, preventing or inhibiting binding of lipopolysaccharide to lipopolysaccharide-binding protein, preventing or inhibiting binding of a TLR ligand (e.g., lipopolysaccharide) to an antigen-presenting cell (e.g., macrophages, dendritic cells, Langerhans cells etc), interacting with the plasma membrane of antigen-presenting cells (e.g., macrophages, dendritic cells, Langerhans cells etc) and down-regulating or impairing lysosome function in antigen-presenting cells (e.g., macrophages, dendritic cells, Langerhans cells etc), and the like.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "corresponds to" or "corresponding to" is meant an antigen which encodes an amino acid sequence that displays substantial sequence similarity or identity to an amino acid sequence in a target antigen. In general the antigen will display at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to at least a portion of the target antigen.

By "effective amount," in the context of modulating an immune response or treating or preventing a disease or condition, is meant the administration of that amount of composition to an individual in need thereof, either in a single dose or as part of a series, that is effective for that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The terms "helminth defense molecules," "HDMs" and the like, as used herein encompasses, without limitation, helminth proteinaceous molecules (e.g., peptides, polypeptides etc) having an amino acid sequence that shares at least 50% (and at least 51% to at least 99% and all integer percentages in between) sequence identity or similarity with the sequence set forth in any one of SEQ ID NOs: 2, 4, 6, 8, 10, 12, 14, 16, 18, 20, 22, 24, 26, 28, 30, 32, 34, 36, 38, 40, 42 or 44, as well as wild type (naturally-occurring) derived from helminths including, but not limited to, *Anoplocephala, Ancylostoma, Ascaris, Baylisascaris, Brugia, Bunostomum, Capillaria, Chabertia, Clonorchis, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Gnathostoma, Habronema, Haemonchus, Hymenolepis, Metastrongylus, Moniezia, Necator, Nematodirus, Nippostrongylus, Oesophagostomum, Onchocerca, Opisthorchis, Ostertagia, Oxyuris, Parascaris, Paragonimus, Schistosoma, Strongylus, Taenia, Toxocara, Trichinella, Strongyloides, Toxascaris, Trichinella, Trichuris, Trichobilharzia, Trichostrongylus, Triodontophorus, Uncinaria* and *Wuchereria*. It further encompasses natural allelic variation of helminth defense molecules that may exist and occur from one organism to another. Also, degree and location of glycosylation or other post-translation modifications may vary depending on the chosen host and the nature of the hosts cellular environment. The term "helminth defense molecules" is also intended to encompass HDM polypeptides in their precursor form, as well as those that have been processed to yield their respective bioactive forms. It further encompasses HDM polypeptides and peptides that have either been chemically modified relative to a reference or naturally-occurring HDM and/or contain one or more amino acid sequence alterations relative to a reference or naturally-occurring HDM and/or contain truncated amino acid sequences relative to a reference or naturally-occurring full-length or precursor HDM. Alternatively, or in addition, HDMs may exhibit different properties relative to a reference or naturally-occurring HDM, including stability, altered specific activity selected from stimulating or inducing an antigen-specific Th2 response, suppressing the development of an antigen-specific Th1 response, stimulating the development in antigen-presenting cells of an alternatively activated phenotype, preventing or inhibiting the activation of antigen-presenting cells by an inflammatory stimulus, binding to lipopolysaccharide, preventing or inhibiting binding of lipopolysaccharide to lipopolysaccharide-binding protein, preventing or inhibiting binding of a TLR ligand (e.g., lipopolysaccharide) to antigen-presenting cells (e.g., macrophages, dendritic cells, Langerhans cells etc), interacting with the plasma membrane of antigen-presenting cells (e.g., macrophages, dendritic cells, Langerhans cells etc) and down-regulating or impairing lysosome function in antigen-presenting cells (e.g., macrophages, dendritic cells, Langerhans cells etc), and the like. The term "HDM" also encompasses proteinaceous molecules with a slightly modified amino acid sequence, for instance, peptides and polypeptides having a modified N-terminal end including N-terminal amino acid deletions or additions, and/or peptides and polypeptides that have been chemically modified relative to a reference or naturally-occurring HDM. HDMs also encompass proteinaceous molecules exhibiting substantially the same or better bioactivity than a reference or naturally-occurring HDM, or, alternatively, exhibiting substantially modified or reduced bioactivity relative to a reference or naturally-occurring HDM. They also include, without limitation, peptides and polypeptides having an amino acid sequence that differs from the sequence of a reference or naturally-occurring HDM by insertion, deletion, or substitution of one or more amino acids and in illustrative examples, encompass proteinaceous molecules that exhibit at least about 10%, 20%, 30%, 40%, 50%, 60%, 70%, 80%, 90%, 100%, 110%, 120%, and 130% of the specific activity of a reference or naturally-occurring HDM that has been produced in the same cell. HDM peptides and polypeptides having substantially the same or improved biological activity relative to a reference or naturally-occurring HDM peptide or polypeptide, encompass molecules that exhibit at least about 10%, 20%, 30%, 40%, 50%, 60%, 70%, 80%, 90%, 100%, 110%, 120%, and 130% of the specific biological activity of the reference or naturally-occurring HDM peptide or polypeptide that has been produced in the same cell type.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

Reference herein to "immuno-interactive" includes reference to any interaction, reaction, or other form of association between molecules and in particular where one of the molecules is, or mimics, a component of the immune system.

By "isolated" is meant material that is substantially or essentially free from components that normally accompany it in its native state. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, i.e., it is not associated with in vivo substances. Similarly, an "isolated" or "purified" proteinaceous molecule (e.g., peptide, polypeptide, protein etc) is substantially free of cellular material or other contaminating molecules from the cell or tissue source from which the proteinaceous molecule is derived, or substantially free from chemical precursors or other chemicals when chemically synthesized. "Substantially free" means that a preparation of HDM proteinaceous molecule is at least 10, 15, 20, 25, 30, 35, 40, 45, 50, 55, 60, 65, 70, 75, 80, 85, 90, 91, 92, 93, 94, 95, 96, 97, 98 or 99% pure. In a preferred embodiment, the preparation of HDM proteinaceous molecule has less than about 30, 25, 20, 15, 10, 9, 8, 7, 6, 5, 4, 3, 2 or 1% (by dry weight), of non-HDMs (also referred to herein as a "contaminating molecules"), or of chemical precursors or non-HDM chemicals. When the HDM is recombinantly produced, it is also desirably substantially free of culture medium, i.e., culture medium represents less than about 20, 15, 10, 5, 4, 3, 2, 1% of the volume of the HDM preparation. The invention includes isolated or purified preparations of at least 0.01, 0.1, 1.0, and 10 milligrams in dry weight.

By "modulating" is meant increasing or decreasing, either directly or indirectly, the immune response of an individual. In certain embodiments, "modulation" or "modulating" means that a desired/selected response (e.g., a tolerogenic or anergic response) is more efficient (e.g., at least 10%, 20%, 30%, 40%, 50%, 60% or more), more rapid (e.g., at least 10%, 20%, 30%, 40%, 50%, 60% or more), greater in magnitude (e.g., at least 10%, 20%, 30%, 40%, 50%, 60% or more), and/or more easily induced (e.g., at least 10%, 20%, 30%, 40%, 50%, 60% or more) than in the absence of an HDM agent.

By "obtained from" is meant that a sample such as, for example, a polynucleotide extract or polypeptide extract is isolated from, or derived from, a particular source.

The term "operably connected" or "operably linked" as used herein means placing a structural gene under the regulatory control of a regulatory element including but not limited to a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e. the genes from which it is derived.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca* mulatta)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc), marine mammals (e.g., dolphins, whales), reptiles (snakes, frogs, lizards etc), and fish. A preferred subject is a human in need of stimulating or inducing an antigen-specific Th2 response, suppressing the development of an antigen-specific Th1 response, stimulating the development in antigen-presenting cells of an alternatively activated phenotype, preventing or inhibiting the activation of antigen-presenting cells by an inflammatory stimulus, binding to lipopolysaccharide, preventing or inhibiting binding of lipopolysaccharide to lipopolysaccharide-binding protein, preventing or inhibiting binding of toll-like receptor (TLR) ligands (e.g., lipopolysaccharide) to antigen-presenting cells, interacting with the plasma membrane of antigen-presenting cells, and down-regulating or impairing lysosome function in antigen-presenting cells, or in need of treatment or prophylaxis of an undesirable or deleterious immune response, including autoimmune diseases, allergies and transplantation associated diseases, which are often associated with the presence or aberrant expression of an antigen of interest. However, it will be understood that the aforementioned terms do not imply that symptoms are present.

By "pharmaceutically acceptable carrier" is meant a solid or liquid filler, diluent or encapsulating substance that can be safely used in topical or systemic administration to an animal, preferably a mammal, including humans.

The term "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide," "peptide," "protein" and "proteinaceous molecule" are used interchangeably herein to refer to molecules comprising or consisting of a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The terms "peptide variant" and "polypeptide variant" and the like refer to peptides and polypeptides that are distinguished from a reference peptide or polypeptide by the addition, deletion or substitution of at least one amino acid residue. In certain embodiments, a peptide or polypeptide variant is distinguished from a reference peptide or polypeptide by one or more substitutions, which may be conservative or non-conservative. In certain embodiments, the peptide or polypeptide variant comprises conservative substitutions and, in this regard, it is well understood in the art that some amino acids may be changed to others with broadly similar properties without changing the nature of the activity of the peptide or polypeptide. Peptide and polypeptide variants also encompass peptides and polypeptides in which one or more amino acids have been added or deleted, or replaced with different amino acid residues.

By "primer" is meant an oligonucleotide which, when paired with a strand of DNA, is capable of initiating the synthesis of a primer extension product in the presence of a suitable polymerizing agent. The primer is preferably single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotide residues to several kilobases or more. Primers can be selected to be "substantially complementary" to the sequence on the template to which it is designed to hybridize and serve as a site for the initiation of synthesis. By "substantially complementary", it is meant that the primer is sufficiently complementary to hybridize with a target polynucleotide. Preferably, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridization conditions. Probes can be labeled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

By "regulatory element" or "regulatory sequence" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

By "regulatory lymphocyte" is meant a lymphocyte that is involved in regulating or suppressing responses and actions of other cells, especially of other immune cells such as B lymphocytes and T helper lymphocytes.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. The present invention contemplates the use in the methods and systems of the present invention of full-length HDM polypeptides as well as their biologically active fragments. Typically, biologically active fragments of a full-length HDM polypeptide may participate in an interaction, for example, an intra-molecular or an intermolecular interaction.

"Similarity" refers to the percentage number of amino acids that are identical or constitute conservative substitutions as defined in Tables 2 and 3 infra. Similarity may be determined using sequence comparison programs such as GAP (Deveraux et al. 1984, *Nucleic Acids Research* 12: 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence," "comparison window", "sequence identity," "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

"Stringency" as used herein, refers to the temperature and ionic strength conditions, and presence or absence of certain organic solvents, during hybridization and washing procedures. The higher the stringency, the higher will be the degree of complementarity between immobilized target nucleotide sequences and the labeled probe polynucleotide sequences that remain hybridized to the target after washing. The term "high stringency" refers to temperature and ionic conditions under which only nucleotide sequences having a high frequency of complementary bases will hybridize. The stringency required is nucleotide sequence dependent and depends upon the various components present during hybridization. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridizes to a complementary probe.

By "suppression," "suppressing" and the like is meant any attenuation or regulation of an immune response, including B lymphocyte and T lymphocyte immune responses, to an antigen or group of antigens. In some embodiments, the attenuation is mediated at least in part by suppressor T lymphocytes (e.g., $CD4^+CD25^+$ regulatory T lymphocytes).

The term "Th1" refers to a subclass of T helper cells that produce inter alia IL-1, IL-2, IL-8, IL-12, IL-18, interferon-gamma (IFN-γ), tumor necrosis factor-alpha (TNF-α), and which elicit inflammatory reactions associated with a cellular, i.e., non-immunoglobulin, response to a challenge. Thus, a Th1 cytokine response or T1 cytokine response encompasses an immune response whose most prominent feature comprises abundant $CD4^+$ helper T cell activation that is associated with increased levels of T1 cytokines (e.g., IL-1, IL-2, IL-8, IL-12, IL-18, IFN-γ, TNF-α, etc.) relative to these cytokine amounts in the absence of activation. A T1 cytokine response can also refer to the production of T1 cytokines from other white blood cells and nonwhite blood cells. A Th1 cytokine response can include abundant CD8 cytotoxic T lymphocyte activity including T1 cytokine production, referred to as Tc1. A Th1 response is typically promoted by CD4 "Th1" T-helper cells however a Th1 response can include CD8 Tc1 T cytotoxic cells.

The term "Th2" refers to a subclass of T helper cells that produce inter alia cytokines, such as IL-4, IL-5, IL-6, IL-10, IL-13, IL-15, etc which are associated with an immunoglobulin (humoral) response to an immune challenge. Thus, a Th2 cytokine response or T2 cytokine response encompasses an immune response whose most prominent feature comprises abundant CD4 helper T cell activation that is associated with increased levels of T2 cytokines (e.g. IL-4, IL-5, IL-6, IL-10, IL-13, IL-15, etc) relative to these cytokine amounts in the absence of activation. A T2 cytokine response can also refer to the production of T2 cytokines from other white blood cells and non-white blood cells. A Th2 cytokine response can include abundant CD8 cytotoxic T lymphocyte activity including T2 cytokine production, referred to as Tc2 responses. A Th2 response is typically promoted by CD4 "Th2" T-helper cells however a Th2 response can include CD8 Tc2T cytotoxic cells.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

By "vector" is meant a polynucleotide molecule, suitably a DNA molecule derived, for example, from a plasmid, bacteriophage, yeast or virus, into which a polynucleotide can be inserted or cloned. A vector may contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

The terms "wild-type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild-type" form of the gene.

2. Helminth Defense Molecules

Figure 1:
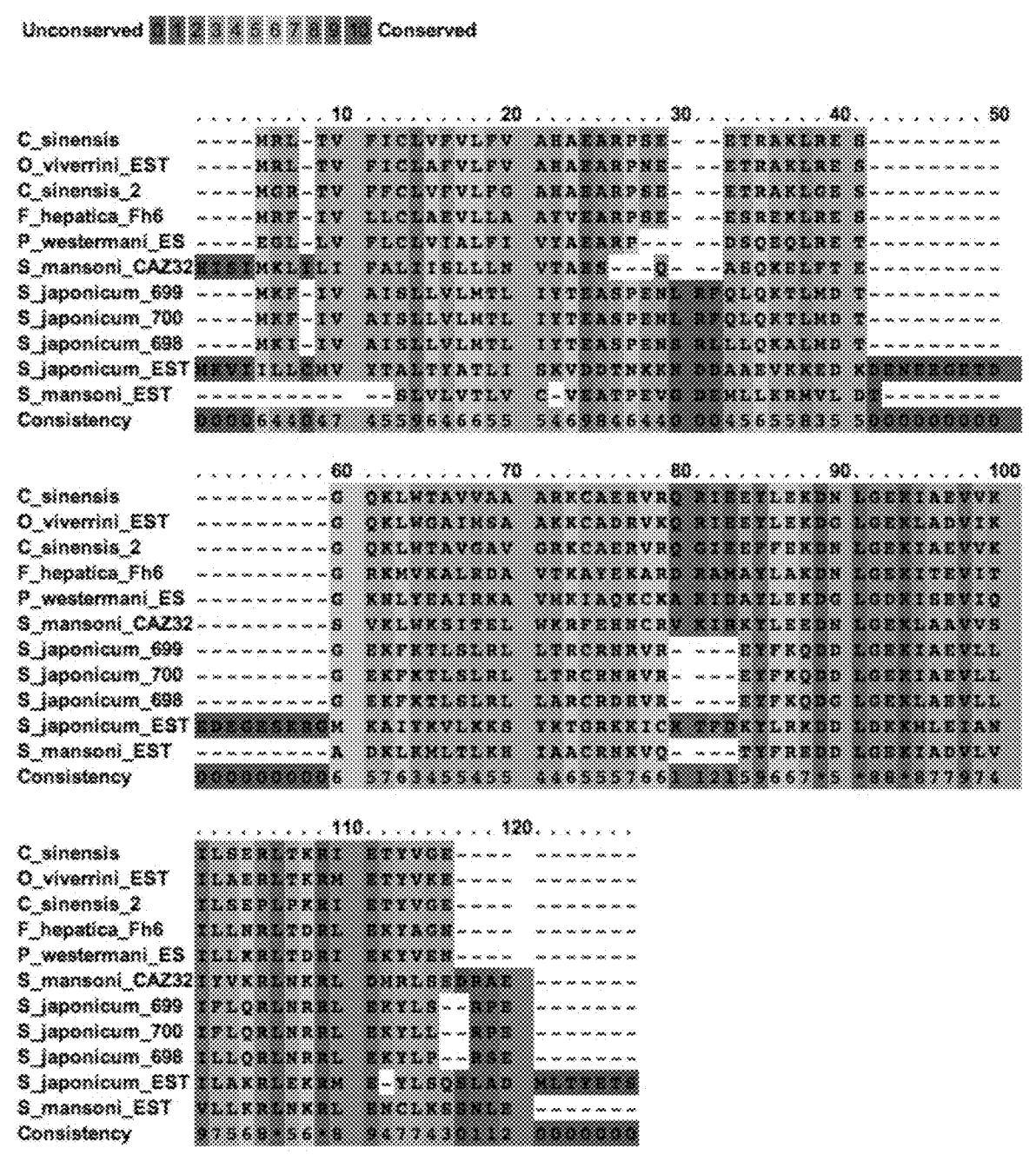

The present invention is based in part on the determination that a 90-residue polypeptide from *F. hepatica*, referred to herein as *F. hepatica* Helminth Defense Molecule-1 (FhHDM-1), as well as C-terminal fragments of this polypeptide, have at least one activity selected from: stimulating the development of an antigen-specific Th2 response, suppressing the development of an antigen-specific Th1 response, stimulating the development in antigen-presenting cells of an alternatively activated phenotype, preventing or inhibiting the activation of antigen-presenting cells by an inflammatory stimulus, binding to lipopolysaccharide, preventing or inhibiting binding of lipopolysaccharide to lipopolysaccharide-binding protein, and preventing or inhibiting binding of a TLR ligand (e.g., lipopolysaccharide) to antigen-presenting cells (e.g., macrophages), interacting with the plasma membrane of antigen-presenting cells and down-regulating or impairing lysosome function in antigen-presenting cells. The present inventors have also determined that when these molecules are administered to animals, they are surprisingly effective as a preventative treatment for T1D and permit the acceptance of islet grafts in the context of established disease. Several homologs of FhHDM-1 have also been identified from other helminths including *C. sinensis, O. viverrini, P. westermani, S. japonicum* and *S. mansoni*. In view of their close structural similarity to FhHDM-1, as for example shown in FIGS. 1 and 2, these homologs and their C-terminal fragments are considered to have the same or similar activity as FhHDM-1. The present inventors thus consider that these Helminth Defense Molecules (HDMs) will be useful in generating tolerogenic responses in animals for treating or preventing undesirable or deleterious immune responses in a range of conditions including ones that manifest in transplant rejection, graft versus host disease, allergies, parasitic diseases, inflammatory diseases and autoimmune diseases.

Accordingly, the present invention provides HDMs in methods and compositions for treating or preventing undesirable or deleterious immune responses in a subject. When included in compositions, the HDMs are suitably combined with a pharmaceutically acceptable carrier or diluent. The HDMs of the present invention can be administered by any suitable route include for example by injection, by topical or mucosal application, by inhalation or via the oral route including modified-release modes of administration to treat or prevent an undesirable or deleterious immune response in a subject.

In some embodiments, the HDMs are obtained from a helminth, non-limiting examples of which include helminths from the phylum Platyhelminthes, representative examples of which include: helminths from the class Turbellaria such as the order Neorhabdocoela (e.g., *Temnocephala* spp.); helminths from the class Monogenea including for example from the subclass Monopisthocotylea (e.g., *Gyrodactylus* spp. and *Tetraonchus* spp.) and the subclass Polyopisthocotylea (e.g., *Microcotyle* spp., *Octomacrum* spp., *Polystoma* spp., *Polystomoides* spp., and *Rajonchocotyle* spp.); helminths from the class Trematoda including for example from the subclass Aspidogastrea (e.g., *Aspidogaster* spp. and *Cotylaspis* spp.), from the subclass Digenea including for example from the order Paramphistomiformes, illustrative examples of which include the family Microscaphidiidae (e.g., *Dictyangium* spp.), the family Notocotylidae (e.g., *Notocotylus notocotylus*); and the family Paramphistomidae (e.g., *Megalodiscus temperatus, Watsonius* spp. and *Zygocotyle lunata*); helminths from the order Hemiuriformes, illustrative examples of which include the family Azygiidae (e.g., *Proterometra* spp.); helminths from the order Echinostomatiformes, illustrative examples of which include the family Echinostomatidae (e.g., *Echinostoma* spp.), the family Fascioloidea (e.g., *Fasciola hepatica, Fascioloides magna* and *Fasciolopsis buski*) and the family Rhopaliasidae (e.g., *Rhopalias* spp.); helminths from the order Strigeiformes including for example from the family Brachylaemidae (e.g., *Leucochloridium* sp, *Postharmostomum helicis* and *Urogonimus dryobatae*), the family Bucephalidae (e.g., *Rhipidocotyle* spp.), the family Diplostomatidae (e.g., *Diplostomulum* spp. and *Uvulifer ambloplitis*); the family Strigeidae (e.g., *Cotylurus* spp.), the family Schistosomatidae (e.g., *Schistosoma* spp. including *S. japonicum*, and *S. mansoni* and *Trichobilharzia* spp.); helminths from the order Opisthorchiformes including for example from the family Cryptogonimidae (e.g., *Acetodextra* spp. and *Allochanthochasmus* spp.), the family Opisthorchiidae (e.g., *Clonorchis sinensis, Opisthorchis* spp. including *O. viverrini* and *Metorchis conjunctus*), the family Heterophyidae (e.g., *Apophallus* spp., *Heterophyes heterophyes* and *Metagonimus yokogawai*); helminths from the order Lepocreadiiformes including for example from the family Lepocreadiidae (e.g., *Apocreadium* spp.); helminths from the order Plagiorchiformes including for example from the suborder Plagiorchiata illustrative examples of which include the family Allocreadiidae (e.g., *Allocreadium* spp. and *Crepidostomum* spp.), the family Auridistomidae (e.g., *Auridistomum* spp.), the family Cephalogonimidae (e.g., *Cephalogonimus* spp.), the family Dicrocoeliidae (e.g., *Conspicuum* spp., *Dicrocoelium dendriticum, Lutztrema* spp., *Platynostomum* spp. and *Zonorchis* spp.), the family Haematoloechidae (e.g., *Haematoloechus medioplexus*), the family Lecithodendriidae (e.g., *Loxogenes* sp and *Parabas-* cus spp.), the family Lissorchiidae (e.g., *Lissorchis fairporti* and *Triganodistomum* spp.), the family Macroderoididae (e.g., *Alloglossidium corti*) the family Microphallidae (e.g., *Microphallus* spp.), the family Plagiorchiidae (e.g., *Styphlodora* spp.), the family Pleorchiidae (e.g., *Pleorchis* spp.), the family Prosthogonimidae (e.g., *Prosthogonimus macrorchis*), the family Telorchiidae (e.g., *Telorchis* spp.); helminths from the suborder Troglotremata including for example from the family Troglotrematidae (e.g., *Paragonimus* spp. including *P. westermani*); helminths from the class Cestoidea including for example from the subclass Cestodaria (e.g., *Gyrocotyle* spp.); from the subclass Eucestoda illustrative examples of which include the order Caryophyllidea (e.g., *Glaridacris catastomus*), the order Cyclophyllidea (e.g., *Anoplocephala* spp., *Choanotaenia* spp., *Dipylidium caninum, Echinococcus granulosus, Echinococcus multilocularis, Hymenolepis* spp., *Hymenolepis diminuta, Hymenolepis (Vampirolepis) nana, Mesocestoides* spp., *Moniezia expansa, Multiceps serialis, Taenia* spp., *Taenia pisiformis* and *Taenia serialis*; helminths from the order Proteocephalata (e.g., *Corallobothrium* spp., *Ophiotaenia* spp. and *Proteocephalus* spp.), helminths from the order Pseudophyllidea (e.g., *Bothriocephalus* spp., *Diplogonoporus grandis, Diphyllobothrium latum, Haplobothrium* spp., *Ligula intestinalis* and *Triaenophorus crassus*); helminths from the order Tetraphyllidea; helminths from the order Trypanorhyncha; helminths from the phylum Nematoda representative examples of which include helminths from the class Aphasmida (=Enoplea) including for example from the order Dioctophymatida, illustrative examples of which include the family Dioctophymatidae (e.g., *Dioctophyme renale*), the family Eustrongylidae (e.g., *Eustrongylides tubifex*); helminths from the order Trichurida including for example from the family Capillaridae (e.g., *Capillaria hepatica* and *Capillaria philippinensis*), the family Trichinellidae (e.g., *Trichinella* spp. including *T. spiralis*), the family Trichuridae (e.g., *Trichuris* spp.); helminths from the class Rhabditae including for example from the order Rhabditidae (e.g., *Strongyloides stercoralis*), from the order Strongylida including for example from the family Ancylostomidae (e.g., *Ancylostoma* spp., *Bunostomum* spp., *Necator* spp. *Placoconus* (=*Arthrocephalus* spp. and *Uncinaria* spp.), the family Angiostrongylidae (e.g., *Angiostrongylus cantonensis*), the family Chabertiidae (e.g., *Chabertia* spp. and *Oesophagostomum* spp.), the family Filaroididae (e.g., *Filaroides* spp.), the family Metastrongylidae (e.g., *Metastrongylus* spp.), the family Strongylidae (e.g., *Cylicocyclus* spp., *Cylicodontophorus* spp., *Cylicostephanus* spp., *Craterostomum* spp., *Oesophagodontus* spp., *Parapoteriostomum* spp., *Petrovinema* spp., *Petrovinema* spp., *Strongylus* spp., *Terniden* spp., *Tridentoinfundibulum* spp., *Triodontophorus* spp. and the subfamily Cyathostominae illustrative examples of which include *Cyathostomum* spp.) the family Trichostrongyloidae (e.g., *Cooperia* spp., *Dictyocaulus* spp., *Haemonchus* spp., *Nematodirus* spp., *Nippostrongylus* spp., *Obeliscoides cuniculi, Ostertagia* spp. and *Trichostrongylus* spp.); helminths from the order Ascaridida (e.g., *Anisakis* spp., *Ascaris* spp., *Baylisascaris procyonis, Parascaris* spp. and *Toxocara* spp. including *T. canis*); helminths from the order Oxyurida (e.g., *Enterobius vermicularis, Cosmocerella* spp. and *Oxyuris* spp.); helminths from the order Spirurida including for example from the suborder Spirurina illustrative examples of which include the family Onchocercidae (e.g., *Brugia malayi, Brugia pahangi, Brugia timori, Cercopithifilaria johnstoni, Dipetalonema* spp., *Dirofilaria* spp., *Loa loa, Mansonella* spp., *Onchocerca* spp. and *Wuchereria* spp. including *W. bancrofti*), the family Gnathostomatidae (e.g., *Gnathostoma* spp.), the family Habronematidae (e.g., *Habronema* spp.) and the family Rhabdochonidae (e.g., *Spinitectus* spp.); helminths from the suborder Camallanina including for example from the family Camallanidae (e.g., *Camallanus oxycephalus*), the family Dracunculidae (e.g., *Dracunculus medinensis* and *Philometra cylindracea*); helminths from the phylum Acanthocephala representative examples of which include helminths from the class Archiacanthocephala (e.g., *Macrocanthorhynchus hirudinaceus* and *Moniliformis* spp.); helminths from the class Palaeacanthocephala including for example from the order Echinorhynchida (e.g., *Leptorhynchoides* spp., *Pomphorhynchus* spp. and *Echinorhynchus* spp.); helminths from the order Polymorphida (e.g., *Plagiorhynchus* spp. and *Polymorphus minutus*); and helminths from the phylum Annelida representative examples of which include helminths from the class Hirudinea including for example from the order Rhynchobdellida illustrative examples of which include from family Glossiphoniidae (e.g., *Placobdella* spp.). In specific embodiments, the HDM is obtained from the class Trematoda. In some embodiments, the HDMs are produced by recombinant DNA techniques or by chemical synthesis.

The HDMs of the present invention include peptides or polypeptides which arise as a result of the existence of alternative translational and post-translational events. The HDMs can be expressed in systems, e.g., cultured cells, which result in substantially the same post-translational modifications present when the HDM is expressed in a native cell, or in systems which result in the alteration or omission of post-translational modifications, e.g., glycosylation or cleavage, present when expressed in a native cell.

In some embodiments, an HDM has any one or more of the following characteristics:

(a) stimulates or induce an antigen-specific Th2 response;

(b) suppresses the development of an antigen-specific Th1 response;

(c) stimulates the development in antigen-presenting cells (e.g., macrophages, dendritic cells, Langerhans cells etc) of an alternatively activated phenotype (e.g., increased expression of any one or more of Arg1, Fizz, Ym1, IL-10, TGF-β, CD206 and CD163);

(d) prevents or inhibits the activation of antigen-presenting cells (e.g., macrophages, dendritic cells, Langerhans cells etc) by an inflammatory stimulus;

(e) binds to lipopolysaccharide;

(f) prevents or inhibits binding of lipopolysaccharide to lipopolysaccharide-binding protein;

(g) prevents or inhibits binding of lipopolysaccharide to antigen-presenting cells (e.g., macrophages, dendritic cells, Langerhans cells etc);

(h) interacts with the plasma membrane of antigen-presenting cells (e.g., macrophages, dendritic cells, Langerhans cells etc); and (i) down-regulates or impairs lysosome function in antigen-presenting cells (e.g., macrophages, dendritic cells, Langerhans cells etc).

The present invention contemplates full-length HDM polypeptides as well as their biologically active fragments. Typically, biologically active fragments of a full-length HDM may participate in an interaction, for example, an intramolecular or an inter-molecular interaction and/or may display any one or more of activities (a) to (i) noted above. Such biologically active fragments include peptides comprising amino acid sequences sufficiently similar to or derived from the amino acid sequences of a (putative) full-length HDM polypeptide, for example, the amino acid sequences shown in SEQ ID NO: 24, 26, 28, 30, 32, 34, 36, 38, 40, 42 and 44, which include less amino acids than a putatively full-length HDM polypeptide, and exhibit at least one activity of that polypeptide (e.g., any one or more of activities (a) to (i) defined above. Typically, biologically active fragments will comprise a domain or motif with at least one activity of a putatively full-length HDM polypeptide and may comprise, consist or consist essentially of an about 27-residue domain, as shown for example in FIG. 2, which is predicted to form an amphipathic helix. In some embodiments, biologically active fragments will comprise an aromatic amino acid residue (e.g., Y or F or modified form thereof) at position 1; a hydrophobic amino acid residue (e.g., aliphatic amino acid residues such as L or modified form thereof, or aromatic amino acid residues such as F, or modified forms thereof) at position 2; D or modified form thereof at position 5, L or modified form thereof at position 7, a charged amino acid residue (e.g., acidic amino acid residues such as E or D, or modified form thereof, or basic amino acid residues such as K, or modified form thereof) at position 9; K or modified form thereof at position 10; an aliphatic amino acid residue (e.g., L, I or M, or modified form thereof) at position 11; an aliphatic amino acid residue (e.g., V or I, or modified form thereof) at position 14; an aliphatic amino acid residues (e.g., V or I, or modified form thereof) at position 17; a hydrophobic amino acid residue (e.g., aliphatic amino acid residues such as L or modified form thereof, or aromatic amino acid residues such as F or Y, or modified forms thereof) at position 18; L or modified form thereof at position 22; a charged amino acid residue (e.g., an acidic amino acid residue such as D, or modified form thereof, or a basic amino acid residue such as K or R, or modified form thereof) at position 24; R or modified form thereof at position 25; an aliphatic amino acid residue (e.g., L, I or M, or modified form thereof) at position 26; and an acidic amino acid residue (e.g., E or D, or modified form thereof) at position 27, relative to the consensus numbering of FIG. 2. In some embodiments, the biologically active fragments will comprise any one or more of: an acidic amino acid residue (e.g., as E, or modified form thereof) or a small amino acid residue (e.g., as A, or modified form thereof), or a basic amino acid residue (e.g., as K or R, or modified form thereof) at position 3; a neutral/polar amino acid residue (e.g., Q or modified form thereof), or a charged amino acid residue (e.g., basic amino acid residues such as K, or modified form thereof, or acidic amino acid residues such as E, or modified form thereof) at position 4; a small amino acid residues (e.g., G, or modified forms thereof), or a neutral/polar amino acid residues (e.g., N, or modified form thereof), or an acidic amino acid residue (e.g., D, or modified form thereof) at position 6; a small amino acid residue (e.g., G, or modified form thereof), or an acidic amino acid residues (e.g., D, or modified form) thereof at position 8; a small amino acid residue (e.g., A, S or T, or modified form thereof), or a hydrophobic amino acid residue including aliphatic amino acid residues (e.g., L, or modified form thereof) at position 12; an acidic amino acid residue (e.g., E or D, or modified form thereof), or a small amino acid residue (e.g., A, or modified form thereof) at position 13; a hydrophobic amino acid residue including aliphatic amino acid residues (e.g., I, L or V, or modified form thereof), or a small amino acid residue (e.g., A, or modified form thereof) at position at position 15; a basic amino acid residue (e.g., K, or modified form thereof), or a neutral/polar amino acid residue (e.g., Q or N, or modified form thereof), or a small amino acid residue (e.g., S or T, or modified form thereof), or a hydrophobic amino acid residue including aliphatic amino acid residues (e.g., L or V, or modified forms thereof) at position 16; a small amino acid residue (e.g., A or S, or modified form thereof), or a hydrophobic amino acid residue including aliphatic amino acid residues (e.g., L or V, or modified forms thereof) at position 19; an acidic amino acid residue (e.g., E, or modified form thereof), or a basic amino acid residue (e.g., K, or modified form thereof), or a neutral/polar amino acid residue (e.g., Q or N, or modified form thereof) at position 20; a basic amino acid residues (e.g., R, or modified form thereof), or a small acid residue (e.g., P, or modified form thereof) at position 21; and a small amino acid residue (e.g., T or P, or modified form thereof), or a neutral/polar amino acid residue (e.g., N, or modified form thereof), or an acidic amino acid residues (e.g., E, or modified form thereof) at position 23, relative to the consensus numbering of FIG. 2.

In other embodiments, biologically active fragments comprise, consist or consist essentially of an about 21-residue domain, as shown in FIG. 19. Suitably, such biologically active fragments may comprise: L or modified form thereof at position 1; G or modified form thereof at position 2; an acidic amino acid residue (e.g., E or D, or modified form thereof) at position 3; K or modified form thereof at position 4; an aliphatic amino acid residue (e.g., L or I, or modified form thereof) at position 5; a small amino acid residue (e.g., A, S or T, or modified form thereof) at position 6; an acidic amino acid residue (e.g., E or D, or modified form thereof) or a small amino acid residue (e.g., A, or modified form thereof) at position 7; V or modified for thereof, at position 8; an aliphatic amino acid residue (e.g., L, I or V, or modified form thereof) at position 9; an aliphatic amino acid residues (e.g., I or V, or modified form thereof) at position 11; a hydrophobic amino acid residue (e.g., aliphatic amino acid residues such as L or modified form thereof, or aromatic amino acid residues such as F or Y, or modified forms thereof) at position 12; an aliphatic amino acid residue (e.g., L or V, or modified form thereof) or a small amino acid residue (e.g., A, or modified form thereof) at position 13; a polar amino acid residue (e.g., Q, N, K or E, or modified form thereof) at position 14; R or modified form thereof at position 15; L or modified form thereof at position 16; a neutral/polar amino acid residue (e.g., N or T, or modified form thereof) at position 17; a charged amino acid residue (e.g., an acidic amino acid residue such as D, or modified form thereof, or a basic amino acid residue such as K or R, or modified form thereof) at position 18; R or modified form thereof at position 19; an aliphatic amino acid residue (e.g., L, I or M, or modified form thereof) at position 20; and an acidic amino acid residue (e.g., E or D, or modified form thereof) at position 21, relative to the consensus numbering of FIG. 19.

A biologically active fragment of a full-length HDM polypeptide can be a polypeptide which is, for example, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or more amino acid residues in length. Suitably, the biologically-active fragment has no less than about 1%, 10%, 25% 50% of an activity of the full-length polypeptide from which it is derived.

The present invention also contemplates HDMs that are variants of wild-type or naturally-occurring HDMs or their fragments. Such "variant" peptides or polypeptides include proteins derived from the native protein by deletion (so-called truncation) or addition of one or more amino acids to the N-terminal and/or C-terminal end of the native protein;

deletion or addition of one or more amino acids at one or more sites in the native protein; or substitution of one or more amino acids at one or more sites in the native protein. Non-limiting examples of such variant HDMs include processed forms of a full-length or precursor HDM, including but not limited to peptides or polypeptides in which the signal peptide domain (from about residue 1 to about residue 27, relative to the consensus numbering shown in FIG. 1) and/or proregion (from about residue 28 to about residue 80, relative to the consensus numbering shown in FIG. 1) have been removed from the precursor form.

Variant proteins encompassed by the present invention are biologically active, that is, they continue to possess the desired biological activity of the native protein. Such variants may result from, for example, genetic polymorphism or from human manipulation.

A HDM peptide or polypeptide may be altered in various ways including amino acid substitutions, deletions, truncations, and insertions. Methods for such manipulations are generally known in the art. For example, amino acid sequence variants of a HDM peptides or polypeptides can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of HDM peptides or polypeptides. Recursive ensemble mutagenesis (REM), a technique which enhances the frequency of functional mutants in the libraries, can be used in combination with the screening assays to identify HDM variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Variant HDM peptides or polypeptides may contain conservative amino acid substitutions at various locations along their sequence, as compared to a parent (e.g., naturally-occurring or reference) HDM amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), *Atlas of protein sequence and structure,* Vol. 5, pp. 345-358, National Biomedical Research Foundation, Washington D.C.; and by Gonnet et al., (1992, *Science,* 256(5062): 14430-1445), however, include proline in the same group as glycine, serine, alanine and threonine. Accordingly, for the purposes of the present invention, proline is classified as a "small" amino acid.

The degree of attraction or repulsion required for classification as polar or non-polar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table 2.

TABLE 2

AMINO ACID SUB-CLASSIFICATION

| SUB-CLASSES | AMINO ACIDS |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alamine, Threonine, Proline |
| Nonpolar/neutral | Alanine, Glycine, Isoleucine, Leucine, Methionine, Phenylalanine, Proline, Tryptophan, Valine |
| Polar/neutral | Asparagine, Histidine, Glutamine, Cysteine, Serine, Threonine, Tyrosine |
| Polar/negative | Aspartic acid, Glutamic acid |
| Polar/positive | Lysine, Arginine |
| Polar/large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional HDM peptide polypeptide can readily be determined by assaying its activity. Conservative substitutions are shown in Table 3 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 3

EXEMPLARY AND PREFERRED
AMINO ACID SUBSTITUTIONS

| ORIGINAL RESIDUE | EXEMPLARY SUBSTUTUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., Biochemistry, third edition, Wm.C. Brown Publishers (1993).

Thus, a predicted non-essential amino acid residue in a HDM peptide or polypeptide is typically replaced with another amino acid residue from the same side chain family. Alternatively, mutations can be introduced randomly along all or part of a HDM gene coding sequence, such as by saturation mutagenesis, and the resultant mutants can be screened for an activity of the parent polypeptide, as described for example herein, to identify mutants which retain that activity. Following mutagenesis of the coding sequences, the encoded peptide or polypeptide can be expressed recombinantly and its activity determined. A "non-essential" amino acid residue is a residue that can be altered from the wild-type sequence of an embodiment peptide or polypeptide without abolishing or substantially altering one or more of its activities. Suitably, the alteration does not substantially alter one of these activities, for example, the activity is at least 20%, 40%, 60%, 70% or 80% of wild-type. Illustrative non-essential amino acid residues include any one or more of the amino acid residues that differ at the same position (e.g., residues $X_1$-$X_{22}$, as defined supra, or residues $J_1$-$J_{14}$, as defined supra) between the wild-type HDM peptides shown in FIG. 2 or 19. By contrast, an "essential" amino acid residue is a residue that, when altered from the wild-type sequence of a reference HDM peptide or polypeptide, results in abolition of an activity of the parent molecule such that less than 20% of the wild-type activity is present. For example, such essential amino acid residues include those that are conserved in HDM peptides or polypeptides across different species, e.g., D (or modified form thereof) at position 5, L (or modified form thereof) at position 7, K (or modified form thereof) at position 9, L (or modified form thereof) at position 22 and R (or modified form thereof) at position 25, relative to the consensus numbering shown in FIG. 2, which are conserved in the C-terminal portions of HDM polypeptides from *F. hepatica, C. sinensis, O. viverrini, P. westermani, S. japonicum* and *S. mansoni*. In other examples, essential amino acid residues include L (or modified form thereof) at position 1, G (or modified form thereof) at position 2, K (or modified form thereof) at position 4, V (or modified form thereof) at position 8, R (or modified form thereof) at position 15, L (or modified form thereof) at position 16 and R (or modified form thereof) at position 19, relative to the consensus numbering shown in FIG. 19, which are conserved in the C-terminal portions of HDM polypeptides from *F. hepatica, O. viverrini, P. westermani, S. japonicum* and *S. mansoni*.

Accordingly, the present invention also contemplates as HDM peptides or polypeptides, variants of the naturally-occurring HDM polypeptide sequences or their biologically-active fragments, wherein the variants are distinguished from the naturally-occurring sequence by the addition, deletion, or substitution of one or more amino acid residues. In general, variants will display at least about 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% similarity to a parent or reference HDM peptide or polypeptide sequence as, for example, set forth in SEQ ID NO: 2, 4, 6, 8, 10, 12, 14, 16, 17, 18, 20, 22, 24, 26, 28, 30, 32, 34, 36, 38, 40, 42, 44, 105, 107, 109, 111, 113, 115, 117, 119, 121 or 122, as determined by sequence alignment programs described elsewhere herein using default parameters. Desirably, variants will have at least 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a parent HDM peptide or polypeptide sequence as, for example, set forth in SEQ ID NO: 2, 4, 6, 8, 10, 12, 14, 16, 17, 18, 20, 22, 24, 26, 28, 30, 32, 34, 36, 38, 40, 42, 44, 105, 107, 109, 111, 113, 115, 117, 119, 121 or 122, as determined by sequence alignment programs described elsewhere herein using default parameters. Variants of a wild-type HDM polypeptide, which fall within the scope of a variant polypeptide, may differ from the wild-type molecule generally by as much 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, or 11 amino acid residues or suitably by as few as 10, 9, 8, 7, 6, 5 4, 3, 2, or 1 amino acid residue(s). In some embodiments, a variant polypeptide differs from the corresponding sequences in SEQ ID NO: 2, 4, 6, 8, 10, 12, 14, 16, 17, 18, 20, 22, 24, 26, 28, 30, 32, 34, 36, 38, 40, 42, 44, 105, 107, 109, 111, 113, 115, 117, 119, 121 or 122 by at least 1 but by less than or equal to 25, 24, 23, 22, 21, 20, 19, 18, 17, 16, 15, 14, 13, 12, 11, 10, 9, 8, 7, 6, 5, 4, 3 or 2 amino acid residues. In other embodiments, it differs from the corresponding sequence in any one of SEQ ID NO: 2, 4, 6, 8, 10, 12, 14, 16, 17, 18, 20, 22, 24, 26, 28, 30, 32, 34, 36, 38, 40, 42, 44, 105, 107, 109, 111, 113, 115, 117, 119, 121 or 122 by at least one 1% but less than or equal to 25%, 24%, 23%, 22%, 21%, 20%, 19%, 18%, 17%, 16%, 15%, 14%, 13%, 12%, 11%, 10%, 9%, 8%, 7% 6%, 5% 4% 3% or 2% of the residues. If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution, as discussed in more detail below.

The HDMs of the present invention also encompass HDM peptide or polypeptides comprising amino acids with modified side chains, incorporation of unnatural amino acid residues and/or their derivatives during peptide, polypeptide or protein synthesis and the use of cross-linkers and other methods which impose conformational constraints on the peptides, portions and variants of the invention. Examples of side chain modifications include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivatization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in Table 4.

TABLE 4

| NON-CONVENTIONAL AMINO ACIDS Non-Conventional Amino Acids | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |

TABLE 4-continued NON-CONVENTIONAL AMINO ACIDS
Non-Conventional Amino Acids

| | |
|---|---|
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | |

The HDMs of the present invention also include peptides and polypeptides that are encoded by polynucleotides that hybridize under stringency conditions as defined herein, especially medium or high stringency conditions, to HDM-encoding polynucleotide sequences, or the non-coding strand thereof, as described below. Illustrative HDM polynucleotide sequences are set forth in SEQ ID NO:1, 3, 5, 7, 9, 11, 13, 15, 17, 19, 21, 23, 25, 27, 29, 31, 33, 35, 37, 39, 41, 43, 104, 106, 108, 110, 112, 114, 116, 118 or 120, or their complements.

In some embodiments, calculations of sequence similarity or sequence identity between sequences are performed as follows:

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 30%, usually at least 40%, more usually at least 50%, 60%, and even more usually at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e., conservative substitution) at the corresponding position in the second sequence, then the molecules are similar at that position.

The percent identity between the two sequences is a function of the number of identical amino acid residues shared by the sequences at individual positions, taking into account the number of gaps, and the length of each gap, which need to be introduced for optimal alignment of the two sequences. By contrast, the percent similarity between the two sequences is a function of the number of identical and similar amino acid residues shared by the sequences at individual positions, taking into account the number of gaps, and the length of each gap, which need to be introduced for optimal alignment of the two sequences.

The comparison of sequences and determination of percent identity or percent similarity between sequences can be accomplished using a mathematical algorithm. In certain embodiments, the percent identity or similarity between amino acid sequences is determined using the Needleman and Wunsch, (1970, *J. Mol. Biol.* 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In specific embodiments, the percent identity between nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. An non-limiting set of parameters (and the one that should be used unless otherwise specified) includes a Blossum 62 scoring matrix with a gap penalty of 12, a gap extend penalty of 4, and a frameshift gap penalty of 5.

In some embodiments, the percent identity or similarity between amino acid or nucleotide sequences can be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to 53010 nucleic acid molecules of the invention. BLAST protein searches can be performed with the XBLAST program, score=50, wordlength=3 to obtain amino acid sequences homologous to 53010 protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

Variants of a reference HDM peptide or polypeptide can be identified by screening combinatorial libraries of mutants, e.g., truncation mutants, of a HDM peptide or polypeptide. Libraries or fragments e.g., N terminal, C terminal, or internal fragments, of a HDM coding sequence can be used to generate a variegated population of fragments for screening and subsequent selection of variants of a reference HDM.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of HDM peptides or polypeptides.

The HDM peptides and polypeptides of the present invention may be prepared by any suitable procedure known to those of skill in the art. For example, the HDM peptides or polypeptides may be produced by any convenient method such as by purifying the peptides or polypeptides from naturally-occurring reservoirs including helminths. Methods of purification include size exclusion, affinity or ion exchange chromatography/separation. The identity and purity of derived HDMs is determined for example by SDS-polyacrylamide electrophoresis or chromatographically such as by high performance liquid chromatography (HPLC). Alternatively, the HDM peptides or polypeptides may be synthesized by chemical synthesis, e.g., using solution synthesis or solid phase synthesis as described, for example, in Chapter 9 of Atherton and Shephard (supra) and in Roberge et al., (1995, *Science*, 269: 202).

In some embodiments, the HDM peptides or polypeptides are prepared by recombinant techniques. For example, the HDM peptides or polypeptides of the invention may be prepared by a procedure including the steps of: (a) preparing a construct comprising a polynucleotide sequence that encodes a HDM peptide or polypeptide and that is operably linked to a regulatory element; (b) introducing the construct into a host cell; (c) culturing the host cell to express the polynucleotide sequence to thereby produce the encoded HDM peptide or polypeptide; and (d) isolating the HDM peptide or polypeptide from the host cell. In illustrative examples, the nucleotide sequence encodes at least a biologically active portion of the sequences set forth in SEQ ID NO: 2, 4, 6, 8, 10, 12, 14, 16, 17, 18, 20, 22, 24, 26, 28, 30, 32, 34, 36, 38, 40, 42, 44, 105, 107, 109, 111, 113, 115, 117, 119, 121 or 122, or a variant thereof. Recombinant HDM peptides or polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

Exemplary nucleotide sequences that encode the HDM peptides and polypeptides of the invention encompass full-length HDM genes as well as portions of the full-length or substantially full-length nucleotide sequences of the HDM genes or their transcripts or DNA copies of these transcripts. Portions of a HDM nucleotide sequence may encode polypeptide portions or segments that retain the biological activity of the native polypeptide. A portion of a HDM nucleotide sequence that encodes a biologically active fragment of a HDM polypeptide may encode at least about 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or more contiguous amino acid residues, or almost up to the total number of amino acids present in a full-length HDM polypeptide.

The invention also contemplates variants of the HDM nucleotide sequences. Nucleic acid variants can be naturally-occurring, such as allelic variants (same locus), homologs (different locus), and orthologs (different organism) or can be non naturally-occurring. Naturally-occurring nucleic acid variants (also referred to herein as polynucleotide variants) such as these can be identified with the use of well-known molecular biology techniques, as, for example, with polymerase chain reaction (PCR) and hybridization techniques as known in the art. Non-naturally occurring polynucleotide variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference HDM peptide or polypeptide. Variant nucleotide sequences also include synthetically derived nucleotide sequences, such as those generated, for example, by using site-directed mutagenesis but which still encode a HDM peptide or polypeptide. Generally, variants of a particular HDM nucleotide sequence will have at least about 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular nucleotide sequence as determined by sequence alignment programs described elsewhere herein using default parameters. In some embodiments, the HDM nucleotide sequence displays at least about 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to a nucleotide sequence selected from any one of SEQ ID NO: 1, 3, 5, 7, 9, 11, 13, 15, 17, 19, 21, 23, 25, 27, 29, 31, 33, 35, 37, 39, 41, 43, 104, 106, 108, 110, 112, 114, 116, 118 or 120, or their complements.

HDM nucleotide sequences can be used to isolate corresponding sequences and alleles from other organisms, particularly other helminths. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other HDM-coding sequences present in a population of cloned genomic DNA fragments or cDNA fragments (i.e., genomic or cDNA libraries) from a chosen organism (e.g., a helminth). Accordingly, the present invention also contemplates polynucleotides that hybridize to reference HDM nucleotide sequences, or to their complements, (e.g., SEQ ID NO: 1, 3, 5, 7, 9, 11, 13, 15, 17, 19, 21, 23, 25, 27, 29, 31, 33, 35, 37, 39, 41, 43, 104, 106, 108, 110, 112, 114, 116, 118 or 120, or their complements) under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a HDM peptide or polypeptide is encoded by a polynucleotide that hybridizes to a disclosed nucleotide sequence under very high stringency conditions. One embodiment of very high stringency conditions includes hybridizing 0.5 M sodium phosphate, 7% SDS at 65° C., followed by one or more washes at 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the T$_m$ for formation of a DNA-DNA hybrid. It is well known in the art that the T$_m$ is the melting temperature, or temperature at which two complementary polynucleotide sequences dissociate. Methods for estimating T$_m$ are well known in the art (see Ausubel et al., supra at page 2.10.8). In general, the T$_m$ of a perfectly matched duplex of DNA may be predicted as an approximation by the formula:

$$T_m=81.5+16.6(\log_{10} M)+0.41(\% \ G+C)-0.63(\% \ \text{formamide})-(600/\text{length})$$

wherein: M is the concentration of Na, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The T$_m$ of a duplex DNA decreases by approximately 1° C. with every increase of 1% in the number of randomly mismatched base pairs. Washing is generally carried out at T$_m$−15° C. for high stringency, or T$_m$−30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% bovine serum albumin), 0.1% SDS and 200 mg/mL denatured salmon sperm DNA) containing labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

The present invention also contemplates the use of HDM chimeric or fusion proteins for treating or preventing undesirable or deleterious immune responses. As used herein, a HDM "chimeric protein" or "fusion protein" includes a HDM peptide or polypeptide linked to a non-HDM peptide or polypeptide. A "non-HDM peptide or polypeptide" refers to a peptide or polypeptide having an amino acid sequence corresponding to a protein which is different from a HDM and which is derived from the same or a different organism. The HDM peptide or polypeptide of the fusion protein can correspond to all or a portion e.g., a fragment described herein of a HDM polypeptide amino acid sequence. In a specific embodiment, a HDM fusion protein includes at least one biologically active portion of a HDM polypeptide. The non-HDM peptide or polypeptide can be fused to the N-terminus or C-terminus of the HDM peptide or polypeptide.

The fusion protein can include a moiety which has a high affinity for a ligand. For example, the fusion protein can be a GST-HDM fusion protein in which the HDM sequence is fused to the C-terminus of the GST sequence. Such fusion proteins can facilitate the purification of recombinant HDM peptide or polypeptide. Alternatively, the fusion protein can be HDM protein containing a heterologous signal sequence at its N-terminus. In certain host cells (e.g., mammalian host cells), expression and/or secretion of HDM peptides or polypeptides can be increased through use of a heterologous signal sequence. In some embodiments, fusion proteins may include all or a part of a serum protein, e.g., an IgG constant region, or human serum albumin.

The HDM fusion proteins of the invention can be incorporated into pharmaceutical compositions and administered to a subject in vivo. They can also be used to modulate the bioavailability of an HDM peptide or polypeptide.

3. Compositions for Modulating Undesirable or Deleterious Immune Responses

The present inventors have determined that HDMs have one or more activities selected from: (a) stimulating or inducing an antigen-specific Th2 response, (b) suppressing the development of an antigen-specific Th1 response, (c) stimulating the development in antigen-presenting cells of an alternatively activated phenotype, (d) preventing or inhibiting the activation of antigen-presenting cells by an inflammatory stimulus, (e) binding to lipopolysaccharide, (f) preventing or inhibiting binding of lipopolysaccharide to lipopolysaccharide-binding protein, (g) preventing or inhibiting binding of toll-like receptor (TLR) ligands (e.g., lipopolysaccharide) to antigen-presenting cells (e.g., macrophages), (h) interacting with the plasma membrane of antigen-presenting cells and (i) down-regulating or impairing lysosome function in antigen-presenting cells. They have also determined that these molecules (j) generate tolerogenic responses in animals for treating or preventing undesirable or deleterious immune responses in a range of conditions including ones that manifest in transplant rejection, graft versus host disease, allergies, parasitic diseases, inflammatory diseases and autoimmune diseases.

In accordance with the present invention, an activity selected from any one or more of (a) to j) as broadly defined above can be achieved using at least one HDM or a polynucleotide from which one is expressible and optionally an antigen to which a tolerogenic response is desired or a polynucleotide from which one is expressible. These tolerogenic agents can be administered in soluble form, in particulate form and/or in the form of antigen-presenting cells that have been contacted ex vivo with at least one HDM or a polynucleotide from which one is expressible and optionally an antigen to which a tolerogenic response is desired or a polynucleotide from which one is expressible.

3.1 Antigen Embodiments

In some embodiments, a HDM as broadly described in Section 2 is administered concurrently with an antigen that corresponds to at least a portion of a target antigen that associates with the undesirable or deleterious immune response, for inducing a tolerogenic immune response to that target antigen. The present invention thus provides compositions for modulating an immune response, especially an undesirable or deleterious immune response, wherein the compositions generally comprise a HDM as defined herein and an antigen that corresponds to at least a portion of a target antigen associated with the undesirable or deleterious immune response.

Illustrative target antigens include alloantigens and self antigens or peptide fragments thereof, which are presented in the context of MHC, as well as soluble proteins and fragments of insoluble complexes, particulate antigens, e.g., bacteria or parasites, and allergens. Thus, exemplary antigens which are useful in the practice of the present invention include, but are not limited to, self antigens that are targets of autoimmune responses, allergens and transplantation antigens. Examples of self antigens include, but are not restricted to, lupus autoantigen, Smith, Ro, La, U1-RNP, fibrillin (scleroderma); proinsulin, insulin, IA2 and GAD65 in diabetes; collagen type II, HC gp39, dnaJp1, citrullinated proteins and peptides e.g., citrullinated type II collagen, vimentin or fibrinogen in rheumatoid arthritis; myelin basic protein and MOG in multiple sclerosis; gliadin in celiac disease; histones, PLP, collagen, glucose-6-phosphate isomerase, thyroglobulin, various tRNA synthetases, acetylcholine receptor (AchR), proteinase-3, myeloperoxidase etc. Examples of allergens include, but are not limited to, Fel d 1 (i.e., the feline skin and salivary gland allergen of the domestic cat *Felis domesticus*, the amino acid sequence of which is disclosed International Publication WO 91/06571), Der p I, Der p II, Der fI or Der fII (i.e., the major protein allergens from the house dust mite dermatophagoides, the amino acid sequence of which is disclosed in International Publication WO 94/24281). Other allergens may be derived, for example from the following: grass, tree and weed (including ragweed) pollens; fungi and moulds; foods such as fish, shellfish, crab, lobster, peanuts, nuts, wheat gluten, eggs and milk; stinging insects such as bee, wasp, and hornet and the chironomidae (non-biting midges); other insects such as the housefly, fruit fly, sheep blow fly, screw worm fly, grain weevil, silkworm, honeybee, non-biting midge larvae, bee moth larvae, mealworm, cockroach and larvae of *Tenebrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives. Transplantation antigens can be derived from donor cells or tissues or from the donor antigen-presenting cells bearing MHC loaded with self antigen in the absence of exogenous antigen.

The antigen(s) may be isolated from a natural source or may be prepared by recombinant techniques as is known in the art. For example, peptide antigens can be eluted from the MHC and other presenting molecules of antigen-presenting cells obtained from a cell population or tissue for which a modified immune response is desired, e.g., an allogeneic tissue or cell population in transplantation medicine. The eluted peptides can be purified using standard protein purification techniques known in the art (Rawson et al., 2000, Cancer Res 60(16), 4493-4498). If desired, the purified peptides can be sequenced and synthetic versions of the peptides produced using standard protein synthesis techniques as for example described below. Alternatively, crude antigen preparations can be produced by isolating a sample of a cell population or tissue for which a modified immune response is desired, and either lysing the sample or subjecting the sample to conditions that will lead to the formation of apoptotic cells (e.g., irradiation with ultra violet or with gamma rays, viral infection, cytokines or by depriving cells of nutrients in the cell culture medium, incubation with hydrogen peroxide, or with drugs such as dexamethasone, ceramide chemotherapeutics and anti-hormonal agents such as Lupron or Tamoxifen). The lysate or the apoptotic cells can then be used as a source of crude antigen for contact with the antigen-presenting cells.

When the antigen is known, it may be conveniently prepared in recombinant form using standard protocols as for example described in: Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6. Typically, an antigen may be prepared by a procedure including the steps of (a) providing an expression vector from which the target antigen or analogue or mimetic thereof is expressible; (b) introducing the vector into a suitable host cell; (c) culturing the host cell to express recombinant polypeptide from the vector; and (d) isolating the recombinant polypeptide.

Alternatively, the antigen can be synthesized using solution synthesis or solid phase synthesis as described, for example, by Atherton and Sheppard (Solid Phase Peptide Synthesis: A Practical Approach, IRL Press at Oxford University Press, Oxford, England, 1989) or by Roberge et al. (1995, *Science* 269: 202).

In some embodiments, the antigen is in the form of one or more peptides. Usually, such peptides are at least 6, 7, 8, 9, 10, 11, 12, 13, 14, 15, 20, 25, 30 amino acid residues in length and suitably no more than about 500, 200, 100, 80, 60, 50, 40 amino acids in length. In some embodiments in which two or more peptides are used, the peptides can be in the form of a plurality of contiguous overlapping peptides whose sequences span at least a portion of a target antigen. Suitably, the peptide sequences are derived from at least about 30, 40, 50, 60, 70, 80, 90, 91, 92, 93, 94, 95, 96, 97, 98, 99% of the sequence corresponding to the target antigen. In some embodiments, each peptide of the plurality of contiguous overlapping peptide fragments can be 30-90 amino acids in length, e.g., 30, 35, 40, 45, 50, 55, 60, 65, 70, 73, 75, 80, 81, 85, 86 and 90 amino acids in length. In various embodiments, the amino acid sequences of contiguous overlapping peptide fragments in the plurality overlap by about 10 to about 15 amino acids, e.g., 10, 11, 12, 13, 14 and 15 amino acids. Exemplary methods for producing such peptide antigens are described, for example, by Astori et al. (2000 *J Immunol*. 165, 3497-3505; and references cited therein) and in U.S. Pat. Appl. Pub. No. 2004/0241178. The antigen may be suitably modified, for example, by lipid modification to modify its physico-chemical properties.

3.2 Peroxiredoxin Embodiments

The present inventors have found that the activity of the HDM peptides and polypeptides of the invention can be enhanced by co-delivery or co-administration of polypeptides with peroxiredoxin activity (also referred to herein as "peroxiredoxin polypeptides" or Prx polypeptides). Accordingly, the present invention also encompasses compositions comprising one or more HDMs and a Prx polypeptide. Prx polypeptides according to the present invention include naturally-occurring Prx polypeptides as for example set forth in SEQ ID NO: 51, 53, 55, 57, 59, 61, 63, 65, 67, 69, 71, 73, 75, 77, 79, 81, 83, 85, 87, 89, 91, 93, 95, 97, 99, 101 or 103, whether in processed or precursor form, their biologically active fragments and variants thereof, wherein the variants have peroxiredoxin activity (e.g., reducing hydrogen peroxide, peroxynitrite, and organic hydroperoxides) and are distinguished from the naturally-occurring sequence by the addition, deletion, or substitution of one or more amino acid residues. In general, variants will display at least about 40%, 45%, 50%, 51%, 52%, 53%, 54%, 55% 6, 57%, 58%, %59% 60%, 61%, 62%, 63%, 64%, 65%, 66%, 67%, 68%, 69% 70%, 71%, 72%, 73%, 74%, 75%, 76%, 77%, 78%, 79%, 80%, 81% o, 82%, 83%, 84%, 85%, 86%, 87%, 88%, 89%, 90%, 91%, 92%, 93%, 94%, 95%, 96%, 97%, 98%, 99% similarity to a parent or reference Prx polypeptide sequence as, for example, set forth in SEQ ID NO: 51, 53, 55, 57, 59, 61, 63, 65, 67, 69, 71, 73, 75, 77, 79, 81, 83, 85, 87, 89, 91, 93, 95, 97, 99, 101 or 103, as determined by sequence alignment programs described elsewhere herein using default parameters. Desirably, variants will have at least 40%, 45%, 50%, 51%, 52%, 53%, 54%, 55%, 6%, %57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a parent Prx polypeptide sequence as, for example, set forth in SEQ ID NO: 51, 53, 55, 57, 59, 61, 63, 65, 67, 69, 71, 73, 75, 77, 79, 81, 83, 85, 87, 89, 91, 93, 95, 97, 99, 101 or 103, as determined by sequence alignment programs described elsewhere herein using default parameters. Variants of a wild-type Prx polypeptide, which fall within the scope of a variant polypeptide, may differ from the wild-type molecule generally by as much 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, or 11 amino acid residues or suitably by as few as 10, 9, 8, 7, 6, 5 4, 3, 2, or 1 amino acid residue(s). In some embodiments, a variant polypeptide differs from the corresponding sequences in SEQ ID NO: 51, 53, 55, 57, 59, 61, 63, 65, 67, 69, 71, 73, 75, 77, 79, 81, 83, 85, 87, 89, 91, 93, 95, 97, 99, 101 or 103 by at least 1 but by less than or equal to 25, 24, 23, 22, 21, 20, 19, 18, 17, 16, 15, 14, 13, 12, 11, 10, 9, 8, 7, 6, 5, 4, 3 or 2 amino acid residues. In other embodiments, it differs from the corresponding sequence in any one of SEQ ID NO: 51, 53, 55, 57, 59, 61, 63, 65, 67, 69, 71, 73, 75, 77, 79, 81, 83, 85, 87, 89, 91, 93, 95, 97, 99, 101 and 103 by at least one 1% but less than or equal to 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3% or 2% of the residues. If the sequence comparison requires alignment, the sequences are typically aligned for maximum similarity or identity, as discussed in Section 2.

Prx polypeptides further encompass polypeptides with peroxiredoxin activity that have either been chemically modified relative to a reference or naturally-occurring Prx polypeptide and/or contain truncated amino acid sequences relative to a reference or naturally-occurring full-length or precursor Prx polypeptide. Prx polypeptides also encompass polypeptides with a slightly modified amino acid sequence, for instance, peptides and polypeptides having a modified N-terminal end including N-terminal amino acid deletions or additions, and/or peptides and polypeptides that have been chemically modified relative to a reference or naturally-occurring Prx polypeptide. Prx polypeptides also encompass polypeptides exhibiting substantially the same or better bioactivity than a reference or naturally-occurring Prx polypeptide, or, alternatively, exhibiting substantially modified or reduced bioactivity relative to a reference or naturally-occurring Prx polypeptide.

Prx polypeptides of the present invention also encompass polypeptides comprising amino acids with modified side chains, incorporation of unnatural amino acid residues and/or their derivatives during peptide, polypeptide or protein synthesis and the use of cross-linkers and other methods which impose conformational constraints on the peptides, portions and variants of the invention, as described for example in Section 2.

In some embodiments, naturally-occurring or wild-type Prx polypeptides are isolated from a particular source by standard methods as known in the art (Donnelly et al., 2005 *Infect Immun* 73: 166-173). In other embodiments, the Prx polypeptides are prepared by recombinant techniques. For example, the Prx polypeptides of the invention may be prepared by a procedure including the steps of: (a) preparing a construct comprising a polynucleotide sequence that encodes a Prx polypeptide and that is operably linked to a regulatory element; (b) introducing the construct into a host cell; (c) culturing the host cell to express the polynucleotide sequence to thereby produce the encoded Prx polypeptide; and (d) isolating the Prx polypeptide from the host cell. In illustrative examples, the nucleotide sequence encodes at least a biologically active portion of the sequences set forth in SEQ ID NO: 51, 53, 55, 57, 59, 61, 63, 65, 67, 69, 71, 73, 75, 77, 79, 81, 83, 85, 87, 89, 91, 93, 95, 97, 99, 101 or 103, or a variant thereof. Recombinant polypeptides can be conveniently prepared using standard protocols as described for example in Section 2.

Exemplary nucleotide sequences that encode the Prx polypeptides of the invention encompass full-length Prx genes as well as portions of the full-length or substantially full-length nucleotide sequences of the Prx genes or their transcripts or DNA copies of these transcripts. Portions of a Prx nucleotide sequence may encode polypeptide portions or segments that retain the biological activity of the native polypeptide. A portion of a Prx nucleotide sequence that encodes a biologically active fragment of a Prx polypeptide may encode at least about 100, 110, 120, 130, 140, 150, 160, 170, 180, 190 or more contiguous amino acid residues, or almost up to the total number of amino acids present in a full-length Prx polypeptide.

Prx nucleotide sequences can be used to isolate corresponding sequences and alleles from other organisms, particularly other parasites including protozoa (e.g., helminths). Accordingly, the present invention also contemplates polynucleotides that hybridize to reference Prx nucleotide sequences, or to their complements, (e.g., SEQ ID NO: 50, 52, 54, 56, 58, 60, 62, 64, 66, 68, 70, 72, 74, 76, 78, 80, 82, 84, 86, 88, 90, 92, 94, 96, 98, 100 or 102, or their complements) under stringency conditions described for example in Section 2, for producing Prx polypeptides according to the present invention.

3.3 Particle Embodiments

In some embodiments, a HDM according to Section 2 and optionally one or both of an antigen according to Section 3.1 and a Prx polypeptide according to Section 3.2 are provided in particulate form. In embodiments in which an HDM and one or both of an antigen and a Prx polypeptide are employed, they may be contained in or otherwise associated with the same particle or with different particles. A variety of particles may be used in the invention, including but not limited to, liposomes, micelles, lipidic particles, ceramic/inorganic particles and polymeric particles, and are typically selected from nanoparticles and microparticles. The particles are suitably sized for phagocytosis or endocytosis by antigen-presenting cells.

Antigen-presenting cells include both professional and facultative types of antigen-presenting cells. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Examples of facultative antigen-presenting cells include but are not limited to activated T cells, astrocytes, follicular cells, endothelium and fibroblasts. In some embodiments, the antigen-presenting cell is selected from monocytes, macrophages, B-lymphocytes, cells of myeloid lineage, dendritic cells or Langerhans cells. In specific embodiments, the antigen-presenting cell expresses CD11c and includes a dendritic cell. In illustrative examples, the particles have a dimension of less than about 100 μm, more suitably in the range of less than or equal to about 500 nm, although the particles may be as large as about 10 μm, and as small as a few nm. Liposomes consist basically of a phospholipid bilayer forming a shell around an aqueous core. Advantages include the lipophilicity of the outer layers which "mimic" the outer membrane layers of cells and that they are taken up relatively easily by a variety of cells. Polymeric vehicles typically consist of micro/nanospheres and micro/nanocapsules formed of biocompatible polymers, which are either biodegradable (for example, polylactic acid) or non-biodegradable (for example, ethylenevinyl acetate). Some of the advantages of the polymeric devices are ease of manufacture and high loading capacity, range of size from nanometer to micron diameter, as well as controlled release and degradation profile.

In some embodiments, the particles comprise an antigen-binding molecule on their surface, which is immuno-interactive with a marker that is expressed at higher levels on antigen-presenting cells (e.g., dendritic cells) than on non-antigen-presenting cells. Illustrative markers of this type include MGL, DCL-1, DEC-205, macrophage mannose R, DC-SIGN or other DC or myeloid specific (lectin) receptors, as for example disclosed by Hawiger et al. (2001, J Exp Med 194, 769), Kato et al. 2003, J Biol Chem 278, 34035), Benito et al. (2004, J Am Chem Soc 126, 10355), Schjetne, et al. (2002, Int Immunol 14, 1423) and van Vliet et al., 2006, Nat Immunol September 24; [Epub ahead of print]) (van Vliet et al., Immunobiology 2006, 211:577-585).

The particles can be prepared from a combination of the HDM and optionally one or both of an antigen to which a tolerogenic response is desired and a Prx polypeptide, and a surfactant, excipient or polymeric material. In some embodiments, the particles are biodegradable and biocompatible, and optionally are capable of biodegrading at a controlled rate for delivery of a therapeutic or diagnostic agent. The particles can be made of a variety of materials. Both inorganic and organic materials can be used. Polymeric and non-polymeric materials, such as fatty acids, may be used. Other suitable materials include, but are not limited to, gelatin, polyethylene glycol, trehalulose, dextran and chitosan. Particles with degradation and release times ranging from seconds to months can be designed and fabricated, based on factors such as the particle material.

3.3.1 Polymeric Particles

Polymeric particles may be formed from any biocompatible and desirably biodegradable polymer, copolymer, or blend. The polymers may be tailored to optimize different characteristics of the particle including: i) interactions between the bioactive agents to be delivered and the polymer to provide stabilization of the bioactive agents and retention of activity upon delivery; ii) rate of polymer degradation and, thereby, rate of agent release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)-hexane anhydride] (PCPH) may be used. Biodegradable polyanhydrides are described in U.S. Pat. No. 4,857,311.

In other embodiments, bulk eroding polymers such as those based on polyesters including poly(hydroxy acids) or poly(esters) can be used. For example, polyglycolic acid (PGA), polylactic acid (PLA), or copolymers thereof may be used to form the particles. The polyester may also have a charged or functionalizable group, such as an amino acid. In illustrative examples, particles with controlled release properties can be formed of poly(D,L-lactic acid) and/or poly (D,L-lactic-co-glycolic acid) ("PLGA") which incorporate a surfactant such as DPPC.

Other polymers include poly(alkylcyanoacrylates), polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

In some embodiments, particles are formed from functionalized polyester graft copolymers, as described in Hrkach et al. (1995, *Macromolecules* 28:4736-4739; and "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M. Ottenbrite et al., Eds., American Chemical Society, Chapter 8, pp. 93-101, 1996.)

Materials other than biodegradable polymers may be used to form the particles. Suitable materials include various non-biodegradable polymers and various excipients. The particles also may be formed of the bioactive agent(s) and surfactant alone.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art, provided that the conditions are optimized for forming particles with the desired diameter.

Methods developed for making microspheres for delivery of encapsulated agents are described in the literature, for example, as described in Doubrow, M., Ed., "Microcapsules and Nanoparticles in Medicine and Pharmacy," CRC Press, Boca Raton, 1992. Methods also are described in Mathiowitz and Langer (1987, *J. Controlled Release* 5, 13-22); Mathiowitz et al. (1987, *Reactive Polymers* 6, 275-283); and Mathiowitz et al. (1988, *J. Appl. Polymer Sci.* 35, 755-774) as well as in U.S. Pat. Nos. 5,213,812, 5,417,986, 5,360,610, and 5,384,133. The selection of the method depends on the polymer selection, the size, external morphology, and crystallinity that is desired, as described, for example, by Mathiowitz et al. (1990, *Scanning Microscopy* 4: 329-340; 1992, *J. Appl. Polymer Sci.* 45, 125-134); and Benita et al. (1984, *J. Pharm. Sci.* 73, 1721-1724).

In solvent evaporation, described for example, in Mathiowitz et al., (1990), Benita; and U.S. Pat. No. 4,272,398 to Jaffe, the polymer is dissolved in a volatile organic solvent, such as methylene chloride. Several different polymer concentrations can be used, for example, between 0.05 and 2.0 g/mL. The bioactive agent(s), either in soluble form or dispersed as fine particles, is (are) added to the polymer solution, and the mixture is suspended in an aqueous phase that contains a surface-active agent such as poly(vinyl alcohol). The aqueous phase may be, for example, a concentration of 1% poly(vinyl alcohol) w/v in distilled water. The resulting emulsion is stirred until most of the organic solvent evaporates, leaving solid microspheres, which may be washed with water and dried overnight in a lyophilizer. Microspheres with different sizes (between 1 and 1000 μm) and morphologies can be obtained by this method.

Solvent removal was primarily designed for use with less stable polymers, such as the polyanhydrides. In this method, the agent is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike the hot-melt microencapsulation method described for example in Mathiowitz et al. (1987, *Reactive Polymers* 6:275), this method can be used to make microspheres from polymers with high melting points and a wide range of molecular weights. Microspheres having a diameter for example between one and 300 microns can be obtained with this procedure.

With some polymeric systems, polymeric particles prepared using a single or double emulsion technique, vary in size depending on the size of the droplets. If droplets in water-in-oil emulsions are not of a suitably small size to form particles with the desired size range, smaller droplets can be prepared, for example, by sonication or homogenation of the emulsion, or by the addition of surfactants.

If the particles prepared by any of the above methods have a size range outside of the desired range, particles can be sized, for example, using a sieve, and further separated according to density using techniques known to those of skill in the art.

The polymeric particles can be prepared by spray drying. Methods of spray drying, such as that disclosed in PCT WO 96/09814 by Sutton and Johnson, disclose the preparation of smooth, spherical microparticles of a water-soluble material with at least 90% of the particles possessing a mean size between 1 and 10 μm.

3.3.2 Ceramic Particles

Ceramic particles may also be used to deliver the bioactive agents of the invention. These particles are typically prepared using processes similar to the well known sol-gel process and usually require simple and room temperature conditions as described for example in Brinker et al. ("Sol-Gel Science: The Physics and Chemistry of Sol-Gel Processing;" Academic Press: San Diego, 1990, p-60), and Avnir et al. (1994, Chem. Mater. 6, 1605). Ceramic particles can be prepared with desired size, shape and porosity, and are extremely stable. These particles also effectively protect doped molecules (polypeptides, drugs etc.) against denaturation induced by extreme pH and temperature (Jain et al., 1998, *J Am. Chem. Soc.* 120, 11092-11095). In addition, their surfaces can be easily functionalized with different groups (Lal et al., 2000, *Chem. Mater.* 12, 2632-2639; Badley et al., 1990, *Langmuir* 6, 792-801), and therefore they can be attached to a variety of monoclonal antibodies and other ligands in order to target them to desired sites in vivo.

Various ceramic particles have been described for delivery in vivo of active agent-containing payloads. For example, British Patent 1 590 574 discloses incorporation of biologically active components in a sol-gel matrix. International Publication WO 97/45367 discloses controllably dissolvable silica xerogels prepared via a sol-gel process, into which a biologically active agent is incorporated by impregnation into pre-sintered particles (1 to 500 μm) or disks. International Publication WO 0050349 discloses controllably biodegradable silica fibres prepared via a sol-gel process, into which a biologically active agent is incorporated during synthesis of the fibre. U.S. Pat. Appl. Pub. 20040180096 describes ceramic nanoparticles in which a bioactive substance is entrapped. The ceramic nanoparticles are made by formation of a micellar composition of the dye. The ceramic material is added to the micellar composition and the ceramic nanoparticles are precipitated by alkaline hydrolysis. U.S. Pat. Appl. Pub. 20050123611 discloses controlled release ceramic particles comprising an active material substantially homogeneously dispersed throughout the particles. These particles are prepared by mixing a surfactant with an apolar solvent to prepare a reverse micelle solution; (b) dissolving a gel precursor, a catalyst, a condensing agent and a soluble active material in a polar solvent to prepare a precursor solution; (c) combining the reverse micelle solution and the precursor solution to provide an emulsion and (d) condensing the precursor in the emulsion. U.S. Pat. Appl. Pub. 20060210634 discloses adsorbing bioactive substances onto ceramic particles comprising a metal oxide (e.g., titanium oxide, zirconium oxide, scandium oxide, cerium oxide and yttrium oxide) by evaporation. Kortesuo et al. (2000, *Int J Pharm.* May 10; 200(2):223-229) disclose a spray drying method to produce spherical silica gel particles with a narrow particle size range for controlled delivery of drugs such as toremifene citrate and dexmedetomidine HCl. Wang et al. (2006, *Int J Pharm.* 308(1-2):160-167) describe the combination of adsorption by porous CaCO3 microparticles and encapsulation by polyelectrolyte multilayer films for delivery of bioactive substances.

3.3.3 Liposomes

Liposomes can be produced by standard methods such as those reported by Kim et al. (1983, *Biochim. Biophys. Acta* 728, 339-348); Liu et al. (1992, *Biochim. Biophys. Acta* 1104, 95-101); Lee et al. (1992, *Biochim. Biophys. Acta.* 1103, 185-197), Brey et al. (U.S. Pat. Appl. Pub. 20020041861), Hass et al. (U.S. Pat. Appl. Pub. 20050232984), Kisak et al. (U.S. Pat. Appl. Pub. 20050260260) and Smyth-Templeton et al. (U.S. Pat. Appl. Pub. 20060204566). Additionally, reference may be made to Copeland et al. (2005, *Immunol. Cell Biol.* 83: 95-105) who review lipid based particulate formulations for the delivery of antigen, and to Bramwell et al. (2005, *Crit Rev Ther Drug Carrier Syst.* 22(2):151-214; 2006, *J Pharm Pharmacol.* 58(6):717-728) who review particulate delivery systems for vaccines, including methods for the preparation of protein-loaded liposomes. Many liposome formulations using a variety of different lipid components have been used in various in vitro cell culture and animal experiments. Parameters have been identified that determine liposomal properties and are reported in the literature, for example, by Lee et al. (1992, *Biochim. Biophys. Acta.* 1103, 185-197); Liu et al. (1992, *Biochim. Biophys. Acta.* 1104, 95-101); and Wang et al. (1989, *Biochem.* 28, 9508-951).

Briefly, the lipids of choice (and any organic-soluble bioactive), dissolved in an organic solvent, are mixed and dried onto the bottom of a glass tube under vacuum. The lipid film is rehydrated using an aqueous buffered solution containing any water-soluble bioactives to be encapsulated by gentle swirling. The hydrated lipid vesicles can then be further processed by extrusion, submitted to a series of freeze-thawing cycles or dehydrated and then rehydrated to promote encapsulation of bioactives. Liposomes can then be washed by centrifugation or loaded onto a size-exclusion column to remove unentrapped bioactive from the liposome formulation and stored at 4° C. The basic method for liposome preparation is described in more detail in Thierry et al. (1992, *Nuc. Acids Res.* 20:5691-5698).

A particle carrying a payload of bioactive agent(s) can be made using the procedure as described in: Pautot et al. (2003, *Proc. Nat. Acad. Sci. USA* 100(19):10718-21). Using the Pautot et al. technique, streptavidin-coated lipids (DPPC, DSPC, and similar lipids) can be used to manufacture liposomes. The drug encapsulation technique described by Needham et al. (2001, *Advanced Drug Delivery Reviews* 53(3): 285-305) can be used to load these vesicles with one or more active agents.

The liposomes can be prepared by exposing chloroformic solution of various lipid mixtures to high vacuum and subsequently hydrating the resulting lipid films (DSPC/CHOL) with pH 4 buffers, and extruding them through polycarbonated filters, after a freezing and thawing procedure. It is possible to use DPPC supplemented with DSPC or cholesterol to increase encapsulation efficiency or increase stability, etc. A transmembrane pH gradient is created by adjusting the pH of the extravesicular medium to 7.5 by addition of an alkalinization agent. A bioactive agent (e.g., a HDM and optionally an antigen to which a tolerogenic response is desired) can be subsequently entrapped by addition of a solution of the bioactive agent in small aliquots to the vesicle solution, at an elevated temperature, to allow accumulation of the bioactive agent inside the liposomes.

Other lipid-based particles suitable for the delivery of the bioactive agents of the present invention such as niosomes are described by Copeland et al. (2005, *Immunol. Cell Biol.* 83: 95-105).

3.3.4 Ballistic Particles

The bioactive agents of the present invention (e.g., a HDM molecule and optionally an antigen to which a tolerogenic response is desired) may be attached to (e.g., by coating or conjugation) or otherwise associated with particles suitable for use in needleless or "ballistic" (biolistic) delivery. Illustrative particles for ballistic delivery are described, for example, in: International Publications WO 02/101412; WO 02/100380; WO 02/43774; WO 02/19989; WO 01/93829; WO 01/83528; WO 00/63385; WO 00/26385; WO 00/19982; WO 99/01168; WO 98/10750; and WO 97/48485. It shall be understood, however, that such particles are not limited to their use with a ballistic delivery device and can otherwise be administered by any alternative technique (e.g., injection or microneedle delivery) through which particles are deliverable to immune cells.

The bioactive agents can be coated or chemically coupled to carrier particles (e.g., core carriers) using a variety of techniques known in the art. Carrier particles are selected from materials which have a suitable density in the range of particle sizes typically used for intracellular delivery. The optimum carrier particle size will, of course, depend on the diameter of the target cells. Illustrative particles have a size ranging from about 0.01 to about 250 µm, from about 10 to about 150 µm, and from about 20 to about 60 µm; and a particle density ranging from about 0.1 to about 25 g/cm3, and a bulk density of about 0.5 to about 3.0 g/cm3, or greater. Non-limiting particles of this type include metal particles such as, tungsten, gold, platinum and iridium carrier particles. Tungsten particles are readily available in average sizes of 0.5 to 2.0 µm in diameter. Gold particles or microcrystalline gold (e.g., gold powder A1570, available from Engelhard Corp., East Newark, N.J.) may also be used. Gold particles provide uniformity in size (available from Alpha Chemicals in particle sizes of 1-3 µm, or available from Degussa, South Plainfield, N.J. in a range of particle sizes including 0.95 µm) and low toxicity. Microcrystalline gold provides a diverse particle size distribution, typically in the range of 0.1-5 µm. The irregular surface area of microcrystalline gold provides for highly efficient coating with the active agents of the present invention.

Many methods are known and have been described for adsorbing, coupling or otherwise attaching bioactive molecules (e.g., hydrophilic molecules such as proteins and nucleic acids) onto particles such as gold or tungsten particles. In illustrative examples, such methods combine a predetermined amount of gold or tungsten with the bioactive molecules, $CaCl_2$) and spermidine. In other examples, ethanol is used to precipitate the bioactive molecules onto gold or tungsten particles (see, for example, Jumar et al., 2004, *Phys Med. Biol.* 49:3603-3612). The resulting solution is suitably vortexed continually during the coating procedure to ensure uniformity of the reaction mixture. After attachment of the bioactive molecules, the particles can be transferred for example to suitable membranes and allowed to dry prior to use, coated onto surfaces of a sample module or cassette, or loaded into a delivery cassette for use in particular particle-mediated delivery instruments.

The formulated compositions may suitably be prepared as particles using standard techniques, such as by simple evaporation (air drying), vacuum drying, spray drying, freeze drying (lyophilization), spray-freeze drying, spray coating, precipitation, supercritical fluid particle formation, and the like. If desired, the resultant particles can be dandified using the techniques described in International Publication WO 97/48485.

3.3.5 Surfactants

Surfactants which can be incorporated into particles include phosphoglycerides. Exemplary phosphoglycerides include phosphatidylcholines, such as the naturally occurring surfactant, L-α-phosphatidylcholine dipalmitoyl ("DPPC"). The surfactants advantageously improve surface properties by, for example, reducing particle-particle interactions, and can render the surface of the particles less adhesive. The use of surfactants endogenous to the lung may avoid the need for the use of non-physiologic surfactants.

Providing a surfactant on the surfaces of the particles can reduce the tendency of the particles to agglomerate due to interactions such as electrostatic interactions, Van der Waals forces, and capillary action. The presence of the surfactant on the particle surface can provide increased surface rugosity (roughness), thereby improving aerosolization by reducing the surface area available for intimate particle-particle interaction.

Surfactants known in the art can be used including any naturally occurring surfactant. Other exemplary surfactants include diphosphatidyl glycerol (DPPG); hexadecanol; fatty alcohols such as polyethylene glycol (PEG); polyoxyethylene-9-lauryl ether; a surface active fatty acid, such as palmitic acid or oleic acid; sorbitan trioleate (Span 85); glycocholate; surfactin; a poloxamer; a sorbitan fatty acid ester such as sorbitan trioleate; tyloxapol and a phospholipid.

3.4 Antigen-Presenting Cell Embodiments

The present invention also contemplates contacting an antigen-presenting cell or its precursor with an HDM and optionally one or both of an antigen to which a tolerogenic response is desired and a Prx polypeptide to produce tolerogenic antigen-presenting cells. Suitably, the antigen-presenting cell is obtained from a subject to be treated (i.e., an autologous antigen-presenting cell) or from a donor that is MHC matched or mismatched with the subject (i.e., an allogeneic antigen-presenting cell). In the latter embodiments, the donor is desirably histocompatible with the subject.

In some embodiments, the antigen-presenting cell is contacted with an HDM as described for example in Section 2, either in soluble form or in particulate form as described for example in Section 3.3, in an amount and for a time sufficient to: (1) stimulate or induce the antigen-presenting cell to elicit an antigen-specific Th2 response, (2) inhibit the antigen-presenting cell from stimulating an antigen-specific Th1 response, (3) stimulate the antigen-presenting cell to develop an alternatively activated phenotype, (4) prevent or inhibit the antigen-presenting cell from activating in response to an inflammatory stimulus, (5) prevent or inhibit the antigen-presenting cell from binding TLR ligands (e.g., lipopolysaccharide), and/or (6) down-regulate or impair lysosome function in the antigen-presenting cell.

In certain examples of the above embodiments, the antigen-presenting cell or its precursor is also contacted with an antigen according to Section 3.1, or with a polynucleotide from which the antigen is expressible, for a time and under conditions sufficient for the antigen or a processed form thereof to be presented by the antigen-presenting cell. Suitably, the antigen is in soluble form or in particulate form as described for example in Section 3.3.

In some examples of the above embodiments, the antigen-presenting cell or its precursor is also contacted with a Prx polypeptide according to Section 3.2, or with a polynucleotide from which the Prx polypeptide is expressible, in an amount and for a time sufficient to enhance at least one HDM activity selected from: (1) stimulating or inducing the antigen-presenting cell to elicit an antigen-specific Th2 response, (2) inhibiting the antigen-presenting cell from stimulating an antigen-specific Th1 response, (3) stimulating the antigen-presenting cell to develop an alternatively activated phenotype, (4) preventing or inhibiting the antigen-presenting cell from activating in response to an inflammatory stimulus, (5) preventing or inhibiting the antigen-presenting cell from binding TLR ligands (e.g., lipopolysaccharide), and/or (6) down-regulating or impairing lysosome function in the antigen-presenting cell. Suitably, the Prx polypeptide is in soluble form or in particulate form as described for example in Section 3.3.

3.4.1 Sources of Antigen-Presenting Cells and their Precursors

Antigen-presenting cells or their precursors can be isolated by methods known to those of skill in the art. The source of such cells will differ depending upon the antigen-presenting cell required for modulating a specified immune response. In this context, the antigen-presenting cell can be selected from dendritic cells, macrophages, monocytes and other cells of myeloid lineage.

Typically, precursors of antigen-presenting cells can be isolated from any tissue, but are most easily isolated from blood, cord blood or bone marrow (Sorg et al., 2001, *Exp Hematol.* 29, 1289-1294; Zheng et al., 2000, *J Hematother Stem Cell Res.* 9, 453-464). It is also possible to obtain suitable precursors from diseased tissues such as rheumatoid synovial tissue or fluid following biopsy or joint tap (Thomas et al., 1994a, *J Immunol.* 153, 4016-4028; Thomas et al., 1994b, *Arthritis Rheum.* 37(4)). Other examples include, but are not limited to liver, spleen, heart, kidney, gut and tonsil (Lu et al., 1994, *J Exp Med.* 179, 1823-1834; McIlroy et al., 2001, *Blood* 97, 3470-3477; Vremec et al., 2000, *J Immunol.* 159, 565-573; Hart and Fabre, 1981, *J Exp Med.* 154(2), 347-361; Hart and McKenzie, 1988, *J Exp Med.* 168(1), 157-170; Pavli et al., 1990, *Immunology* 70(1), 40-47).

Leukocytes isolated directly from tissue provide a major source of antigen-presenting cell precursors. Typically, these precursors can only differentiate into antigen-presenting cells by culturing in the presence or absence of various growth factors. According to the practice of the present invention, the antigen-presenting cells may be so differentiated from crude mixtures or from partially or substantially purified preparations of precursors. Leukocytes can be conveniently purified from blood or bone marrow by density gradient centrifugation using, for example, Ficoll Hypaque which eliminates neutrophils and red cells (peripheral blood mononuclear cells or PBMCs), or by ammonium chloride lysis of red cells (leukocytes or white blood cells). Many precursors of antigen-presenting cells are present in peripheral blood as non-proliferating monocytes, which can be differentiated into specific antigen-presenting cells, including macrophages and dendritic cells, by culturing in the presence of specific cytokines.

Tissue-derived precursors such as precursors of tissue dendritic cells or of Langerhans cells are typically obtained by mincing tissue (e.g., basal layer of epidermis) and digesting it with collagenase or dispase followed by density gradient separation, or selection of precursors based on their expression of cell surface markers. For example, Langerhans cell precursors express CD1 molecules as well as HLA-DR and can be purified on this basis.

In some embodiments, the antigen-presenting cell precursor is a precursor of macrophages. Generally these precursors can be obtained from monocytes of any source and can be differentiated into macrophages by prolonged incubation in the presence of medium and macrophage colony stimulating factor (M-CSF) (Erickson-Miller et al., 1990, Int J Cell Cloning 8, 346-356; Metcalf and Burgess, 1982, J Cell Physiol. 111, 275-283).

In other embodiments, the antigen presenting cell precursor is a precursor of Langerhans cells. Usually, Langerhans cells can be generated from human monocytes or CD34+ bone marrow precursors in the presence of granulocyte/macrophage colony-stimulating factor (GM-CSF), IL-4/TNFα and TGFβ (Geissmann et al., 1998, J Exp Med. 187, 961-966; Strobl et al., 1997a, Blood 90, 1425-1434; Strobl et al., 1997b, dv Exp Med Biol. 417, 161-165; Strobl et al., 1996, J Immunol. 157, 1499-1507).

In still other embodiments, the antigen-presenting cell precursor is a precursor of dendritic cells. Several potential dendritic cell precursors can be obtained from peripheral blood, cord blood or bone marrow. These include monocytes, CD34+ stem cells, granulocytes, CD33+CD11c+DC precursors, and committed myeloid progenitors—described below.

Monocytes:

Monocytes can be purified by adherence to plastic for 1-2 h in the presence of tissue culture medium (e.g., RPMI) and serum (e.g., human or foetal calf serum), or in serum-free medium (Anton et al., 1998, Scand J Immunol. 47, 116-121; Araki et al., 2001, Br J Haematol. 114, 681-689; Mackensen et al., 2000, Int J Cancer 86, 385-392; Nestle et al., 1998, Nat Med. 4, 328-332; Romani et al., 1996, J Immunol Meth. 196, 137-151; Thurner et al., 1999, J Immunol Methods 223, 1-15). Monocytes can also be elutriated from peripheral blood (Garderet et al., 2001, J Hematother Stem Cell Res. 10, 553-567). Monocytes can also be purified by immunoaffinity techniques, including immunomagnetic selection, flow cytometric sorting or panning (Araki et al., 2001, supra; Battye and Shortman, 1991, Curr. Opin. Immunol. 3, 238-241), with anti-CD14 antibodies to obtain CD14hi cells. The numbers (and therefore yield) of circulating monocytes can be enhanced by the in vivo use of various cytokines including GM-CSF (Groopman et al., 1987, N Engl J Med. 317, 593-598; Hill et al., 1995, J Leukoc Biol. 58, 634-642). Monocytes can be differentiated into dendritic cells by prolonged incubation in the presence of GM-CSF and IL-4 (Romani et al., 1994, J Exp Med. 180, 83-93; Romani et al., 1996, supra). A combination of GM-CSF and IL-4 at a concentration of each at between about 200 to about 2000 U/mL, more preferably between about 500 to about 1000 U/mL and even more preferably between about 800 U/mL (GM-CSF) and 1000 U/mL (IL-4) produces significant quantities of immature dendritic cells, i.e., antigen-capturing phagocytic dendritic cells. Other cytokines which promote differentiation of monocytes into antigen-capturing phagocytic dendritic cells include, for example, IL-13.

CD34+ Stem Cells:

Dendritic cells can also be generated from CD34+ bone marrow derived precursors in the presence of GM-CSF, TNFα±stem cell factor (SCF, c-kitL), or GM-CSF, IL-4±flt3L (Bai et al., 2002, Int J Oncol. 20, 247-53; Chen et al., 2001, Clin Immunol. 98, 280-292; Loudovaris et al., 2001, J Hematother Stem Cell Res. 10, 569-578). CD34+ cells can be derived from a bone marrow aspirate or from blood and can be enriched as for monocytes using, for example, immunomagnetic selection or immunocolumns (Davis et al., 1994, J Immunol Meth. 175, 247-257). The proportion of CD34+ cells in blood can be enhanced by the in vivo use of various cytokines including (most commonly) G-CSF, but also flt3L and progenipoietin (Fleming et al., 2001, Exp Hematol. 29, 943-951; Pulendran et al., 2000, J Immunol. 165, 566-572; Robinson et al., 2000, J Hematother Stem Cell Res. 9, 711-720).

Other Myeloid Progenitors:

DC can be generated from committed early myeloid progenitors in a similar fashion to CD34+ stem cells, in the presence of GM-CSF and IL-4/TNF. Such myeloid precursors infiltrate many tissues in inflammation, including rheumatoid arthritis synovial fluid (Santiago-Schwarz et al., 2001, J Immunol. 167, 1758-1768). Expansion of total body myeloid cells including circulating dendritic cell precursors and monocytes, can be achieved with certain cytokines, including flt-3 ligand, granulocyte colony-stimulating factor (G-CSF) or progenipoietin (pro-GP) (Fleming et al., 2001, supra; Pulendran et al., 2000, supra; Robinson et al., 2000, supra). Administration of such cytokines for several days to a human or other mammal would enable much larger numbers of precursors to be derived from peripheral blood or bone marrow for in vitro manipulation. Dendritic cells can also be generated from peripheral blood neutrophil precursors in the presence of GM-CSF, IL-4 and TNFα (Kelly et al., 2001, Cell Mol Biol. (Noisy-le-grand) 47, 43-54; Oehler et al., 1998, J Exp Med. 187, 1019-1028). It should be noted that dendritic cells can also be generated, using similar methods, from acute myeloid leukaemia cells (Oehler et al., 2000, Ann Hematol. 79, 355-362).

Tissue DC Precursors and Other Sources of APC Precursors:

Other methods for DC generation exist from, for example, thymic precursors in the presence of IL-3+/−GM-CSF, and liver DC precursors in the presence of GM-CSF and a collagen matrix. Transformed or immortalised dendritic cell lines may be produced using oncogenes such as v-myc as for example described by (Paglia et al., 1993, J Exp Med. 178(6):1893-1901) or by myb (Banyer and Hapel, 1999, J Leukoc Biol. 66(2):217-223; Gonda et al., 1993, Blood. 82(9):2813-2822).

Circulating DC Precursors:

These have been described in human and mouse peripheral blood. One can also take advantage of particular cell surface markers for identifying suitable dendritic cell precursors. Specifically, various populations of dendritic cell precursors can be identified in blood by the expression of CD11c and the absence or low expression of CD14, CD19, CD56 and CD3 (O'Doherty et al., 1994, Immunology 82, 487-493; O'Doherty et al., 1993, J Exp Med. 178, 1067-1078). These cells can also be identified by the cell surface markers CD13 and CD33 (Thomas et al., 1993b, J Immunol. 151(12), 6840-6852). A second subset, which lacks CD14, CD19, CD56 and CD3, known as plasmacytoid dendritic cell precursors, does not express CD11c, but does express CD123 (IL-3R chain) and HLA-DR (Farkas et al., 2001, Am J Pathol. 159, 237-243; Grouard et al., 1997, J Exp Med. 185, 1101-1111; Rissoan et al., 1999, Science 283, 1183-

1186). Most circulating CD11c+ dendritic cell precursors are HLA-DR+, however some precursors may be HLA-DR−. The lack of MHC class II expression has been clearly demonstrated for peripheral blood dendritic cell precursors (del Hoyo et al., 2002, *Nature* 415, 1043-1047).

Optionally, CD33+CD14−/lo or CD11c+HLA−DR+, lineage marker-negative dendritic cell precursors described above can be differentiated into more mature antigen-presenting cells by incubation for 18-36 h in culture medium or in monocyte conditioned medium (Thomas et al., 1993b, supra; Thomas and Lipsky, 1994, *J Immunol.* 153, 4016-4028; O'Doherty et al., 1993, supra). Alternatively, following incubation of peripheral blood non-T cells or unpurified PBMC, the mature peripheral blood dendritic cells are characterised by low density and so can be purified on density gradients, including metrizamide and Nycodenz (Freudenthal and Steinman, 1990, *Proc Natl Acad Sci USA* 87, 7698-7702; Vremec and Shortman, 1997, *J Immunol.* 159, 565-573), or by specific monoclonal antibodies, such as but not limited to the CMRF-44 mAb (Feamley et al., 1999, *Blood* 93, 728-736; Vuckovic et al., 1998, *Exp Hematol.* 26, 1255-1264). Plasmacytoid dendritic cells can be purified directly from peripheral blood on the basis of cell surface markers, and then incubated in the presence of IL-3 (Grouard et al., 1997, supra; Rissoan et al., 1999, supra). Alternatively, plasmacytoid DC can be derived from density gradients or CMRF-44 selection of incubated peripheral blood cells as above.

In general, for dendritic cells generated from any precursor, when incubated in the presence of activation factors such as monocyte-derived cytokines, lipopolysaccharide and DNA containing CpG repeats, cytokines such as TNF-α, IL-6, IFN-α, IL-1β, necrotic cells, re-adherence, whole bacteria, membrane components, RNA or polyIC, immature dendritic cells will become activated (Clark, 2002, *J Leukoc Biol.* 71, 388-400; Hacker et al., 2002, *Immunology* 105, 245-251; Kaisho and Akira, 2002, *Biochim Biophys Acta* 1589, 1-13; Koski et al., 2001, *Crit Rev Immunol.* 21, 179-1890. This process of dendritic cell activation is inhibited in the presence of NF-κB inhibitors (O'Sullivan and Thomas, 2002, *J Immunol.* 168, 5491-5498).

3.4.2 Ex Vivo Delivery of HDM and Optionally an Antigen and/or a Prx Polypeptide HDMs can be delivered into antigen-presenting cells in various forms, including in nucleic acid and proteinaceous form. The HDMs may be soluble or particulate. In nucleic acid embodiments, the HDM is typically in the form of a nucleic acid construct from which a HDM is expressible. The amount of soluble or particulate HDM to be placed in contact with antigen-presenting cells can be determined empirically by routine methods known to persons of skill in the art. Typically antigen-presenting cells are incubated with an HDM (e.g., 0.1-100 μg/mL), generally for about 10 min to about 18 hours (e.g., about 10 min, 20 min, 30 min, 1, 2, 3, 4, 5, 6, 7, 8, 9, 10, 11, 12, 13, 14, 15, 16, 17, 18 hours) at 35° C.-38° C., or for as much time as required to (1) stimulate or induce the antigen-presenting cells to elicit an antigen-specific Th2 response, (2) inhibit the antigen-presenting cells from stimulating an antigen-specific Th1 response, (3) stimulate the antigen-presenting cells to develop an alternatively activated phenotype, (4) prevent or inhibit the antigen-presenting cells from activating in response to an inflammatory stimulus, (5) prevent or inhibit the antigen-presenting cells from binding TLR ligands (e.g., lipopolysaccharide), and/or (6) down-regulate or impair lysosome function in the antigen-presenting cells.

In some embodiments where a Prx polypeptide is concurrently delivered with an HDM and optionally an antigen, the amount of soluble or particulate Prx polypeptide to be placed in contact with antigen-presenting cells is determined empirically by routine methods known to persons of skill in the art. Suitably, the antigen-presenting cell is incubated with a Prx polypeptide (e.g., 0.1-100 μg/mL) for about 1 to about 18 hours (e.g., about 1, 2, 3, 4, 5, 6, 7, 8, 9, 10, 11, 12, 13, 14, 15, 16, 17, 18 hours).

In antigen embodiments, antigen-presenting cells are typically incubated with antigen for about 1 to 6 h at 37° C., although it is also possible to expose antigen-presenting cells to antigen for the duration of incubation with growth factors and HDM. Usually, for purified antigens and peptides, 0.1-10 μg/mL is suitable for producing antigen-specific antigen-presenting cells. Dendritic cells are exposed to apoptotic bodies in approximately 1:1 ratio, and bacteria (Albert et al., 1998, International Publication WO 99/42564; Corinti et al., 1999, *J Immunol.* 163(6), 3029-3036). The antigen should be exposed to the antigen-presenting cells for a period of time sufficient for those cells to internalize the antigen. The time and dose of antigen necessary for the cells to internalize and present the processed antigen may be determined using pulse-chase protocols in which exposure to antigen is followed by a washout period and exposure to a read-out system e.g., antigen reactive T cells. Once the optimal time and dose necessary for cells to express processed antigen on their surface is determined, a protocol may be used to prepare cells and antigen for inducing tolerogenic responses. Those of skill in the art will recognize in this regard that the length of time necessary for an antigen-presenting cell to present an antigen may vary depending on the antigen or form of antigen employed, its dose, and the antigen-presenting cell employed, as well as the conditions under which antigen loading is undertaken. These parameters can be determined by the skilled artisan using routine procedures.

In some embodiments, the delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, *Immunomethods* 4, 229-235), osmotic lysis of pinosomes after pinocytic uptake of soluble antigen (Moore et al., 1988, *Cell* 54, 777-785), coupling of antigens to potent adjuvants (Aichele et al., 1990, *J. Exp. Med.* 171, 1815-1820; Gao et al., 1991, *J. Immunol.* 147, 3268-3273; Schulz et al., 1991, *Proc. Natl. Acad. Sci. USA* 88, 991-993; Kuzu et al., 1993, *Euro. J. Immunol.* 23, 1397-1400; and Jondal et al., 1996, *Immunity* 5, 295-302), exosomes (Zitvogel et al., 1998 *Nat Med.* 4, 594-600; 2002, *Nat Rev Immunol.* 2, 569-79), and apoptotic cell delivery of antigen (Albert et al., 1998, *Nature* 392, 86-89; Albert et al., 1998, *Nature Med.* 4, 1321-1324; and in International Publications WO 99/42564 and WO 01/85207). Recombinant bacteria (e.g., *Escherichia coli*) or transfected host mammalian cells may be pulsed onto dendritic cells (as particulate antigen, or apoptotic bodies respectively) for antigen delivery. Such a delivery system might be logically combined with a HDM. Recombinant chimeric virus-like particles (VLPs) have also been used as vehicles for delivery of exogenous heterologous antigen to the MHC class I processing pathway of a dendritic cell line (Bachmann et al., 1996, *Eur. J. Immunol.*, 26(11), 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3), 248-256 and U.S. Pat. No. 6,352,697), phospholipases (see, e.g., Camilli et al., 1991, *J Exp. Med.* 173, 751-754), pore-forming toxins (e.g., an alpha-toxin), natural cytolysins of gram-positive bacteria, such as listeriolysin O (LLO, e.g., Mengaud et al., 1988, *Infect. Immun.* 56, 766-772 and Portnoy et al., 1992, *Infect. Immun.* 60, 2710-2717), streptolysin O (SLO, e.g., Palmer et al., 1998, *Biochemistry* 37(8), 2378-2383) and perfringolysin O (PFO, e.g., Rossjohn et al., *Cell* 89(5), 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., 1992, *Infect. Immun.* 60, 2710-2717).

The cytolysin may be provided together with a pre-selected antigen in the form of a single composition or may be provided as a separate composition, for contacting the antigen-presenting cells. In some embodiments, the cytolysin is fused or otherwise linked to the antigen, wherein the fusion or linkage permits the delivery of the antigen to the cytosol of the target cell. In other embodiments, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In specific embodiments of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory element which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of nonvirulent, non-pathogenic bacteria may be used; exemplary microbes are relatively well characterised strains, particularly laboratory strains of *E. coli*, such as MC4100, MC1061, DH5.alpha., etc. Other bacteria that can be engineered for the invention include well-characterised, nonvirulent, non-pathogenic strains of *Listeria monocytogenes, Shigella flexneri, Mycobacterium, Salmonella, Bacillus subtilis*, etc. In particular embodiments, the bacteria are attenuated to be non-replicative, non-integrative into the host cell genome, and/or non-motile inter- or intra-cellularly.

The delivery vehicles described above can be used to deliver one or more antigens to virtually any antigen-presenting cell capable of endocytosis of the subject vehicle, including phagocytic and non-phagocytic antigen-presenting cells. In embodiments when the delivery vehicle is a microbe, the subject methods generally require microbial uptake by the target cell and subsequent lysis within the antigen-presenting cell vacuole (including phagosomes and endosomes).

In other embodiments, a HDM and optionally one or both of an antigen of interest and a Prx polypeptide can be produced inside an antigen-presenting cell by introduction of one or more expression constructs that encode the HDM and/or the antigen and/or the Prx polypeptide. As described, for example, in U.S. Pat. No. 5,976,567 (Inex), the expression of natural or synthetic nucleic acids is typically achieved by operably linking a nucleic acid of interest to a regulatory element (e.g., a promoter, which may be either constitutive or inducible), suitably incorporating the construct into an expression vector, and introducing the vector into a suitable host cell. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, prokaryotes, or both, (e.g., shuttle vectors) and selection markers for both prokaryotic and eukaryotic systems. Vectors may be suitable for replication and integration in prokaryotes, eukaryotes, or both. See, Giliman and Smith (1979), *Gene* 8: 81-97; Roberts et al. (1987), *Nature* 328: 731-734; Berger and Kimmel, Guide to Molecular Cloning Techniques, Methods in Enzymology, volume 152, Academic Press, Inc., San Diego, Calif. (Berger); Sambrook et al. (1989), MOLECULAR CLONING—A LABORATORY MANUAL (2nd ed.) Vol. 1-3, Cold Spring Harbor Laboratory, Cold Spring Harbor Press, N.Y., (Sambrook); and F. M. Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel).

Expression vectors containing regulatory elements from eukaryotic viruses such as retroviruses are typically used for expression of nucleic acid sequences in eukaryotic cells. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

While a variety of vectors may be used, it should be noted that viral expression vectors are useful for modifying eukaryotic cells because of the high efficiency with which the viral vectors transfect target cells and integrate into the target cell genome. Illustrative expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2), 205-208), Vigna and Naldini (2000, *J. Gene Med.* 2(5), 308-316), Kay et al. (2001, *Nat. Med.* 7(1), 33-40), Athanasopoulos, et al. (2000, *Int. J Mol. Med.* 6(4),363-375) and Walther and Stein (2000, *Drugs* 60(2), 249-271).

The polypeptide or peptide-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the HDM and/or antigen in a mammalian host using methods that take advantage of codon usage bias, or codon translational efficiency in specific mammalian cell or tissue types as set forth, for example, in International Publications WO 99/02694 and WO 00/42215. Briefly, these latter methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5%, 10%, 15%, 20%, 25%, 30%, more preferably 35%, 40%, 50%, 60%, 70% or more of the existing codons of a parent polynucleotide.

The expression vector is compatible with the antigen-presenting cell in which it is introduced such that the antigen-encoding polynucleotide is expressible by the cell. The expression vector is introduced into the antigen-presenting cell by any suitable means which will be dependent on the particular choice of expression vector and antigen-presenting cell employed. Such means of introduction are well-known to those skilled in the art. For example, introduction can be effected by use of contacting (e.g., in the case of viral vectors), electroporation, transformation, transduction, conjugation or triparental mating, transfection, infection membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art. Alternatively, the vectors are introduced by means of cationic lipids, e.g., liposomes. Such liposomes are commercially available (e.g., Lipofectin®, Lipofectamine™, and the like, supplied by Life Technologies, Gibco BRL, Gaithersburg, Md.).

3.5 Antigen-Specific Regulatory Lymphocytes

The present invention also contemplates antigen-specific regulatory B or T lymphocytes, especially T lymphocytes, which suppress or down regulate a Th1 response in an antigen-specific fashion to representation of the antigen. In some embodiments, the lymphocytes actively regulate prior immune responses or subsequent priming to that antigen.

In some embodiments, antigen-specific regulatory T lymphocytes are produced by contacting an antigen-specific antigen-presenting cell as defined above with a population of T lymphocytes, which may be obtained from any suitable source such as spleen or tonsil/lymph nodes but is preferably obtained from peripheral blood. The T lymphocytes can be used as crude preparations or as partially purified or substantially purified preparations, which are suitably obtained using standard techniques as, for example, described in "Immunochemical Techniques, Part G: Separation and Characterization of Lymphoid Cells" (*Meth. in Enzymol.* 108, Edited by Di Sabato et al., 1984, Academic Press). This includes rosetting with sheep red blood cells, passage across columns of nylon wool or plastic adherence to deplete adherent cells, immunomagnetic or flow cytometric selection using appropriate monoclonal antibodies as described (Cavanagh et al., 1998; Thomas et al., 1993a).

The preparation of T lymphocytes is contacted with the antigen-specific antigen-presenting cells of the invention for an adequate period of time to stimulate the development of antigen-specific regulatory lymphocytes. This period will generally be at least about 1 day, and up to about 5 days. Generally, the proliferation of regulatory T lymphocytes produced after this procedure is short-lived and they produce IL-10 in an antigen-specific manner.

In specific embodiments, a population of antigen-presenting cell precursors is cultured in the presence of a heterogeneous population of T lymphocytes, which is suitably obtained from peripheral blood, together with a HDM and an antigen to which a modified immune response is required, or with a polynucleotide from which the antigen is expressible. These cells are cultured for a period of time and under conditions sufficient for:

(i) the precursors to differentiate into antigen-presenting cells;

(ii) the HDM to elicit at least one activity selected from (1) stimulating or inducing the antigen-presenting cells to elicit an antigen-specific Th2 response, (2) inhibiting the antigen-presenting cells from stimulating an antigen-specific Th1 response, (3) stimulating the antigen-presenting cells to develop an alternatively activated phenotype, (4) preventing or inhibiting the antigen-presenting cells from activating in response to an inflammatory stimulus, (5) preventing or inhibiting the antigen-presenting cells from binding TLR ligands, and/or (6) down-regulating or impairing lysosome function in the antigen-presenting cells;

(iii) the antigen, or processed form thereof, to be presented by the antigen-presenting cells; and (iv) the antigen-presenting cells to stimulate the development of a subpopulation of T lymphocytes that suppress or down regulate a Th1 response in an antigen-specific fashion to representation of the antigen; this can occur using Ficoll-purified PBMC plus antigen plus HDM since such a preparation contains both monocytes (e.g., macrophage and dendritic cell precursors and T lymphocytes).

The antigen-specific antigen-presenting cells may induce one or more types of antigen-specific regulatory lymphocytes, especially regulatory T lymphocytes. Several populations of regulatory T lymphocytes are known to inhibit the response of other (effector) lymphocytes in an antigen-specific manner including, for example, Tr1 lymphocytes, Th3 lymphocytes, Th2 lymphocytes, $CD8^+CD28^-$ regulatory T lymphocytes, natural killer (NK) T lymphocytes and γδ T lymphocytes.

Tr1 lymphocytes can emerge after several rounds of stimulation of human blood T cells by allogeneic monocytes in the presence of IL-10. This subpopulation secretes high levels of IL-10 and moderate levels of TGFβ but little IL-4 or IFNγ (Groux et al., 1997, *Nature* 389:737-742).

The Th3 regulatory subpopulation refers to a specific subset induced following antigen delivery via the oral (or other mucosal) route. They produce predominantly TGFβ, and only low levels of IL-10, IL-4 or IFNγ, and provide specific help for IgA production (Weiner et al., 2001, *Microbes Infect* 3:947-954). They are able to suppress both Th1 and Th2-type effector T cells.

Th2 lymphocytes produce high levels of IL-4, IL-5 and IL-10 but low IFNγ and TGFβ. Th2 lymphocytes are generated in response to a relative abundance of IL-4 and lack of IL-12 in the environment at the time of presentation of their cognate peptide ligands (O'Garra and Arai, 2000, *Trends Cell Biol* 10:542-550). T lymphocyte signalling by CD86 may also be important for generation of Th2 cells (Lenschow et al., 1996, *Immunity* 5:285-293; Xu et al., 1997, *J Immunol* 159:4217-4226).

A distinct CD8$^+$CD28$^-$ regulatory or "suppressor" subset of T lymphocytes can be induced by repetitive antigenic stimulation in vitro. They are MHC class I-restricted, and suppress CD4$^+$ T cell responses.

NK T lymphocytes, which express the NK cell marker, CD161, and whose TCR are V$\alpha$24J$\alpha$Q in human and V$\alpha$14J$\alpha$281 in mouse, are activated specifically by the non-polymorphic CD1d molecule through presentation of a glycolipid antigen (Kawano et al., 1997, *Science* 278:1626-1629). They have been shown to be immunoregulatory in a number of experimental systems. They are reduced in number in several autoimmune models before disease onset, and can reduce incidence of disease upon passive transfer to non-obese diabetic (NOD) mice. Administration of the glycolipid, $\alpha$-galactosyl ceramide ($\alpha$-gal cer), presented by CD1 d, also results in accumulation of NKT lymphocytes and amelioration of diabetes in these mice (Naumov et al., 2001, *Proc Natl Acad Sci USA* 98:13838-13843).

$\gamma\delta$ T lymphocytes have been implicated in the downregulation of immune responses in various inflammatory diseases and in the suppression of inflammation associated with induction of mucosal tolerance. The tolerance induced by mucosal antigen was transferable to untreated recipient mice by small numbers of $\gamma\delta$ T cells (McMenamin et al., 1995, *J Immunol* 154:4390-4394; McMenamin et al., 1994, *Science* 265:1869-1871). Moreover, mucosal tolerance induction was blocked by the administration of the GL3 antibody that blocks $\gamma\delta$ T cell function (Ke et al., 1997, *J Immunol* 158:3610-3618).

Thus, the present invention provides means to generate large quantities of antigen-specific regulatory lymphocytes by stimulating lymphocytes with antigen-specific antigen-presenting cells that have been made tolerogenic using the HDM molecules of the present invention. In order for the lymphocytes to exhibit tolerance, they may be stimulated with HDM-treated antigen-presenting cells e.g., for minimally at least about 1 day, usually at least about 3 to 5 days.

The efficiency of inducing lymphocytes, especially T lymphocytes, to exhibit tolerance to a specified antigen can be determined by assaying immune responses to that antigen including, but not limited to, assaying T lymphocyte cytolytic activity in vitro using for example the antigen-specific antigen-presenting cells as targets of antigen-specific cytolytic T lymphocytes (CTL); assaying antigen-specific T lymphocyte proliferation (see, e.g., Vollenweider and Groscurth, 1992, *J Immunol Meth.* 149, 133-135), measuring B cell response to the antigen using, for example, Elispot assays, and Elisa assays; interrogating cytokine profiles; or measuring delayed-type hypersensitivity (DTH) responses by test of skin reactivity to a specified antigen (see, e.g., Chang et al. 1993, *Cancer Res.* 53, 1043-1050).

4. Pharmaceutical Formulations

In accordance with the present invention, bioactive agents selected from an HDM or a polynucleotide from which one is expressible as described for example in Section 2; and optionally one or more ancillary agents selected from: (A) antigens to which a tolerogenic response is desired as described for example in Section 3.1; (B) Prx polypeptides as described for example in Section 3.2; (C) particles as described for example in Section 3.3;

(D) antigen-presenting cells as described for example in Section 3.4; and (D) antigen-specific regulatory lymphocytes as described for example in Section 3.5 are useful in compositions and methods for modifying an immune response, especially for inducing a tolerogenic response including the suppression of a future or existing immune response, to one or more target antigens. These compositions are useful, therefore, for treating or preventing an undesirable immune response including, for example, transplant rejection, graft versus host disease, allergies, parasitic diseases, inflammatory diseases and autoimmune diseases.

Examples of transplant rejection, which can be treated or prevented in accordance with the present invention, include rejections associated with transplantation of bone marrow and of organs such as heart, liver, pancreas, kidney, lung, eye, skin etc.

Examples of allergies include seasonal respiratory allergies; allergy to aeroallergens such as hayfever; allergy treatable by reducing serum IgE and eosinophilia; asthma; eczema; animal allergies, food allergies; latex allergies; dermatitis; or allergies treatable by allergic desensitisation.

Autoimmune diseases and related conditions that can be treated or prevented by the present invention include, for example, psoriasis, systemic lupus erythematosus, myasthenia gravis, stiff-man syndrome, thyroiditis, Sydenham chorea, rheumatoid arthritis, ankylosing spondylitis, autoimmune aplastic anemia, autoimmune hemolytic anemia, Churg Strauss disease, scleroderma, Wegener granulomatosus, Wiskott Aldrich syndrome, type 1 diabetes mellitus (T1DM) and multiple sclerosis. Examples of inflammatory disease include Crohn's disease, chronic inflammatory eye diseases, chronic inflammatory lung diseases and chronic inflammatory liver diseases, autoimmune hemolytic anemia, idiopathic leucopoenia, ulcerative colitis, dermatomyositis, scleroderma, mixed connective tissue disease, irritable bowel syndrome, systemic lupus erythromatosus (SLE), multiple sclerosis, myasthenia gravis, Guillan-Barre syndrome (antiphospholipid syndrome), primary myxoedema, thyrotoxicosis, pernicious anemia, autoimmune atrophic gastris, alopecia totalis, Addison's disease, insulin-dependent diabetes mellitus (IDDM), Goodpasture's syndrome, Behcet's syndrome, Sjogren's syndrome, rheumatoid arthritis, sympathetic ophthalmia, Hashimoto's disease/hypothyroiditis, celiac disease/dermatitis herpetiformis, adult-onset idiopathic hypoparathyroidism (AOIH), amyotrophic lateral sclerosis, and demyelinating disease primary biliary cirrhosis, mixed connective tissue disease, chronic active hepatitis, polyendocrine failure, vitiligo, Celiac disease, chronic active hepatitis, CREST syndrome, dermatomyositis, dilated cardiomyopathy, eosinophilia-myalgia syndrome, epidermolysis bullosa acquisita (EBA), giant cell arteritis, Graves' disease/hyperthyroiditis, scleroderma, chronic idiopathic thrombocytopenic purpura, peripheral neuropathy, diabetic neuropathy, hemochromatosis, Henoch-Schonlein purpura, idiopathic IgA nephropathy, insulin-dependent diabetes mellitus (IDDM), Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, and septic shock. Other unwanted immune reactions that can also be treated or prevented by the present invention include antibodies to recombinant therapeutic agents such as anti-factor VIII antibodies in hemophilia or anti-insulin antibodies in diabetes.

In specific embodiments, the undesirable or deleterious immune response is an organ-specific disease, non-limiting examples of which include T1DM, thyroiditis, adrenal insufficiency, alopecia, atrophic gastritis, vitiligo, premature ovarian failure, autoimmune polyendocrine syndromes (APS), parathyroiditis, hypoparathyroidism, autoimmune adrenal insufficiency (Addison's disease), autoimmune hepatitis, Sjogren's syndrome, celiac disease, exocrine pancreatitis, keratitis and mucocutaneous candidiasis.

The above compositions are, therefore, useful for treating or preventing an unwanted or deleterious immune response in a patient, which comprises administering to the patient a pharmaceutical composition comprising one or more of bioactive agents (A), (B), (C) or (D) above. The pharmaceutical composition may comprise a pharmaceutically acceptable carrier or diluent. In some embodiments, the compositions are administered to individuals having the unwanted or deleterious immune response. In other embodiments, the compositions are administered to at-risk individuals who are autoantibody positive and/or HLA haplotype identified at risk e.g., Type 1 diabetes first degree relatives with at least one and desirably two or more autoantibodies positive (see, e.g., Scofield, R. H., 2004. *Lancet* 363, 1544; Berglin et al., 2004, *Arthritis Res Ther.* 6, R30336; Harrison et al., 2004, Diabetes Care 27, 2348), or individuals at risk of rheumatoid arthritis, with one or two HLA susceptibility genes and positive anti-CCP antibodies (Klarskog et al. 2006, *Arthritis Rheum.* 54: 38) (Rantapaa-Dahlqvist S et al. 2003, *Arthritis Rheum.* 48:2741).

Pharmaceutical compositions suitable for use in the present invention include compositions wherein the bioactive agents are contained in an effective amount to achieve their intended purpose. The dose of active compound(s) administered to a patient should be sufficient to achieve a beneficial response in the patient over time such as a reduction in at least one symptom associated with the unwanted or deleterious immune response, which is suitably associated with a condition selected from an allergy, an autoimmune disease and a transplant rejection. The quantity or dose frequency of the pharmaceutically active compounds(s) to be administered may depend on the subject to be treated inclusive of the age, sex, weight and general health condition thereof. In this regard, precise amounts of the active compound(s) for administration will depend on the judgement of the practitioner. In determining the effective amount of the active compound(s) to be administered in the treatment or prophylaxis of the unwanted or deleterious immune response, the practitioner may evaluate inflammation, proinflammatory cytokine levels, lymphocyte proliferation, cytolytic T lymphocyte activity and regulatory T lymphocyte function. In any event, those of skill in the art may readily determine suitable dosages of the antagonist and antigen.

Accordingly, the bioactive agents are administered to a subject to be treated in a manner compatible with the dosage formulation, and in an amount that will be prophylactically and/or therapeutically effective. The amount of the composition to be delivered, generally in the range of from 0.01 µg/kg to 100 µg/kg of bioactive molecule (e.g., HDM, antigen etc) per dose, depends on the subject to be treated. In some embodiments, and dependent on the intended mode of administration, the HDM-containing compositions will generally contain about 0.1% to 90%, about 0.5% to 50%, or about 1% to about 25%, by weight HDM, the remainder being suitable pharmaceutical carriers and/or diluents etc and optionally the antigen. The dosage of the inhibitor can depend on a variety of factors, such as mode of administration, the species of the affected subject, age and/or individual condition. In other embodiments, and dependent on the intended mode of administration, antigen-containing compositions will generally contain about 0.1% to 90%, about 0.5% to 50%, or about 1% to about 25%, by weight of antigen, the remainder being suitable pharmaceutical carriers and/or diluents etc and the HDM.

Depending on the specific condition being treated, the particles may be formulated and administered systemically, topically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, transcutaneous, intradermal, intramedullary delivery (e.g., injection), as well as intrathecal, direct intraventricular, intravenous, intraperitoneal, intranasal, or intraocular delivery (e.g., injection). For injection, the bioactive agents of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

The compositions of the present invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the bioactive agents of the present invention can be formulated readily using pharmaceutically acceptable carriers well known in the art into dosages suitable for oral administration, which is also contemplated for the practice of the present invention. Such carriers enable the bioactive agents of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the particles in water-soluble form. Additionally, suspensions of the bioactive agents may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances that increase the viscosity of the suspension, such as sodium carboxymethyl cellulose, sorbitol, or dextran. Optionally, the suspension may also contain suitable stabilisers or agents that increase the solubility of the compounds to allow for the preparation of highly concentrated solutions.

Pharmaceutical preparations for oral use can be obtained by combining the bioactive agents with solid excipients and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, eg. by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of particle doses.

Pharmaceuticals which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The bioactive agents of the present invention may be administered over a period of hours, days, weeks, or months, depending on several factors, including the severity of the condition being treated, whether a recurrence of the condition is considered likely, etc. The administration may be constant, e.g., constant infusion over a period of hours, days, weeks, months, etc. Alternatively, the administration may be intermittent, e.g., bioactive agents may be administered once a day over a period of days, once an hour over a period of hours, or any other such schedule as deemed suitable.

The bioactive agents of the present invention may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In some particulate embodiments of the present invention, the particles of a formulation may advantageously have diameters of less than 50 µm, suitably less than 10 µm.

In some particulate embodiments, the bioactive agents are administered for active uptake by cells, for example by phagocytosis, as described for example in U.S. Pat. No. 5,783,567 (Pangaea). In some embodiments, phagocytosis by these cells may be improved by maintaining a particle size typically below about 20 µm, and preferably below about 11 µm.

In specific particulate embodiments, bioactive agents in particulate form are delivered directly into the bloodstream (i.e., by intravenous or intra-arterial injection or infusion) if uptake by the phagocytic cells of the reticuloendothelial system (RES), including liver and spleen, is desired. Alternatively, one can target, via subcutaneous injection, take-up by the phagocytic cells of the draining lymph nodes. The particles can also be introduced intradermally (i.e., to the APCs of the skin, such as dendritic cells and Langerhans cells) for example using ballistic or microneedle delivery. Illustrative particle-mediated delivery techniques include explosive, electric or gaseous discharge delivery to propel carrier particles toward target cells as described, for example, in U.S. Pat. Nos. 4,945,050, 5,120,657, 5,149,655 and 5,630,796. Non-limiting examples of microneedle delivery are disclosed in International Publication Nos. WO 2005/069736 and WO 2005/072630 and U.S. Pat. Nos. 6,503,231 and 5,457,041.

In other specific particulate embodiments, the route of particle delivery is via the gastrointestinal tract, e.g., orally. Alternatively, the particles can be introduced into organs such as the lung (e.g., by inhalation of powdered microparticles or of a nebulized or aerosolized solution containing the microparticles), where the particles are picked up by the alveolar macrophages, or may be administered intranasally or buccally. Once a phagocytic cell phagocytoses the particle, the HDM and optionally the antigen are released into the interior of the cell.

Accordingly, the present invention provides for the induction of tolerance to an antigen that is associated with an unwanted or deleterious immune response including without limitation autoimmune diseases, allergies, transplantation associated diseases and organ-specific diseases. In some embodiments, therefore, the present invention provides for the induction of tolerance to an autoantigen for the treatment of autoimmune diseases by co-administering the antigen to which tolerance is desired, or a polynucleotide from which the antigen is expressible, along with a HDM or a polynucleotide from which the HDM is expressible. In an illustrative example of this type, autoantibodies directed against the acetylcholine receptor (AChR) are observed in patients with Myasthenia gravis, and, accordingly, AChR-antigen or antigen-expressing vectors may be used in the invention to be delivered in conjunction with a HDM or a polynucleotide from which the HDM is expressible to treat and/or prevent Myasthenia gravis.

In still other embodiments, an individual who is a candidate for a transplant from a non-identical twin may suffer from rejection of the engrafted cells, tissues or organs, as the engrafted antigens are foreign to the recipient. Prior tolerance of the recipient individual to the intended graft abrogates or reduces later rejection. Reduction or elimination of chronic anti-rejection therapies may be achieved by administering concurrently to the recipient of the transplant one or more transplantation antigens or a polynucleotide from which they are expressible and a HDM or a polynucleotide from which the HDM is expressible optionally in combination with a Prx polypeptide or a nucleic acid molecule from which one is expressible.

In further embodiments, sensitization of an individual to an industrial pollutant or chemical, such as may be encountered on-the-job, presents a hazard of an immune response. Prior tolerance of the individual's immune system to the chemical may be desirable to prevent the later occupational development of an immune response. In these cases, it is generally desirable to administer concurrently to the individual the chemical reacted with the individual's endogenous proteins, together with a HDM or a polynucleotide from which the HDM is expressible optionally in combination with a Prx polypeptide or a nucleic acid molecule from which one is expressible.

Notably, even in diseases where the pathogenic autoantigen is unknown, bystander suppression may be induced using antigens present in the anatomical vicinity of the pathogenesis and a HDM. For example, autoantibodies to collagen are observed in rheumatoid arthritis and, accordingly, collagen or a collagen-expressing construct (see e.g. Choy, 2000, *Curr Opin Investig Drugs* 1: 58-62) may be utilized, together with a HDM or a HDM-expressing construct in order to treat rheumatoid arthritis. Furthermore, tolerance to beta cell autoantigens may be utilized to prevent development of type 1 diabetes (see e.g. Bach and Chatenoud, 2001, *Ann Rev Immunol.* 19: 131-161) in a similar manner.

As another example, auto-antibodies directed against myelin oligodendrocyte glycoprotein (MOG) are observed in autoimmune encephalomyelitis and in many other CNS diseases as well as multiple sclerosis (see e.g. Iglesias et al., 2001, Glia 36: 22-34). Accordingly, co-delivery of a MOG antigen or MOG antigen-expressing constructs with a HDM or HDM-expressing construct allows for treatment or prevention of multiple sclerosis as well as related autoimmune disorders of the central nervous system.

When antigen-presenting cells or regulatory lymphocytes are employed, the cells can be introduced into a patient by any means (e.g., injection), which produces the desired modified immune response to an antigen or group of antigens. The cells may be derived from the patient (i.e., autologous cells) or from an individual or individuals who are MHC-matched or -mismatched (i.e., allogeneic) with the patient. In specific embodiments, autologous cells are injected back into the patient from whom the source cells were obtained. The injection site may be subcutaneous, intraperitoneal, intramuscular, intradermal, or intravenous. The cells may be administered to a patient already suffering from the unwanted immune response or who is predisposed to the unwanted immune response in sufficient number to prevent or at least partially arrest the development, or to reduce or eliminate the onset of, that response. The number of cells injected into the patient in need of the treatment or prophylaxis may vary depending on inter alia, the antigen or antigens and size of the individual. This number may range for example between about $10^3$ and $10^{11}$, and usually between about $10^5$ and $10^7$ cells (e.g., macrophages, dendritic cells etc or their precursors). Single or multiple administrations of the cells can be carried out with cell numbers and pattern being selected by the treating physician. The cells should be administered in a pharmaceutically acceptable carrier, which is non-toxic to the cells and the individual. Such carrier may be the growth medium in which the cells were grown, or any suitable buffering medium such as phosphate buffered saline. The cells may be administered alone or as an adjunct therapy in conjunction with other therapeutics known in the art for the treatment or prevention of unwanted immune responses for example but not limited to glucocorticoids, methotrexate, D-penicillamine, hydroxychloroquine, gold salts, sulfasalazine, TNFα or interleukin-1 inhibitors, and/or other forms of specific immunotherapy. In specific embodiments, the antigen-presenting cells are pre-contacted with one or more antigens associated with the unwanted or deleterious immune response to provide antigen-specific tolerogenic antigen presenting cells or are administered concurrently to the subject with one or more such antigens.

In order that the invention may be readily understood and put into practical effect, particular preferred embodiments will now be described by way of the following non-limiting examples.

EXAMPLES

Example 1

Characterization of Native FhHDM-1

Total adult *F. hepatica* secretory proteins (ES) were separated by size exclusion chromatography as shown in FIG. 3. (A). Peak 1 contains FhHDM-1 and this was purified to homogeneity using RP-HPLC as shown in panel (B). Panel C shows total ES proteins (S), peak 1 (1) and HPLC-pure native FhHDM-1 (2).

FhHDM-1 was identified by N-terminal sequencing which generated sequence SEESREKLRE (SEQ ID NO:142) and LC-MS/MS (matched peptide ITEVITILLNR [SEQ ID NO:141]) by searching against a *Fasciola* EST database. The FhHDM-1 coding region was confirmed by cloning and sequencing the FhHDM-1cDNA. Panel D shows the primary sequence of FhHDM-1. The predicted signal peptide for classical secretion is in italics.

Example 2

A Novel Family of FhHDM-1-Like Molecules

Figure 4:
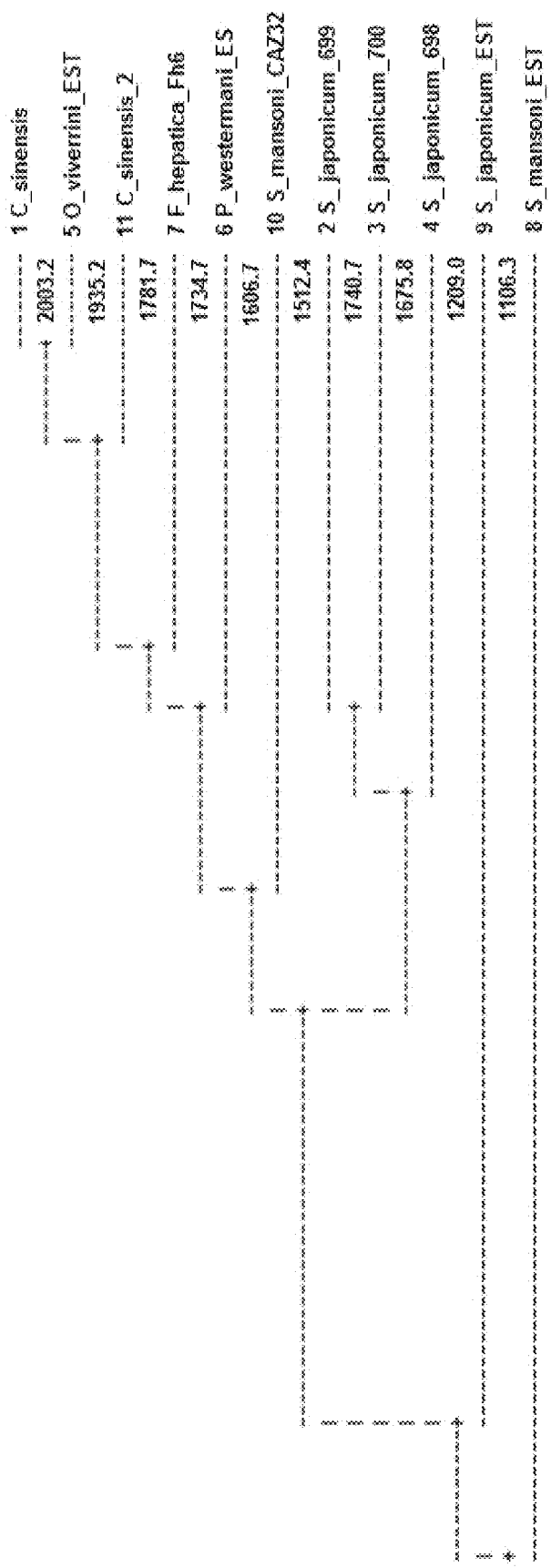
FIG. 4 is a diagrammatic representation showing a phylogenetic analysis of HDMs from C. sinensis (CsHDM-1 and CsHDM-2), O. viverrini (OvHDM-1), F. hepatica (FhHDM-1), P. westermani (PwHDM-1), S. mansoni (SmHDM-1 and SmHDM-2) and S. japonicum (SjHDM-1, SjHDM-2, SjHDM-3 and SjHDM-4).

BLAST searches against protein and nucleotide databases identified a family of FhHDM-1 homologues in related trematode species, as shown in FIG. 1. A phylogenetic analysis shown in FIG. 4 reveals that FhHDM-1 segregates with similar molecules from the Asian flukes (*C. sinensis, O. viverrini* and *P. westermani*) while those of the blood flukes *S. mansoni* and *S. japonicum* form a separate lineage.

Example 3

Expression of FhHDM-1 During the *Fasciola* Life-Cycle

Figure 5:
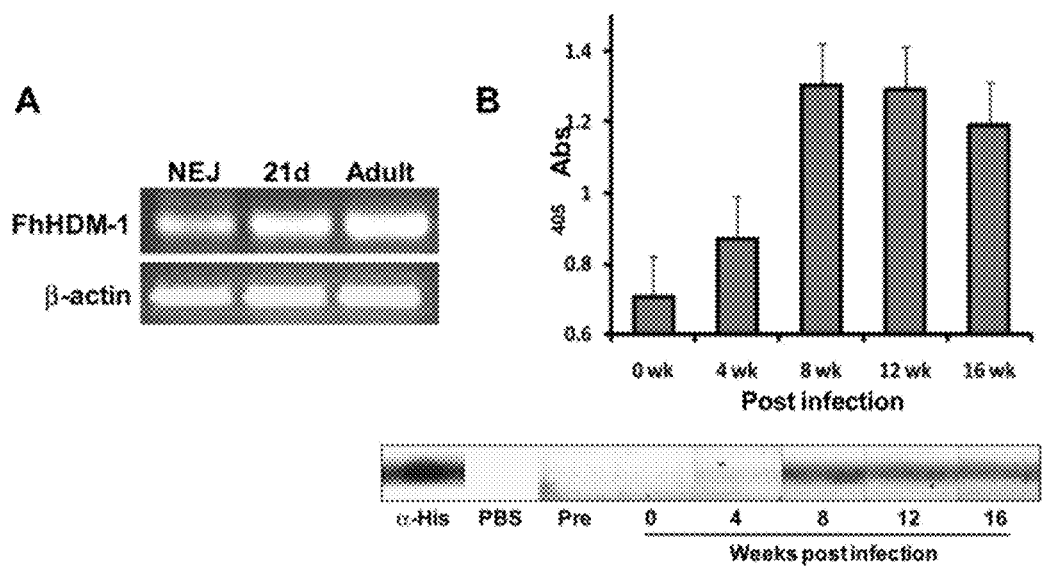
FIG. 5 is a photographic representation showing expression of FhHDM-1 during the Fasciola lifecycle. (A) RT-PCR analysis using mRNA from Fasciola larvae (NEJ), 21 day-old immature worms (21d) and adult flukes (adult). (B) ELISA showing that sera from sheep infected with F. hepatica recognize FhHDM-1.
Figure 6:
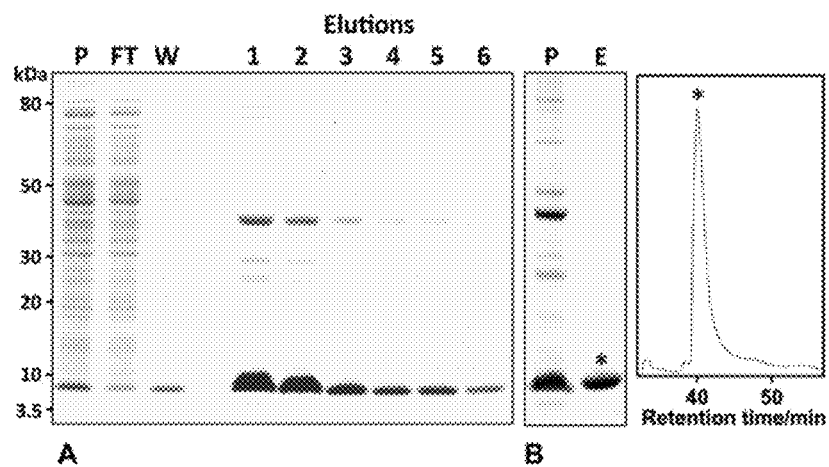
FIG. 6 is a photographic and graphical representation showing production and purification of recombinant FhHDM-1. Full-length FhHDM-1 (minus the N-terminal signal peptide) was expressed in E. coli and purified using Ni-agarose chromatography (A) and RP-HPLC (B).

RT-PCR using mRNA from *Fasciola* larvae (NEJ), 21 day-old immature worms (21d) and adult flukes (adult) shows that FhHDM-1 is constitutively expressed (see, FIG. 5, panel A). An ELISA of sera from sheep infected with *F. hepatica* shows that these sera recognise FhHDM-1 (see, FIG. 4, panel B). The ELISA results were confirmed by western blot analysis (FIG. 6).

Example 4

FhHDM-1 Induces the Alternative Activation of Macrophages

Figure 7:
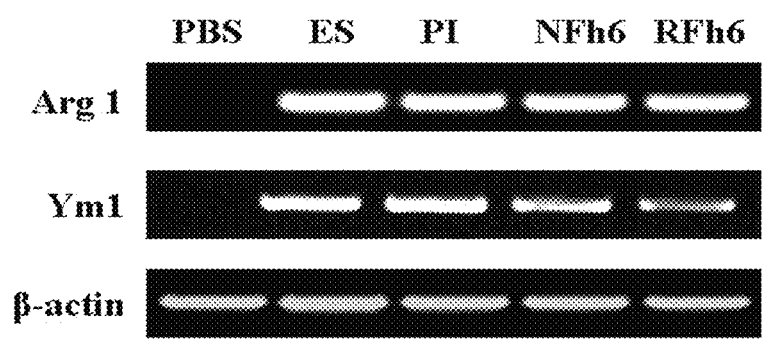
FIG. 7 is a photographic representation showing the results of a RT-PCR analysis of macrophage RNA isolated from Balb/c mice given three i.p. injections of 5 µg native FhHDM-1 (NFh6) or recombinant FhHDM-1 (FH6). This analysis showed increased expression of Arg-1 and Ym1, indicating that the macrophages had developed an alternatively activated phenotype.
Figure 8:
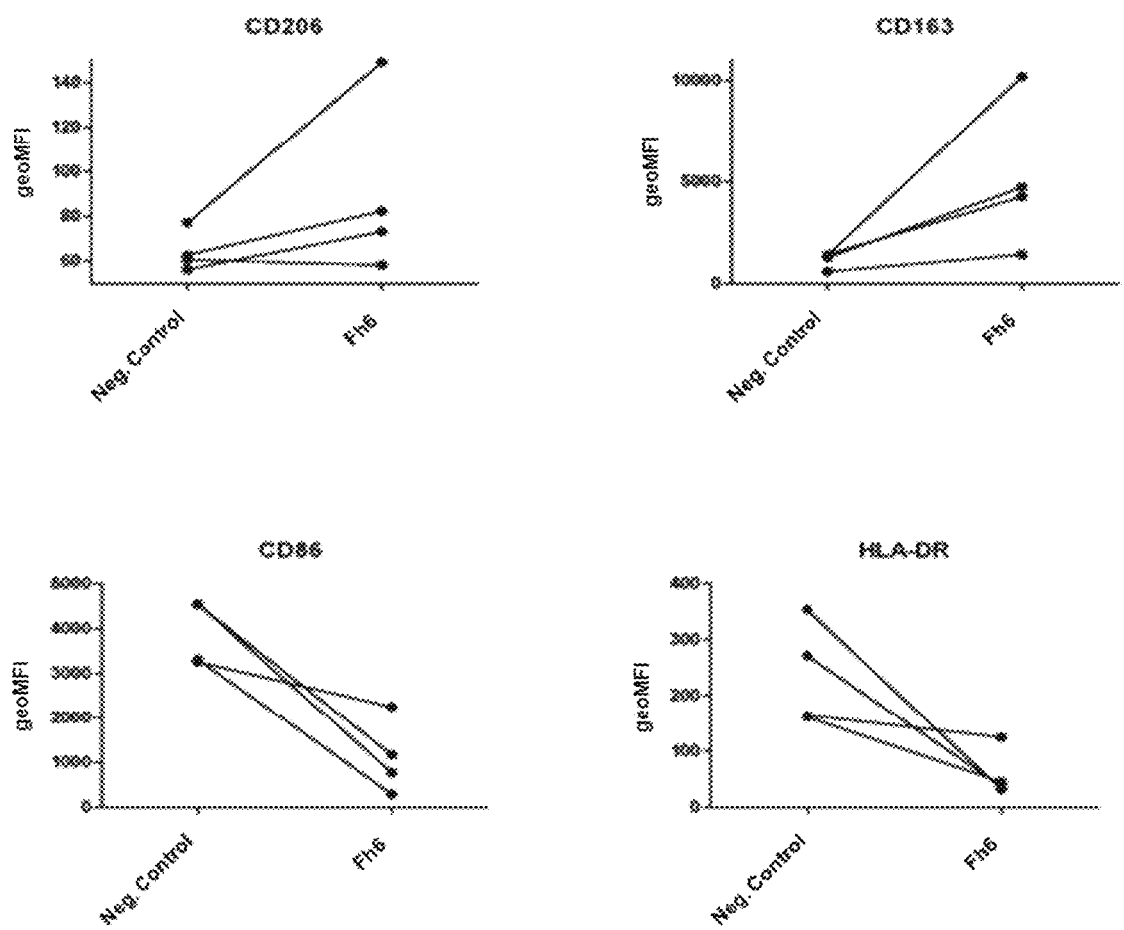
FIG. 8 is a graphical representation showing that human monocytes stimulated for 40 h with 10 µg/mL FhHDM-1 have increased expression of markers of alternative activation (CD163 and CD206) and decreased expression of markers of the classical phenotype (CD86 and HLA-DR), as measured by flow cytometry.

Balb/c mice were given three intraperitoneal (i.p.) injections of 5 μg native (NFh6) or recombinant FhHDM-1. Isolated peritoneal macrophages showed increased expression of Arg-1 and Ym1 (see, FIG. 7), indicating an alternatively activated phenotype. FIG. 8 shows that when human monocytes are stimulated for 40 h with 10 μg/mL FhHDM-1, they have increased expression of markers of alternative activation (CD163 and CD206) and decreased expression of markers of the classical phenotype (CD86 and HLA-DR), as measured by flow cytometry.

Example 5

FhHDM-1 and a C-Terminal Peptide Neutralize the Effects of LPS

Recombinant FhHDM-1 and FhHDM-1 C-Terminal Peptide Bind LPS

Figure 9:
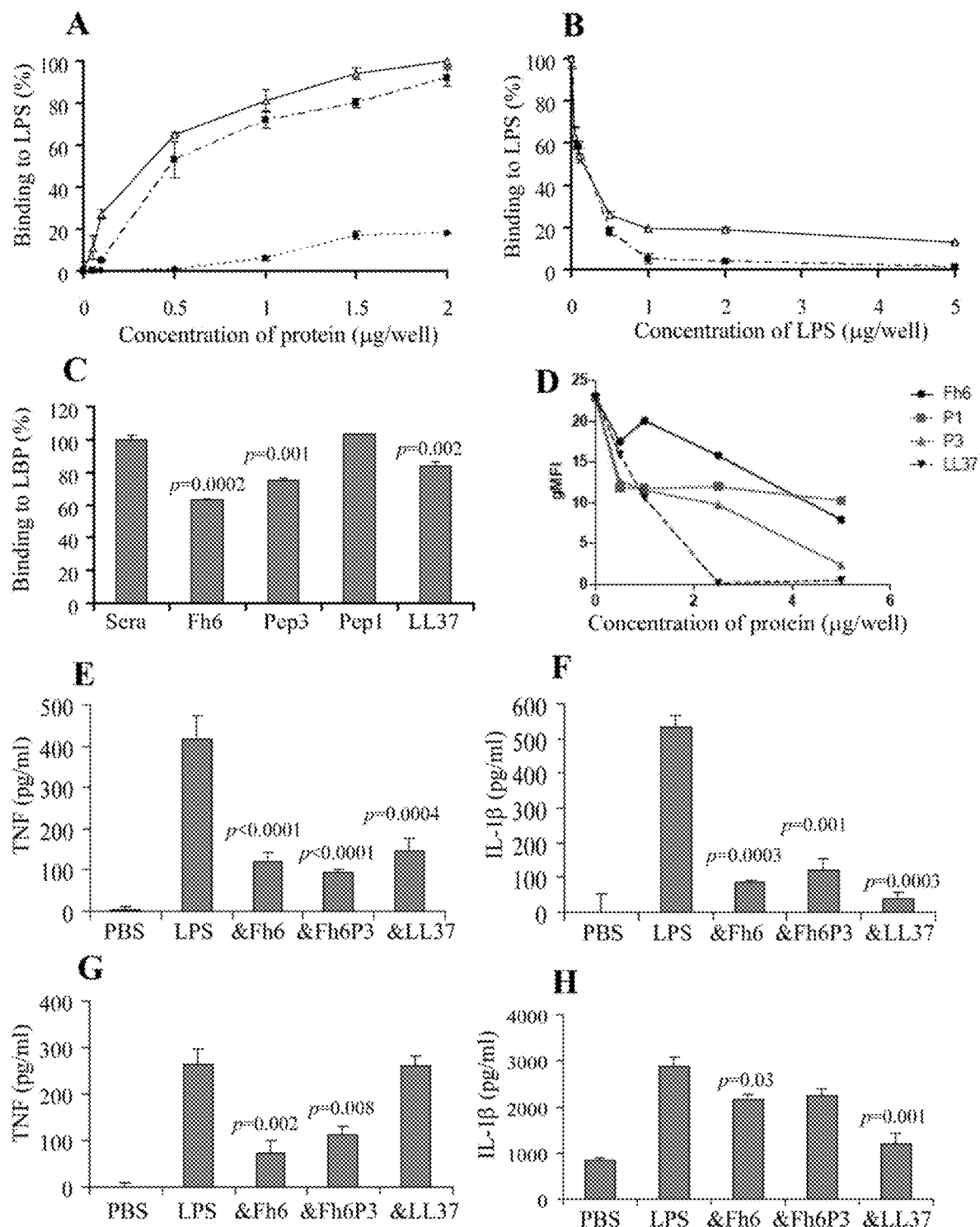
FIG. 9 is a graphical representation showing LPS neutralization by FhHDM-1. The ability of FhHDM-1 (Δ), FhHDM-1 p1 (●) or FhHDM-1 p3 (■) to bind to LPS was investigated by (A) incubating a range of concentrations of proteins (0.02-2 µg/well) in an LPS-coated (100 ng/well) microtitre plate. Bound peptides were detected by ELISA using rabbit anti-FhHDM-1 as a primary antibody. (B) FhHDM-1 or derived peptides (0.1 µg) were incubated in the presence of LPS (0.05-5 µg/well) and bound peptides measured as described above. Binding of peptides to the LPS-immobilized plates was expressed as a percentage of that measured for 2 µg (for panel A) or 0.1 µg (for panel B) of FhHDM-1. Data are the means±SD from three separate experiments. (C) FhHDM-1 and FhHDM-1 p3 but not FhHDM-1 p1 reduced the interaction between LPS and LBP as effectively as LL-37. LPS-coated microtitre plates were incubated with 5 µg/well of LL-37, FhHDM-1 or derived peptides for 1 h prior to the addition of 10% human sera in PBS. Interaction of LBP with LPS was measured by ELISA using an anti-LBP primary antibody and expressed as a percentage of that detected for 10% sera in the absence of added peptides. Data are the mean±SD of three separate experiments. Statistical significance was calculated using the student t-test and represent a comparison to the binding of 10% sera to immobilized LPS. (D) Binding of FITC-conjugated LPS to RAW264.7 cells was inhibited by LL-37, FhHDM-1 and peptides. RAW264.7 cells ($5 \times 10^5$ cells/mL) were incubated with 1 µg/mL of FITC-conjugated LPS in the presence of increasing concentrations (0.1-10 µg/mL) of FhHDM-1, FhHDM-1 p1 and FhHDM-1 p3 and LL-37 in RPMI 1640 containing 10% FBS for 20 min at 4° C. The binding of FITC-LPS was analyzed by flow cytometry. LPS binding was expressed as a percentage of the mean fluorescence obtained for the addition of FITC-LPS to cells in the absence of peptides. Data are the mean±SD of two independent experiments. (E) FhHDM-1 and FhHDM-1 p3 both suppress the inflammatory response induced by LPS in mice. BALB/c mice were intra-peritoneally injected with 1 µg of LPS alone or combined with 1 µg of FhHDM-1, FhHDM-1 p3 or LL-37. Two hours later, sera was collected and serum levels of TNF and (F) IL-10 measured by ELISA. (G) Peritoneal macrophages were isolated, cultured unstimulated in media overnight and then levels of TNF and (H) IL-10 in the culture measured by ELISA. Data are the mean±SD of six mice in each group. Statistical significance represents a comparison to the levels of cytokines secreted by mice given LPS only.

The ability of FhHDM-1 and derived peptides to bind LPS from *E. coli* O111:B4 was determined by ELISA using rabbit anti-FhHDM-1 as a primary antibody (FIG. 9A). Both full-length recombinant FhHDM-1 and the C-terminal peptide AMAYLAKDNLGEKITEVITILLNRLTDRLEKYAG [SEQ ID NO:46; FhHDM-1 p3](containing the complete amphipathic helix) bound to LPS in a concentration-dependent manner. However, peptide FhHDM-1 p1, KARDRAMAYLAKDNLGEKITEVITILLNRL [SEQ ID NO:47], in which the amphipathic helix is truncated, did not bind to LPS. The specific interaction between FhHDM-1 and LPS was supported by experiments in which FhHDM-1 and FhHDM-1 p3 were mixed with increasing concentrations of LPS during the ELISA. As shown in FIG. 9B, both molecules bound to free LPS in solution and were therefore unable to bind LPS immobilised on the ELISA plate.

Recombinant FhHDM-1 and FhHDM-1 p3 Block the Interaction of LPS with LPS-Binding Protein (LPB)

The ability of FhHDM-1 and derived peptides to block the interaction of LPS with LPB was assessed by ELISA using an anti-LBP primary antibody. Since it is a well-characterised α-helical Defense peptide, human defense peptide LL-37 was used for comparison. As shown in FIG. 9C, both full-length FhHDM-1 (p=0.0002) and FhHDM-1 p3 (p=0.001) significantly reduced the interaction between LPS and LBP as effectively as LL-37 (p=0.002). However, FhHDM-1 p1 did not block the interaction of LPS with LPB. Thus, the ability of FhHDM-1 to block the interaction of LPS with LPB is mediated by its conserved C-terminal domain.

Recombinant FhHDM-1 and FhHDM-1 p3 inhibit Binding of FITC-LPS to RA W264.7 Macrophages The effect of FhHDM-1 and derived peptides on the binding of FITC-LPS to CD14+ cells was determined by flow cytometry of the murine macrophage cell line RAW264.7. The assay was performed at 4° C. to inhibit endocytosis thus ensuring that only cell surface interactions were observed. When incubated with RAW264.7 cells in the absence of the parasite molecules or LL-37, FITC-LPS bound to the cells strongly compared to untreated control cells. Binding of FITC-LPS to the macrophages was most strongly inhibited by LL-37 (FIG. 9D). Like LL-37, FhHDM-1 p3 also considerably reduced FITC-LPS binding, almost abolishing cell surface labelling when used at 5 µg/mL (FIG. 9D). Full-length FhHDM-1 and FhHDM-1 p1 also reduced binding of FITC-LPS to the cells in a dose-dependent manner albeit to a lesser extent to LL-37 or FhHDM-1 p3.

Recombinant FhHDM-1 and FhHDM-1 p3 Suppress LPS-Induced Inflammatory Response in Mice Human Defense peptides protect against harmful inflammatory responses by preventing activation of macrophages by classical TLR ligands such as LPS (Scott et al. 2002, *J. Immunol.* 169, 3883-3891). Here, the inventors employed a murine model to examine whether FhHDM-1 and derived peptides can suppress LPS-induced Th1 inflammation. BALB/c mice were injected intra-peritoneally with 1 µg of LPS alone or LPS combined with 1 µg of FhHDM-1, FhHDM-1 p3 or LL-37. Two hours later, sera was collected and serum levels of the pro-inflammatory mediators TNF and IL-10 were measured by ELISA. Serum levels of TNF and IL-10 were markedly elevated following injection of LPS alone indicating that an inflammatory response was elicited in the mice (FIGS. 9E and 9F). However, administration of LPS mixed with 1 µg of FhHDM-1, FhHDM-1 p3 or LL-37 led to a significant reduction in serum levels of TNF and IL-10 in treated mice (FIGS. 9E and 9F). Because macrophages are the main source of pro-inflammatory mediators in this murine model of inflammation, peritoneal macrophages were isolated from treated mice (LPS±FhHDM-1, peptides or LL-37 as described above), cultured unstimulated in media overnight and then levels of TNF and IL-10 in the culture media were measured by ELISA. For those mice injected with LPS alone, levels of both TNF and IL-10 were elevated compared with PBS-treated mice, again demonstrating that an inflammatory response had been induced (FIGS. 9G and 9H). However, the inventors found that the level of TNF secreted from macrophages treated with LPS mixed with FhHDM-1 or FhHDM-1 p3 were significantly reduced compared with macrophages derived from animals pre-treated with LPS alone. Interestingly, LL-37 did not significantly reduce secretion of TNF from macrophages in this assay (FIG. 9G). Treatment with full-length recombinant FhHDM-1 or LL-37 (but not FhHDM-1 p3) significantly inhibited LPS-induced secretion of IL-10 from peritoneal macrophages (FIG. 9H). Collectively, these data demonstrate that FhHDM-1, and its C-terminal region, are capable of protecting mice against LPS-induced inflammation by reducing secretion of pro-inflammatory cytokines from macrophages.

The findings may be summarized as follows:

1) Full-length FhHDM-1 and peptide 3 (but not peptide 1) bind directly to LPS. This would likely reduce the amount of LPS that is free to bind its receptor. (Both full-length and peptide 3 have the complete amphipathic helix whereas peptide 1 does not).

2) Full-length FhHDM-1 and peptide 3 (but not peptide 1) block the interaction of LPS with LPS-binding protein (LPB). LPS binds to LPB and transfers it to CD14. The LPs-CD14 complex then initiate downstream signalling via interaction with TLRs. The parasite molecules block this first step.

3) Full-length FhHDM-1 and peptide 3 (and to a lesser extent peptide 1) inhibit binding of FITC-labelled LPS to RAW264.7 macrophages. This is likely due to the direct binding of LPS by the parasite molecules and confirms the biological relevance of point 1 above.

4) Human Defense peptides such as LL-37 protect against harmful inflammatory responses by preventing activation of macrophages by classical TLR ligands such as LPS. The inventors have now shown that full-length FhHDM-1 and peptide 3 suppress LPS-induced inflammatory response (i.e. reduced levels of TNF and IL-10 in serum and secreted by peritoneal macrophages) in mice.

Collectively, these data demonstrate that FhHDM-1, and its C-terminal region, are capable of protecting mice against LPS-induced inflammation by reducing secretion of pro-inflammatory cytokines from macrophages.

Materials and Methods

Measurement of the LPS-Binding Activities of FhHDM-1 and Derived Peptides

Microtiter plates (96 well; Nunc) were coated with E. coli LPS (100 ng/well; serotype 111:B4; Sigma) in PBS for 3 h at 37° C., following which the plates were rinsed thoroughly under running water and air-dried overnight. After blocking excess binding sites with 1% BSA/PBS, FhHDM-1 or derived peptides (0.02-2.0 µg/well in PBS) were added to the plate which was then incubated for 1 h at 37° C. Binding of FhHDM-1 or peptides to LPS was detected by the addition of affinity-purified rabbit anti-FhHDM-1 (1:5000 dilution in 0.1% BSA/PBS) for 1 h at 37° C., followed by AP-conjugated goat anti-rabbit IgG (Sigma; 1:2000 dilution in 0.1% BSA/PBS). Following 1 h incubation at 37° C., binding was visualised by the addition of p-nitrophenol phosphate substrate (Sigma; 100 µl/well) and absorbance read at 405 nm. Alternatively, FhHDM-1 or derived peptides (0.1 µg/well) were added to LPS-coated plates in the presence of LPS (0.05 to 5.0 µg/well) in PBS. Bound peptide was then determined by the addition of anti-FhHDM-1 antibody as described above.

Assay for the interaction of LPS with LBP

LPS-LBP binding was examined as previously described (Nagaoka et al. 2002, Clin. Diagn. Lab. Immunol. 9, 972-982). Briefly, PBS containing 0.1-10% mouse sera was added to an LPS-coated microtiter plate (100 ng/well) and incubated for 1 h at 37° C. Bound LBP was detected by the addition of anti-LBP antibody (Santa Cruz; 1:500 dilution in 0.1% BSA/PBS) followed by AP-conjugated rabbit anti-goat IgG (Sigma; 1:1000 dilution on 0.1% BSA/PBS) and visualised by adding p-nitrophenol phosphate substrate and absorbance read at 405 nm. To examine the effect of FhHDM-1 or derived peptides on the interaction between LPS and LBP, LPS-coated microtiter plates were pre-incubated with either FhHDM-1, FhHDM-1 p1 or FhHDM-1 p3 (0.01-10 µg/mL) for 1 h at 37° C. prior to the addition of 10% mouse sera in PBS and assayed as described above.

Assay for Binding of FITC-Conjugated LPS to RAW 264.7 Cells

RAW 264.7 cells (5×10$^5$/mL) were incubated with FITC-conjugated LPS (100 ng/mL) in the absence or presence of FhHDM-1 or derived peptides (0.01 to 10 µg/mL) in RPMI 1640 containing 10% FBS for 20 min at 4° C. After cells were washed with PBS, the binding of FITC-conjugated LPS was analysed by measuring median fluorescence intensity using a LSR II flow cytometer (BD Bioscience).

The Effects of FhHDM-1 and Derived Peptides on Endotoxin-Induced Inflammation

Six week-old female BALB/c mice were purchased from ARC (Perth, Australia) and maintained according to the guidelines of the University of Technology Sydney Animal Care and Ethics committee. For the analysis for endotoxin-induced inflammation, mice were intra-peritoneally injected with 1 µg of E. coli LPS (serotype 111:B4; Sigma) either with or without 1 µg FhHDM-1 or derived peptides. After 2 h mice were sacrificed by cervical dislocation. Plasma was isolated from cardiac blood by centrifugation at 2000×g for 10 min and levels of circulating IL-10 and TNF measured by ELISA (BD Pharmingen). Additionally, the peritoneal cavities of mice were lavaged and peritoneal macrophages isolated by adherence to plastic as previously described (Donnelly et al. 2010, J. Biol. Chem. 285, 3383-3392). Macrophages were incubated overnight in RPMI 1640 supplemented with 10% FCS and supernatants were analysed for the presence of IL-10 and TNF by ELISA.

Example 6

FhHDM-1 Interacts with the Plasma Membrane of Primary Human Macrophages

Figure 10:
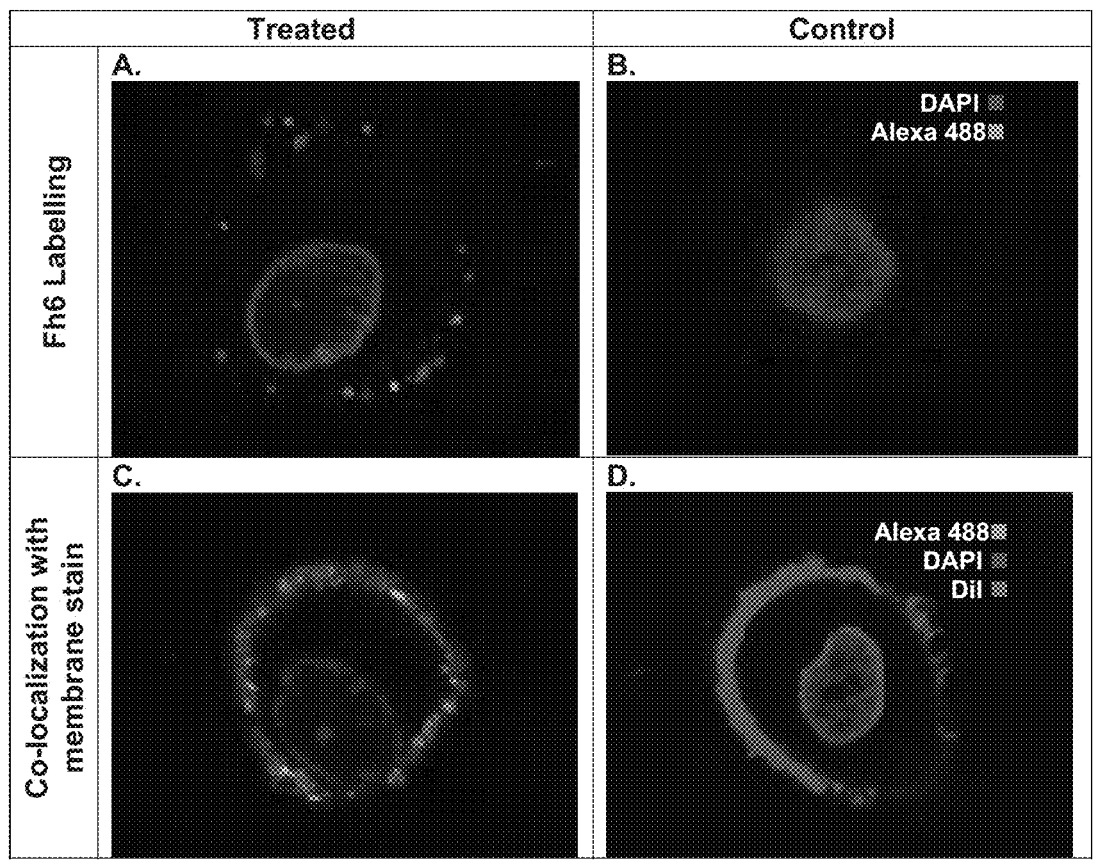
FIG. 10 is a photographic representation showing representative immunofluorescent images obtained by confocal microscopy at an original magnification 100× of primary human macrophages (A) and (C) incubated with recombinant FhHDM-1 (10 µg/mL for 2 h). Images (B) and (D) were experimental controls incubated with media only. Cells were stained with mouse anti-His MAb (1/2000), goat-anti-mouse Alexa-488-conjugated secondary antibody (1/1000) (green staining) and DiI plasma membrane stain (red staining). DAPI was used for identification of the cell nucleus (blue staining).

Confocal microscopy of primary human macrophages incubated with FhHDM-1, as shown in FIG. 10, reveals that FDHM-1 interacts with the plasma membrane of the macrophages.

Example 7

Down-Regulation of Macrophage Lysosomal Proteins by FhHDM-1

Figure 11:
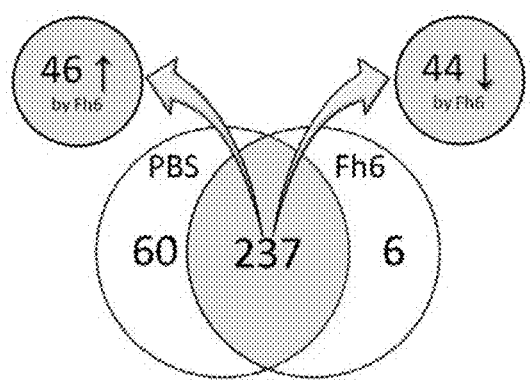
FIG. 11 is a diagrammatic representation showing a Venn diagram of soluble proteins identified in primary human macrophages.

Proteomics analysis of primary human macrophages treated with recombinant FhHDM-1 or PBS shows that 60 proteins are uniquely expressed in the PBS-treated sample and 6 in the FhHDM-1-treated sample. 237 proteins were present in both samples however, 42 of these proteins were up-regulated following FhHDM-1 treatment whereas 44 proteins were down-regulated. These results are summarized in FIG. 11. Of interest, the proteomic analysis revealed that the KEGG pathways are down-regulated in primary human macrophages in response to FhHDM-1 treatment (see, Table 5).

TABLE 5

KEGG PATHWAYS ARE DOWN-REGULATED IN PRIMARY HUMAN MACROPHAGES BY FHHDM-1 TREATMENT

| Pathway | Accession | Protein |
| --- | --- | --- |
| Lysosome | P08962 | CD63 molecule |
|  | A8K0B6 | N-acylsphingosine amidohydrolase (acid ceramidase) 1 |
|  | P11117 | Lysosomal Acid Phosphatase 2 |
|  | P16278 | Galactosidase, beta 1 |
|  | P15586 | Glucosamine (N-acetyl)-6-sulfatase |
|  | P10253 | Glucosidase, alpha; acid |
|  | P08236 | Glucuronidase, beta |
|  | P06865 | Hexosaminidase A (alpha polypeptide) |
|  | P11279 | Lysosomal-associated membrane protein 1 |
|  | Q13488 | T-cell, immune regulator 1, ATPase, H+ transporting, lysosomal V0 subunit A3 |
|  | Q00610 | Clathrin, heavy chain (Hc) |
|  | P07686 | Hexosaminidase B (beta polypeptide) |
|  | O00754 | Mannosidase, alpha, class 2B, member 1 |
|  | P07602 | Prosaposin |
| Oxidative Phosphorylation | P56385 | ATP synthase, H+ transporting, mitochondrial F0 complex, subunit E |
|  | P36542 | ATP synthase, H+ transporting, mitochondrial F1 complex, gamma polypeptide 1 |
|  | O75348 | ATPase, H+ transporting, lysosomal 13 kDa, V1 subunit G1 |
|  | Q6PJ05 | ATPase, H+ transporting, lysosomal 34 kDa, V1 subunit D |

TABLE 5-continued

KEGG PATHWAYS ARE DOWN-REGULATED IN PRIMARY HUMAN MACROPHAGES BY FHHDM-1 TREATMENT

| Pathway | Accession | Protein |
|---|---|---|
| | P20674 | Cytochrome c oxidase subunit Va |
| | P25705 | ATP synthase, H+ transporting, mitochondrial F1 complex, alpha subunit 1, cardiac muscle |
| | Q13488 | T-cell, immune regulator 1, ATPase, H+ transporting, lysosomal V0 subunit A3 |
| | P22695 | Ubiquinol-cytochrome c reductase core protein II |
| Glycosaminoglycan degradation | P16278 | Galactosidase, beta 1 |
| | P15586 | Glucosamine (N-acetyl)-6-sulatase |
| | P08236 | Glucuronidase, beta |
| | P06865 | Hexosaminidase A (alpha polypeptide) |
| | P07686 | Hexosaminidase B (beta polypeptide) |
| Other glycan degradation | P16278 | Galactosidase, beta 1 |
| | P06865 | Hexosaminidase A (alpha polypeptide) |
| | P07686 | Hexosaminidase B (beta polypeptide) |
| | O00754 | Mannosidase, alpha, class 2B, member 1 |
| Pentose Phosphate Pathways | O95336 | 6-phosphogluconolactonase |
| | P11413 | Glucose-6-phosphate dehydrogenase |
| | P29401 | Transketolase |
| Glycosphingolipid biosynthesis | P16278 | Galactosidase, beta 1 |
| | P06865 | Hexosaminidase A (alpha polypeptide) |
| | P07686 | Hexosaminidase B (beta polypeptide) |
| TCA cycle | O75390 | Citrate synthase |
| | P62820 | Dihydrolipoamide S-succinyltransferase (E2 component of 2-oxo-glutarate complex) |
| | O75874 | Isocitrate dehydrogenase 1 (NADP+), soluble |

*Proteins in bold are uniquely expressed by PBS-treated macrophages

The above results indicate that FhHDM-1 treatment of primary macrophages down-regulates their lysosomal proteins.

Example 8

FhHDM-1 P3 Reduces Immune Cell Invasion of Pancreatic Islets in Type I Diabetes Model Non-obese diabetic (NOD) mice (model of Type 1 diabetes) were given 6 injections (on every second day) of proteinaceous compound beginning at 5 weeks of age and animals were sacrificed at 10 weeks of age (i.e. when insulitis develops). Subsequently, formalin-fixed, paraffin-embedded pancreata was stained with haematoxylin and eosin to assess islet inflammation (i.e., insulitis).

Islet insulitis was scored as 0 (healthy islet), 1 (peri-insulitis up to 25% of islet occupied by leukocytes), 2 (leukocytic infiltration from 25% up to 50% of islet mass), 3 (leukocytic infiltration from 50% up to 75% of islet mass) or 4 (less than 25% of islet mass present). Accordingly, the greater the percentage of islets with higher insulitis scores the worse the prognosis for diabetes development would be for that animal. Additionally, if as a group the treated animals had a lower percentage of islets with insulitis as compared to the control group, then the treatment was considered to have some putative efficacy in reducing immune cell invasion into the islets.

Figure 12:
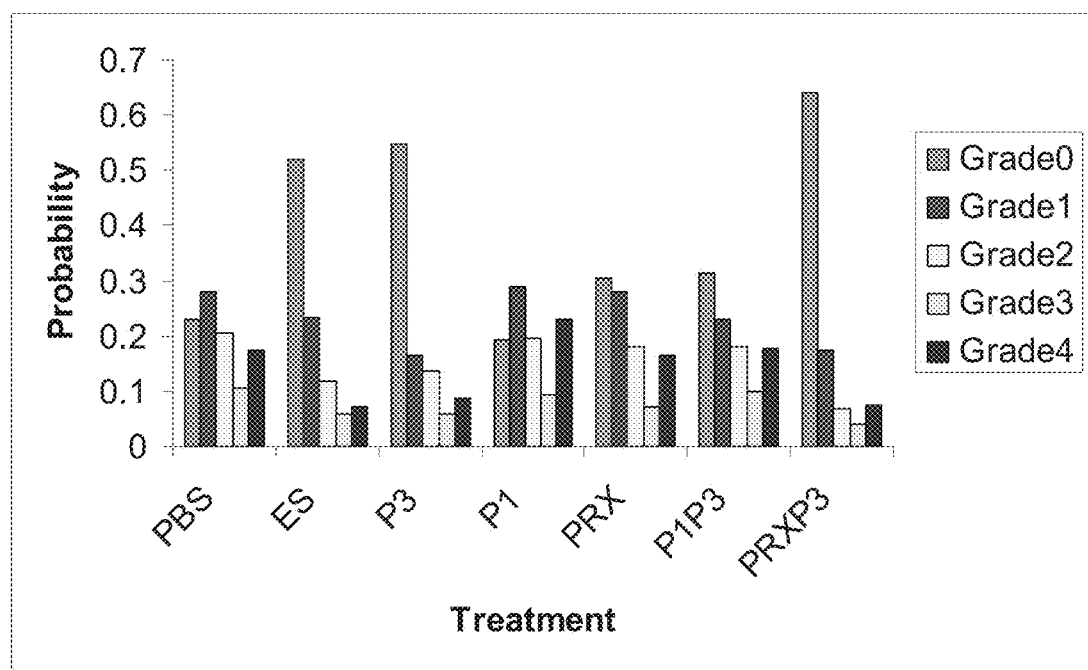
FIG. 12 is a graphical representation showing that FhHDM-1 P3 significantly reduces insulitis in a murine model of type I diabetes. Abbreviations are as follows for the various treatment groups: PBS (phosphate buffered saline, i.e., vehicle control); ES (excretory/secretory product from F. hepatica, previously shown to reduce insulitis [immune cell invasion into the islets] and prevent disease); F. hepatica PRX (peroxiredoxin); FhHDM-1 P1 (peptide 1); FhHDM-1 P3 (peptide 3); PRXP3 (peroxiredoxin and peptide 3); and P1P3 (peptide 1 and peptide 3).

Inspection of the results shown in FIG. 12 clearly shows that FhHDM-1 P3 alone reduces immune cell invasion of pancreatic islets with the same efficacy as ES (i.e., total adult *F. hepatica* secretory proteins, from which FhHDM-1 was derived). The results also show that FhHDM-1 P1 has no significant activity in reducing that immune cell invasion and that the activity of FhHDM-1 P3 was enhanced by co-administration of *F. hepatica* PRX (i.e., peroxiredoxin).

Example 9

HDM Protects Nod Mice from Developing Diabetes

Female NOD mice (n=10) were given recombinant HDM (10 μg in 100 μL sterile PBS) by intraperitoneal (i.p.) injection on alternate days beginning at 4 weeks of age for a total of 6 injections. Control mice were given 100 μL of sterile PBS on the same days. Blood glucose levels were measured once a week, from the age of 13 weeks, using Accu-check Advantage blood glucose strips (Roche). Animals were sacrificed when they became overtly diabetic; as defined by two random blood glucose concentrations above 12 mM. Statistical analysis of the times the animal was sacrificed was performed using survival analysis.

Figure 13:
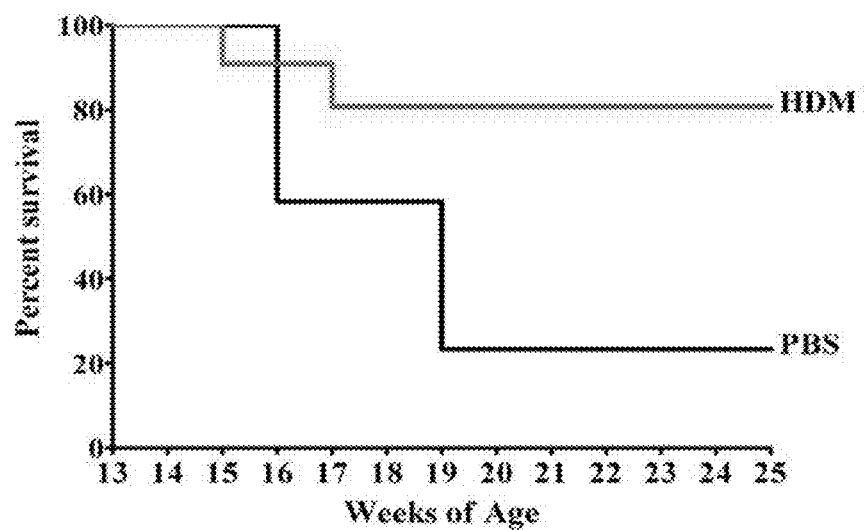
FIG. 13 is a graphical representation showing that FhHDM-1 protects NOD mice from developing diabetes. FhHDM-1 was given to female NOD mice aged 4 weeks. 10 µg of FhHDM-1 was delivered i.p. in PBS on alternate days for a total of 6 doses. Blood glucose readings were taken weekly and mice with two consecutive readings >14 mmol/L were deemed diabetic.

The results shown in FIG. 13 demonstrate that at 18 weeks of age, 80% of HDM-treated mice were normoglycaemic, compared to only 18% of vehicle (PBS)-treated mice (p=0.0078). This level of protection was sustained for another 7 weeks.

Example 10

Macrophages Isolated from the Peritoneal Cavity of HDM Treated Mice Secrete Significantly More IL-10 Compared to Untreated Mice Female NOD mice (n=6) were given recombinant HDM (10 μg in 100 μL sterile PBS) by intraperitoneal (i.p.) injection on alternate days beginning at 4 weeks of age for a total of 6 injections. Control mice were given 100 μL of sterile PBS on the same days. 24 h after the last injection mice were sacrificed and peritoneal cells harvested by lavage. Macrophages were isolated from peritoneal lavages based upon their adherent properties, and cultured overnight at 37° C. in RPMI supplemented with FCS. The quantity of IL-10 secreted into the media was measured by ELISA.

Figure 14:
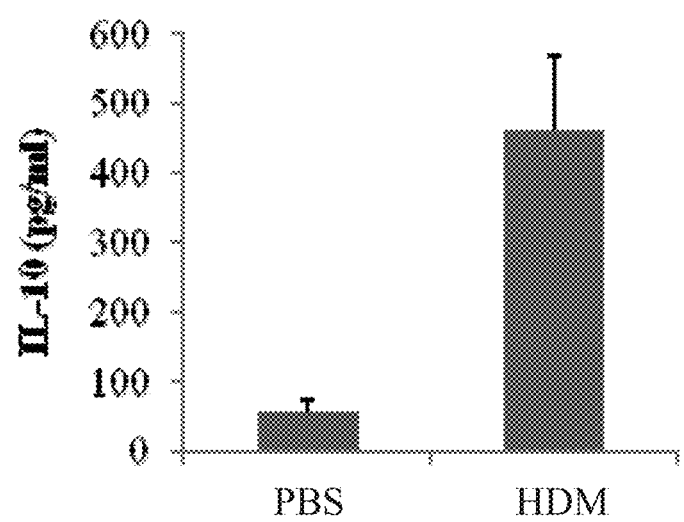
FIG. 14 is a graphical representation showing that macrophages isolated from the peritoneal cavity of FhHDM-1-treated NOD mice secrete significantly more IL-10, as compared to untreated mice. FhHDM-1 was given to female NOD mice aged 4 weeks. 10 µg of FhHDM-1 was delivered i.p. in PBS on alternate days for a total of 6 doses. 24 h after the last injection, macrophages were isolated from the peritoneal lavage and cultured in RPMI supplemented with FCS for 12 h. IL-10 secreted into the media was measured by ELISA.

The results presented in FIG. 14 reveal that macrophages isolated from the peritoneal cavity of NOD mice treated with HDM secreted significantly more (p=0.032) IL-10 compared to macrophages isolated from untreated NOD mice.

Example 11

HDM Treatment Inhibits the Inflammatory Response to Bacterial Lipopolysaccharide In Vivo Female BALB/c mice (n=5) were given a single intraperitoneal injection of 1 μg of recombinant HDM two hours prior to an intraperitoneal injection of 1 μg of *E. coli* lipopolysaccharide. Four hours later, mice were sacrificed and blood and peritoneal cells were harvested. Peritoneal macrophages were isolated from lavage fluid based upon their adherent properties, and cultured overnight at 37° C. in RPMI supplemented with FCS. The quantities of inflammatory cytokines in both sera and culture media from macrophages were measured by ELISA.

Figure 15:
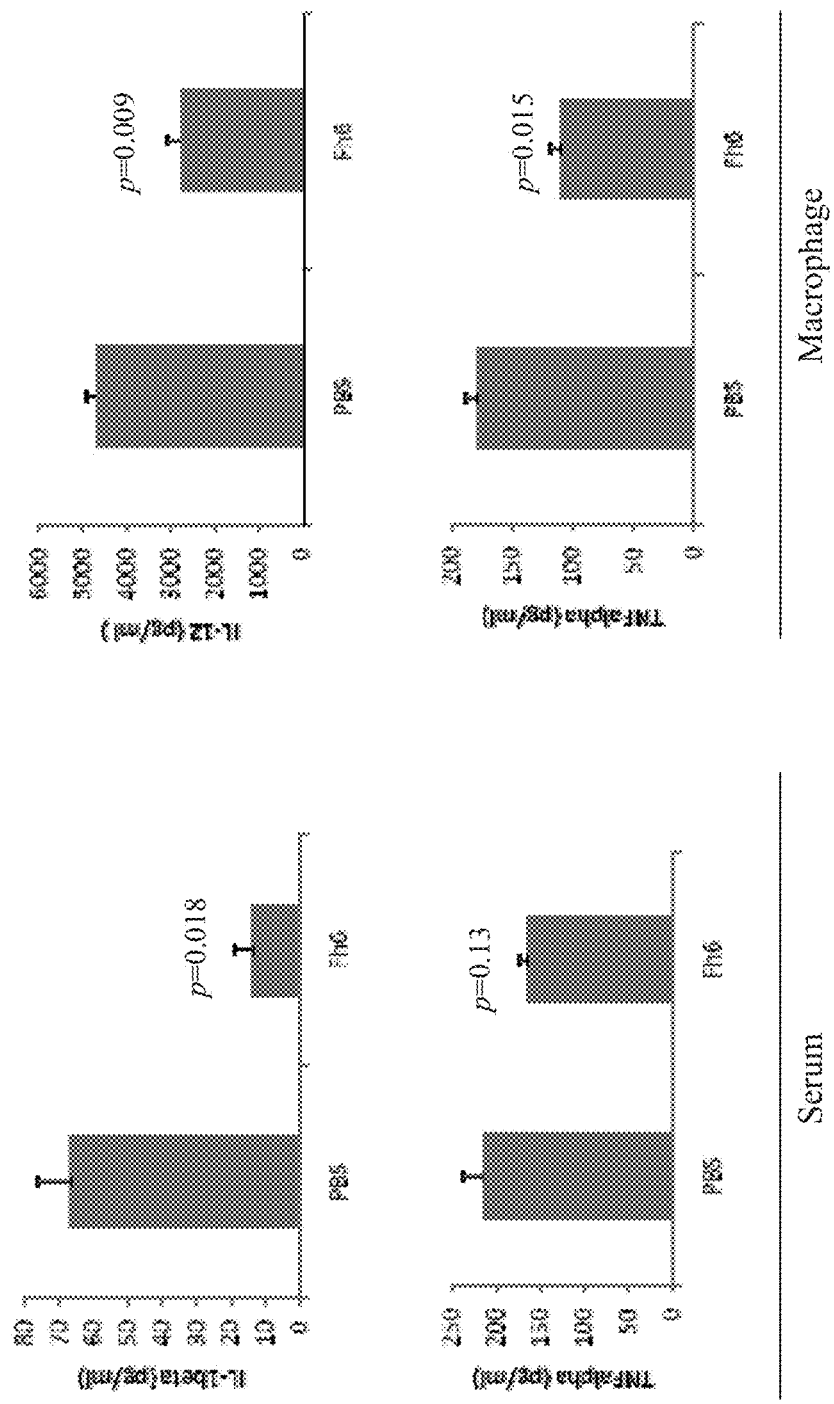
FIG. 15 is a graphical representation showing that FhHDM-1 treatment inhibits the inflammatory response to bacterial lipopolysaccharide in vivo. Female BALB/c mice were given 1 μg of FhHDM-1 i.p. and 2 h later given 1 μg of E. coli LPS i.p. After another 4 h, mice were sacrificed and serum and peritoneal macrophages assessed for the presence of inflammatory cytokines.

The results presented in FIG. 15 demonstrate that macrophages isolated from the peritoneal cavity of BALB/c mice treated with HDM secreted significantly less IL-12 (p=0.009) and TNFα (p=0.015) in response to exposure to LPS, compared to macrophages isolated from untreated mice. In addition, the levels of inflammatory cytokine IL-10

Example 12

FhHDM P3 Prevents ATP Induced Macrophage Cell Death

Raw macrophages were pre-treated with either HDM (20 µg/mL) or FhHDM-1 P3 (20 µg/mL) for 1 h, washed and then cultured in the presence of ATP (5 mM) for 2 h. The culture supernatants were collected and assayed for LDH activity with an LDH release kit. The amount of LDH release by cells treated with ATP only was used to represent 100% cytotoxicity.

Figure 16:
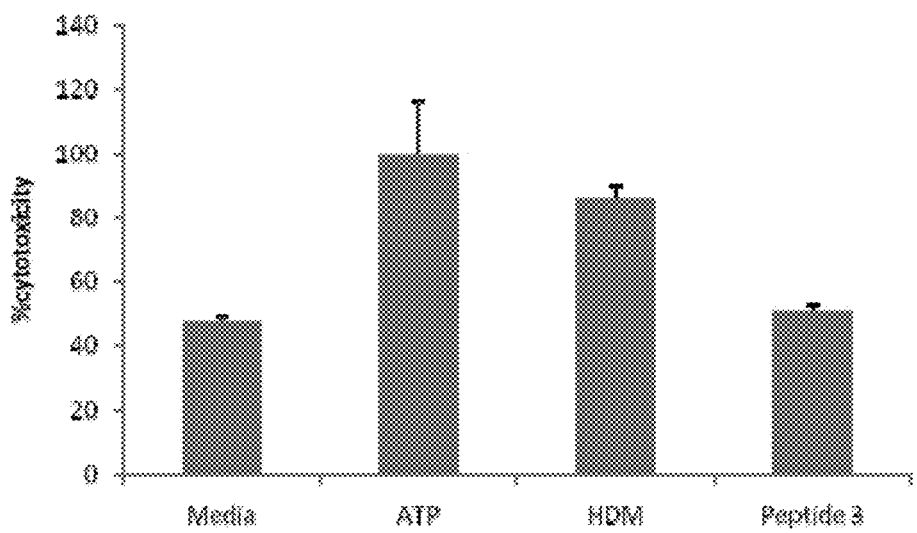
FIG. 16 is a graphical representation showing that FhHDM-1 P3 prevents ATP induced cell death in RAW macrophages. RAW macrophages were pretreated with either FhHDM-1 (20 μg/mL) or FhHDM-1 p3 (20 μg/mL) for 1 h, then washed and cultured in the presence of ATP (5 mM) for 2 h. Cell death (% cytotoxicity) was quantified according to the amount of LDH released by the cells into culture media.

The results presented in FIG. 16 show that FhHDM-1 P3 derived from full-length FhHDM-1 inhibited LDH release induced by ATP stimulation. Macrophages treated with this peptide recorded the same level of cell death as those cells cultured in media alone. In comparison, pre-treatment of cells with the full-length recombinant FhHDM-1 had no significant effect on the cytotoxicity of ATP.

Example 13

FhHDM-1 C-Terminal Peptides and Peptide Homologs Inhibit ATPase Activity Associated with Lysosomal Membranes A cellular fraction enriched for lysosomes was prepared by sequential centrifugation of RAW264.7 macrophage lysates. The lysosome pellet was extracted with water and the resulting lysosomal membranes were recovered and assayed (with or without HDM peptides) for ATPase activity using a commercially available kit.

Figure 17:
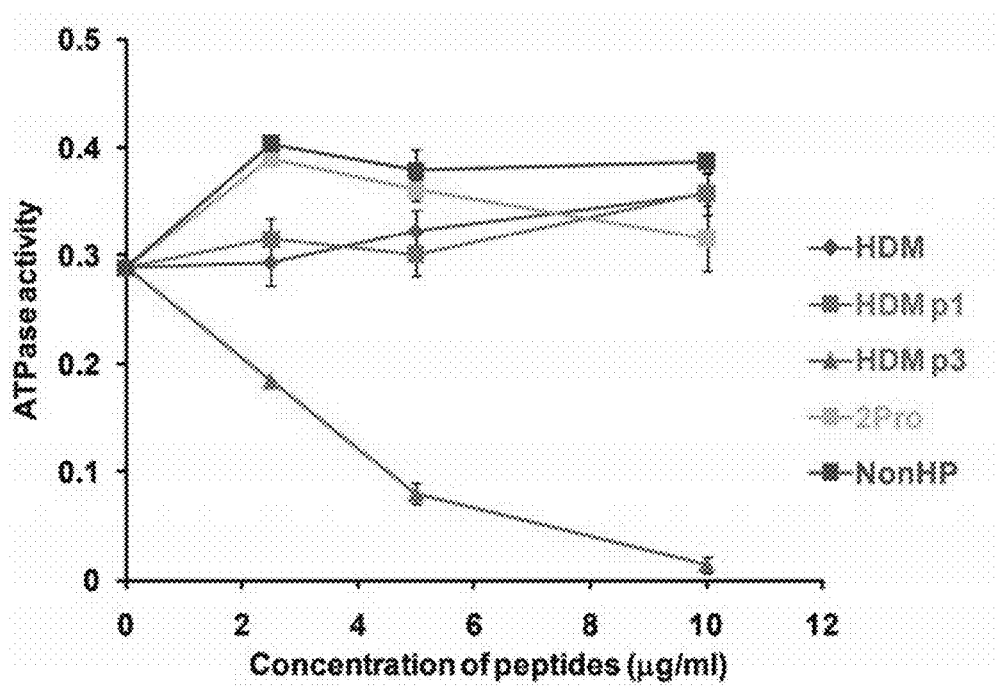
FIG. 17 is a graphical representation showing that FhHDM-1 P3 inhibits ATPase activity associated with lysosomal membranes in a concentration-dependent manner. A cellular fraction enriched for lysosomes was prepared by sequential centrifugation of RAW264.7 macrophage lysates. The lysosomal membranes were recovered and assayed (with or without HDM peptides) for ATPase activity using a commercially available kit.

The results presented in FIG. 17 show that HDM-1p3 inhibited ATPase activity associated with lysosomal membranes (equivalent to vATPase activity) in a concentration-dependent manner. HDMp2, HDMp3_27 and a consensus HDM sequence (Cons_p3) were also inhibitory (data not shown). In contrast, full-length HDM as well as synthetic peptide analogues with a truncated C-terminal amphipathic helix (HDM-1p1), disrupted helical structure (2Pro) or where the hydrophobic face of the C-terminal amphipathic helix has been knocked-out (nonHP) did not inhibit ATPase activity even at the highest concentrations tested. An alignment of these peptide sequences is shown in FIG. 18.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

SEQUENCE LISTING

A Sequence Listing forms part of this patent application. Sequence Listings in ASCII format which form part of this application were created on Jun. 1, 2016 (186,960 bytes; entitled "33321-US-1-PCT_ST25.txt"), Oct. 27, 2016 (192,340 bytes; entitled "33321-US-1-PCT_ST25.txt"), May 25, 2017 (192,770 bytes; entitled "7409861_00005_Amended_Sequence Listing_ST25.txt"), and Sep. 21, 2018 (195,260 bytes; entitled "Amended_sequence_listing_ST25.txt"). All of these sequence listings are incorporated by reference herein in their entirety.

---

What is claimed is:

1. A method for suppressing a tumor necrosis factor- or interleukin-1β-mediated immune response in a subject, the method comprising administering to the subject an effective amount of an isolated proteinaceous molecule, or a composition comprising the isolated proteinaceous molecule, wherein the proteinaceous molecule comprises an amphipathic helix, and wherein the isolated proteinaceous molecule comprises the amino acid sequence set forth in SEQ ID NO:46.

2. The method according to claim 1, wherein the amphipathic helix comprises the amino acid sequence set forth in SEQ ID NO:2.

3. The method according to claim 1, wherein the proteinaceous molecule comprises or consists essentially of the amino acid sequence set forth in SEQ ID NO: 24.

4. The method according to claim 1, wherein the composition further comprises a pharmaceutically acceptable carrier or diluent.

5. The method according to claim 1, wherein administration of the composition comprising the proteinaceous molecule suppresses an immune response associated with a transplant rejection.

6. The method according to claim 1, wherein the proteinaceous molecule lacks a native signal peptide.

7. A method according to claim 1, further comprising administering to the subject at least one ancillary agent, wherein the ancillary agent is an antigen that corresponds to a target antigen to which a tolerogenic response is desired.

8. A method according to claim 7, wherein the proteinaceous molecule and/or ancillary agent are contained in or otherwise associated with a particle.

9. A method according to claim 7, wherein the proteinaceous molecule and/or ancillary agent are contained in a single particle.

10. A method according to claim 7, wherein the proteinaceous molecule and/or ancillary agent are contained in different particles.

11. A method according claim 10, wherein each particle is capable of being taken up by an immune cell.

12. The method according to claim 1, wherein administration of the composition comprising the proteinaceous molecule suppresses an immune response associated with graft versus host disease.

13. The method according to claim 1, wherein administration of the composition comprising the proteinaceous molecule suppresses an immune response associated with inflammatory diseases.

14. The method according to claim 1, wherein administration of the composition comprising the proteinaceous molecule suppresses an immune response associated with autoimmune diseases.

15. The method according to claim 1, further comprising administering to the subject at least one ancillary agent, wherein the ancillary agent is a nucleic acid molecule from which the antigen is expressible.

16. The method according to claim 1, further comprising administering to the subject at least one ancillary agent, wherein the ancillary agent is a peroxiredoxin.

17. The method according to claim 1, further comprising administering to the subject at least one ancillary agent, wherein the ancillary agent is a nucleic acid molecule from which peroxiredoxin is expressible.

* * * * *